(12) United States Patent
Stranix et al.

(10) Patent No.: US 6,608,100 B1
(45) Date of Patent: Aug. 19, 2003

(54) HIV PROTEASE INHIBITORS BASED ON AMINO ACID DERIVATIVES

(75) Inventors: Brent Richard Stranix, Pointe-Claire (CA); Gilles Sauvé, Laval (CA); Abderrahim Bouzide, Laval (CA); Alexandre Coté, Chomedey Laval (CA); Gervais Bérubé, Trois-Rivières (CA); Patrick Soucy, Beaconsfield (CA); Yongsen Zhao, Montreal (CA); Jocelyn Yelle, Laval (CA)

(73) Assignee: Pharmacor Inc., Laval (CA)

( * ) Notice: Subject to any disclaimer, the term of this patent is extended or adjusted under 35 U.S.C. 154(b) by 0 days.

(21) Appl. No.: 10/244,622

(22) Filed: Sep. 17, 2002

Related U.S. Application Data

(62) Division of application No. 09/781,219, filed on Feb. 13, 2001, now Pat. No. 6,506,786.

(51) Int. Cl.$^7$ .................. A61K 31/404; C07D 207/09; A61P 43/00

(52) U.S. Cl. ................ 514/419; 548/403; 548/482

(58) Field of Search .................. 514/419; 548/403, 548/482

(56) References Cited

U.S. PATENT DOCUMENTS

| | | | |
|---|---|---|---|
| 5,013,861 A | 5/1991 | Weller, III et al. | 560/34 |
| 5,527,829 A | 6/1996 | Kalish | 514/604 |
| 5,614,522 A | 3/1997 | Talley et al. | 514/237.8 |
| 5,714,605 A | 2/1998 | Vazquez et al. | 544/106 |
| 5,776,718 A | 7/1998 | Palmer et al. | 435/23 |
| 5,965,588 A | 10/1999 | Vazquez et al. | 514/357 |
| 6,022,994 A | 2/2000 | Vazquez et al. | 564/89 |

FOREIGN PATENT DOCUMENTS

| | | |
|---|---|---|
| EP | 0532466 | 3/1993 |
| WO | WO 95 24385 | 9/1995 |

OTHER PUBLICATIONS

Poduska, et al, 1965, Collection Czech. Chem. Commun., 30(7), 2410–2433.*
GArrity, et al, 1993, TEtrahedron Letters, 34(35), 5531–4.*
Lasky L.A. et al., Cell vol. 50, p.975–985 (1987).
Meek et al., Nature, 343, pp. 90–92 (1990).
Matayoshi et al (Science 247: 954–954, 1990).
J.Org.Chem 44, 4841 (1979).

* cited by examiner

Primary Examiner—Joseph K. McKane
Assistant Examiner—Andrea D. Small
(74) Attorney, Agent, or Firm—Ronald S. Kosie; Robert Brouillette; Gaetan Prince

(57) ABSTRACT

A compound selected from the group consisting of a compound of formula I $$\underset{R_2}{\overset{R_1}{\underset{|}{N}}}-\overset{Cx}{\underset{|}{C}}-(CH_2)_n-\underset{H}{\overset{|}{N}}-\overset{Y}{\underset{|}{C}}-\underset{R_5}{\overset{|}{C}}-\underset{R_4}{\overset{R_3}{N}},\qquad I$$

a compound of formula II $$\underset{R_2}{\overset{R_1}{\underset{|}{N}}}-\overset{Cx}{\underset{|}{C}}-(CH_2)_n-\underset{H}{\overset{|}{N}}-\overset{Y}{\underset{|}{C}}-\underset{R_a}{\overset{R_4}{N}}\qquad II$$

and when the compound of formula I and II comprises an amino group pharmaceutically acceptable ammonium salts thereof, wherein $R_1$, $R_2$, Cx, n, $R_3$, $R_4$, $R_5$, Y are as defined in the specification.

10 Claims, No Drawings

HIV PROTEASE INHIBITORS BASED ON AMINO ACID DERIVATIVES

This application is a divisional of U.S. patent application Ser. No. 09/781,219, filed Feb. 13, 2001 now U.S. Pat. No. 6,506,786 Jan. 14, 2003.

TECHNICAL FIELD OF THE INVENTION

The present invention concerns amino acid derivatives possessing aspartyl protease inhibitory properties, in particular Nε-amino acid substituted L-lysine derivatives (and analogs) possessing aspartyl protease inhibitory properties. It describes also the synthetic methodology used to make these derivatives and their biological applications. In addition, this invention relates to different pharmaceutical compositions comprising these compounds. The compounds and the pharmaceutical compositions of this invention have been shown to inhibit the activity of HIV aspartyl protease, an enzyme essential for virus maturation. The inhibitory property may be advantageously used to provide compounds with antiviral properties against HIV viruses, including the HIV-1 and HIV-2 viruses.

BACKGROUND OF THE INVENTION

The HIV (human immunodeficiency virus) retrovirus is responsible for causing the disease known as AIDS (acquired immunodeficiency syndrome). HIV infection is characterized by a period immediately following infection, called asymptomatic, which is devoid of clinical manifestations in the patient. Progressive HIV-induced destruction of the immune system then leads to increased susceptibility to opportunistic infections, which eventually produces a syndrome called AIDS-related complex (ARC) characterized by symptoms such as persistent generalized lymphadenopathy, fever, weight loss, followed itself by full blown AIDS.

As the first step of its replication cycle, the HIV-1 retrovirus attaches primarily to the CD4 receptor (a 58 kDa transmembrane protein) to gain entry into susceptible cells, through high-affinity interactions between the viral envelope glycoprotein (gp 120) and a specific region of the CD4 molecule found in CD4 (+) T-helper lymphocytes and other cells carrying the receptor (Lasky L. A. et al., Cell vol. 50, p. 975–985 (1987)). The HIV genetic material, in the form of RNA, is then transcribed into DNA by a viral enzyme carried by the virus called reverse transcriptase. The viral DNA now called provirus is then transported into the cell nucleus in the form of a preintegration complex and attached to the cell DNA by another viral enzyme called integrase. Following integration, the viral DNA then serves as a template for viral gene expression by the host transcription system The primary RNA transcripts made from the provirus are synthesized by the host cell RNA polymerase II whose activity is modulated by two virus-encoded proteins, Tat and Rev. The viral proteins are expressed mainly in the form of polyproteins. After the infected cell has produced all the different HIV polyproteins and genetic material, they assemble at the cell membrane and are released from the cell in the form of an immature viral particle. A third viral enzyme known as protease then cleaves the polyproteins to give the mature, infectious viral particle. The polyproteins that are cleaved by the HIV protease are the Gag and Gag-Pol precursors, whose cleavage gives rise to structural proteins and viral enzymes.

A number of synthetic antiviral agents have been designed to block various stages in the replication cycle of HIV, although only those developed against the viral enzymes have reached the market so far. The latter include compounds which block viral reverse transcriptase (for example, didanosine and zidovudine (AZT)), or the viral protease (for example, ritonavir and indinavir). Although these drugs have improved significantly the survival time and quality of life of AIDS patients, the administration of most of these agents leads to unwanted side effects, such as anemia, neurotoxicity and bone marrow suppression.

Anti-protease compounds represent the most recent drugs developed to block HIV replication. These compounds inhibit the formation of infectious virions by interfering with the processing of viral polyprotein precursors by the viral protease. The antiviral potential of HIV protease inhibitors was first demonstrated using peptidic inhibitors. Such peptidic compounds, however, are typically large and complex molecules that tend to exhibit poor bioavailability and limited stability in the body. New compounds devoid of these drawbacks are urgently needed to treat HIV infections. In addition, mutations arising during HIV replication lead to resistance to the currently available protease inhibitors, so new compounds with original structure are desirable to fight these resistant viral strains.

SUMMARY OF THE INVENTION

The present invention provides a novel class of compounds, including their pharmaceutically acceptable derivatives. These compounds have an affinity for aspartyl proteases, in particular, HIV aspartyl protease. Therefore, these compounds are useful as inhibitors of such proteases. These compounds can be used alone or in combination with other therapeutic or prophylactic. agents for the treatment or prophylaxis of viral infection.

According to a preferred embodiment, the compounds of this invention are capable of inhibiting HIV viral replication in human CD4+ T-cells, by inhibiting the ability of HIV aspartyl protease to catalyse the hydrolysis of peptide bonds present in viral Gag and Gag-Pol polyproteins. These novel compounds can thus serve to reduce the production of infectious virions from acutely and chronically infected cells, and can inhibit the initial or further infection of host cells. Accordingly, these compounds are useful as therapeutic and prophylactic agents to treat or prevent infection by HIV-1 and HIV-2, which may result in asymptomatic infection, AIDS-related complex (ARC), acquired immunodeficiency syndrome (AIDS), AIDS-related dementia, or similar diseases of the immune system, and related viruses such as HTLV-I and HTLV-II, and simian immunodeficiency virus.

It is the m objective of this invention to provide a novel class of molecules that are aspartyl protease inhibitors, and particularly, HIV aspartyl protease inhibitors.

The present invention relates to a class of Nε-amino acid substituted L-lysine derivatives (including its lower and higher homologues and analogs) as well as their pharmaceutically acceptable derivatives (e.g. salts).

Accordingly, the present invention in accordance with one aspect thereof provides a compound of formula I

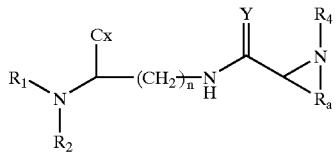

I a compound of formula II

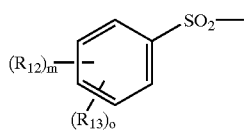

II and when the compound of formula I and II comprises an amino group pharmaceutically acceptable ammonium salts thereof, wherein n is 3 or 4 wherein Y is O, S or N—CN wherein Cx is selected from the group consisting of —COOM, COOR$_6$, —CHO, —CH$_2$OR$_7$, —CH$_2$OCOR$_8$, —CONHR$_9$ and —CONR$_{10}$R$_{11}$, wherein M is an alkali metal (e.g. Na, K, Cs, etc.) or alkaline earth metal (Ca, Mg, etc.), wherein R$_1$ is selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, wherein R$_2$ is selected from the group consisting of a benzenesulfonyl group of formula III,

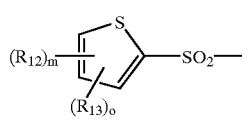

III and a thiophenesulfonyl group of formula IV,

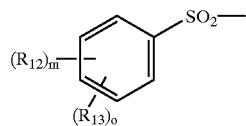

IV wherein R$_3$ is selected from the group consisting of H, a straight or branched alkyl group of 1 to 6 carbon atoms, a phenyl or a benzyl group wherein R$_4$ is selected from the group consisting of H, a group of formula IIIa

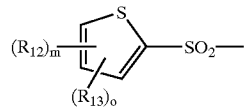

IIIa a group of formula IVa

IVa

C$_6$H$_{11}$—, C$_5$H$_{10}$N—CH$_2$CH$_2$—, OC$_4$H$_8$N—CH$_2$CH$_2$— (i.e. morpholine-4-CH$_2$CH$_2$—), C$_6$H$_5$CH$_2$CH$_2$—, 2,3-(CH$_3$O)$_2$C$_6$H$_3$CH$_2$—, C$_6$H$_5$—, 2-C$_5$H$_4$N (i.e. 2-pyridinyl), 3-C$_5$H$_4$N (i.e. 3-pyridinyl), 4-C$_5$H$_4$N (i.e. 4-pyridinyl), 3-quinolyl, C$_6$H$_5$CS—, 2-naphthyl-SO$_2$— and a group of formula R$_{4C}$—CO—, R$_{4C}$ being selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, (e.g. CH$_3$—, iso-butyl, isopropyl, tert-butyl, tert-butyl-CH$_2$—), CF$_3$, 1-pyrrolidinyl, 4-morpholinyl, tetrahydro-3-furanyloxy, 4-CH$_3$OC$_6$H$_4$NH—, CH$_3$NH—, HOCH$_2$CH$_2$NH—, 9-fluorenyl-CH$_2$O —, tert-butylO—, iso-butylO—, C$_6$H$_5$CH$_2$O —, CH$_3$O —, unsubstituted C$_6$H$_5$—, C$_6$H$_5$— substituted by one or more members (e.g. one or two) selected from the group consisting of F, Cl, Br, I, —CF$_3$, —NO$_2$, —NR$_{10}$R$_{11}$, —NHCOR$_{10}$, —OR$_{10}$, —SR$_{10}$, —COOR$_{10}$, —COR$_{10}$ and —CH$_2$OH, unsubstituted C$_6$H$_5$CH$_2$—, C$_6$H$_5$CH$_2$— substituted by one or more members (e.g. one or two) selected from the group consisting of F, Cl, Br, I, —CF$_3$, —NO$_2$, —NR$_{10}$R$_{11}$, —NHCOR$_{10}$, —OR$_{10}$, —SR$_{10}$, —COOR$_{10}$, —COR$_{10}$ and —CH$_2$OH, unsubstituted C$_6$H$_5$CH$_2$CH$_2$—, and C$_6$H$_5$CH$_2$CH$_2$— substituted by one or more members (e.g. one or two) selected from the group consisting of F, Cl, Br, I, —CF$_3$, —NO$_2$, —NR$_{10}$R$_{11}$, —NHCOR$_{10}$, —OR$_{10}$, —SR$_{10}$, —COOR$_{10}$, —COR$_{10}$ and —CH$_2$OH, wherein R$_5$ is selected from the group consisting of H, a straight or branched alkyl group of 1 to 8 carbon atoms, (e.g. CH$_3$—, CH$_3$CH$_2$CH$_2$—, CH$_3$CH$_2$CH$_2$CH$_2$—, iso-C$_4$H$_9$—, C$_6$H$_{11}$CH$_2$—), HOCH$_2$—, C$_6$H$_5$CH$_2$OCH$_2$—, benzyl-OCH(CH$_3$), HO$_2$CCH$_2$—, HO$_2$CCH$_2$CH$_2$—, NC—CH$_2$—, H$_2$NC(O)CH$_2$—, H$_2$NC(O)CH$_2$CH$_2$—, 4—CH$_3$C$_6$H$_4$CH$_2$SCH$_2$—, CH$_3$SCH$_2$CH$_2$—, H$_2$NCH$_2$CH$_2$CH$_2$CH$_2$—, C$_6$H$_5$—, C$_6$H$_5$CH$_2$—, C$_6$H$_5$CH(OH)—, C$_6$H$_5$CH(CN)—, C$_6$F$_5$CH$_2$—, 4-(9-fluorenylmethoxycarbonyl)-NHCH$_2$—C$_6$H$_4$CH$_2$—, C$_5$H$_4$N-2-CH$_2$— (i.e. pyridine-2—CH$_2$—), C$_5$H$_4$N-3-CH$_2$— (i.e. pyridine-3-CH$_2$—), C$_5$H$_4$N-4-CH$_2$— (i.e. pyridine-4-CH$_2$—), 2-thiophene-CH$_2$—, indole-3-CH$_2$—, 2-benzothiophene-CH$_2$—, Nτ-benzyl-imidazole-4-CH$_2$—, imidazole-4-CH$_2$—, thiazole-4-CH$_2$— and substituted benzyl (e.g. benzyl substituted by a group being as defined for R$_{12}$ below, e.g. 4-tert-butyl-C$_6$H$_4$CH$_2$—, 4-HOC$_6$H$_4$CH$_2$—, 4-benzyl-O—C$_6$H$_4$CH$_2$—, 4—NO$_2$C$_6$H$_4$CH$_2$—, 2-FC$_6$H$_4$CH$_2$—, 3-FC$_6$H$_4$CH$_2$—, 4-FC$_6$H$_4$CH$_2$—), wherein Ra represents a member selected from the group consisting of

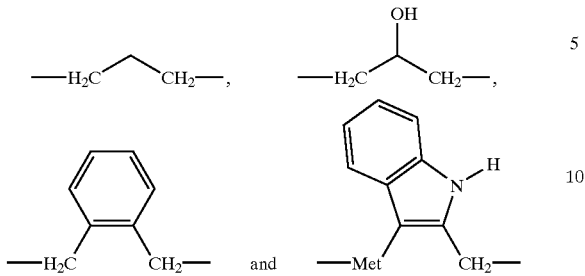

wherein Met is a methylene linked to the α' nitrogen wherein $R_6$ is selected from the group consisting of H, a straight or branched alkyl group of 1 to 4 carbon atoms and glycyl wherein $R_7$ is selected from the group consisting of H, a straight or branched alkyl group of 1 to 4 carbon atoms wherein $R_8$ is selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part and 1 to 3 carbon atoms in the alkyl part thereof, wherein $R_9$ is selected from the group consisting of H, a straight or branched alkyl group of 1 to 4 carbon atoms, —OH, —$NH_2$ and —$CH_2CH_2OH$ wherein $R_{10}$ and $R_{11}$ are independently selected from the group consisting of H, a straight or branched alkyl group of 1 to 4 carbon atoms wherein m is 0 or 1 wherein o is 0 or 1 wherein $R_{12}$ and $R_{13}$ are independently selected from the group consisting of H, a straight or branched alkyl group of 1 to 4 carbon atoms, F, Cl, Br, I, —$CF_3$, —$NO_2$, —$NR_{10}R_{11}$, —$NHCOR_{10}$, —$OR_{10}$, —$OCH_2C_6H_5$, —$SR_{10}$, —$COOR_{10}$, —$COR_{10}$ and —$CH_2OH$, $R_{10}$ and $R_{11}$ being as defined herein.

More particularly, this invention provides a compound of formula IA

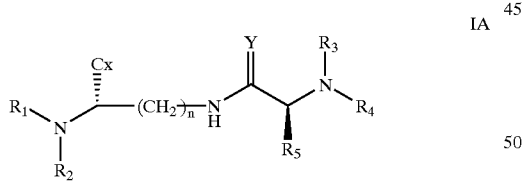

and when the compound of formula IA comprises an amino group pharmaceutically acceptable ammonium salts thereof, wherein n is 3 or 4 wherein Y is O, S or N—CN wherein Cx is selected from the group consisting of —COOM, $COOR_6$, —CHO, —$CH_2OR_7$, —$CH_2OCOR_8$, —$CONHR_9$ and —$CONR_{10}R_{11}$, wherein M is an alkali metal (e.g. Na, K, Cs, etc.) or alkaline earth metal, wherein $R_1$ is selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, wherein $R_2$ is selected from the group consisting of a benzenesulfonyl group of formula III,

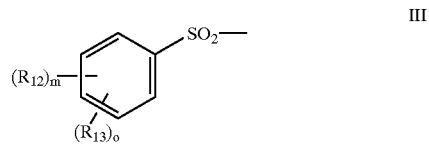

and a thiophenesulfonyl group of formula IV,

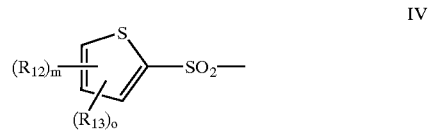

wherein $R_3$ is selected from the group consisting of H, a straight or branched alkyl group of 1 to 6 carbon atoms, a phenyl or a benzyl group wherein $R_4$ is selected from the group consisting of H, $C_6H_{11}$—, $C_5H_{10}N$—$CH_2CH_2$—, $OC_4H_8N$—$CH_2CH_2$— (i.e. morpholine-4-$CH_2CH_2$—), $C_6H_5CH_2CH_2$—, 2,3-$(CH_3O)_2C_6H_3CH_2$—, $C_6H_5$—, 2-$C_5H_4N$, 3-$C_5H_4N$, 4-$C_5H_4N$, 3-quinolyl, $CH_3CO$—, $CF_3CO$, $C_6H_5CO$—, $C_6H_5CS$—, 4-$CH_3OC_6H_4CH_2CO$—, $C_6H_5CH_2CH_2CO$—, iso-butyl-CO—, iso-propyl-CO—, tert-butyl-CO—, tert-butyl-$CH_2CO$—, 1-pyrrolidine-CO—, 4-morpholine-CO—, carbotetrahydro-3-furanyloxy, 4-$CH_3OC_6H_4NHCO$—, $CH_3NHCO$—, $HOCH_2CH_2NHCO$—, 9-fluorenylmethoxycarbonyl, tert-butylO-CO—, iso-butylO-CO—, $C_6H_5CH_2O$—CO—$CH_3O$—CO—, $C_6H_5SO_2$—, 4-$CH_3C_6H_4SO_2$—, 4-$CF_3C_6H_4SO_2$—, 4-$NO_2C_6H_4SO_2$—, 4-$NH_2C_6H_4SO_2$—, 4-$AcNHC_6H_4SO_2$—, 4-$FC_6H_4SO_2$—, 4-$ClC_6H_4SO_2$—, 4-$BrC_6H_4SO_2$—, 4-$CH_3OC_6H_4SO_2$—, 2-thiophene-$SO_2$— and 2-naphthyl-$SO_2$— wherein $R_5$ is selected from the group consisting of H, $CH_3$—, $CH_3CH_2CH_2$—, $CH_3CH_2CH_2CH_2$—, iso-$C_4H_9$—, $C_6H_{11}CH_2$—, $HOCH_2$—, $C_6H_5CH_2OCH_2$—, benzyl-OCH($CH_3$), $HO_2CCH_2$—, $HO_2CCH_2CH_2$—, NC—$CH_2$—, $H_2NC(O)CH_2$—, $H_2NC(O)CH_2CH_2$—, 4-$CH_3C_6H_4CH_2SCH_2$—, $CH_3SCH_2CH_2$—, $H_2NCH_2CH_2CH_2CH_2$—, $C_6H_5$—, $C_6H_5CH_2$—, $C_6F_5CH_2$—, 4-tert-butyl-$C_6H_4CH_2$—, 4-$HOC_6H_4CH_2$—, 4-benzyl-O—$C_6H_4CH_2$—, 4-$NO_2C_6H_4CH_2$—, 4-(9-fluorenylmethoxycarbonyl) $NHCH_2$—$C_6H_4CH_2$—, 2-$FC_6H_4CH_2$—, 3-$FC_6H_4CH_2$—, 4-$FC_6H_4CH_2$—, $C_5H_4N$-2-$CH_2$—, $C_5H_4N$-3-$CH_2$—, $C_5H_4N$-4-$CH_2$—, 2-thiophene-$CH_2$—, indole-3-$CH_2$—, 2-benzothiophene-$CH_2$—, Nτ-benzyl-imidazole-4-$CH_2$— and thiazole-4-$CH_2$— wherein $R_6$ is selected from the group consisting of H, a straight or branched alkyl group of 1 to 4 carbon atoms and glycyl wherein $R_7$ is selected from the group consisting of H, a straight or branched alkyl group of 1 to 4 carbon atoms wherein $R_8$ is selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part and 1 to 3 carbon atoms in the alkyl part thereof, wherein $R_9$ is selected from the group consisting of H, a straight or branched alkyl group of 1 to 4 carbon atoms, —OH, —$NH_2$ and —$CH_2CH_2OH$ wherein $R_{10}$ and $R_{11}$ are independently selected from the group consisting of H, a straight or branched alkyl group of 1 to 4 carbon atoms wherein m is 0 or 1 wherein o is 0 or 1 wherein $R_{12}$ and $R_{13}$ are independently selected from the group consisting of H, a straight or branched alkyl group of 1 to 4 carbon atoms, F, Cl, Br, I, —$CF_3$, —$NO_2$, —$NR_{10}R_{11}$, —$NHCOR_{10}$, —$OR_{10}$, —$OCH_2C_6H_5$, —$SR_{10}$, —$COOR_{10}$, —$COR_{10}$ and —$CH_2OH$, $R_{10}$ and $R_{11}$ being as defined herein.

This invention also provides a compound of formula Ia

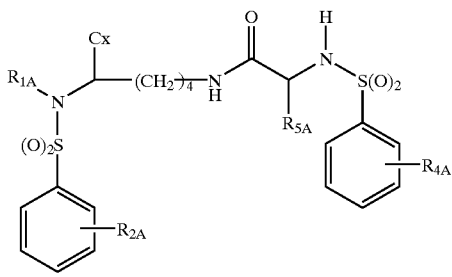

and when the compound of formula Ia comprises an amino group pharmaceutically acceptable ammonium salts thereof, wherein Cx is selected from the group consisting of —COOM and —$CH_2OH$, M being an alkali metal or alkaline earth metal, wherein $R_{1A}$ is selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, wherein $R_{2A}$ and $R_{4A}$ are independently selected from the group consisting of H, a straight or branched alkyl group of 1 to 4 carbon atoms, F, Cl, Br, I, —$CF_3$, —$NO_2$, —$NR_{10}R_{11}$, —$NHCOR_{10}$, —$OR_{10}$, —$OCH_2C_6H_5$, —$SR_{10}$, —$COOR_{10}$, —$COR_{10}$ and —$CH_2OH$, wherein $R_{5A}$ is selected from the group consisting of H, a straight or branched alkyl group of 1 to 8 carbon atoms, (e.g. $CH_3$—, $CH_3CH_2CH_2$—, $CH_3CH_2CH_2CH_2$—, iso-$C_4H_9$—, $C_6H_{11}CH_2$—), $HOCH_2$—, $C_6H_5CH_2OCH_2$—, benzyl-$OCH(CH_3)$, $HO_2CCH_2$—, $HO_2CCH_2CH_2$—, NC—$CH_2$—, $H_2NC(O)CH_2$—, $H_2NC(O)CH_2CH_2$—, 4-$CH_3C_6H_4CH_2SCH_2$—, $CH_3SCH_2CH_2$—, $H_2NCH_2CH_2CH_2CH_2$—, $C_6H_5$—, $C_6H_5CH_2$—, $C_6H_5CH(OH)$—, $C_6H_5CH(CN)$—, $C_6F_5CH_2$—, 4-(9-fluorenylmethoxycarbonyl)-$NHCH_2$—$C_6H_4CH_2$—, $C_5H_4N$-2-$CH_2$— (i.e. pyridine-2-$CH_2$—), $C_5H_4N$-3-$CH_2$— (i.e. pyridine-3-$CH_2$—), $C_5H_4N$-4-$CH_2$— (i.e. pyridine-4-$CH_2$—), 2-thiophene-$CH_2$—, indole-3-$CH_2$—, 2-benzothiophene-$CH_2$—, Nτ-benzyl-imidazole-4-$CH_2$—, imidazole-4-$CH_2$—, thiazole-4-$CH_2$— and substituted benzyl (e.g. benzyl substituted by a group as defined for $R_{2A}$, e.g. 4-tert-butyl-$C_6H_4CH_2$—, 4-$HOC_6H_4CH_2$—, 4-benzyl-O—$C_6H_4CH_2$—, 4-$NO_2C_6H_4CH_2$—, 2-$FC_6H_4CH_2$—, 3-$FC_6H_4CH_2$—, 4-$FC_6H_4CH_2$—), and wherein $R_{10}$ and $R_{11}$ are as defined herein.

This invention also provides a compound of formula Ib

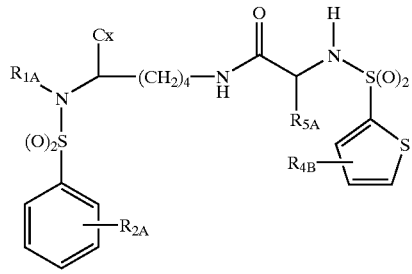

and when the compound of formula Ib comprises an amino group pharmaceutically acceptable ammonium salts thereof, wherein Cx is selected from the group consisting of —COOM, and —$CH_2OH$, M being an alkali metal or alkaline earth metal, wherein $R_{1A}$ is selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, wherein $R_{2A}$ and $R_{4B}$ are independently selected from the group consisting of H, a straight or branched alkyl group of 1 to 4 carbon atoms, F, Cl, Br, I, —$CF_3$, —$NO_2$, —$NR_{10}R_{11}$, —$NHCOR_{10}$, —$OR_{10}$, —$OCH_2C_6H_5$, —$SR_{10}$, —$COOR_{10}$, —$COR_{10}$ and —$CH_2OH$, wherein $R_{5A}$ is selected from the group consisting of H, a straight or branched alkyl group of 1 to 8 carbon atoms, (e.g. $CH_3$—, $CH_3CH_2CH_2$—, $CH_3CH_2CH_2CH_2$—, iso-$C_4H_9$—, $C_6H_{11}CH_2$—), $HOCH_2$—, $C_6H_5CH_2OCH_2$—, benzyl-$OCH(CH_3)$, $HO_2CCH_2$—, $HO_2CCH_2CH_2$—, NC—$CH_2$—, $H_2NC(O)CH_2$—, $H_2NC(O)CH_2CH_2$—, 4-$CH_3C_6H_4CH_2SCH_2$—, $CH_3SCH_2CH_2$—, $H_2NCH_2CH_2CH_2CH_2$—, $C_6H_5$—, $C_6H_5CH_2$—, $C_6H_5CH(OH)$—, $C_6H_5CH(CN)$—, $C_6F_5CH_2$—, 4-(9-fluorenylmethoxycarbonyl)-$NHCH_2$—$C_6H_4CH_2$—, $C_5H_4N$-2-$CH_2$— (i.e. pyridine-2-$CH_2$—), $C_5H_4N$-3-$CH_2$— (i.e. pyridine-3-$CH_2$—), $C_5H_4N$-4-$CH_2$— (i.e. pyridine-4-$CH_2$—), 2-thiophene-$CH_2$—, indole-3-$CH_2$—, 2-benzothiophene-$CH_2$—, Nτ-benzyl-imidazole-4-$CH_2$—, imidazole-4-$CH_2$—, thiazole-4-$CH_2$— and substituted benzyl (e. g. benzyl substituted by a group as defined for $R_{2A}$, e.g. 4-tert-butyl-$C_6H_4CH_2$—, 4-$HOC_6H_4CH_2$—, 4-benzyl-O—$C_6H_4CH_2$—, 4-$NO_2C_6H_4CH_2$—, 2-$FC_6H_4CH_2$—, 3-$FC_6H_4CH_2$—, 4-$FC_6H_4CH_2$—), and wherein $R_{10}$ and $R_{11}$ are as defined herein.

This invention also provides a compound of formula Ic

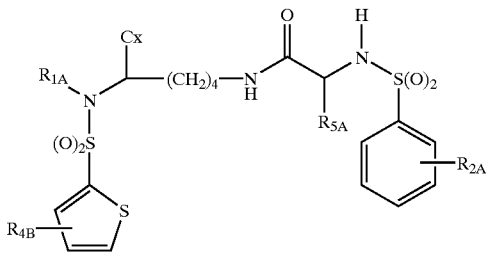

and when the compound of formula Ic comprises an amino group pharmaceutically acceptable ammonium salts thereof, wherein Cx is selected from the group consisting of —COOM and —CH$_2$OH, M being an alkali metal or alkaline earth metal, wherein R$_{1A}$ is selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, wherein R$_{2B}$ and R$_{4B}$ are independently selected from the group consisting of H, a straight or branched alkyl group of 1 to 4 carbon atoms, F, Cl, Br, I, —CF$_3$, —NO$_2$, —NR$_{10}$R$_{11}$, —NHCOR$_{10}$, —OR$_{10}$, —OCH$_2$C$_6$H$_5$, —SR$_{10}$, —COOR$_{10}$, —COR$_{10}$ and —CH$_2$OH, wherein R$_{5A}$ is selected from the group consisting of H, a straight or branched alkyl group of 1 to 8 carbon atoms, (e.g. CH$_3$—, CH$_3$CH$_2$CH$_2$—,CH$_3$CH$_2$CH$_2$CH$_2$—, iso-C$_4$H$_9$—, C$_6$H$_{11}$CH$_2$—), HOCH$_2$—, C$_6$H$_5$CH$_2$OCH$_2$—, benzyl-OCH(CH$_3$), HO$_2$CCH$_2$—, HO$_2$CCH$_2$CH$_2$—, NC—CH$_2$—, H$_2$NC(O)CH$_2$—, H$_2$NC(O)CH$_2$CH$_2$—, 4-CH$_3$C$_6$H$_4$CH$_2$SCH$_2$—, CH$_3$SCH$_2$CH$_2$—, H$_2$NCH$_2$CH$_2$CH$_2$CH$_2$—, C$_6$H5—, C$_6$H$_5$CH$_2$—, C$_6$H$_5$CH(OH)—, C$_6$H$_5$CH(CN)—, C$_6$F$_5$CH$_2$—, 4-(9-fluorenylmethoxycarbonyl)-NHCH$_2$—C$_6$H$_4$CH$_2$—, C$_5$H$_4$N-2-CH$_2$— (i.e. pyridine-2—CH$_2$—), C$_5$H$_4$N-3-CH$_2$— (i.e. pyridine-3-CH$_2$—), C$_5$H$_4$N-4-CH$_2$— (i.e. pyridine-4-CH$_2$—), 2-thiophene-CH$_2$—, indole-3-CH$_2$—, 2-benzothiophene-CH$_2$—, Nτ-benzyl-imidazole-4-CH$_2$—, imidazole-4-CH$_2$—, thiazole-4-CH$_2$— and substituted benzyl (e.g. benzyl substituted by a group as defined for R$_{2A}$, e.g. 4-tert-butyl-C$_6$H$_4$CH$_2$—, 4-HOC$_6$H$_4$CH$_2$—, 4-benzyl-O—C$_6$H$_4$CH$_2$—, 4-NO$_2$C$_6$H$_4$CH$_2$—, 2-FC$_6$H$_4$CH$_2$—, 3-FC$_6$H$_4$CH$_2$—, 4-FC$_6$H$_4$CH$_2$—), and wherein R$_{10}$ and R$_{11}$ are as defined herein.

This invention also provides a compound of formula Id

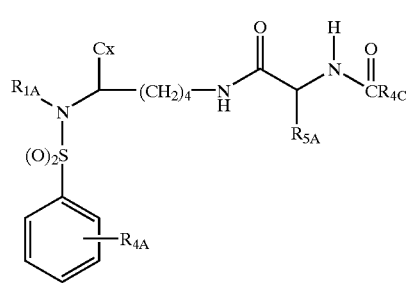

Id and when the compound of formula Id comprises an amino group pharmaceutically acceptable ammonium salts thereof, wherein Cx is selected from the group consisting of —COOM and —CH$_2$OH, M being an alkali metal or alkaline earth metal, wherein R$_{1A}$ is selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, wherein R$_{4A}$ is selected from the group consisting of H, a straight or branched alkyl group of 1 to 4 carbon atoms, F, Cl, Br, I, —CF$_3$, —NO$_2$, —NR$_{10}$R$_{11}$, —NHCOR$_{10}$, —OR$_{10}$, —OCH$_2$C$_6$H$_5$, —SR$_{10}$, —COOR$_{10}$, —COR$_{10}$ and —CH$_2$OH, wherein R$_{4C}$ is selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, (e.g. CH$_3$—, iso-butyl, iso-propyl, tert-butyl, tert-butyl-CH$_2$—), CF$_3$, pyrrolidine, 4-morpholine, tetrahydro-3-furanyloxy, 4-CH$_3$OC$_6$H$_4$NH—, CH$_3$NH—, HOCH$_2$CH$_2$NH—, 9-fluorenyl-CH$_2$O—, tert-butylO—, iso-butylO—, C$_6$H$_5$CH$_2$O—, CH$_3$O—, unsubstituted C$_6$H$_5$—, C$_6$H$_5$— substituted by one or more members (e.g. one or two) selected from the group consisting of F, Cl, Br, I, —CF$_3$, —NO$_2$, —NR$_{10}$R$_{11}$, —NHCOR$_{10}$, —OR$_{10}$, —SR$_{10}$, —COOR$_{10}$, —COR, and —CH$_2$OH, unsubstituted C$_6$H$_5$CH$_2$—, C$_6$H$_5$CH$_2$— substituted by one or more members (e.g. one or two) selected from the group consisting of F, Cl, Br, I, —CF$_3$, —NO$_2$, —NR$_{10}$R$_{11}$, —NHCOR$_{10}$, —OR$_{10}$, —SR$_{10}$, —COOR$_{10}$, —COR$_{10}$ and —CH$_2$OH, unsubstituted C$_6$H$_5$CH$_2$CH$_2$—, and C$_6$H$_5$CH$_2$CH$_2$— substituted by one or more members (e.g. one or two) selected from the group consisting of F, Cl, Br, I, —CF$_3$, —NO$_2$, —NR$_{10}$R$_{11}$, —NHCOR$_{10}$, —OR$_{10}$, —SR$_{10}$, —COOR$_{10}$, —COR$_{10}$ and —CH$_2$OH, wherein R$_{5A}$ is selected from the group consisting of H, a straight or branched alkyl group of 1 to 8 carbon atoms, (e.g. CH$_3$—, CH$_3$CH$_2$CH$_2$—,CH$_3$CH$_2$CH$_2$CH$_2$—, iso-C$_4$H$_9$—, C$_6$H$_{11}$CH$_2$—), HOCH$_2$—, C$_6$H$_5$CH$_2$OCH$_2$—, benzyl-OCH(CH$_3$), HO$_2$CCH$_2$—, HO$_2$CCH$_2$CH$_2$—, NC—CH$_2$—, H$_2$NC(O)CH$_2$—, H$_2$NC(O)CH$_2$CH$_2$—, 4-CH$_3$C$_6$H$_4$CH$_2$SCH$_2$—, CH$_3$SCH$_2$CH$_2$—, H$_2$NCH$_2$CH$_2$CH$_2$CH$_2$—, C$_6$H$_5$—, C$_6$H$_5$CH$_2$—, C$_6$H$_5$CH(OH)—, C$_6$H$_5$CH(CN)—, C$_6$F$_5$CH$_2$—, 4-(9-fluorenylmethoxycarbonyl)-NHCH$_2$—C$_6$H$_4$CH$_2$—, C$_5$H$_4$N-2-CH$_2$— (i.e. pyridine-2-CH$_2$—), C$_5$H$_4$N-3-CH$_2$— (i.e. pyridine-3-CH$_2$—), C$_5$H$_4$N-4-CH$_2$— (i.e. pyridine-4-CH$_2$—), 2-thiophene-CH$_2$- indole-3-CH$_2$—, 2-benzothiophene-CH$_2$—, Nτ-benzyl-imidazole-4-CH$_2$—, Imidazole-4-CH$_2$—, thiazole-4-CH$_2$— and substituted benzyl (e.g. benzyl substituted by a group as defined for R$_{2A}$, e.g. 4-tert-butyl-C$_6$H$_4$CH$_2$—, 4-HOC$_6$H$_4$CH$_2$—, 4-benzyl-O—C$_6$H$_4$CH$_2$—, 4-NO$_2$C$_6$H$_4$CH$_2$—, 2-FC$_6$H$_4$CH$_2$—, 3-FC$_6$H$_4$CH$_2$—, 4-FC$_6$H$_4$CH$_2$—), and wherein R$_{10}$ and R$_{11}$ are as defined herein.

In addition, this invention provides pharmaceutical compositions in which these novel compounds of formula I or II, (as well as of formula IA, Ia, Ib, Ic and Id) derived from L-lysine or L-lysine derivatives (as well as lower and higher homologues) are used to inhibit aspartyl proteases, including HIV aspartyl protease, thus providing protection against HIV infection. Thus the present invention provides a pharmaceutical composition comprising a pharmaceutically acceptable carrier and a pharmaceutically effective amount of at least one compound of formula I, formula II (as well as of formulae IA, Ia, Ib, Ic, and Id) and as applicable pharmaceutically acceptable ammonium salts thereof.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "pharmaceutically effective amount" refers to an amount effective in treating HIV infection in a patient.

The term "prophylactically effective amount" refers to an amount effective in preventing HIV infection in a patient. As used herein, the term "patient" refers to a mammal, including a human.

The terms "pharmaceutically acceptable carrier", "pharmaceutically acceptable adjuvant" and "physiologically acceptable vehicle" refer to a non-toxic carrier or adjuvant that may be administered to a patient, together with a compound of this invention, and which does not destroy the pharmacological activity thereof.

The compounds of this invention include pharmaceutically acceptable derivatives of the compounds of formula I, formula II (as well as of formulae IA, Ia, IB, Ic, and Id) and as applicable pharmaceutically acceptable ammonium salts thereof. A "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an antivirally active metabolite or residue thereof. Salts derived from appropriate bases include alkali metal (e.g., sodium), alkaline earth metal (e.g., magnesium), ammonium and $N-(C_{1-4}alkyl)_4^+$ salts.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

Pharmaceutically acceptable salts of the compounds of this invention include those derived from pharmaceutically acceptable inorganic and organic acids and bases. Examples of such acid salts include: acetate, adipate, alginate, aspartate, benzoate, benzenesulfonate, bisulfate, butyrate, citrate, camphorate, camphorsulfonate, cyclopentanepropionate, digluconate, dodecylhydrogensulfate, dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

This invention also envisions the quaternization of any basic nitrogen containing groups of the compounds disclosed herein. The basic nitrogen can be quaternized with any agents known to those of ordinary skill in the art including, for example, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides, and aralkyl halides including benzyl and phenethyl bromides. Water or oil-soluble or dispersible products may be obtained by such quaternization.

The compounds of this invention are readily prepared using conventional techniques from commercially available and inexpensive starting materials. The relative ease of synthesis of the products described herein represents a marked advantage for the large scale preparation of these compounds. In general, the derivatives of the present invention may be readily obtained through sequences recognized by those knowledgeable in the art as straightforward. These sequences are presented in schemes 1 to 7 discussed below.

Scheme 1 illustrates a generic example for the preparation of a key intermediate needed for the synthesis of HIV protease inhibitors.

Note:
a) For scheme 1, $R_1$ represents an alkyl or cycloalkylalkyl side chain as defined above
b) $R_2$ represents a benzenesulfonyl group of formula III, a thiophenesulfonyl group of formula IV, a 1-naphthylsulfonyl, a 2-naphthylsulfonyl or a 8-quinolinesulfonyl group as defined above As shown in scheme 1, the Nα,Nα-disubstituted L-lysine derivative 5 was obtained from commercially available L-lysine 1 in a four-step reaction sequence. This preparation uses the cyclic form of L-lysine in order to manipulate the Nα-amino group without the need for protective groups. First, L-lysine was transformed into L-α-amino-ε-caprolactam 2 upon treatment with hydrochloric acid in methanol followed by neutralization with sodium hydroxide. The caprolactam 2 is also commercially available. Reductive alkylation of derivative 2 with an appropriate aldehyde and $NaBH(OAc)_3$ in dichloroethane lead to the Nα-alkylamino-ε-caprolactam 3. Then, sulfonation with an arylsulfonyl chloride or a substituted-arylsulfonyl chloride in the presence of triethylamine in dichloromethane gave compound 4 in excellent yields. The Nα,Nα-disubstituted L-lysine derivative 5 was obtained quantitatively by acid hydrolysis of the cyclic amide 4.

Scheme 1

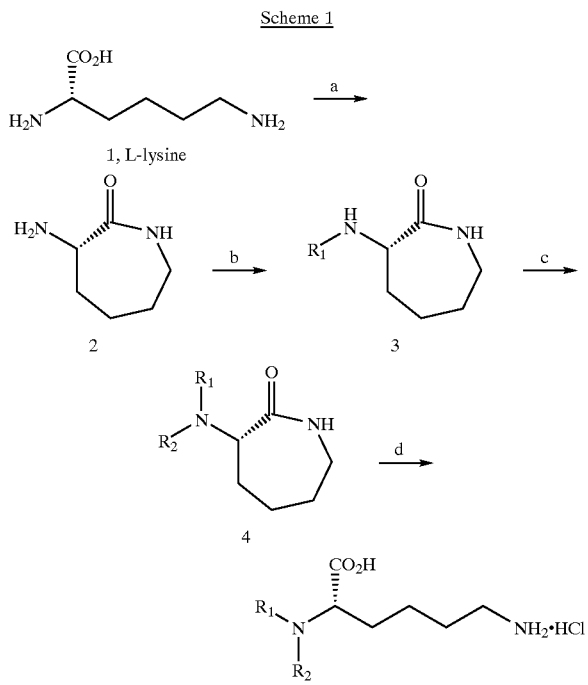

Reagents: a) 1) $MeOH/H^+$ (99.4%); 2) NaOMe, $NH_4Cl$, pH 11.5 (85%); b)Aldehyde $NaBH(OAc)_3$, DCE; c) arylsulfonyl chloride or substituted-arylsulfonyl chloride; TEA, $CH_2Cl_2$, 3h; d) 6N HCl, 12 h Scheme 2 illustrates the preparation of HIV protease inhibitors bearing either a carboxylic function, compound 6, or an alcohol function, compound 8, on the final product. In other words, this scheme shows the synthesis of a L-lysine derivative or a (2S) 2,6-diaminohexanol derivative Note:
a) For scheme 2, $R_1$ and $R_2$ are as defined above
b) $R_3$ represents H, a straight or branched alkyl group of 1 to 6 carbon atoms, a phenyl or a benzyl group
c) $R_4$ is as defined above
d) $R_5$ represents an amino acid side chain as defined above Following the indications summarized in Scheme 2, derivative 5 is linked with a substituted amino acid using N,N-carbonyldiimidazole as the activating reagent to yield derivative 6 in good to excellent yield. The various N-acylated (or N-sulfonated) amino acids needed for the coupling reaction were prepared from the appropriate amino acid and acyl chloride (or sulfonyl chloride) using the Schotten-Baumen procedure. Alternatively, derivative 5 is treated with trimethylsilyl chloride in methanol (HCl generated in situ) and the resulting methyl ester intermediate is reduced with lithium aluminum hydride (LAH) in THF to afford 7 in good yields. The (2S) 2,6-diaminohexanol derivative 7 is linked to a substituted amino acid derivative as it is described above for the synthesis of derivative 6.

be achieved upon activation of the acid 6 with DCC in the presence of a catalytic amount of N,N-dimethylaminopyridine and an alcohol. The amide 10 can be obtained as described earlier for the preparation of compound 6, see scheme 2.

Note:

a) For scheme 3, $R_1$, $R_2$, $R_3$, $R_4$ and $R_5$ are as described above

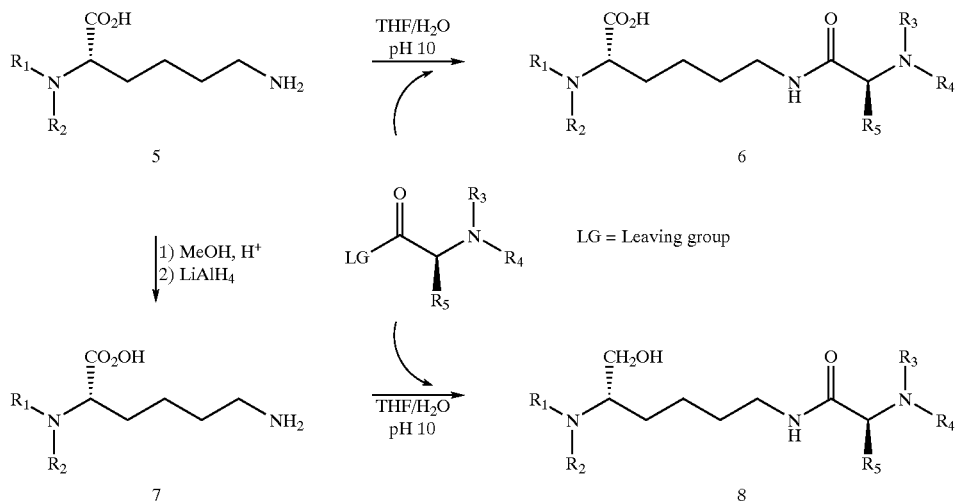

The L-lysine divative 6 can be further transformed into a variety of esters 9 as well as amide derivative 10 as shown in scheme 3. These transformations are done under standard reaction conditions. For example, the synthesis of ester 9 can b) $R_{10}$ and $R_{11}$, same or different, represent an H or a straight or branched alkyl group of 1 to 4 carbon atoms.

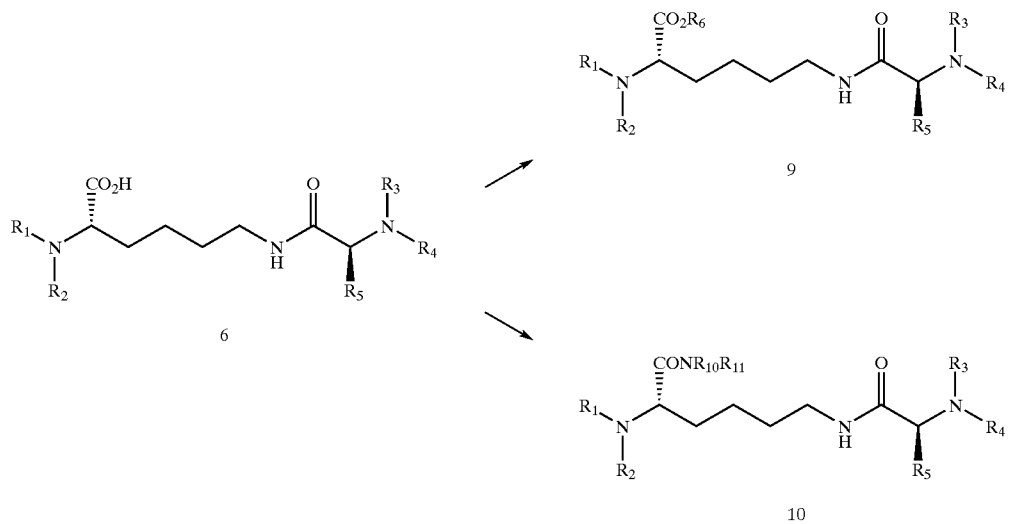

Scheme 4 presents a second approach for the preparation of HIV protease inhibitors of formula 6 and 8. It proceeds by using commercially available Nε-benzyloxycarbonyl-L-lysine methyl ester hydrochloride (11) as the starting material Reductive alkylation of derivative 11 with an appropriate aldehyde and sodium cyanoborohydride provided the derivative 12. Then, sulfonation with benzenesulfonyl chloride (or substituted-benzenesulfonyl chloride) in the presence of triethylamine (or diisopropylethylamine) in dichloromethane gave compound 13 in excellent yields for the two first steps. Removal of the benzyloxycarbonyl group (Z group) by hydrogen gas in presence of 10% Pd/C yielded the free Nε-amino derivative 14 quantitatively. Acylation of 14 with a substituted amino acid N-hydroxysuccinimide ester provided derivative 15 in excellent yields. The desired HIV protease inhibitors 6 and 8 are easily obtained from the methyl ester 15 by hydrolysis with sodium hydroxide in a mixture of THF and methanol giving the acid 6 or by reduction with LAH giving the alcohol 8, both in excellent yields. It is noteworthy that, under basic hydrolysis of 15 to produce compound 6, some racemization may occur. However, it is not the case when compound 15 is reduced with LAH to give derivative 8.

Note:

a) For scheme 4, $R_1$, $R_2$, $R_3$, $R_4$ and $R_5$ are as described above

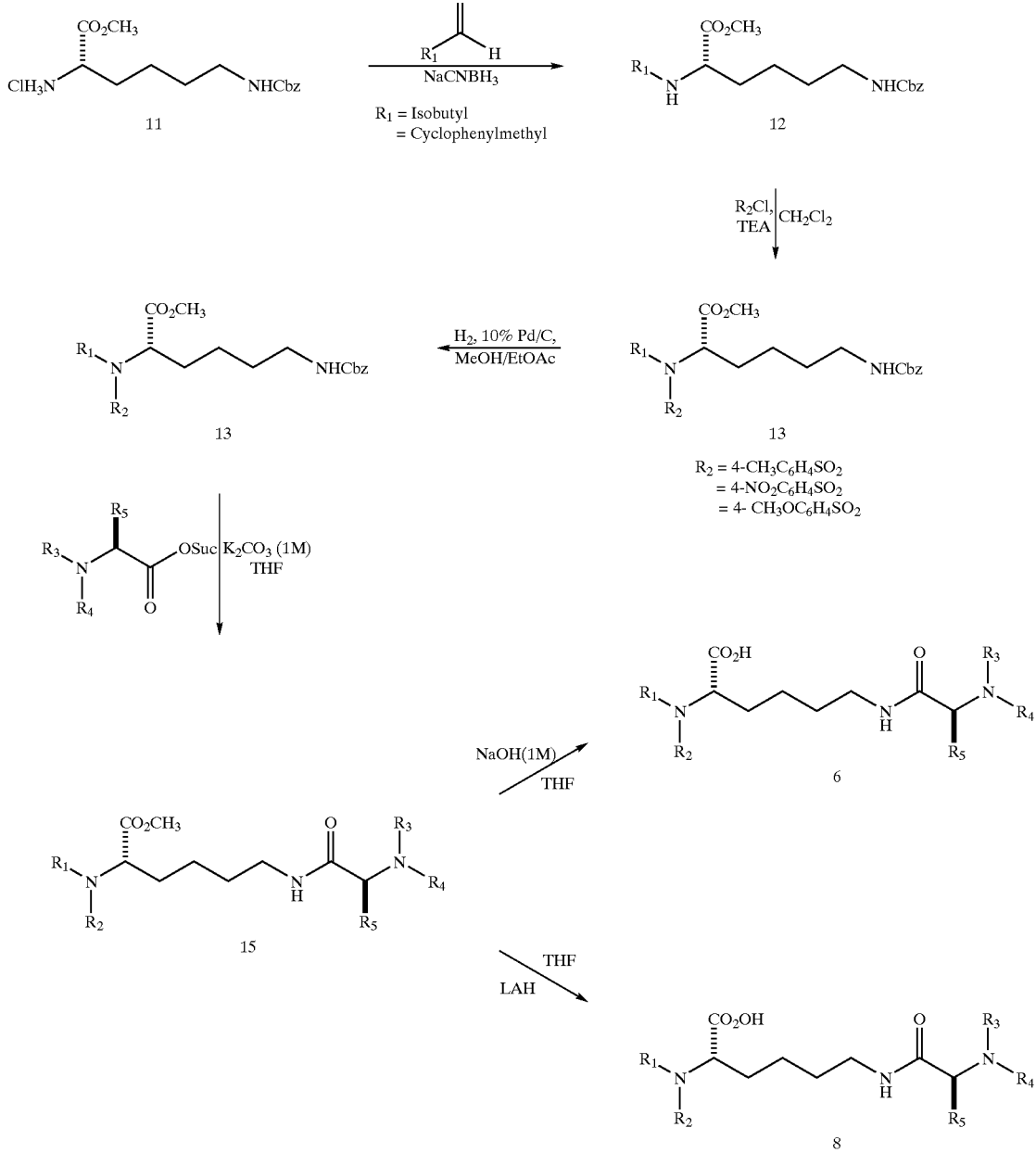

Scheme 5 illustrates the preparation of an anti-protease derivative using a solid phase methodology in accordance with the present invention (see example 21). Any suitable solid phase substrate could be used in such preparation (K.

Burgess, Solid phase organic synthesis, Wiley-Interscience, 2000).

resin with TFA in $CH_2Cl_2$ leads to the desired L-lysine derivative 19.

Scheme 5

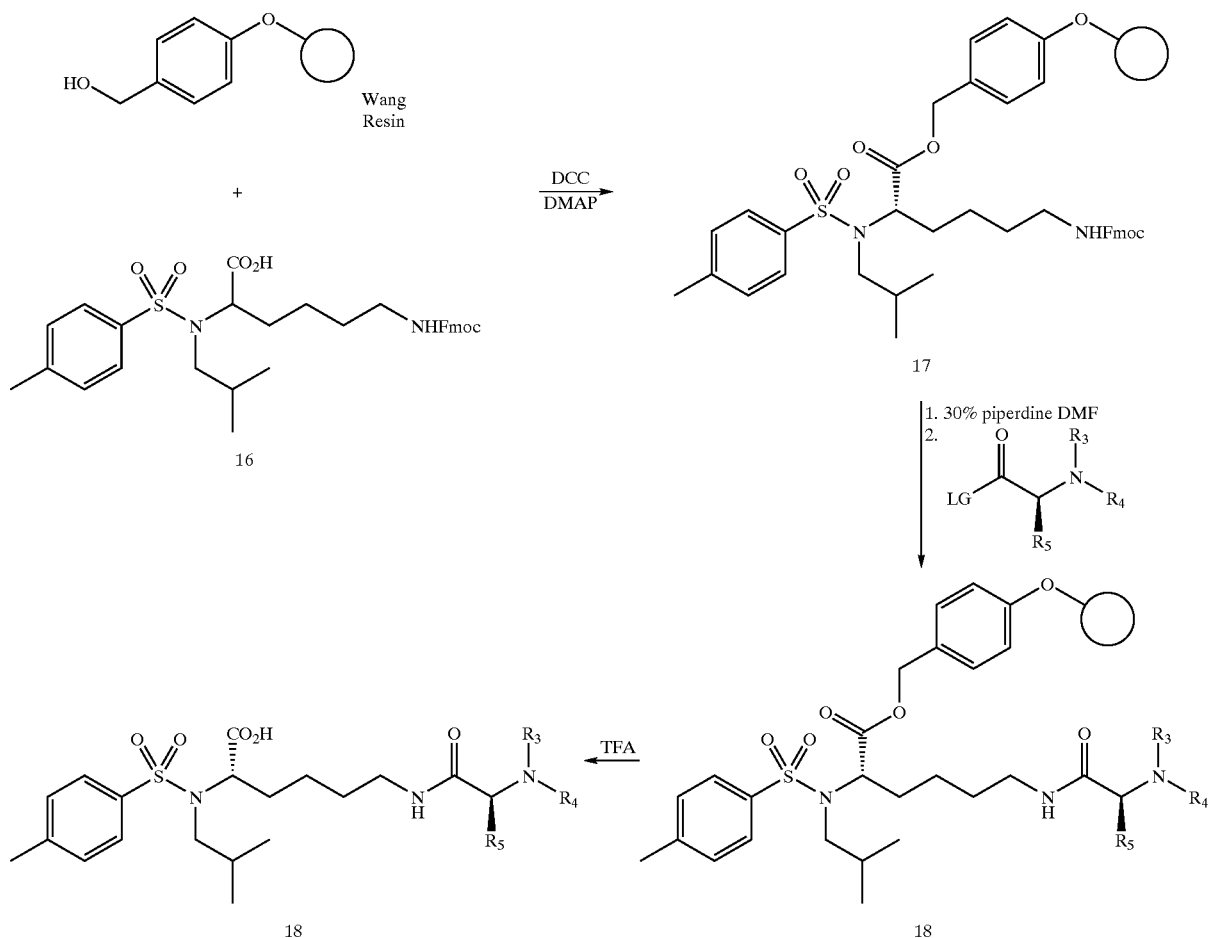

= Any suitable solid phase support could be used, such as, for example, polystyrene (Ps) see K. Burgess, Solid phase organic synthesis, Wiley-Interscience, 20 00.

LG = Leaving group

Note:
a) For scheme 4, $R_1$ is iso-butyl, $R_2$ is 4-methylbenzenesulfonyl, $R_3$, $R_4$ and $R_5$ are as described above This process allows the introduction of pharmacophores to a $N\alpha,N\alpha$-disubstituted-L-lysine derivative (such as 16) via the N-terminal function. Thus, in scheme 5, $N\alpha$-isobutyl-$N\alpha$-(4-methylbenzenesulfonyl)-$N\epsilon$-(9-fluorenylmethoxycarbonyl)-L-lysine 16 is immobilized on a p-benzyloxybenzylalcohol resin (Wang resin) in DMF for a period of 16 h. The resulting component 17 contained 0.28 meq. of L-lysine derivative / g of resin. At this stage, after removal of the Fmoc protective group under standard reaction conditions (30% piperidine in DMF see T. W. Greene and P. G. M. Wuts, Protective groups in Organic Synthesis, $3^{rd}$ Edition, John Wiley & Sons, Inc. 2000), the resin can be coupled with a variety of N-acylated (or N-sulfonated) amino acids to give component 18. The N-acylated (or N-sulfonated) amino acids are activated with N-hydroxysuccinimide and DCC in DMF. Cleavage of the Scheme 6 illustrates the preparation of substituted glycine derivatives used for the synthesis of several HIV protease inhibitors in accordance with the present invention (see examples 114 and 158 below for specific descriptions of the synthesis of such glycine derivatives):

In scheme 6 a), N-phenylglycine 20 is treated with an excess butyllithium to give the dianion intermediate to which an appropriate alkyl halide (or arylalkyl halide or tosylate) is added and reacted for a period of 16 h. The final products 21 are obtained in good to excellent yields. An appropriate alkyl halide is defined as bearing a $R_3$ component which can sustain strong basic reaction conditions.

In scheme 6 b), methyl bromoacetate 22 is treated with benzylamine in $CH_2Cl_2$ at room temperature for 16 h. The N-benzylglycine methyl ester derivative 23 was obtained in 86% yield. This intermediate can be either acylated with a carboxylic acid derivative and DCC in THF or sulfonated with an appropriate sulfonyl chloride and triethylamine in $CH_2Cl_2$ to give derivative 24 or 25 as desired in good to excellent yields.

Scheme 6

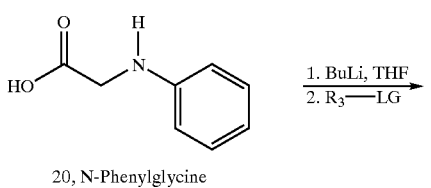

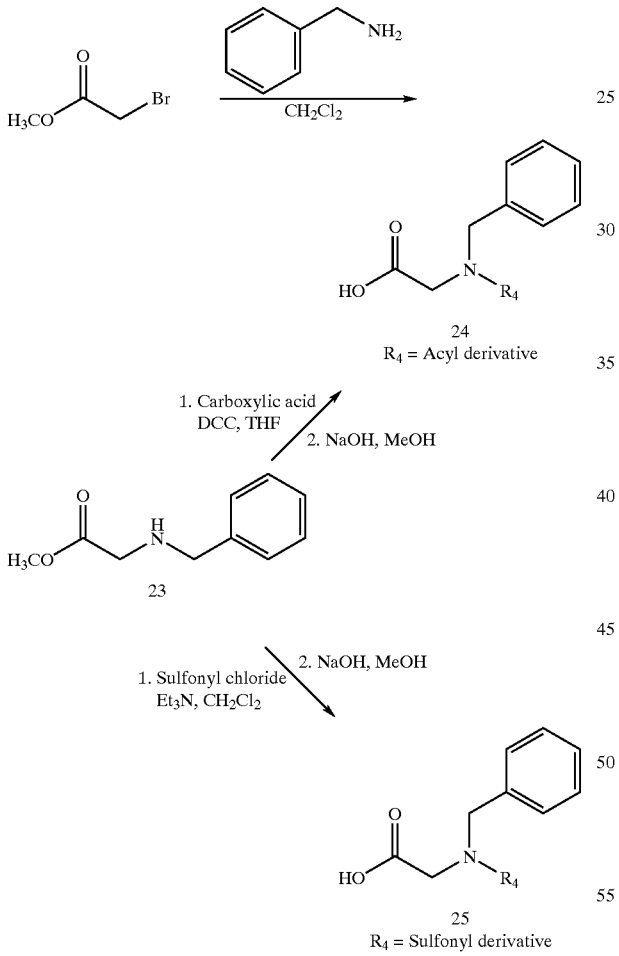

Scheme 7 shows another methodology for the formation of Nε-substituted-glycyl-L-lysine HIV protease inhibitors via the Nε-iodoacetyl-L-lysine derivative 26 (see example 105 for the detailed description of the synthesis of derivative 26 and its use). Thus, Nα,Nα-disubstituted-L-lysine derivative 5 potassium salt is initially treated with chloroacetyl chloride in the presence of DIEA in THF to give the Nα,Nα-disubstituted-Nε-chloroacetyl-L-lysine intermediate. This intermediate is transformed into the iodoacetyl derivative 26 upon treatment with sodium iodide in dry acetone. Compound 26 is then heated at reflux with a primary (or secondary) amine in the presence of of DIEA in THF to yield the desired Nε-substituted-glycyl-L-lysine derivative 6. In scheme 7, a primary amine is used so $R_3$=H and $R_5$=H.

Scheme 7

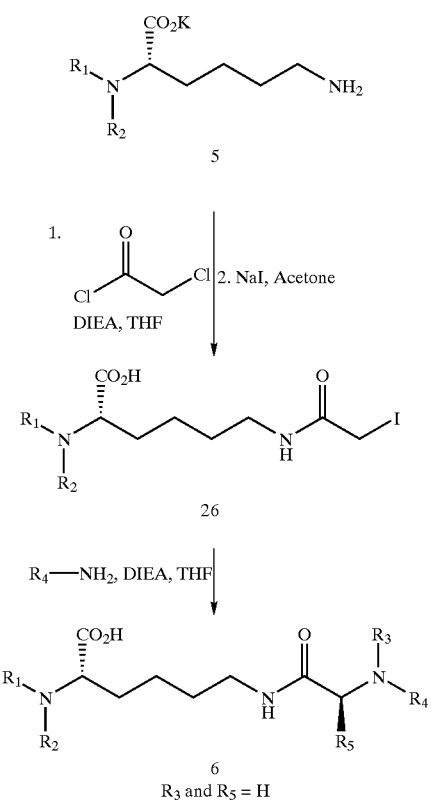

As it can be appreciated by the skilled artisan, the above synthetic schemes are not intended to be a comprehensive list of all means by which the compounds described and claimed in this application may be synthesized. Further methods will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

As discussed above, the novel compounds of the present invention are excellent ligands for aspartyl proteases, particularly HIV-1 protease. Accordingly, these compounds are capable of targeting and inhibiting late stage events in the replication, i.e. the processing of the viral polyproteins by HIV encoded protease. Compounds according to this invention advantageously inhibit the ability of the HIV-1 virus to infect immortalized human T cells over a period of days, as determined by an assay measuring the amount of extracellular p24 antigen—a specific marker of viral replication (see, Meek et al., Nature, 343, pp. 90–92 (1990)).

In addition to their use in the prophylaxis or treatment of HIV or HTLV infection, the compounds according to this invention may also be used as inhibitory or interruptive agents for other viruses which depend on aspartyl proteases, similar to HIV or HTLV aspartyl proteases, for obligatory events in their life cycle. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production and reproduction of infectious virions, particularly from acutely and chronically infected cells. The compounds of this invention advantageously inhibit aspartyl proteases, thus blocking the ability of aspartyl proteases to catalyse the hydrolysis of peptide bonds.

The compounds of this invention may be employed in a conventional manner for the treatment or prevention of HIV, HTLV, and other viruses, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period of time against viral infections, such as HIV infection. As such, the novel protease inhibitors of this invention can be administered as agents for treating or preventing viral infections, including HIV infection, in a mammal.

The compounds of this invention may be administered to a healthy or HIV-infected patient either as a single agent or in combination with other antiviral agents which interfere with the replication cycle of HIV. By administering the compounds of this invention with other antiviral agents which target different events in the viral life cycle, the therapeutic effect of these compounds is potentiated. For instance, the co-administered antiviral agent can be one which targets early events in the viral life cycle, such as attachment to the cell receptor and cell entry, reverse transcription and viral DNA integration into cellular DNA. Antiviral agents targeting such early life cycle events include among others polysulfated polysaccharides, sT4 (soluble CD4) and other compounds which block binding of virus to CD4 receptors on CD4 bearing T-lymphocytes and other CD4(+) cells, or inhibit fusion of the viral envelope with the cytoplasmic membrane, and didanosine (ddI), zalcitabine (ddC), stavudine (d4T), zidovudine (AZT) and lamivudine (3TC) which inhibit reverse transcription. Other anti-retroviral and antiviral drugs may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformate, eflornithine, ribavirin, acyclovir, alpha interferon and trimenotrexate. Additionally, other types of drugs may be used to potentiate the effect of the compounds of this invention, such as viral uncoating inhibitors, inhibitors of Tat or Rev trans-activating proteins, antisense molecules or inhibitors of the viral integrase. These compounds may also be co-administered with other inhibitors of HIV aspartyl protease.

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce the potential of resistance to single agent therapies, while minimizing any associated toxicity. These combinations may also increase the efficacy of the conventional agent without increasing the associated toxicity. Preferred combination therapies include the administration of a compound of this invention with AZT, 3TC, ddI; ddC, d4T or other reverse transcriptase inhibitors.

Alternatively, the compounds of this invention may also be co-administered with other HIV protease inhibitors such as Ro 31-8959 (Saquinavir; Roche), L-735,524 (Indinavir; Merck), AG-1343 (Nelfinavir; Agouron), A-84538 (Ritonavir; Abbott), ABT-378/r (Lopinavir; Abbott), and VX-478 (Amprenavir; Glaxo) to increase the effect of therapy or prophylaxis against various viral mutants or members of other HIV quasi species.

We prefer administering the compounds of this invention as single agents or in combination with retroviral reverse transcriptase inhibitors, or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbamate sodium, tumor necrosis factor, naltrexone and rEPO) antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds of this invention can also be used as inhibitory agents for other viruses that depend on similar aspartyl proteases for obligatory events in their life cycle. These viruses include, but are not limited to, retroviruses causing AIDS-like diseases such as simian immunodeficiency viruses, HIV-2, HTLV-I-and HTLV-II. In addition, the compounds of this invention may also be used to inhibit other aspartyl proteases and, in particular, other human aspartyl proteases including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. We prefer oral administration or administration by injection. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are amino acid, water, Ringer's solution and isotonic sodium chloride solution. In addition, sterile, fixed oils are conventionally employed as a solvent or suspending medium For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv. or a similar alcohol.

The pharmaceutical compositions of this invention may be orally administered in any orally acceptable dosage form including, but not limited to, capsules, tablets, and aqueous suspension and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene or polyoxypropylene compound, emulsifying wax and water. Alternatively, the pharmaceutical compositions can be formulated with a suitable lotion or cream containing the active compound suspended or dissolved in a carrier. Suitable carriers include, but are not limited to, mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis, upon any recurrence of disease symptoms.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide by an aspartyl protease, or may be derivatized to bind to a stable resin as a tethered substrate for affinity chromatography applications. These and other uses which characterize commercial aspartyl protease inhibitors will be evident to those of ordinary skill in the art.

Enzymatic Assay for Determining the Inhibition Constant (Ki) of Synthetic Compounds Targeting the HIV Protease This is a fluorometric assay based on the cleavage by protease of a substrate carrying a donor group (EDANS) and an acceptor group (DABCYL) on each side of the cleavage site, interacting together through fluorescence resonance energy transfer (FRET) as described by Matayoshi et al. (Science 247:954–954, 1990).

After calculation of Vo and Vi, the inhibition constant (Ki) of the compound is determined using the equation of Henderson:

$$\frac{Vo}{Vi} = 1 + \frac{[I]}{Ki_{app}}$$

Where $$Ki = \frac{Ki_{app}}{1 + \frac{[S]}{Km}}$$

where

Vo=the enzyme's initial velocity

Vi=the enzyme velocity in the presence of the inhibitory compound,

[I]=inhibitor concentration, [S]=substrate concentration,

Km=Michaelis-Menten constant and $Ki_{app}$=apparent Ki

Graphs are traced and the Ki determined using GraphPad Prism software v. 3.0.

The compounds listed in Tables 1 and 2 were prepared by following Scheme 1, 2, 3, 4, 5, 6 or 7; the numbers of the compounds listed in the table correspond to the example numbers presented in the experimental section (see examples below). The activities of the compounds are also listed in the same tables demonstrating their potential usefulness. In Table 1 are shown compounds of formula I wherein Y, n, Cx, $R_1$, $R_2$, $R_3$, $R_4$ and $R_5$ are as presented in Table 1. In Table 2 are shown compounds of formula II wherein Y, n, Cx, R, $R_2$, $R_4$ and $R_a$ are as presented in Table 2.

In the description herein, the following abbreviations are used:

| Abbreviation | Meaning |
| --- | --- |
| Ac | Acetyl |
| AcOH | Acetic acid |
| ARC | AIDS-related complex |
| AIDS | Acquired Immunodeficiency Syndrome |
| AZT | 3-Azido-3-deoxythymine (Zidovudine) |
| Bn | benzyl |

-continued

| Abbreviation | Meaning |
| --- | --- |
| Boc | tert-Butoxycarbonyl |
| i-Bu | iso-Butyl |
| t-Bu | tert-Butyl |
| CAM | Cerium ammonium molybdate |
| DABCYL | 4-[[4'-(dimethylamino)phenyl]azo]benzoic acid |
| DCC | Dicyclohexylcarbodiimide |
| DCE | Dichloroethane |
| DCM | Dichloromethane |
| DMAP | N,N-dimethylaminopyridine |
| DIEA | N,N-Diisopropylethylamine |
| DMF | Dimethylformamide |
| DNA | Deoxyribonucleic acid |
| EDANS | 5-[(2'-aminoethyl)amino]naphthalene sulfonic acid |
| EDC | 1-Ethyl-3-(3-dimethylaminopropyl)carbodiimide hydrochloride |
| EtOAc | Ethyl acetate |
| EtOH | Ethyl alcohol |
| Fmoc | 9-Fluorenylmethoxycarbonyl |
| g | Gram |
| HIV-1, -2 | Human immunodeficiency virus type 1, type 2 |
| HOBt | 1-Hydroxybenzotriazole |
| HPLC | High performance liquid chromatography |
| HTLV-I, -II | Human T-cell lymphotropic virus type I, type II |
| IL-2 | Interleukin-2 |
| Kg | Kilogram |
| LAH | Lithium aluminum hydride |
| LC-MS | Liquid chromatography-mass spectrometry |
| M | Molar |
| MeOH | Methyl alcohol |
| mg | Milligram |
| MP | Melting point |
| min | Minute |
| mol | Mole |
| mL | Milliliter |
| mmol | Millimole |
| nM | Nanomolar |
| i-Pr | iso-Propyl |
| rEPO | Recombinant erythropoietin |
| RNA | Ribonucleic acid |
| 3TC | 2',3'-Dideoxy-3-thiacytidine |
| TFA | Trifluoroacetic acid |
| H TFA | Trifluoroacetic acid ammonium salt |
| THF | Tetrahydrofuran |
| Z | Benzyloxycarbonyl |

EXAMPLES

In order that this invention be more fully understood, the following examples are set forth. These examples are for the purpose of illustration only and are not to be construed as limiting the scope of the invention in any way.

Materials and Methods

Analytical thin layer chromatography (TLC) was carried out with 0.25 mm silica gel E. Merck 60 $F_{254}$ plates and eluted with the indicated solvent systems. Preparative chromatography was performed by flash chromatography, using silica gel 60 (EM Science) with the indicated solvent systems and positive air pressure to allow proper rate of elution. Detection of the compounds was carried out by exposing eluted plates (analytical or preparative) to iodine, UV light and/or treating analytical plates with a 2% solution of p-anisaldehyde in ethanol containing 3% sulfuric acid and 1% acetic acid followed by heating. Alternatively, analytical plates can be treated with a 0.3% ninhydrin solution in ethanol containing 3% acetic acid and/or a CAM solution made of 20 g $(NH_4)_6Mo_7O_{24}$ and 8.3 g $Ce(SO_4)_2$ polyhydrate in water (750 mL) containing concentrated sulfuric acid (90 mL).

Preparative HPLC were perform on a Gilson apparatus equipped with a C18 column, a 215 liquid handler module and 15 mL/min capacity head pumps. The HPLC is operated with a Gilson UniPoint System Software. A solvent gradient was used starting from H$_2$O/CH$_3$CN (95%:5%) to 100% CH$_3$CN over 25 min, and 100% CH$_3$CN for a further 20 mill to clean the column.

Unless otherwise indicated, all starting materials were purchased from a commercial source such as Aldrich Co. or Sigma Co.

Nuclear magnetic resonance (NMR) spectra were recorded on a Bruker AMX 500 equipped with a reversed or QNP probe. Samples were dissolved in deuterochloroform (CDCl$_3$), deuteroacetone (acetone-d$_6$) or deuterodimethylsulfoxide (DMSO-d$_6$) for data acquisition using tetramethylsilane as internal standard. Chemical shifts (δ) are expressed in parts per million (ppm), the coupling constants (J) are expressed in hertz (Hz) whereas multiplicities are denoted as s for singlet, d for doublet, dd for doublet of doublets, t for triplet, q for quartet, m for multiplet, and br s for broad singlet.

General Procedures
A. Preparation of N-acylated (or N-sulfonated) amino acids (Schotten-Baumen procedure)

To a solution of an amino acid (10 mmol) in 25 mL IN NaOH and 5 mL saturated Na$_2$CO$_3$ (resulting solution at pH 10) was added an acyl chloride (or a sulfonyl chloride, or a chloroformate) (12 mmol) dissolved in 10 mL acetone over a period of 20 min. Afterwards, the reaction mixture was stirred at room temperature for 2 h. The alkaline solution was extracted once with ether (50 mL) and the aqueous phase was acidified with 1N HCl to form a pasty oil. This was extracted twice with 20 mL CHCl$_3$, and the combined organic phases were washed with 10 mL 1N HCl. The organic phase was dried over MgSO$_4$, filtered and evaporated to an oil which crystallized on standing. The solid was recrystallized from either dichloromethane, ether, hexanes or without solvent as indicated in each specific example. The purity was evaluated by LC-MS and/or $^1$H NMR and was found to be ranging from 85 to 99%.
B. Coupling reaction of N-acylated (or N-sulfonated) amino acid with the Nϵ-NH$_2$ of a L-lysine derivative Depending on the nature of the reagents, various methods were used to link the two amino acid portions together.
a) N,N-carbonyldiimidazole Method Nα-isobutyl-Nα-(4-methylbenzenesulfonyl)-L-lysine hydrochloride (or other L-lysine derivative) (100 mg, 0.25 mmol) was weighed in the Bohdahn robotic reaction vessels. The solid was then added to 1 mL 3.3M Cs$_2$CO$_3$ solution to which 2 mL of THF was added. The tube was then stirred vigorously. The resulting mixture was treated with N-acylated (or N-sulfonated) amino acid (0.3 mmol) activated by N,N-carbonyldiimidazole (0.3 mmol) dissolved in THF (1 mL). The stirring was continued for 2 h. Afterwards, EtOAc (3 mL) was added and the organic phase was removed. The organic phase was washed with 1N HCl and again separated. Evacuation of the solvent gave a crude product which was resolved by HPLC. The yield of the reactions will be indicated in each specific example.
b) Solid Phase Method Preparation of Solid-phase Bound Nα-isobutyl-Nα-(4-methylbenzenesulfonyl)-Nϵ-(9-fluorenylmethoxycarbonyl)-L-lysine Nα-isobutyl-Nα-(4-methylbenzenesulfonyl)-Nϵ-(9-fluorenylmethoxycarbonyl)-L-lysine (1.51 g, 2.6 mmol) was dissolved in DCM (70 nL) containing DCC (1.5 g). The solution was stirred at room temperature for 8 h and then filtered. The filtrate was added to 5.0 g dried washed Wang resin (0.73 meq/g) to which 150 mg N,N-dimethylaminopyridine (DMAP) was added. The suspension was stirred at room temperature for 12 h. Then, the resin was filtered and washed successively with DCM (100 mL, 2×), 1:1 DCM: MeOH (100 nL, 3×), MeOH (50 mL, 2×) and ether (100 mL). The resin was again swollen in DCM to which acetic anhydride (20 mL) was added. It was left to stand for 3 h and then filtered and washed as above. The resulting resin was dried at room temperature in a dessicator in vacuo. The resulting resin (5.92 g) contained 0.28 meq/g L-lysine derivative.

NB: Same preparation for solid-phase bound Nα-isobutyl-Nα-(4-nitrobenzenesulfonyl)-Nϵ-(9-fluorenylmethoxycarbonyl)-L-lysine (see example 28).

Deprotection

In a typical experiment, 450 mg (0.125 mmol) of resin was added to a syringe type reaction vessel with Teflon frits and stopcock. The resin was swollen with DCM and washed after 15 min. It was treated with 30% piperidine in DMF (4 mL) and left for 15 min before being successively washed with DMF (5 mL, 2×), DCM (5 mL, 4×), and ether (5 mL, 4×). This process was repeated once.

Coupling

In a typical experiment, 0.5 mmol of N-acylated (or N-sulfonated) amino acid was added to a solution of N-hydroxysuccinimide (0.5 mmol) and DCC (0.5 mmol) in DMF (3 mL). The acid was activated for 3 h and filtered directly into the resin containing vessel. The coupling reaction was allowed to proceed for 12 h at room temperature. The resin was then washed successively with DCM, MeOH and ether as described above then dried in vacuo.

Cleavage

The dried resin was swollen with DCM, filtered and treated with 95% TFA (4 mL). The resulting mixture was stirred for a period of 3 h. Then, the solution was filtered off and evaporated. The residue was triturated with ether and the pasty solid placed under high vacuum for 4 h The solid was purified by preparative HPLC to give the final coupled product. The yield of the reactions will be indicated in each specific example.
c) Dicyclohexylcarbodiimide (DCC) method Nα-isobutyl-Nα-(4-methylbenzenesulfonyl)-L-lysine potassium salt (or other L-lysine potassium salt derivative) (1 mmol) was weighed in a round bottom flask and was suspended in THF (20 mL). This suspension was treated with a 1N NaOH (1.5 mL) to pH 10. In another reaction vessel, a solution of N-protected amino acid (1 mmol) in THF (25 ML), was treated with 115 mg of N-hydroxysuccinimide (1 mmol) and 206 mg DCC (1 mmol). The resulting mixture was stirred at room temperature for 4 h. Afterwards, the precipitate was filtered off and the filtrate was added to the initial suspension with vigorous stirring. After 2 h, a 2 mL aliquot of water was added resulting in a clear solution. The stirring was continued for 12 h. Then, EtOAc (50 nL) was added and the organic phase was washed successively with 1N NaOH (50 mL), with 1N HCl (50 mL) and finally with brine (50 mL). The organic phase was removed and dried with Na$_2$SO$_4$. The solvent was evaporated and the product was purified (in whole or in part) by preparative HPLC or by trituration with ether. The yield of the reactions will be indicated in each specific example.

d) 1-Ethyl-3-(3-dimethylaminopropyl)carbodiimide hydrochloride (EDC) method

A solution of Nα-isobutyl-Nα-(4-methylbenzenesulfonyl)-L-lysinol (1.63 g) in EtOAc (16 mL) was prepared (100 mg/ mL, 0.29 mmol/mL). A second solution containing EDC (2.5 g) and HOBt (1.34 g) in DMF was prepared (0.5 mmol / mL). To Bohdan robotic test tubes were then added a series of N-substituted amino acids (0.5 mmol) to which a 1 mL aliquot of the EDC:HOBt solution was added. After 20 min, a 1 mL aliquot of the lysinol solution was added. The resulting solutions were stirred at room temperature for 6 h. Afterwards, a 5 mL aliquot of 10% citric acid aqueous solution was added to each test tube and the solutions were extracted with EtOAc (50 mL). The organic phase were evaporated and the residue obtained in each test tube was purified by HPLC. The yield of the reactions will be indicated in each specific example.

C. Removal of the N-tert-butoxycarbonyl (Boc) group

To a series of Boc protected products (100 mg) in Bohdan test tubes was added 2 mL of $CH_2Cl_2$:TFA (1:1). Gas evolution was observed and the solutions were stirred for 20 min. The solvents were evacuated and the resulting thick oil was triturated with cold ether. The ether was decanted away and the remaining products were placed in a high vacuum desiccator for 12 h to give solid foams. The yield of the reactions will be indicated in each specific example.

D. Sodium Salt Formation

The L-lysine product (100 mg) was dissolved in MeCN (1 mL). The solution was added to 5 mL $H_2O$ to form a turbid suspension. A 1N NaOH solution (1 mol eq) was slowly added to the turbid suspension which became clear. The solution was frozen solid and lyophilized to yield a white powder (100%).

E. Catalytic Hydrogenation

To a series of nitro compounds (100 mg) dissolved in argon saturated MeOH (10 mL) was added 10% Pd/C (50 mg) followed by formic acid 98% (0.1 mL). The suspensions were saturated with $H_2$ and kept under positive pressure using a $H_2$ filled balloons. After 4–6 h stirring, the $H_2$ was purged out and the solutions were filtered through thin pads of celite. The clear solutions were then evacuated, triturated with ether and resolved by preparative HPLC. The yield of the reactions will be indicated in each specific example.

F. General Procedure for the Thiomidation Reaction

To a stirred solution of amide (1 mmol) in dry THF (10 mL) was added Lawesson's reagent (606 mg, 1.5 mmol). The reaction was stirred overnight then concentrated and purified by flash chromatography using hexane/EtOAc as eluent to afford the desired thioamide.

G. General Procedure for the Reduction of Esters with $LiAlH_4$

To a stirred solution of the ester (1 mmol) in THF was added at 0° C. $LiAlH_4$ (1.5 mmol). The mixture was stirred at room temperature for 3 h. The hydride excess was neutralised with HCl 1N and the reaction was extracted with EtOAc. The organic phase was dried ($MgSO_4$) and concentrated. The crude was purified by flash chromatography.

H. Substitution Reaction on an Iodoacetamide Derivative

To a solution of Nα-isobutyl-Nα-(4-methylbenzenesulfonyl)-Nε-iodoacetyl-L-lysine (1.0 eq.) in THF (10 mL) was added DIEA (2.0–3.0 eq.) and an amine derivative (2.0–4.0 eq.). The reaction mixture was stirred overnight at room temperature. Then, a 2N HCl solution (2 mL) was added and the resulting mixture was extracted with EtOAc (20 mL, 3×). The organic phase was dried $MgSO_4$ and evaporated to an oil. The crude material was purified by preparative HPLC.

Specific Examples for the Preparation of Derivatives of General Formula I

The following compounds were prepared either from a L-amino acid or, when indicated, from a derivative of a D-amino acid using the procedures summarized in schemes 1, 2, 3, 4, 5, 6 and 7.

Example 1

Preparation of Nα-isobutyl-Nα-(4-methylbenzenesulfonyl)-Nε-[N'α-(4-methylbenzenesulfonyl)-L-phenylalanyl]-L-lysine Step A. Preparation of L-lysine methyl ester dihydrochloride MeOH (J. Org. Chem 44, 4841 (1979))

To a stirred suspension of L-lysine monohydrochloride (190.7 g, 1.08 mol) in MeOH (3 L) was added (via a cannula) trimethylsilylchloride (350 mL). The mixture quickly became clear and homogeneous. The solution was stirred at reflux for 3 h and then at room temperature for 2 h. The reaction flask was left overnight in a refrigerator cooled to −75 ° C. The large crystals obtained were filtered, washed with cold MeOH (100 mL) and dried in vacuo for 24 h at room temperature. L-lysine methyl ester dihydrochloride MeOH (275.8 g) was obtained in 99.4% yield.

$^1$H NMR (DMSO-$d_6$): δ 1.36 (m, 1H), 1.45 (m, 1H), 1.58 (m, 2H), 1.81 (m, 2H), 2.74 (br s, 2H), 3.11 (s, 3H), 3.72 (s, 3H), 3.94 (t, J=4.0, 1H), 8.12 (br s, 3H), 8.72 (br s, 3H).

Step B. Preparation of L-α-amino-ε-caprolactam hydrochloride (J. Org. Chem. 44, 4841 (1979))

Sodium methylate 58.73 g (1 mole) was dissolved in cold MeOH (1 L). About one half of this solution was cannulated into a solution of L-lysine methyl ester dihydrochloride MeOH (132.5 g, 0.5 mole) in 1 L MeOH. The suspension was allowed to warm and dissolved. The remainder sodium methylate was added with concurrent apparition of NaCl. The mixture was then allowed to reflux for 4 h, after which 5 g of $NH_4Cl$ was added. The solution then sat at RT for 18 h and was filtered through celite. Evaporation of the MeOH resulted in a thick opaque syrup. The excess NaCl was removed by redissolving the mixture in boiling glyme (100 mL, 2×), filtering through celite and evaporating in vacuo. The resulting clear oil was taken up in ethanol and acidified with 12 N HCl. Cooling gave a mass of fine white needles which were filtered and dried in vacuo to yield 69.71 g, 85% of the title compound. MP 301–306 ° C.

[α]d=−24.8 (c=3.4, 1N HCl). $^1$H NMR (DMSO-$d_6$): δ 1.17 (q, J=12.6, 1H), 1.45 (q, J=12.6, 1H), 1.58 (q, J=12.6, 1H), 1.71 (d, J=12.6, 1H), 1.86 (d, J=12.6, 1H), 1.94 (d, J=12.6, 1H), 3.03 (m, 1H), 3.15 (m, 1H), 4.03 (d, J=12.6, 1H), 8.12 (br s, 1H), 8.22 (br s, 3H). $^{13}$C NMR (DMSO-$d_6$): δ 28.2, 29.7, 29.9, 41.6, 53.4, 173.2. LC-MS: 129.1 (M+H)$^+$, 99% pure.

Step C. Preparation of Nα-isobutyl-L-α-amino-ε-caprolactam

L-α-amino-ε-caprolactam (60.0 g, 0.47 mol) was dissolved in dichloroethane (DCE, 100 mL) containing isobutyraldehyde (37.0 g, 0.5 mole) and stirred until the heat evolved was dissipated. Then, DCE (2 L) and AcOH (35 mL) were added to the solution followed by 0.5 mole of powdered $NaBH(OAc)_3$. The slightly turbid mixture was stirred at 60° C. for 2 h, and at room temperature for 12 h. The solution was treated with 1M $K_2CO_3$ (1 L)and stirred for a further 2 h. The DCE layer was dried with $MgSO_4$, filtered and evaporated. The oil thus obtained crystallizes slowly on standing (87 g, 94.5%) and was used without further purification in the next step. MP 52–54° C. A small sample was converted to the hydrochloride salt by adding the solid to a solution of 1N HCl in 95% EtOH.

$^1$H NMR (CDCl$_3$): δ 0.93 (d, J=6.5, 3H), 0.97 (d, J=6.5, 3H), 1.39 (t, J=9.8, 1H), 1.47 (m, 1H), 1.78–1.65 (m, 2H), 2.00–1.93 (m, 2H), 2.32–2.2 (m, 2H), 2.38 (t, J=9.7, 1H), 3.16 (m, 3H), 6.62 (s, 1H (NH)).

Step D. Preparation of Nα-isobutyl-Nα-(4-methylbenzenesulfonyl)-L-α-amino-ε-caprolactam The compound prepared in step C of this example (10.0 g, 51 mmol, free base) was dissolved in DCM (100 mL) and treated with diisopropylethylamine (10 mL) followed by freshly recrystallized 4-methylbenzenesulfonyl chloride (11.4 g, 57.3 mmol). The mixture was stirred overnight (TLC shows the reaction to be complete after 2 h). The solution was extracted with 1 N HCl and the organic layer was dried and evaporated. Then, the residue was dissolved in boiling $CHCl_3$ (5 mL), diluted with hexanes (200 mL) and placed in the refrigerator for 3 h. The precipitated product was filtered off and air dried giving 15.5 g of pure product. MP 49–51° C.

$^1$H NMR ($CDCl_3$): δ 0.74 (d, J=6.2,3H), 0.80 (d, J=6.2, 3H), 1. 12 (q, J=8.3, 1H), 1.56–1.73 (m, 4H), 1.84–1.87 (m, 1H), 1.96–1.99 (m, 1H), 2.33 (s, 3H), 2.86–2.89 (m, 1H), 2.97–2.98 (m 1H), 3.1–3.06 (m, 2H), 3.21–3.26 (m, 1H), 4.48 (d, J=10.6, 1H), 5.7 (s, 1H (NH)), 7.29 (d, J=7.7, 2H), 7.59 (d, J=7.7, 2H).

Step E. Preparation of Nα-isobutyl-Nα-(4-methylbenzenesulfonyl)-L-lysine hydrochloride A mixture of Nα-isobutyl-Nα-(4-methylbenzenesulfonyl)-L-α-amino-ε-caprolactam (13.5 g, 40 mmol), AcOH (4 mL) and 6N HCl (200 mL) was refluxed for 12 h until all solids had disappeared. Afterwards, the solution was evaporated to give 11.0 g, 77% of the hydrochloride salt.

$^1$H NMR (DMSO-$d_6$): δ 0.72 (dd, J=5.8,6.4, 6H), 1.13–1.17 (m, 2H), 1.17–1.24 (m 2H), 1.42–1.48 (m, 2H), 2.3 (s, 3H), 2.67 (t, J=7.2, 2H), 2.80–2.91 (m, 2H), 4.13 (t, J=7.2, 1H), 7.22 (d, J=8.5, 2H), 7.64 (d, J=8.5, 2H).

Step F. Preparation of Nα-isobutyl-Nα-(4-methylbenzenesulfonyl)-Nε-[N'α-(4-methylbenzenesulfonyl)-L-phenylalanyl]-L-lysine A suspension of Nα-isobutyl-Nα-(4-methylbenzenesulfonyl)-L-lysine hydrochloride (600 mg) in THF (20 mL) was treated with a 1N NaOH (1.5 mL) to pH 10. A solution of commercially available Nα-(4-methylbenzenesulfonyl)-L-phenylalanine acid chloride (250 mg) in dry THF (20 mL) was added to the suspension and stirred for 2 h. Afterwards, water (2 mL) was added resulting in a clear solution. The reaction mixture was stirred for 12 h. Then, EtOAc (30 mL) was added and the organic phase was washed with 1N HCl. The organic phase was removed. Evaporation of the solvent gave a crude product which was triturated with ether to yield 750 mg (76%) of the title compound.

$^1$H NMR ($CDCl_3$): δ 0.77 (d, J=6.3, 3H), 0.80 (d, J=6.3, 3H), 1.00–1.11 (m, 4H), 1.23–1.25 (m, 1H), 1.70–1.74 (m, 1H), 1.89–1.93 (m, 1H), 2.30 (s, 3H), 2.32 (s, 3H), 2.59–2.67 (m, 2H), 2.87 and 2.93 (ABX, J=14.1, 4.2, 2H), 3.85 (t, J=5.9, 1H), 3.63 (t, J=6.9, 1H), 6.90–7.10 (m, 7H), 7.24 (d, J=8.0, 2H), 7.44 (d, J=8.1, 2H), 7.73 (d, J=8.1, 2H). LC-MS: 656.2 (M–H)$^-$, 98% pure.

Example 2

Preparation of Nα-isobutyl-Nα-(4-methylbenzenesulfonyl)-Nε-[N'α-(4-methylbenzenesulfonyl)-L-tryptophanyl]-L-lysine Step A. Preparation of Nα-(4-methylbenzenesulfonyl)-L-tryptophan L-tryptophan was reacted with 4-methylbenzenesulfonyl chloride under the conditions used in general procedure A giving the title compound which was recrystallised from DCM (58%).

$^1$H NMR ($CDCl_3$): δ 2.33 (s, 3H), 2.9–3.11 (m, 2H), 3.91 (t, J=7.0, 1H), 6.86–7.01 (m, 3H), 7.25 (d, J=6.9, 2H), 7.34 (t, J=6.8, 1H), 7.45 (d, J=6.9, 2H), 8.15 (d, J=6.1, 1H). LC-MS: 357 (M–H)$^-$, 99% pure.

Step B. Preparation of Nα-isobutyl-Nα-(4-methylbenzenesulfonyl)-Nε-[N'α-(4-methylbenzenesulfonyl)-L-tryptophanyl]-L-lysine The title compound was prepared from Nα-isobutyl-Nα-(4-methylbenzenesulfonyl)-L-lysine (150 mg, 0.42 mmol, example 1, step E) as described in general procedure Bc using Nα-(4-methylbenzenesulfonyl)-L-tryptophan (180 mg, 0.5 mmol) which was prepared in step A of this example. The final product was triturated with ether to yield 180 mg (69%) of the desired material.

$^1$H NMR (DMSO-$d_6$): δ 0.77 (d, J=6.3, 3H), 0.80 (d, J=6.3, 3H), 1.00–1.11 (m, 4H), 1.32–1.35 (m, 1H), 1.70–1.74 (m, 1H), 1.83–1.88 (m, 1H), 2.26 (s, 3H), 2.34 (s, 3H), 2.59–2.67 (m, 2H), 2.92 and 2.87 (ABX, J=13.1, 2.8, 2H), 3.80 (t, J=6.5, 1H), 4.11 (t, J=7.2, 1H), 6.85 (t, J=7.1, 1H), 7.00 (t, J=4.0,2H), 7.10 (d, J=7.1, 2H), 7.28 (d, J=4.0, 1H), 7.33 (m 3H), 7.43 (d, J=7.1, 2H), 7.60 (d, J=7.1, 2H), 7.71 (t, J=5.4, 1H), 7.80 (d, J=8.0, 1H). LC-MS: 695.2 (M–H)$^-$, 99% pure.

Example 3

Preparation of Nα-isobutyl-Nα-(4-methylbenzenesulfonyl)-Nε-[N'α-(4-acetamidobenzenesulfonyl)-L-phenylalanyl]-L-lysine Step A. Preparation of Nα-(4-acetamidobenzenesulfonyl)-L-phenylalanine L-phenylalanine was reacted with 4-acetamidobenzenesulfonyl chloride under the conditions used in general procedure A giving the title compound which was recrystallised from DCM (52%).

LC-MS: 362 (M–H)$^-$, 95% pure.

Step B. Preparation of Nα-isobutyl-Nα-(4-methylbenzenesulfonyl)-Nε-[N'α-(4-acetamidobenzenesulfonyl)-L-phenylalanyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-acetamidobenzenesulfonyl)-L-phenylalanine (102 mg, 0.29 mmol) which was prepared in step A of this example. The final product was triturated with ether to yield 101 mg (57%) of the desired material.

LC-MS: 699.2 (M–H)$^-$, 95% pure.

Example 4

Preparation of Nα-isobutyl-Nα-(4-methylbenzenesulfonyl)-Nε-(N'α-benzenesulfonyl-L-tryptophanyl)-L-lysine Step A. Preparation of Nα-benzenesulfonyl-L-tryptophan L-tryptophan was reacted with benzenesulfonyl chloride under the conditions used in general procedure A giving the title compound which was recrystallised from DCM (26%).

$^1$H NMR ($CDCl_3$): δ 2.86–3.26 (m, 2H), 3.93 (t, J=5.0, 1H), 6.92–7.00 (m, 3H), 7.28 (d, J=7.0, 2H), 7.30–7.34 (m, 3H), 7.55 (d, J=6.0, 1H), 8.24 (d, J=6.0, 1H). LC-MS: 343 (M–H)$^-$, 99% pure.

Step B. Preparation of Nα-isobutyl-Nα-(4-methylbenzenesulfonyl)-Nε-(N'α-benzenesulfonyl-L-tryptophanyl)-L-lysine The title compound was prepared from Nα-isobutyl-Nα-(4-methylbenzenesulfonyl)-L-lysine (1.0 g, 2.9 mmol, example 1, step E) as described in general procedure Bc using Nα-benzenesulfonyl-L-tryptophan (1.72 g, 5 mmol) which was prepared in step A of this example. The final product was triturated with ether to yield 1.7 g of the crude material. Purification of 500 mg of the crude material by HPLC gave 322 mg (64%) of pure adduct.

$^1$H NMR (CDCl$_3$): δ 0.78 (d, J=6.3, 3H), 0.81 (d, J=6.3, 3H), 0.94–1.03 (m, 4H), 1.32–1.35 (m, 1H), 1.46–1.49 (m, 1H), 1.83–1.88 (m, 1H), 2.35 (s, 3H), 2.82–2.99 (m, 4H), 3.95 (t, J=6.5, 1H), 4.21 (t, J=7.2, 1H), 6.85 (t, J=4.5, 1H), 7.09 (t, J=4.5, 1H), 7.23–7.31 (m, 6H), 7.42 (t, J=4.5, 1H), 7.60 (d, J=6.8, 2H), 7.73 (d, J=6.8, 2H). LC-MS: 681.2 (M−H)$^−$, 99% pure.

Example 5

Preparation of Nα-isobutyl-Nα-(4-aminobenzenesulfonyl)-Nε-[N'α-(4-aminobenzenesulfonyl)-L-tryptophanyl]-L-lysine Step A. Preparation of Nα-(4-nitrobenzenesulfonyl)-L-tryptophan L-tryptophan was reacted with 4-nitrobenzenesulfonyl chloride under the conditions used in general procedure A giving Nα-(4-nitrobenzenesulfonyl)-L-tryptophan which was recrystallised from DCM (56%).

LC-MS: 388 (M−H)$^−$, 99% pure.

Step B. Preparation of Nα-isobutyl-Nα-(4-nitrobenzenesulfonyl)-L-(α-amino-ε-caprolactam Nα-isobutyl-L-α-amino-ε-caprolactam (example 1, step C) (4.14 g, 21.1 mmol, free base) was dissolved in DCM (50 mL) and treated with diisopropylethylamine (6.0 mL, 30 mmol) followed by freshly recrystallized 4-nitrobenzenesulfonyl chloride (5.09 g, 21.7 mmol). The mixture was stirred overnight (TLC shows the reaction to be complete after 2 h). The solution was extracted with 1N HCl and the organic layer was dried and evaporated. Then, the residue was dissolved in boiling MeOH (250 mL) and placed in the refrigerator for 3 h. The thin needles obtained were filtered off and air dried giving 6.9 g (83%) of pure product. MP 152–154° C.

$^1$H NMR (CDCl$_3$): δ 0.93 (d, J=6.0, 3H), 0.96 (d, J=6.0, 3H), 1.39 (t, J=12.0, 1H), 1.65–1.85 (m, 3H), 2.08–2.18 (m, 3H), 3.06 (dd, J=14.2, 8.5, 1H), 3.35 (dd, J=14.2, 8.5, 1H), 4.65 (d, J=8.7, 1H), 5.7 (s, 1H (NH)), 7.92 (d, J=8.8, 2H), 8.3 (d, J=8.8, 2H).

Step C. Preparation of Nα-isobutyl-Nα-(4-nitrobenzenesulfonyl)-L-lysine hydrochloride A mixture of Nα-isobutyl-Nα-(4-nitrobenzenesulfonyl)-L-(α-amino-ε-caprolactam (1.0 g, 2.7 mmol), AcOH (4 mL) and 6N HCl (10 mL) was refluxed for 12 h until all solids had disappeared. Afterwards, the solution was evaporated to give 1.12 g, 100% of the hydrochloride salt.

[α]d=−16.7 (c=0.36 in MeOH); $^1$H NMR (DMSO-d$_6$): δ 0.79 (d, J=6.8, 3H), 0.86 (d, J=6.8, 3H), 1.25 (t, J=11.9, 2H), 1.32–1.28 (m 2H), 1.58–1.45 (m, 2H), 1.85–1.75 (m, 2H), 2.7 (m, 3H (NH)), 2.83–2.87 (m, 1H), 3.03–3.07 (m, 1H), 4.21 (t, J=10.1, 1H), 8.10 (d, J=7.9, 2H), 8.37 (d, J=7.9, 2H).

Step D. Preparation of Nα-isobutyl-Nα-(4-aminobenzenesulfonyl)-Nε-[N'α-(4-aminobenzenesulfonyl)-L-tryptophanyl]-L-lysine The title compound was prepared from Nα-isobutyl-Nα-(4-nitrobenzenesulfonyl)-L-lysine hydrochloride (200 mg, 0.52 mmol, step C) as described in general procedure Bc using Nα-(4-nitrobenzenesulfonyl)-L-tryptophan (300 mg, 0.8 mmol) which was prepared in step A of this example. The intermediate derivative was reduced following the indications of general procedure E. The final product was purified by HPLC to give 101 mg (53%) of pure adduct.

$^1$H NMR (DMSO-d$_6$): δ 0.73 (d, J=6.3, 3H), 0.75 (d, J=6.3, 3H), 1.00–1.11 (m, 4H), 1.32–1.35 (m 1H), 1.66–1.69 (m, 1H), 1.83–1.88 (m, 1H), 2.48 (br s, 6H), 2.59–2.67 (m, 2H), 2.84–2.96 (m, 2H), 3.80 (t, J=6.5, 1H), 4.01 (t, J=7.2, 1H), 6.46 (d, J=7.1, 2H), 6.52 (d, J=7.1, 2H), 6.85 (t, J=4.0, 1H), 7.09 (t, J=4.0, 2H), 7.28 (d, J=7.1, 1H), 7.33 (d, J=7.1, 2H), 7.60 (t, J=4.0, 1H). LC-MS: 697.2 (M−H)$^−$, 98% pure.

Example 6

Preparation of Nα-isobutyl-Nα-(4-methylbenzenesulfonyl)-Nε-[N'α-(4-nitrobenzenesulfonyl)-L-tryptophanyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-nitrobenzenesulfonyl)-L-tryptophan (120 mg, 0.3 mmol) which was prepared in step A of example 5. The final product was purified by HPLC to give 66 mg (36%) of pure adduct.

LC-MS: 726.2 (M−H)$^−$, 99% pure.

Example 7

Preparation of Nα-isobutyl-Nα-(4-methylbenzenesulfonyl)-Nε-[N'α-(4-methylbenzenesulfonyl)-D-phenylalanyl]-L-lysine Step A. Preparation of Nα-(4-methylbenzenesulfonyl)-D-phenylalanine D-phenylalanine was reacted with 4-methylbenzenesulfonyl chloride under the conditions used in general procedure A giving the title compound which was recrystallised from ether (18%).

LC-MS: 318 (M−H)$^−$, 98% pure.

Step B. Preparation of Nα-isobutyl-Nα-(4-methylbenzenesulfonyl)-Nε-[N'α-(4-methylbenzenesulfonyl)-D-phenylalanyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-methylbenzenesulfonyl)-D-phenylalanine (160 mg, 0.5 mmol) which was prepared in step A of this example. The final product was triturated with ether to yield 49 mg (29%) of the desired material.

LC-MS: 656.2 (M−H)$^−$, 99% pure.

Example 8

Preparation of Nα-isobutyl-Nα-(4-methylbenzenesulfonyl)-Nε-(N'α-benzenesulfonyl-L-phenylalanyl)-L-lysine Step A. Preparation of Nα-benzenesulfonyl-L-phenylalanine L-phenylalanine was reacted with benzenesulfonyl chloride under the conditions used in general procedure A giving the title compound which was recrystallised from ether (50%).

LC-MS: 349 (M−H)$^−$, 95% pure.

Step B. Preparation of Nα-isobutyl-Nα-(4-methylbenzenesulfonyl)-Nε-(N'α-benzenesulfonyl-L-phenylalanyl)-L-lysine The title compound was prepared from Nα-isobutyl-Nα-(4-methylbenzenesulfonyl)-L-lysine hydrochloride (120 mg, 0.34 mmol, example 1, step E) as described in general procedure Bc using Nα-benzenesulfonyl-L-phenylalanine (300 mg, 1.0 mmol) prepared in step A of this example. The final product was purified by preparative HPLC to yield 107 mg (56%) of the desired material.

$^1$H NMR (CDCl$_3$): δ 0.74 (d, J=6.3, 3H), 0.80 (d, J=6.3, 3H), 1.10–1.21 (m, 2H), 1.26–1.33 (m, 2H), 1.70–1.74 (m,

1H), 1.89–1.93 (m, 2H), 2.39 (s, 3H), 2.79–2.89 (m, 2H), 3.85 (t, J=5.9, 1H), 4.29 (t, J=6.9, 1H), 6.90 (d, J=6.2, 2H), 7.08–7.29 (m, 6H), 7.35 (t, J=6.2, 2H), 7.44 (d, J=8.1, 2H), 7.73 (d, J=8.1, 2H). LC-MS: 642.2 (M–H)$^-$, 99% pure.

Example 9

Preparation of Nα-isobutyl-Nα-(4-methylbenzenesulfonyl)-Nε-[N'α-(4-chlorobenzenesulfonyl)-L-phenylalanyl]-L-lysine Step A. Preparation of Nα-(4-chlorobenzenesulfonyl)-L-phenylalanine L-phenylalanine was reacted with 4-chlorobenzenesulfonyl chloride under the conditions used in general procedure A giving the title compound which was recrystallised neat (30%).

LC-MS: 338 (M–H)$^-$, 98% pure.

Step B. Preparation of Nα-isobutyl-Nα-(4-methylbenzenesulfonyl)-Nε-[N'α-(4-chlorobenzenesulfonyl)-L-phenylalanyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-chlorobenzenesulfonyl)-L-phenylalanine (89 mg, 0.3 mmol) prepared in step A of this example. The final product was purified by preparative HPLC to yield 56 mg (33%) of the desired material.

$^1$H NMR (DMSO-d$_6$): δ 0.74 (d, J=6.3, 3H), 0.80 (d, J=6.3, 3H), 1.00–1.11 (m, 4H), 1.23–1.25 (m, 1H), 1.70–1.74 (m, 1H), 1.89–1.93 (m, 1H), 2.32 (s, 3H), 2.59–2.67 (m, 2H), 2.84 and 2.95 (ABX, J=14.1, 6.8, 2H), 3.85 (t, J=5.9, 1H), 4.11 (t, J=6.9, 1H), 7.02–7.21 (m, 7H), 7.24 (d, J=8.0, 1H), 7.54 (d, J=8.1, 2H), 7.73 (d, J=8.1, 2H), 8.07 (d, J=6.4, 1H). LC-MS: 677.2 (M–H)$^-$, 99% pure.

Example 10

Preparation of Nα-isobutyl-Nα-(4-methylbenzenesulfonyl)-Nε-[N'α-(4-nitrobenzenesulfonyl)-L-phenylalanyl]-L-lysine Step A. Preparation of Nα-(4-nitrobenzenesulfonyl)-L-phenylalanine L-phenylalanine was reacted with 4-nitrobenzenesulfonyl chloride under the conditions used in general procedure A giving the title compound which was recrystallised in ether (37%). LC-MS: 349 (M–H)$^-$, 98% pure.

Step B. Preparation of Nα-isobutyl-Nα-(4-methylbenzenesulfonyl)-Nε-[N'α-(4-nitrobenzenesulfonyl)-L-phenylalanyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-nitrobenzenesulfonyl)-L-phenylalanine (125 mg, 0.5 mmol) prepared in step A of this example. The final product was purified by preparative HPLC to yield 91 mg (52%) of the desired material.

LC-MS: 687.2 (M–H)$^-$, 98% pure.

Example 11

Preparation of Nα-isobutyl-Nα-(4-methylbenzenesulfonyl)-Nε-[N'α-(4-methylbenzenesulfonyl)-L-tyrosyl]-L-lysine Step A. Preparation of Nα-(4-methylbenzenesulfonyl)-L-tyrosine L-tyrosine was reacted with 4-methylbenzenesulfonyl chloride under the conditions used in general procedure A giving the title compound which was recrystallised neat (15%).

LC-MS: 334 (M–H)$^-$, 95% pure.

Step B. Preparation of Nα-isobutyl-Nα-(4-methylbenzenesulfonyl)-Nε-[N'α-(4-methylbenzenesulfonyl)-L-tyrosyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-methylbenzenesulfonyl)-L-tyrosine (160 mg, 0.5 mmol) prepared in step A of this example. The final product was purified by preparative HPLC to yield 78 mg (46%) of the desired material.

LC-MS: 672.2 (M–H)$^-$, 99% pure.

Example 12

Preparation of Nα-isobutyl-Nα-(4-methylbenzenesulfonyl)-Nε-[N'α-(4-aminobenzenesulfonyl)-L-tryptophanyl]-L-lysine The title compound was prepared from Nα-isobutyl-Nα-(4-methylbenzenesulfonyl)-L-lysine hydrochloride (200 mg, 0.59 mmol, example 1, step E) as described in general procedure Bc using Nα-(4-nitrobenzenesulfonyl)-L-tryptophan (300 mg, 0.75 mmol) prepared in step A of example 5. The intermediate, Nα-isobutyl-Nα-(4-methylbenzenesulfonyl)-Nε-[N'α-(4-nitrobenzenesulfonyl)-L-tryptophanyl]-L-lysine, was reduced following the conditions of general procedure E. The final product was purified by preparative HPLC to yield 266 mg (58%) of the desired material.

1H NMR (DMSO-d$_6$): δ 0.74 (d, J=6.3, 3H), 0.80 (d, J=6.3, 3H), 1.00–1.11 (m, 4H), 1.32–1.35 (m, 1H), 1.70–1.74 (m, 1H), 1.83–1.88 (m, 1H), 2.34 (s, 3H), 2.59–2.67 (m, 2H), 2.84–2.96 (m, 2H), 3.86 (t, J=6.5, 1H), 4.13 (t, J=7.2, 1H), 6.85 (t, J=4.0, 1H), 7.00 (t, J=4.0, 2H), 7.10 (d, J=7.1, 2H), 7.28 (d, J=4.0, 1H), 7.33 (m, 3H), 7.43 (d, J=7.1, 2H), 7.60 (d, J=7.0, 2H), 7.71 (t, J=4.1, 1H), 7.80 (d, J=8.0, 1H). LC-MS: 725.2 (M–H)$^-$, 98% pure.

Example 13

Preparation of Nα-isobutyl-Nα-(4-methylbenzenesulfonyl)-Nε-[N'α-(4-nitrobenzenesulfonyl)-L-alanyl]-L-lysine Step A. Preparation of Nα-(4-nitrobenzenesulfonyl)-L-alanine L-alanine was reacted with 4-nitrobenzenesulfonyl chloride under the conditions used in general procedure A giving the title compound which was recrystallised neat (9%). This compound was used without further purification in the next step.

Step B. Preparation of Nα-isobutyl-Nα-(4-methylbenzenesulfonyl)-Nε-[N'α-(4-nitrobenzenesulfonyl)-L-alanyl]-L-lysine The title compound was prepared from No-isobutyl-Nα-(4-methylbenzenesulfonyl)-L-lysine hydrochloride (100 mg, 0.29 mmol, example 1, step E) as described in general procedure Bc using Nα-(4-nitrobenzenesulfonyl)-L-alanine (140 mg, 0.5 mmol) prepared in step A of this example. The final product was purified by preparative HPLC to yield 10 mg (6.5%) of the desired material.

LC-MS: 611.2 (M–H)$^-$, 99% pure.

Example 14

Preparation of Nα-isobutyl-Nα-(4-methylbenzenesulfonyl)-Nε-[N'α-(benzenesulfonyl)-L-norvalyl]-L-lysine Step A. Preparation of Nα-benzenesulfonyl-L-norvaline L-norvaline was reacted with benzenesulfonyl chloride under the conditions used in general procedure A giving the title compound which was recrystallised neat (33%). This compound was used without further purification in the next step.

Step B. Preparation of Nα-isobutyl-Nα-(4-methylbenzenesulfonyl)-Nε-[N'α-(benzenesulfonyl)-L-norvalyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-benzenesulfonyl-L-norvaline (120 mg, 0.5 mmol) prepared in step A of this example. The final product was purified by preparative HPLC to yield 15 mg (10%) of the desired material.

LC-MS: 594.3 (M–H)⁻, 99% pure.

Example 15

Preparation of Nα-isobutyl-Nα-(4-methylbenzenesulfonyl)-Nε-[N'α-(benzenesulfonyl)-L-norleucyl]-L-lysine Step A. Preparation of Nαc-benzenesulfonyl-L-norleucine L-norleucine was reacted with benzenesulfonyl chloride under the conditions used in general procedure A giving the title compound which was recrystallised neat (25%). Tis compound was used without further purification in the next step.

Step B. Preparation of Nα-isobutyl-Nα-(4-methylbenzenesulfonyl)-Nε-[N'α-(benzenesulfonyl)-L-norleucyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-benzenesulfonyl-L-norleucine (125 mg, 0.5 mmol) prepared in step A of this example. The final product was purified by preparative HPLC to yield 13 mg (8.5%) of the desired material.

LC-MS: 608.3 (M–H)⁻, 99% pure.

Example 16

Preparation of Nα-isobutyl-Nα-(4-methylbenzenesulfonyl)-Nε-[N'α-(4-nitrobenzenesulfonyl)-L-leucyl]-L-lysine Step A. Preparation of Nα-(4-nitrobenzenesulfonyl)-L-leucine L-leucine was reacted with 4-nitrobenzenesulfonyl chloride under the conditions used in general procedure A giving the title compound which was recrystallised neat (66%). This compound was used without further purification in the next step.

Step B. Preparation of Nα-isobutyl-Nα-(4-methylbenzenesulfonyl)-Nε-[N'α-(4-nitrobenzenesulfonyl)-L-leucyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-nitrobenzenesulfonyl)-L-leucine (150 mg, 0.5 mmol) prepared in step A of this example. The final product was purified by preparative HPLC to yield 28 mg (17%) of the desired material.

LC-MS: 653.3 (M–H)⁻, 99% pure.

Example 17

Preparation of Nα-isobutyl-Nα-(4-methylbenzenesulfonyl)-Nε-[N'α-(benzenesulfonyl)-4-trans-hydroxy-L-prolyl]-L-lysine Step A. Preparation of Nα-benzenesulfonyl-4-trans-hydroxy-L-proline 4-trans-hydroxy-L-proline was reacted with benzenesulfonyl chloride under the conditions used in general procedure A giving the title compound which was recrystallised neat (21%). This compound was used without further purification in the next step.

Step B. Preparation of Nα-isobutyl-Nα-(4-methylbenzenesulfonyl)-Nε-[N'α-(benzenesulfonyl)-4-trans-hydroxy-L-prolyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-benzenesulfonyl-4-trans-hydroxy-L-proline (130 mg, 0.5 mmol) prepared in step A of this example. The final product was purified by preparative HPLC to yield 9 mg (6%) of the desired material.

LC-MS: 608.3 (M–H)⁻, 99% pure.

Example 18

Preparation of Nα-isobutyl-Nα-(4-methylbenzenesulfonyl)-Nε-[N'α-(4-fluorobenzenesulfonyl)-L-phenylalanyl]-L-lysine Step A. Preparation of Nα-(4-fluorobenzenesulfonyl)-L-phenylalanine L-phenylalanine was reacted with 4-fluorobenzenesulfonyl chloride under the conditions used in general procedure A giving the title compound which was recrystallised in ether (40%).

LC-MS: 322 (M–H)⁻, 99% pure.

Step B. Preparation of Nα-isobutyl-Nα-(4-methylbenzenesulfonyl)-Nε-[N'α-(4-fluorobenzenesulfonyl)-L-phenylalanyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-fluorobenzenesulfonyl)-L-phenylalanine (160 mg, 0.5 mmol) prepared in step A of this example. The final product was purified by preparative HPLC to yield 87 mg (52%) of the desired material.

$^1$H NMR (DMSO-d$_6$): δ 0.74 (d, J=6.3, 3H), 0.80 (d, J=6.3, 3H), 1.00–1.11 (m, 4H), 1.23–1.25 (m, 1H), 1.70–1.74 (m, 1H), 1.89–1.93 (m, 1H), 2.32 (s, 3H), 2.65 (m, 2H), 2.85 and 2.95 (ABX, J=16.1 7.1, 22H), 3.88 (t, J=6.0, 1H), 4.11 (t, J=6.9, 1H), 7.02–7.21 (m, 7H), 7.24 (d, J=8.0, 1H), 7.54 (d, J=8.1, 2H), 7.73 (d, J=8.1, 2H), 8.15 (d, J=6.6, 1H). LC-MS: 660.2 (M–H)⁻, 99% pure.

Example 19

Preparation of Nα-isobutyl-Nα-(4-methylbenzenesulfonyl)-Nε-[N'α-(2-naphthylsulfonyl)-L-phenylalanyl]-L-lysine Step A. Preparation of Nα-(2-naphthylsulfonyl)-L-phenylalanine L-phenylalanine was reacted with 2-naphthylsulfonyl chloride under the conditions used in general procedure A giving the title compound which was recrystallised in ether (51%).

LC-MS: 352 (M–H)⁻, 95% pure.

Step B. Preparation of Nα-isobutyl-Nα-(4-methylbenzenesulfonyl)-Nε-[N'α-(2-naphthylsulfonyl)-L-phenylalanyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(2-naphthylsulfonyl)-L-phenylalanine (175 mg, 0.5 mmol) prepared in step A of this example. The final product was purified by preparative HPLC to yield 55 mg (32%) of the desired material.

LC-MS: 692.3 (M–H)⁻, 99% pure.

Example 20

Preparation of Nα-isobutyl-Nα-(4-methylbenzenesulfonyl)-Nε-[N'α-(4-bromobenzenesulfonyl)-L-phenylalanyl]-L-lysine Step A. Preparation of Nα-(4-bromobenzenesulfonyl)-L-phenylalanine L-phenylalanine was reacted with 4-bromobenzenesulfonyl chloride under the conditions used in general procedure A giving the title compound which was recrystallised in ether (18%).

LC-MS: 383 (M–H)⁻, 99% pure.

Step B. Preparation of Nα-isobutyl-Nα-(4-methylbenzenesulfonyl)-Nε-[N'α-(4-bromobenzenesulfonyl)-L-phenylalanyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-bromobenzenesulfonyl)-L-phenylalanine (190 mg, 0.5 mmol) prepared in step A of this example. The final product was purified by preparative HPLC to yield 56 mg (30%) of the desired material.

1H NMR (DMSO-$d_6$): δ 0.74 (d, J=6.3, 3H), 0.80 (d, J=6.3, 3H), 1.00–1.11 (m, 4H), 1.23–1.25 (m, 1H), 1.70–1.74 (m, 1H), 1.89–1.93 (m, 1H), 2.32 (s, 3H), 2.60–2.68 (m, 2H), 2.86 and 2.97 (ABX,J=14.1, 7.1, 2H), 3.96 (t, J=6.1, 1H), 4.11 (t, J=6.9, 1H),6.99–7.22 (m, 7H), 7.24 (d, J=8.0, 1H), 7.54 (d, J=8.1, 2H), 7.73 (d, J=8.1, 2H), 8.11 (d, J6.5, 1H). LC-MS: 721.2 (M–H)⁻, 99% pure.

Example 21

Preparation of Nα-isobutyl-Nα-(4-methylbenzenesulfonyl)-Nε-[N'α-(4-methylbenzenesulfonyl)-glycyl]-L-lysine Step A. Preparation of Nα-(4-methylbenzenesulfonyl)-glycine Glycine was reacted with 4-methylbenzenesulfonyl chloride under the conditions used in general procedure A giving the title compound which was recrystallised neat (60%).

LC-MS: 228 (M–H)⁻, 99% pure.

Step B. Preparation of Nα-isobutyl-Nα-(4-methylbenzenesulfonyl)-Nε-(9-fluorenylmethoxycarbonyl)-L-lysine The title compound was prepared from Nα-isobutyl-Nα-(4-methylbenzenesulfonyl)-L-lysine by following the indications of general example Bc using commercially available N-(9-fluorenylmethoxycarbonyloxy) succinimide instead of the usual combination of reactants i.e. N-protected amino acid, N-hydroxysuccinimide and DCC.

¹H NMR (CDCl₃): 0.79 (d, J=7.1, 3H), 0.81 (d, J=7.1, 3H), 1.12–1.25 (m, 2H), 1.30–1.40 (m, 2H), 1.42–1.50 (m, 2H), 1.78–1.90 (m, 2H), 2.36 (s, 3H), 2.85 (m, 2H), 2.88 and 3.04 (ABX, J=14.3, 7.3, 2H), 4.16–4.21 (m, 2H), 4.28 (d, J=7.0, 2H), 7.30–7.42 (m, 6H), 7.60 (m, 4H), 7.88 (d, J=7.5, 2H), 12.69 (br s, 1H).

Step C. Preparation of Nα-isobutyl-Nα-(4-methylbenzenesulfonyl)-Nε-[N'α-(4-methylbenzenesulfonyl)-glycyl]-L-lysine The title compound was prepared from solid phase bound Nα-isobutyl-Nα-(4-methylbenzenesulfonyl)-Nε-(9-fluorenylmethoxycarbonyl)-L-lysine (step B) as described in general procedure Bb using Nα-(4-methylbenzenesulfonyl)-glycine (110 mg, 0.5 mmol) prepared in step A of this example. The final product was purified by preparative HPLC to yield 30 mg (42%) of the desired material.

¹H NMR (CDCl₃): δ 0.73 (d, J=6.9, 6H), 1.23–1.25 (m, 2H), 1.45–1.52 (m, 3H), 1.89–1.99 (m, 2H), 2.32 (s, 6H), 2.94–3.03 (m, 2H), 3.16 (m, 2H), 3.55 (t, J=5.9, 1H), 4.27 (t, J=7.2, 1H), 7.26 (d, J=8.1, 4H), 7.73 (d, J=8.1, 4H). LC-MS: 566.5 (M–H)⁻, 85% pure.

Example 22

Preparation of Nα-isobutyl-Nα-(4-methylbenzenesulfonyl)-Nε-(N'α-benzenesulfonyl-L-leucyl]-L-lysine Step A. Preparation of Nα-benzenesulfonyl-L-leucine L-leucine was reacted with benzenesulfonyl chloride under the conditions used in general procedure A giving the title compound which was recrystallised neat (31%). This compound was used without further purification in the next step Step B. Preparation of Nα-isobutyl-Nα-(4-methylbenzenesulfonyl)-Nε-(N'α-benzenesulfonyl-L-leucyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-benzenesulfonyl-L-leucine (130 mg, 0.5 mmol) prepared in step A of this example. The final product was purified by preparative HPLC to yield 30 mg (39%) of the desired material.

¹H NMR (CDCl₃): δ 0.72 (d, J=6.0, 3H), 0.75 (d, J=6.0, 3H), 0.78–0.81 (m, 6H), 1.20–1.22 (m, 2H), 1.32–1.34 (m, 2H), 1.52–1.55 (m, 1H), 1.78–2.04 (m, 3H), 2.32 (s, 3H), 2.81–3.01 (m, 4H), 3.56 (t, J=5.2, 1H), 4.25 (t, J=6.0, 1H), 7.21–7.29 (m, 2H), 7.42–7.45 (m, 2H), 7.52 (t, J=6.1, 1H), 7.71 (d, J=7.8, 2H), 7.81 (d, J=7.8, 2H). LC-MS: 608.2 (M–H)⁻, 90% pure.

Example 23

Preparation of Nα-isobutyl-Nα-(4-methylbenzenesulfonyl)-Nε-[N'α-(4-trifluoromethylbenzenesulfonyl)-L-phenylalanyl]-L-lysine Step A. Preparation of Nα-(4-trifluoromethylbenzenesulfonyl)-L-phenylalanine L-phenylalanine was reacted with 4-trifluoromethylbenzenesulfonyl chloride under the conditions used in general procedure A giving the title compound which was recrystallised neat (18%).

LC-MS: 369 (M–H)⁻, 98% pure.

Step B. Preparation of Nα-isobutyl-Nα-(4-methylbenzenesulfonyl)-Nε-[N'α-(4-trifluoromethylbenzenesulfonyl)-L-phenylalanyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-trifluoromethylbenzenesulfonyl)-L-phenylalanine (180 mg, 0.5 mmol) prepared in step A of this example. The final product was purified by preparative HPLC to yield 50 mg (56%) of the desired material.

LC-MS: 710.2 (M–H)⁻, 80% pure.

Example 24

Preparation of Nα-isobutyl-Nα-(4-methylbenzenesulfonyl)-Nε-[N'α-(2-thiophenesulfonyl)-L-phenylalanyl]-L-lysine Step A. Preparation of Nα-(2-thiophenesulfonyl)-L-phenylalanine L-phenylalanine was reacted with 2-thiophenesulfonyl chloride under the conditions used in general procedure A giving the title compound which was recrystallised from ether (93%).

LC-MS: 310 (M–H)⁻, 99% pure.

Step B. Preparation of Nα-isobutyl-Nα-(4-methylbenzenesulfonyl)-Nε-[N'α-(2-thiophenesulfonyl)-L-phenylalanyl]-L-lysine The title compound was prepared from Nα-isobutyl-Nα-(4-methylbenzenesulfonyl)-L-lysine hydrochloride (250 mg, 0.61 mmol, example 1, step E) as described in general procedure Bc using Nα-(2-thiophenesulfonyl)-L-phenylalanine (155 mg, 0.5 mmol) which was prepared in step A of this example. The crude material was purified by HPLC to give 272 mg (66%) of pure adduct.

$^1$H NMR (DMSO-d$_6$): δ 0.77 (d, J=6.3, 3H), 0.80 (d, J=6.3, 3H), 1.00–1.11 (m, 4H), 1.32–1.35 (m, 1H), 1.70–1.74 (m, 1H), 1.83–1.88 (m, 1H), 2.34 (s, 3H), 2.59–2.67 (m, 2H), 2.92 and 2.96 (ABX, J=16.5, 7.1, 2H), 3.90 (t, J=6.5, 1H), 4.11 (t, J=7.2, 1H), 7.00 (t, J=4.0, 1H), 7.10–7.21 (m, 5H), 7.30 (d, J=4.0, 1H), 7.34 (d, J=8.1, 2H), 7.63 (d, J=8.1, 2H), 7.77 (d, J=4.0, 1H), 7.81 (t, J=5.3, 1H), 8.22 (d, J=8.1, 1H). LC-MS: 648.5 (M–H)⁻, 99% pure.

Example 25

Preparation of Nα-isobutyl-Nα-(4-methylbenzenesulfonyl)-Nε-(N'α-benzenesulfonyl)-L-asparagyl]-L-lysine Step A. Preparation of Nα-benzenesulfonyl-L-asparagine L-asparagine was reacted with benzenesulfonyl chloride under the conditions used in general procedure A giving the title compound which was recrystallised neat (29%). This compound was used without further purification in the next step.

Step B. Preparation of Nα-isobutyl-Nα-(4-methylbenzenesulfonyl)-Nε-(N'α-benzenesulfonyl)-L-asparagyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-benzenesulfonyl-L-asparagine (350 mg, 1.0 mmol) prepared in step A of this example. The final product was purified by preparative HPLC to yield 70 mg (91%) of the desired material.

$^1$H NMR (CDCl$_3$): δ 0.78 (d, J=6.3, 3H), 0.81 (d, J=6.3, 3H), 0.94–1.13 (m, 4H), 1.32–1.35 (m, 1H), 1.66–1.69 (m, 1H), 1.83–1.88 (m, 1H), 2.10–2.29 (m, 2H), 2.35 (s, 3H), 2.38 (s, 3H), 2.82 and 2.99 (ABX, J=12.6, 8.1, 2H), 4.00 (t, J=6.5, 1H), 4.11 (t, J=7.2, 1H), 7.21 (d, J=7.9, 2H), 7.32 (d, J=7.9, 2H), 7.55–7.64 (m, 3H), 7.77 (d, J=7.8, 2H). LC-MS: 609.1 (M–H)⁻, 99% pure.

Example 26

Preparation of Nα-isobutyl-Nα-(4-methylbenzenesulfonyl)-Nε-[N'α-(4-methylbenzenesulfonyl)-L-4-nitrophenylalanyl]-L-lysine Step A. Preparation of Nα-(4-methylbenzenesulfonyl)-L-4-nitrophenylalanine L-4-nitrophenylalanine was reacted with 4-methylbenzenesulfonyl chloride under the conditions used in general procedure A giving the title compound which was recrystallised neat (14%).

LC-MS: 364 (M–H)⁻, 98% pure.

Step B. Preparation of Nα-isobutyl-Nα-(4-methylbenzenesulfonyl)-Nε-[N'α-(4-methylbenzenesulfonyl)-L-4-nitrophenylalanyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-methylbenzenesulfonyl)-L-4-nitrophenylalanine (180 mg, 0.5 mmol) prepared in step A of this example. The final product was purified by preparative HPLC to yield 25 mg (28%) of the desired material.

LC-MS: 701.1 (M–H)⁻, 95% pure.

Example 27

Preparation of Nα-isobutyl-Nα-(4-methylbenzenesulfonyl)-Nε-[N'α-(4-methylbenzenesulfonyl)-L-phenylglycyl]-L-lysine Step A. Preparation of Nα-(4-methylbenzenesulfonyl)-L-phenylglycine L-phenylglycine was reacted with 4-methylbenzenesulfonyl chloride under the conditions used in general procedure A giving the title compound which was recrystallised neat (21%).

LC-MS: 288 (M–H)⁻, 99% pure.

Step B. Preparation of Nα-isobutyl-Nα-(4-methylbenzenesulfonyl)-Nε-[N'α-(4-methylbenzenesulfonyl)-L-phenylglycyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-methylbenzenesulfonyl)-L-phenylglycine (150 mg, 0.5 mmol) prepared in step A of this example. The final product was purified by preparative HPLC to yield 55 mg (68%) of the desired material.

LC-MS: 642.1 (M–H)⁻, 95% pure.

Example 28

Preparation of Nα-isobutyl-Nα-(4-nitrobenzenesulfonyl)-Nε-[N'α-(4-acetamidobenzenesulfonyl)-L-phenylalanyl]-L-lysine Step A. Preparation of Nα-isobutyl-Nα-(4-nitrobenzenesulfonyl)-Nε-(9-fluorenylmethoxycarbonyl)-L-lysine Nα-isobutyl-Nα-(4-nitrobenzenesulfonyl)-L-lysine hydrochloride (1 mmol, example 5, step C) was partially dissolved in K$_2$CO$_3$ (1M)/THF/CH$_3$CN (4 mL/4 mL/4 mL). To this suspension was added N-(9-fluorenylmethoxycarbonyloxy) succinimide (371 mg, 1.10 mmol). The reaction turned slowly to colorless and was left stirring for 1 h. HCl (1M) was added until acidic pH and the reaction mixture was extracted twice with EtOAc. The combined organic layers were washed with brine, dried over MgSO$_4$ and concentrated. The residue was purified by flash chromatography eluting with a mixture of hexane/EtOAc containing 0.4% AcOH to yield 88% of the title compound which was used without further purification in the next step.

Step B. Preparation of Nα-isobutyl-Nα-(4-nitrobenzenesulfonyl)-Nε-[N'α-(4-acetamidobenzenesulfonyl)-L-phenylalanyl]-L-lysine The title compound was prepared from solid phase bound Nα-isobutyl-Nα-(4-nitrobenzenesulfonyl)-Nε-(9-fluorenylmethoxycarbonyl)-L-lysine (step A) as described in general procedure Bb using Nα-(4-acetamidobenzenesulfonyl)-L-phenylalanine (400 mg, 1.2 mmol) which was prepared in step A of example 3. The final product was purified by preparative HPLC to yield 55 mg (60%) of the desired material.

LC-MS: 730.1 (M–H)⁻, 95% pure.

Example 29

Preparation of Nε-isobutyl-Nα-(4-nitrobenzenesulfonyl)-Nε-[N'α-(2-thiophenesulfonyl)-L-phenylalanyl]-L-lysine The title compound was prepared from solid phase bound Nα-isobutyl-Nα-(4-nitrobenzenesulfonyl)-Nε-(9- fluorenylmethoxycarbonyl)-L-lysine as described in general procedure Bb using Nα-(2-thiophenesulfonyl)-L-phenylalanine (300 mg, 1.2 mmol) which was prepared in step A of example 24. The final product was purified by preparative HPLC to yield 46 mg (54%) of the desired material.

LC-MS: 679.0 (M–H)⁻, 95% pure.

Example 30

Preparation of Nα-isobutyl-Nα-(4-methylbenzenesulfonyl)-Nε-(N'α-acetyl-L-phenylalanyl)-L-lysine Step A. Preparation of Nα-acetyl-L-phenylalanine L-phenylalanine was reacted with acetyl chloride under the conditions used in general procedure A giving the title compound which was recrystallised from ether (97%). This compound is also commercially available.

LC-MS: 206 (M–H)⁻, 99% pure.

Step B. Preparation of Nα-isobutyl-Nα-(4-methylbenzenesulfonyl)-Nε-(N'α-acetyl-L-phenylalanyl)-L-lysine The title compound was prepared from Nα-isobutyl-Nα-(4-methylbenzenesulfonyl)-L-lysine (150 mg, 0.42 mmol, example 1, step E) as described in general procedure Bc using Nα-acetyl-L-phenylalanine (207 mg, 1.0 mmol) which was prepared in step A of this example. The final product was purified by preparative HPLC to yield 121 mg (59%) of the desired material.

¹H NMR (CDCl₃): δ 0.83 (d, J=6.9, 6H), 1.08–1.11 (m, 2H), 1.23–1.25 (m, 2H), 1.45–1.52 (m, 1H), 1.89–1.99 (m and s (1.90), 5H), 2.32 (s, 3H), 2.94–3.09 (m, 6H), 4.23 (t, 1H J=5.9), 4.61 (m, 1H), 7.09–7.26 (m, 7H), 7.73 (d, J=8.1, 2H). LC-MS: 544.2 (M–H)⁻, 99% pure.

Example 31

Preparation of Nα-isobutyl-Nα-(4-methylbenzenesulfonyl)-Nε-(N'α-benzyloxycarbonyl-L-phenylalanyl)-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using commercially available Nα-benzyloxycarbonyl-L-phenylalanine (300 mg, 1.2 mmol). The final product was purified by preparative HPLC to yield 33 mg (37%) of the desired material.

LC-MS: 636.2 (M–H)⁻, 99% pure.

Example 32

Preparation of Nα-isobutyl-Nα-(4-methylbenzenesulfonyl)-Nε-[N'α-(4-methylbenzenesulfonyl)-L-seryl]-L-lysine Step A. Preparation of Nα-(4-methylbenzenesulfonyl)-L-serine L-serine was reacted with 4-methylbenzenesulfonyl chloride under the conditions used in general procedure A giving the title compound which was recrystallised neat (44%). This compound was used without further purification in the next step.

Step B. Preparation of Nα-isobutyl-Nα-(4-methylbenzenesulfonyl)-Nε-[N'α-(4-methylbenzenesulfonyl)-L-seryl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-methylbenzenesulfonyl)-L-serine (150 mg, 1.2 mmol) prepared in step A of this example. The final product was purified by preparative HPLC to yield 35 mg (46%) of the desired material.

¹H NMR (CDCl₃): δ 0.78–0.82 (m, 6H), 1.18–1.22 (m, 2H), 1.38–1.41 (m, 2H), 1.50–1.52 (m, 1H), 1.79–1.96 (m, 2H), 2.32 (s, 6H), 2.85–2.97 (m, 2H), 3.06–3.19 (m, 2H), 3.82 (br s, 1H), 4.23 (t, J=6.9, 1H), 7.25 (d, J=8.0, 4H), 7.70 (d, J=8.0, 4H). LC-MS: 596.1 (M–H)⁻, 95% pure.

Example 33

Preparation of Nα-isobutyl-Nα-(4-methylbenzenesulfonyl)-Nε-[N'α-(4-methylbenzenesulfonyl)-L-cyclohexylalanyl]-L-lysine Step A. Preparation of Nα-(4-methylbenzenesulfonyl)-L-cyclohexylalanine L-cyclohexylalanine was reacted with 4-methylbenzenesulfonyl chloride under the conditions used in general procedure A giving the title compound which was recrystallised neat (14%).

LC-MS: 324 (M–H)⁻, 95% pure.

Step B. Preparation of Nα-isobutyl-Nα-(4-methylbenzenesulfonyl)-Nε-[N'α-(4-methylbenzenesulfonyl)-L-cyclohexylalanyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-methylbenzenesulfonyl)-L-cyclohexylalanine (350 mg, 1.2 mmol) prepared in step A of this example. The final product was purified by preparative HPLC to yield 19 mg (22%) of the desired material.

¹H NMR (CDCl₃): δ 0.73–1.73 (m, 24H), 1.89–1.99 (m, 2H), 2.39 (s, 6H), 2.94–3.19 (m, 4H), 3.65 (t, J=5.9, 1H), 4.33 (t, J=7.2, 1H), 7.26 (d, J=8.1, 4H), 7.73 (d, J=8.1, 4H). LC-MS: 662.2 (M–H)⁻, 95% pure.

Example 34

Preparation of Nα-isobutyl-Nα-(4-methylbenzenesulfonyl)-Nε-[N'α-(4-methylbenzenesulfonyl)-L-glutaminyl]-L-lysine Step A. Preparation of Nα-(4-methylbenzenesulfonyl)-L-glutamine L-glutamine was reacted with 4-methylbenzenesulfonyl chloride under the conditions used in general procedure A giving the title compound which was recrystallised neat (11%). This compound was used without further purification in the next step.

Step B. Preparation of Nα-isobutyl-Nα-(4-methylbenzenesulfonyl)-Nε-[N'α-(4-methylbenzenesulfonyl)-L-glutaminyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-methylbenzenesulfonyl)-L-glutamine (360 mg, 1.2 mmol) prepared in step A of this example. The final product was purified by preparative HPLC to yield 18 mg (21%) of the desired material.

LC-MS: 637.2 (M–H)⁻, 80% pure.

Example 35

Preparation of Nα-isobutyl-Nα-(4-methylbenzenesulfonyl)-Nε-[N'α-(4-methylbenzenesulfonyl)-L-2-thiophenylalanyl]-L-lysine Step A. Preparation of Nα-(4-methylbenzenesulfonyl)-L-2-thiophenylalanine L-2-thiophenylalanine was reacted with 4-methylbenzenesulfonyl chloride under the conditions used in general procedure A giving the title compound which was recrystallised neat (33%). This compound was used without further purification in the next step.

Step B. Preparation of Nα-isobutyl-Nα-(4-methylbenzenesulfonyl)-Nε-[N'α-(4-methylbenzenesulfonyl)-L-2-thiophenylalanyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-methylbenzenesulfonyl)-L-2-thiophenylalanine (390 mg, 1.2 mmol) prepared in step A of this example. The final product was purified by preparative HPLC to yield 15 mg (18%) of the desired material.

LC-MS: 662.1 (M–H)−, 85% pure.

Example 36

Preparation of Nα-isobutyl-Nα-(4-methylbenzenesulfonyl)-Nε-[N'α-(9-fluorenylmethoxycarbonyl)-L-seryl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using commercially available Nα-(9-fluorenylmethoxycarbonyl)-L-serine (390 mg, 1.2 mmol). The final product was purified by preparative HPLC to yield 15 mg (18%) of the desired material.

LC-MS: 664.3 (M–H)−, 95% pure.

Example 37

Preparation of Nα-isobutyl-Nα-(4-methylbenzenesulfonyl)-Nε-[N'α-(9-fluorenylmethoxycarbonyl)-L-cyclohexylalanyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using commercially available Nα-(9-fluorenylmethoxycarbonyl)-L-cyclohexylalanine (470 mg, 1.2 mmol). The final product was purified by preparative HPLC to yield 11 mg (12%) of the desired material.

LC-MS: 730.6 (M–H)−, 95% pure.

Example 38

Preparation of Nα-isobutyl-Nα-(4-methylbenzenesulfonyl)-Nε-[N'α-(4-methylbenzenesulfonyl)-L-glutamyl]-L-lysine Step A. Preparation of Nα-(4-methylbenzenesulfonyl)-L-glutamic acid L-glutamic acid was reacted with 4-methylbenzenesulfonyl chloride under the conditions used in general procedure A giving the title derivative (20%) which was used without purification in the next step.

Step B. Preparation of Nα-isobutyl-Nα-(4-methylbenzenesulfonyl)-Nε-[N'α-(4-methylbenzenesulfonyl)-L-glutamyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-methylbenzenesulfonyl)-L-glutamic acid (360 mg, 1.2 mmol) prepared in step A of this example. The final product was purified by preparative HPLC to yield 20 mg (25%) of the desired material.

LC-MS: 640.3 (M+H)+, 99% pure.

Example 39

Preparation of Nα-isobutyl-Nα-(4-methylbenzenesulfonyl)-Nε-[N'α-(4-methylbenzenesulfonyl)-L-lysyl]-L-lysine Step A. Preparation of Nα-(4-methylbenzenesulfonyl)-Nε-tert-butoxycarbonyl-L-lysine Nε-tert-butoxycarbonyl-L-lysine was reacted with 4-methylbenzenesulfonyl chloride under the conditions used in general procedure A giving the title derivative which was used without purification in the next step.

Step B. Preparation of Nα-isobutyl-Nα-(4-methylbenzenesulfonyl)-Nε-[N'α-(4-methylbenzenesulfonyl)-L-lysyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-methylbenzenesulfonyl)-Nε-tert-butoxycarbonyl-L-lysine (360 mg, 1.2 mmol) prepared in step A of this example. The final product was purified by preparative HPLC to yield 10 mg (12%) of the desired material.

LC-MS: 637.2 (M–H)−, 99% pure.

Example 40

Preparation of Nα-isobutyl-Nα-(4-methylbenzenesulfonyl)-Nε-[N'α-(4-methylbenzenesulfonyl)-O-benzyl-L-seryl]-L-lysine The title compound was prepared from solid phase bound Nα-isobutyl-Nα-(4-methylbenzenesulfonyl)-Nε-(9-fluorenylmethoxycarbonyl)-L-lysine (200 mg, 0.1 mmol) in a similar fashion to general procedure Bb using commercially available Nα-(9-fluorenylmethoxycarbonyl)-O-benzyl-L-serine (100 mg, 0.24 mmol) with DCC (100 mg, 0.48 mmol) and HOBt (50 mg, 0.37 mmol) as the activating reagents. The intermediate adduct was again deprotected and coupled with 4-methylbenzenesulfonyl chloride in $CH_2Cl_2$ before being cleaved from the resin with TFA. The final product was purified by preparative HPLC to yield 30 mg (42%) of the desired material.

$^1$H NMR (DMSO-$d_6$): δ 0.78 (d, J=6.5, 3H), 0.82 (d, J=6.6, 3H), 1.15–1.45 (m, 5H), 1.84 (m, 1H), 1.95 (m, 1H), 2.34 (s, 3H), 2.36 (s, 3H), 2.79 (m, 2H), 2.91 (m, 2H), 3.42 (t, J=5.7, 2H), 3.92 (t, J=6.1, 1H), 4.04 (m, 1H), 4.37 (d, J=5.7, 2H), 7.21 (d, J=7.3, 2H), 7.23–7.33 (m, 7H), 7.65 (d, J=8.2, 2H), 7.71 (d, J=7.7, 2H), 7.93 (t, J=4.0, 1H), 7.95 (br s, 1H). LC-MS: 688 (M+H)+, 99% pure.

Example 41

Preparation of Nα-isobutyl-Nα-(4-methylbenzenesulfonyl)-Nε-[N'α-(4-methylbenzenesulfonyl)-L-aspartyl]-L-lysine Step A. Preparation of Nα-(4-methylbenzenesulfonyl)-L-aspartic acid L-aspartic acid was reacted with 4-methylbenzenesulfonyl chloride under the conditions used in general procedure A giving the title derivative (40%) which was used without purification in the next step.

Step B. Preparation of Nα-isobutyl-Nα-(4-methylbenzenesulfonyl)-Nε-[N'α-(4-methylbenzenesulfonyl)-L-aspartyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-methylbenzenesulfonyl)-L-aspartic acid (340 mg, 1.2 mmol) prepared in step A of this example. The final product was purified by preparative HPLC to yield 20 mg (26%) of the desired material.

LC-MS: 624.1 (M–H)−, 99% pure.

Example 42

Preparation of Nα-isobutyl-Nα-(4-methylbenzenesulfonyl)-Nε-[N'α-(4-methylbenzenesulfonyl)-L-3-(2-thianaphthyl)-alanyl]-L-lysine Step A. Preparation of 4-methylbenzenesulfonyl-L-3-(2-thianaphthyl)-alanine L-3-(2-thianaphthyl)-alanine was reacted with 4-methylbenzenesulfonyl chloride under the conditions used in general procedure A giving the title derivative which was recrystallised neat (34%). This compound was used without further purification in the next step.

Step B. Preparation of Nα-isobutyl-Nα-(4-methylbenzenesulfonyl)-Nε-[N'α-(4-methylbenzenesulfonyl)-L-3-(2-thianaphthyl)-alanyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using 4-methylbenzenesulfonyl-L-3-(2-thianaphthyl)-alanine (450 mg, 1.2 mmol) prepared in step A of this example. The final product was purified by preparative HPLC to yield 25 mg (28%) of the desired material.

$^1$H NMR (CDCl$_3$): δ 0.85–0.89 (m, 6H), 1.08–1.15 (m, 2H), 1.32–1.36 (m, 2H), 1.50–1.53 (m, 2H), 1.85–1.89 (r, 2H), 2.24 (s, 3H), 2.96–3.12 (m, 4H), 3.84–3.86 (m, 1H), 4.22 (t, J=5.4, 1H), 6.90 (d, J=6.8, 2H), 7.06 (s, 1H), 7.19–7.28 (m, 8H), 7.46 (d, J=6.8, 1H), 7.74 (d, J=6.8, 2H).

LC-MS: 714.2 (M+H)$^+$, 99% pure.

Example 43

Preparation of Nα-(4-aminobenzenesulfonyl)-Nα-isobutyl-Nε-[N'α-(4-methylbenzenesulfonyl)-L-tryptophanyl]-L-lysine The title compound was prepared from Nα-isobutyl-Nα-(4-nitrobenzenesulfonyl)-L-lysine hydrochloride (350 mg, 1.0 mmol, example 5, step C) as described in general procedure Bc using Nα-(4-methylbenzenesulfonyl)-L-tryptophan (335 mg, 1.1 mmol) which was prepared in step A of example 2. The final product was purified by preparative HPLC to yield 650 mg (90%) of Nα-(4-nitrobenzenesulfonyl)-Nα-isobutyl-Nε-[N'α-(4-methylbenzenesulfonyl)-L-tryptophanyl]-L-lysine. The latter derivative (300 mg) was hydrogenolysed following the indications of general procedure E. Purification by HPLC gave the desired material (235 mg, 75%).

$^1$H NMR(DMSO-d$_6$): δ 0.74 (d, J=6.3, 3H), 0.80 (d, J=6.3, 3H), 1.00–1.11 (m, 4H), 1.32–1.35 (m, 1H), 1.70–1.74 (m, 1H), 1.83–1.88 (m, 1H), 2.34 (s, 3H), 2.59–2.67 (m, 2H), 2.84–2.96 (m, 2H), 3.80 (t, J=6.5, 1H), 4.11 (t, J=7.2, 1H), 6.85 (t, J=5.2, 1H), 7.00 (t, J=4.0, 2H), 7.10 (d, J=5.3, 2H), 7.28 (d, J=4.0, 1H), 7.33 (m, 3H), 7.43 (d, J=6.9, 2H), 7.60 (d, J=6.9, 2H), 7.71 (t, J=6.9, 1H), 7.80 (d, J=8.0, 1H). LC-MS: 696.8 (M–H)$^-$, 99% pure.

Example 44

Preparation of Nα-(4-aminobenzenesulfonyl)-Nα-isobutyl-Nε-(N'α-benzenesulfonyl-L-phenylalanyl)-L-lysine The title compound was prepared from Nα-isobutyl-Nα-(4-nitrobenzenesulfonyl)-L-lysine (385 mg, 1.0 mmol, example 5, step C) as described in general procedure Bc using Nα-benzenesulfonyl-L-phenylalanine (335 mg, 1.1 mmol) which was prepared in step A of example 8. The final product was purified by preparative HPLC to yield 550 mg (85%) of Nα-(4-nitrobenzenesulfonyl)-Nα-isobutyl-Nε-(N'α-benzenesulfonyl)-L-phenylalanyl)-L-lysine. The latter derivative (200 mg) was hydrogenolysed following the indications of general procedure E. Purification by HPLC gave the desired material (129 mg, 65%).

$^1$H NMR (CDCl$_3$): δ 0.75 (d, J=7.1, 3H), 0.88 (d, J=7.1, 3H), 1.0–1.1 (m, 2H), 1.16–1.23 (m, 1H), 1.56–1.58 (m, 1H), 1.72–1.73 (m, 1H), 1.82–1.91 (m, 1H), 2.79–2.96 (m, 2H), 3.867 (t, J=6.2, 1H), 4.09 (t, J=6.1, 1H), 5.59 (s, 1H), 6.55 (d, J=7.5, 2H), 7.05 (d, J=7.1, 2H), 7.11–7.19 (m, 4H), 7.38 (d, J=6.9, 2H), 7.42 (t, J=7.1, 2H), 7.51 (d, J=7.1, 2H), 8.01 (d, J=7.1, 1H).

LC-MS: 643.2 (M–H)$^-$, 99% pure.

Example 45

Preparation of Nα-isobutyl-Nα-(4-methylbenzenesulfonyl)-Nε-[N'α-(4-methylbenzenesulfonyl)-L-tryptophanyl]-L-lysine 2,3-dihydroxypropyl ester A solution of Nα-isobutyl-Nα-(4-methylbenzenesulfonyl)-Nε-[N'α-(4-methylbenzenesulfonyl)-L-tryptophanyl]-L-lysine (product of example 2, 70 mg, 0.1 mmol) in DMF (1 mL) was treated with glycerol (100 mg) and EDC (100 mg, 0.5 mmol) and stirred overnight. The solution is then poured in 5% citric acid and extracted with EtOAc (5 mL). The solvent was evaporated and the residue was purified by preparative HPLC to yield 30 mg (40%) of the desired ester.

LC-MS: 769.3 (M–H)$^-$, 99% pure.

Example 46

Preparation of Nα-(4-aminobenzenesulfonyl)-Nα-isobutyl-Nε-[N'α-(2-thiophenesulfonyl)-L-phenylalanyl]-L-lysine The title compound was prepared from Nα-isobutyl-Nα-(4-nitrobenzenesulfonyl)-L-lysine hydrochloride (400 mg, 1.03 mmol, example 5, step C) as described in general procedure Bc using Nα-(2-thiophenesulfonyl)-L-phenylalanine (311 mg, 1.2 mmol) which was prepared in step A of example 24. The final product was purified by preparative HPLC to yield 550 mg (80%) of Nα-isobutyl-Nα-(4-nitrobenzenesulfonyl)-Nε-[N'α-(2-thiophenesulfonyl)-L-phenylalanyl]-L-lysine. The latter derivative was hydrogenolysed following the indications of general procedure E. Purification by HPLC gave the desired material (400 mg, 65%).

$^1$H NMR(DMSO-d$_6$): δ 0.78 (q, J=6.9, 6H), 1.00–1.11 (m, 4H), 1.32–1.35(m, 1H), 1.70–1.74 (m, 1H), 1.83–1.88 (m, 1H), 2.59–2.67 (m, 2H), 2.74–2.96 (m, 4H), 3.90 (t, J=6.5, 1H), 4.11 (t, J=7.2, 1H), 6.50 (d, J=8.1, 2H), 6.95 (t, J=4.0, 1H), 7.10–7.21 (m, 5H), 7.30 (d, J=4.0, 1H), 7.34 (d, J=8.1, 2H), 7.77 (d, J=4.0, 1H), 7.81 (t, J=5.3, 1H), 8.22 (d, J=8.1, 1H). LC-MS: 649.8 (M–H)$^-$, 98% pure.

Example 47

Preparation of Nα-(4-aminobenzenesulfonyl)-Nα-isobutyl-Nε-[N'α-(4-methylbenzenesulfonyl)-L-asparagyl]-L-lysine Step A. Preparation Nα-(4-methylbenzenesulfonyl)-L-asparagine L-asparagine was reacted with 4-methylbenzenesulfonyl chloride under the conditions used in general procedure A giving the title compound which was recrystallised from ether (40%).

$^1$H NMR (CDCl$_3$): δ 2.20–2.23 (m, 1H), 2.33 (s, 3H), 2.42–2.50 (m, 1H), 4.00–4.03 (br s, 1H), 6.8 (s, 1H), 7.26 (s, 2H), 7.51 (s, 2H).

Step B. Preparation of Nα-(4-aminobenzenesulfonyl)-Nα-isobutyl-Nε-[N'α-(4-methylbenzenesulfonyl)-L-asparagyl]-L-lysine The title compound was prepared from Nα-isobutyl-Nα-(4-nitrobenzenesulfonyl)-L-lysine hydrochloride (400 mg, 1.03 mmol, example 5, step C) as described in general procedure Bc using Nα-(4-methylbenzenesulfonyl)-L-asparagine (286 mg, 1.0 mmol) which was prepared in step A this example. The final product, Nα-isobutyl-Nα-(4-nitrobenzenesulfonyl)-Nε-[N'α-(4-methylbenzenesulfonyl)-L-asparagyl]-L-lysine was subsequently hydrogenolysed following the indications of general procedure E. Purification by HPLC gave the desired material (185 mg, 76%).

$^1$H NMR (CDCl$_3$): δ 0.78 (d, J=6.3, 3H), 0.81 (d, J=6.3, 3H), 0.94–1.13 (m, 4H), 1.32–1.35 (m, 1H), 1.66–1.69 (m, 1H), 1.83–1.88 (m, 1H), 2.10–2.29 (m, 2H), 2.31 (s, 3H), 2.82–2.99 (m, 2H), 3.95 (t, J=6.5, 1H), 4.11 (t, J=7.2, 1H), 6.80 (d, J=8.0, 2H), 7.19 (d, J=7.9, 2H), 7.32 (d, J=7.9, 2H), 7.64 (d, J=8.0, 2H). LC-MS: 624.8 (M–H)$^-$, 98% pure.

Example 48

Preparation of Nα-isobutyl-Nα-(4-methylbenzenesulfonyl)-Nε-(N'α-benzyloxycarbonyl-L-asparagyl)-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using commercially available Nα-benzyloxycarbonyl-L-asparagine (319 mg, 1.2 mmol). The final product was purified by preparative HPLC to yield 46 mg (41%) of the desired material.

LC-MS: 603.1 (M–H)$^-$, 98% pure.

Example 49

Preparation of Nα-(4-aminobenzenesulfonyl)-Nα-isobutyl-Nε-[N'α-(2-thiophenesulfonyl)-L-phenylalanyl]-L-lysine hydrazide A solution of Nα-(4-aminobenzenesulfonyl)-Nα-isobutyl-Nε-[N'α-(2-thiophenesulfonyl)-L-phenylalanyl]-L-lysine (650 mg, 1.0 mmol, example 46) dissolved in EtOAc (20 mL) was treated with p-nitrophenol (139 mg, 1.0 mmol) and DCC (206 mg, 1.0 mmol) and was left in a refrigerator overnight. Afterwards, the precipitate was filtered off through celite and the solvent evaporated. The crude residue was used without further purification. A portion of the residue (55 mg, 0.072 mmol) was added to a solution of hydrazine hydrate in ethanol (1M, 10 mL). The resulting solution was stirred for 3 h before evaporation of the solvent. The residue was purified by preparative HPLC to yield 25 mg, 30% of the desired material.

LC-MS: 663.1 (M–H)$^-$, 95% pure.

Example 50

Preparation of Nα-isobutyl-Nα-(4methylbenzenesulfonyl)-Nε-(N'α-benzoyl-L-phenylalanyl)-L-lysine Step A. Preparation of Nα-benzoyl-L-phenylalanine L-phenylalanine was reacted with benzoyl chloride under the conditions used in general procedure A giving the title compound which was recrystallised from ether (60%).

$^1$H NMR (CDCl$_3$): δ 3.21–3.39 (m, 2H), 5.09 (q, J=6.6, 1H), 7.10–7.27 (m, 5H), 7.42 (t, J=6.9, 2H), 7.5 (t, J=7.0, 1H), 7.68 (d, J=6.9, 2H). LC-MS: 268 (M–H)$^-$, 99% pure.

Step B. Preparation of Nα-isobutyl-Nα-(4-methylbenzenesulfonyl)-Nε-(N'α-benzoyl-L-phenylalanyl)-L-lysine The title compound was prepared from solid phase bound Nα-isobutyl-N(-(4-methylbenzenesulfonyl)-Nε-(9-fluorenylmethoxycarbonyl)-L-lysine as described in general procedure Bb using Nα-benzoyl-L-phenylalanine (321 mg, 1.2 mmol). The final product was purified by preparative HPLC to yield 44 mg (58%) of the desired material.

$^1$H NMR (CDCl$_3$): δ 0.83 (d, J=6.9, 6H), 1.08–1.11 (m, 2H), 1.23–1.25 (m, 2H), 1.45–1.52 (m, 1H), 1.89–1.99 (m, 5H), 2.31 (s, 3H), 2.94–3.19 (m, 6H), 4.24 (t, J=6.9, 1H), 4.89 (t, J=5.9, 1H), 7.19–7.26 (m, 7H), 7.30 (t, J=7.9, 2H), 7.46 (t, J=7.8, 1H), 7.73–7.82 (m, 4H). LC-MS: 606.2 (M–H)$^-$, 98% pure.

Example 51

Preparation of Nα-isobutyl-Nα-(4-methylbenzenesulfonyl)-Nε-[N'α-(4-morpholinecarbonyl)-L-phenylalanyl]-L-lysine Step A. Preparation of Nα-(4-morpholinecarbonyl)-L-phenylalanine L-phenylalanine was reacted with 4-morpholinecarbonyl chloride under the conditions used in general procedure A giving the title compound which was recrystallised from ether (69%).

$^1$H NMR (CDCl$_3$): δ 3.11–3.39 (m, 6H), 3.57 (s, 4H), 4,65 (q, J=6.6, 1H), 7.10–7.27 (m, 5H).

Step B. Preparation of Nα-isobutyl-Nα-(4-methylbenzenesulfonyl)-Nε-[N'α-(4-morpholinecarbonyl)-L-phenylalanyl]-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-(4-morpholinecarbonyl)-L-phenylalanine (330 mg, 1.2 mmol). The final product was purified by preparative HPLC to yield 41 mg (53%) of the desired material.

LC-MS: 615.2 (M–H)$^-$, 95% pure.

Example 52

Preparation of Nα-isobutyl-Nα-(4-methylbenzenesulfonyl)-Nε-(N'α-pivaloyl-L-phenylalanyl)-L-lysine Step A. Preparation of Nα-pivaloyl-L-phenylalanine L-phenylalanine was reacted with pivaloyl chloride under the conditions used in general procedure A giving the title compound which was recrystallised from hexanes (40%).

$^1$H NMR (CDCl$_3$): δ 1.16 (s 9H), 3.12–3.31 (m, 2H), 4.85 (t, J=5.1, 1H), 7.11–7.32 (m, 5H).

Step B. Preparation of Nα-isobutyl-Nα-(4-methylbenzenesulfonyl)-Nε-(N'α-pivaloyl-L-phenylalanyl)-L-lysine The title compound was prepared from solid phase bound Nα-isobutyl-Nα-(4-methylbenzenesulfonyl)-Nε-(9-fluorenylmethoxycarbonyl)-L-lysine as described in general procedure Bb using Nα-pivaloyl-L-phenylalanine (300 mg, 1.2 mmol). The final product was purified by preparative HPLC to yield 49 mg (66%) of the desired material.

LC-MS: 586.1 (M–H)$^-$, 95% pure.

Example 53

Preparation of Nα-isobutyl-Nα-(4-methylbenzenesulfonyl)-Nε-[N'α-(2-thiophenesulfonyl)-L-tryptophanyl]-L-lysine Step A. Preparation of Nα-(2-thiophenesulfonyl)-L-tryptophan L-tryptophan was reacted with 2-thiophenesulfonyl chloride under the conditions used in general procedure A giving the title compound which was recrystallised from DCM (32%).

$^1$H NMR (CDCl$_3$): δ 2.9–3.11 (m, 2H), 3.91 (t, J=7.0, 1H), 6.86–7.01 (m, 4H), 7.21–7.3 (m, 3H), 7.70 (s, 1H), 8.38 (s, 1H).

Step B. Preparation of Nα-isobutyl-Nα-(4-methylbenzenesulfonyl)-Nε-[N'α-(2-thiophenesulfonyl)-L-tryptophanyl]-L-lysine The title compound was prepared from Nα-isobutyl-Nα-(4-nethylbenzenesulfonyl)-L-lysine (100 mg, 0.29 mmol, example 1, step E) as described in general procedure Bc using Nα-(2-thiophenesulfonyl)-L-tryptophan (90 mg, 0.3 mmol) which was prepared in step A of this example. The final product was triturated with ether to yield 12 mg (6%) of the desired material.

LC-MS: 687.2 (M–H)$^-$, 85% pure.

Example 54

Preparation of Nα-isobutyl-Nα-(2-thiophenesulfonyl)-Nε-[N'α-(4-methylbenzenesulfonyl)-L-phenylalanyl]-L-lysine Step A. Preparation of Nα-isobutyl-Nα-(2-thiophenesulfonyl)-L-α-amino-ε-caprolactam Nα-isobutyl-L-α-amino-ε-caprolactam (example 1, step C) (2.56 g, 14.0 mmol, free base) was dissolved in DCM (50 mL) and treated with diisopropylethylamine (4.0 mL, 20 mmol) followed by freshly recrystallized 2-thiophenenesulfonyl chloride (2.56 g, 14.0 mmol). The mixture was stirred overnight (TLC shows the reaction to be complete after 2 h). The solution was extracted with 1N HCl and the organic layer was dried and evaporated. Then, the residue was dissolved in boiling MeOH (150 mL) and placed in the refrigerator for 3 h. The thin needles obtained were filtered off and air dried giving 3.6 g (78%) of pure product. This compound was used without further purification in the next step.

Step B. Preparation of Nα-isobutyl-Nα-(2-thiophenesulfonyl)-L-lysine hydrochloride A mixture of Nα-isobutyl-Nα-(2-thiophenesulfonyl)-L-(α-amino-ε-caprolactam (3.5 g, 10.1 mmol), AcOH (12 mL) and 6N HCl (50 mL) was refluxed for 6 h until all solids had disappeared. Afterwards, the solution was evaporated to give 2.8 g, 71% of the hydrochloride salt.

$^1$H NMR (DMSO-d$_6$): δ 0.72 (dd, J=5.8, 6.4, 6H), 1.13–1.17 (m, 2H), 1.42–1.46 (m, 2H), 1.79–1.87 (m, 2H), 2.67 (t, J=7.2, 2H), 2.80–2.91 (m, 2H), 4.13 (t, J=7.2, 1H), 7.11 (t, J=5.1, 1H), 7.50 (d, J=5.5, 1H), 7.85 (d, J=5.6, 1H).

Step C. Preparation of Nα-isobutyl-Nα-(2-thiophenesulfonyl)-Nε-[N'α-(4-methylbenzenesulfonyl)-L-phenylalanyl]-L-lysine A suspension of Nα-isobutyl-Nα-(2-thiophenesulfonyl)-L-lysine hydrochloride (150 mg, 0.5 mmol), in THF (20 mL) was treated with a 1N NaOH (0.5 mL) to pH 10. A solution of commercially available Nα-(4-methylbenzenesulfonyl)-L-phenylalanine acid chloride (150 mg, 0.4 mmol), in dry THF (10 nL) was added to the suspension and stirred for 4 h. Afterwards, water (2 mL) was added resulting in a clear solution. Then, EtOAc (30 mL) was added and the organic phase was washed with 1N HCl. The organic phase was removed. Evaporation of the solvent gave a crude product which was purified by preparative HPLC to yield 150 mg (57%) of the title compound.

$^1$H NMR (DMSO-d$_6$): δ 0.79 (d, J=6.3, 3H), 0.82 (d, J=6.3, 3H), 1.00–1.11 (m, 4H), 1.23–1.25 (m, 1H), 1.80–1.84 (m, 1H), 1.89–1.98 (m, 1H), 2.32 (s, 3H), 2.59–2.67 (m, 2H), 2.84 and 2.95 (ABX, J=15.5, 4.8,2H), 3.88 (t, J=6.0, 1H), 4.21 (t, J=6.9, 1H), 7.04 (d, J=7.6, 2H), 7.12–7.21 (m, 5H), 7.35–7.44 (m, 3H), 7.87 (d, J=7.61, 2H). LC-MS: 648.5 (M–H)$^-$, 98% pure.

Example 55

Preparation of Nα-isobutyl-Nα-(4-methylbenzenesulfonyl)-Nε-[N'α-isobutyl-N'α-(4-methylbenzenesulfonyl)-glycyl]-L-lysine Step A. Preparation of Nα-isobutyl-Nα-(4-methylbenzenesulfonyl)-glycine The title compound was prepared in a three-step sequence from tert-butyl bromoacetate. Initially, tert-butyl bromoacetate (1.91 g, 10 mmol) dissolved in isobutylamine (60 mmol) was stirred at room temperature for 2 h. The reaction mixture was filtered and the excess isobutylamine was distilled yielding 80% of pure N-isobutyl glycine tert-butyl ester. Secondly, the intermediate was reacted with 4-methylbenzenesulfonyl chloride (8 mmol) as described for the preparation of Nα-isobutyl-Nα-(4-methylbenzenesulfonyl)-L-α-amino-ε-caprolactam presented in example 1 (step D). In this case, triethylamine was used instead of diisopropylethylamine. Thirdly, deprotection of the tert-butyl ester with TFA provided the final product quantitatively (two last steps).

$^1$H NMR (CDCl$_3$): δ 0.80 (br s, 6H), 1.75–1.82 (m, 1H), 2.32 (s, 3H), 2.85–2.9 (br s, 2H), 3.83 (s, 2H), 7.26 (d, J=7.9, 2H), 7.6 (d, J=7.9, 2H). LC-MS: 286 (M–H)$^-$, 99% pure.

Step B. Preparation of Nα-isobutyl-Nα-(4-methylbenzenesulfonyl)-Nε-[N'α-isobutyl-N'α-(4-methylbenzenesulfonyl)-glycyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-isobutyl-Nα-(4-methylbenzenesulfonyl)-glycine (90 mg, 0.3 mmol) which was prepared in step A of this example. The final product was triturated with ether to yield 40 mg (21%) of the desired material.

LC-MS: 623.8 (M–H)$^-$, 95% pure.

Example 56

Preparation of Nα-(4-aminobenzenesulfonyl)-Nα-isobutyl-Nε-[N'α-(4-acetylaminobenzenesulfonyl)-L-phenylalanyl]-L-lysine The title compound was prepared from Nα-(4-aminobenzenesulfonyl)-Nα-isobutyl-L-lysine (100 mg, 0.29 mmol, example 166, step B) as described in general procedure Bc using Nα-(4-acetamidobenzenesulfonyl)-L-phenylalanine (110 mg, 0.3 mmol) which was prepared in step A of example 3. The final product was purified by HPLC to give 50 mg (23%) of pure adduct.

LC-MS: 700.8 (M–H)$^-$, 95% pure.

Example 57

Preparation of Nα-isobutyl-Nα-(4-methylbenzenesulfonyl)-Nε-[N'α-(2-thiophenesulfonyl)-L-phenylalanyl]-L-lysine methyl ester The title compound was prepared by treating Nα-isobutyl-Nα-(4-methylbenzenesulfonyl)-Nε-[N'α-(2-thiophenesulfonyl)-L-phenylalanyl]-L-lysine (60 mg, 0.1 mmol, example 24) dissolved in MeOH (2 mL) with DCC (1 eq.). The reaction mixture was stirred at room temperature for a period of 2 h. Filtration and evaporation of the solvent followed by HPLC purification gave the desired methyl ester (15 mg, 22%).

LC-MS: 662.1 (M–H)$^-$, 99% pure.

Example 58

Preparation of Nα-isobutyl-Nα-(4-methylbenzenesulfonyl)-Nε-[N'α-(2-thiophenesulfonyl)-L-phenylalanyl]-L-lysinamide A solution of Nα-isobutyl-Nα-(4-methylbenzenesulfonyl)-NF-[N'α-(2-thiophenesulfonyl)-L- phenylalanyl]-L-lysine (650 mg, 1.0 mmol, example 24) dissolved in EtOAc (10 mL) was treated with p-nitrophenol (139 mg, 1.0 mmol) and DCC (206 mg, 1.0 mmol) and was left in a refrigerator overnight. Afterwards, the precipitate was filtered off through celite and the solvent evaporated. The crude intermediate was used without further purification in the next step. A portion of the intermediate (25 mg, 0.03 mmol) was added to a solution of ammonia in ethanol (1M, 10 mL). The resulting solution was stirred for 3 h before evaporation of the solvent. The residue was purified by preparative HPLC to yield 2.6 mg, 11% of the desired material.

LC-MS: 647.2 (M–H)⁻, 99% pure.

Example 59

Preparation of Nα-isobutyl-Nα-(4-methylbenzenesulfonyl)-Nε-[N'α-(2-thiophenesulfonyl)-L-phenylalanyl]-L-lysine N-hydroxylamide A portion of the crude intermediate of example 58 above, (25 mg, 0.03 mmol) was added to a solution of hydroxylamine in ethanol (1M, 10 mL). The resulting solution was stirred for 3 h before evaporation of the solvent. The residue was purified by preparative HPLC to yield 4.0 mg, 18% of the desired material.

LC-MS: 663.1 (M–H)⁻, 99% pure.

Example 60

Preparation of Nα-isobutyl-Nα-(4-methylbenzenesulfonyl)-Nε-[N'α-(2-thiophenesulfonyl)-L-phenylalanyl]-L-lysine ethanolamide A portion of the crude intermediate of example 58 above, (25 mg, 0.03 mmol) was added to a solution of ethanolamine in ethanol (1M, 10 mL). The resulting solution was stirred for 3 h before evaporation of the solvent. The residue was purified by preparative H[PLC to yield 15 mg, 21% of the desired material.

LC-MS: 691.2 (M–H)⁻, 99% pure.

Example 61

Preparation of Nα-isobutyl-Nα-(4-methylbenzenesulfonyl)-Nε-[N'α-(4-methylbenzenesulfonyl)-L-asparagyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(4-methylbenzenesulfonyl)-L-asparagine (90 mg, 0.3 mmol) which was prepared in step A of example 47. The final product was triturated with ether to yield 95 mg (15%) of the desired material.

¹H NMR (CDCl₃): δ 0.78 (d, J=6.3, 3H), 0.81 (d, J=6.3, 3H), 0.99–1.03 (m, 4H), 1.32–1.35 (m, 1H), 1.66–1.69 (m, 1H), 1.83–1.88 (m, 1H), 2.10–2.29 (, 2H), 2.35 (s, 3H), 2.38 (s, 3H), 2.82 and 2.99 (m, 2H), 3.95 (t, J=6.5, 1H), 4.11 (t, J=7.2, 1H), 7.19 (d, J=7.9, 2H), 7.32 (d, J=7.9, 2H), 7.55–7.64 (m, 4H). LC-MS: 625.8 (M+H)⁺, 97% pure.

Example 62

Preparation of Nα-isobutyl-Nα-(4methylbenzenesulfonyl)-Nε-(N'α-pivaloyl-L-asparagyl)-L-lysine Step A. Preparation of Nα-pivaloyl-L-asparagine L-asparagine was reacted with pivaloyl chloride under the conditions used in general procedure A giving the title compound which was recrystallised neat (80%). This compound was used without further purification in the next step.

Step B. Preparation of Nα-isobutyl-Nα-(4-methylbenzenesulfonyl)-Nε-(N'α-pivaloyl-L-asparagyl)-L-lysine The title compound was prepared from Nα-isobutyl-Nα-(4-methylbenzenesulfonyl)-L-lysine (100 mg, 0.29 mmol, example 1, step E) as described in general procedure Bc using Nα-pivaloyl-L-asparagine (65 mg, 0.3 mmol) which was prepared in step A this example. The final product was purified by preparative HPLC to yield 21 mg (12%) of the desired material.

LC-MS: 555.7 (M+H)⁺, 90% pure.

Example 63

Preparation of Nα-isobutyl-Nα-(4-methylbenzenesulfonyl)-Nε-(N'α-benzoyl-L-asparagyl)-L-lysine Step A. Preparation of Nα-benzoyl-L-asparagine L-asparagine was reacted with benzoyl chloride under the conditions used in general procedure A giving the title compound which was recrystallised neat (90%). This compound was used without further purification in the next step.

Step B. Preparation of Nα-isobutyl-Nα-(4-methylbenzenesulfonyl)-Nε-(N'α-benzoyl-L-asparagyl)-L-lysine The title compound was prepared from Nα-isobutyl-Nα-(4-methylbenzenesulfonyl)-L-lysine (100 mg, 0.29 mmol, example 1, step E) as described in general procedure Bc using Nα-benzoyl-L-asparagine (70 mg, 0.3 mmol) which was prepared in step A this example. The final product was purified by preparative HPLC to yield 14 mg (9%) of the desired material.

LC-MS: 575.2 (M+H)⁺, 99% pure.

Example 64

Preparation of Nα-isobutyl-Nα-(4-methylbenzenesulfonyl)-Nε-['α-(2-thiophenesulfonyl)-L-phenylalanyl]-L-lysine hydrazide A portion of the crude intermediate of example 58 above, (50 mg, 0.06 mmol) was added to a solution of hydrazine in ethanol (1M, 10 mL). The resulting solution was stirred for 3 h before evaporation of the solvent. The residue was purified by preparative HPLC to yield 25 mg, 60% of the desired material.

LC-MS: 664.2 (M–H)⁻, 99% pure.

Example 65

Preparation of Nα-isobutyl-Nα-(4-methylbenzenesulfonyl)-Nε-[1,2,3,4-tetrahydroisoquinoline-N'-(4-methylbenzenesulfonyl)-3-carbonyl]-L-lysine This particular preparation is based in scheme 4 of this invention.

Step A. Preparation of Nα-isobutyl-Nε-benzyloxycarbonyl-L-lysine methyl ester

To a stirred solution of commercially available Nε-benzyloxycarbonyl-L-lysine methyl ester hydrochloride (9.92 g, 30 mmol), AcOH (6 mL) and NaCNBH₃ (33 mmol) in MeOH (250 mL) at 0° C. was added a solution of isobutyraldehyde (3.01 mL, 33 mmol) in MeOH (80 mL).

The solution was warmed to room temperature and stirred for 2 h A saturated solution of K₂CO₃ (150 mL) was added and the solution was decanted from the solid and coevaporated on vacuo. The residue was partitioned between EtOAc (300 mL) and H₂O(200 mL). The organic layer was washed with K₂CO₃ (1M) and with brine, then dried and concentrated. The crude was used in the next step without further purification.

Step B. Preparation of Nα-isobutyl-Nα-(4-methylbenzenesulfonyl)-Nε-benzyloxycarbonyl-L-lysine methyl ester To a stirred solution of Nα-isobutyl-Nε-benzyloxycarbonyl-L-lysine methyl ester (336 mg, 1 mmol) in CH₂Cl₂ (2 mL) was added 4-methylbenzenesulfonyl chloride (286 mg, 1.5 mmol) and triethylamine (174 μL, 1 mmol). The reaction mixture was allowed to stir for 3 days, then it was diluted with 1N HCl and extracted with CH₂Cl₂. The organic layer was dried (MgSO₄) and concentrated. The crude was flash chromatographed using hexane/EtOAc as eluent to obtain the corresponding sulfonamide.

Yield: 71% (steps A and B)

¹H NMR (DMSO-d₆): δ 0.84 (d, J=7.2, 3H), 0.86 (d, J=6.3, 3H), 1.30–1.68 (m, 5H), 1.88–2.00 (m, 2H), 2.42 (s, 3H), 2.92 and 3.00 (ABX, J=14.7, 8.2, 2H), 3.18 (m, 2H), 3.50 (s, 3H), 4.40 (t, J=7.4, 1H), 4.78 (br s, 1H), 5.11 (s, 2H), 7.27–7.71 (m, 9H).

Step C. Preparation of Nα-isobutyl-Nα-(4-methylbenzenesulfonyl)-L-lysine methyl ester Pd/C 10% (120 mg) was added to a solution of the above sulfonamide (491 mg, 1 mmol) in EtOAc/MeOH (3 mL/3 mL). The suspension was flushed with H₂ and maintained under H₂ pressure until complete consumption of the starting material. The insoluble material was filtered off, and the filtrate was concentrated under reduced pressure to give the desired amine in quantitative yield. This compound was used without purification in the next step.

Step D. Preparation of Nα-isobutyl-Nα-(4-methylbenzenesulfonyl)-Nε-[1,2,3,4-tetrahydroisoquinoline-N'-(tert-butoxycarbonyl)-3-carbonyl]-L-lysine methyl ester To a stirred solution of the above crude amine in THF/K₂CO₃ (1M) (3 mL/3 mL) was added 1,2,3,4-tetrahydroisoquinoline-N'-(tert-butoxycarbonyl)-3-carboxylic acid N-hydroxysuccinimide ester (451 mg, 1.2 mmol). The reaction mixture was stirred overnight then diluted with 1N HCl and extracted with EtOAc. The organic layer was dried (MgSO₄) and concentrated. The crude was purified by flash chromatography using hexane/EtOAc as the eluent to afford the desired product.

Step E. Preparation of Nα-isobutyl-Nα-(4-methylbenzenesulfonyl)-Nε-[1,2,3,4-tetrahydroisoquinoline-N'-(tert-butoxycarbonyl)-3-carbonyl]-L-lysine The above ester (314 mg, 0.5 mmol) was dissolved in THF/MeOH (2 mL/1 mL), to which was added NaOH (0.6 mmol). The reaction mixture was stirred until complete consumption of the starting ester, then diluted with 1N HCl until acidic pH and extracted with EtOAc. The organic phase was dried (MgSO₄) and concentrated to give the desired acid in quantitative yield.

Overall yield: 62% (steps C, D and E)

¹H NMR (DMSO-d₆): δ 0.80 (d, J=6.5, 3H), 0.83 (d, J=6.6, 3H), 1.00–1.30 (m, 4H), 1.35 (s, 9H), 1.42 (m, 1H), 1.70–1.92 (m, 2H), 2.35 (s, 3H), 2.80–3.10 (m, 6H), 4.12 (m, 1H), 4.35 (m, 1H), 4.50–4.65 (m, 2H), 7.15 (m, 4H), 7.35 (d, J=8.0, 2H), 7.65 (d, J=8.0, 2H), 7.78 (m, 1H).

Step F. Preparation of Nα-isobutyl-Nα-(4-methylbenzenesulfonyl)-Nε-[1,2,3,4-tetrahydroisoquinoline-3-carbonyl]-L-lysine trifluoroacetic acid salt The title product was prepared by treating a solution of Nα-isobutyl-Nα-(4-methylbenzenesulfonyl)-Nε-[1,2,3,4-tetrahydroisoquinoline-N'-(tert-butoxycarbonyl)-3-carbonyl]-L-lysine (614 mg, 1 mmol, step E) in CH₂Cl₂ (5 mL) with TFA (3 mL) for 3 h The ammonium salt was isolated in quantitative yield.

¹H NMR (DMSO-d₆): δ 0.80 (d, J=6.5, 3H), 0.83 (d, J=6.8, 3H), 1.22–1.57 (m, 5H), 1.82–1.98 (m, 2H), 2.38 (s, 3H), 2.88–3.22 (m, 5H), 3.30 (d, J=16.5, 1H), 4.10–4.40 (m 4H), 7.25 (m, 4H), 7.40 (d, J=7.4, 2H), 7.69 (d, J=7.5, 2H), 8.60 (s, 1H), 9.40 (br s, 1H), 9.63 (br s, 1H).

Step G. Preparation of Nα-isobutyl-Nα-(4-methylbenzenesulfonyl)-Nε-[1,2,3,4-tetrahydroisoquinoline-N'-(4-methylbenzenesulfonyl)-3-carbonyl]-L-lysine The final product was prepared from Nα-isobutyl-Nα-(4-methylbenzenesulfonyl)-Nε-[1,2,3,4-tetrahydroisoquinoline-3-carbonyl]-L-lysine trifluoroacetic acid salt (step F above) following the indications of step B of this example. The desired material was obtained in 71% yield.

¹H NMR (DMSO-d₆): δ 0.80 (d, J=6.5, 3H), 0.83 (d, J=6.8, 3H), 1.00–1.40 (m, 5H), 1.68–1.90 (m, 2H), 2.33 (s, 3H), 2.35 (s, 3H), 2.70–3.00 (m, 6H), 4.12 (m, 1H), 4.42–4.53 (m, 3H), 7.10–7.40 (m, 8H), 7.63 (d, J=8.2, 4H), 7.90 (m, 1H), 12.70 (br s, 1H).

Example 66

Preparation of Nα-isobutyl-Nα-(4-methylbenzenesulfonyl)-Nε-[N'α-(4-methylbenzenesulfonyl)-D-phenylalanyl]-D-lysine The title compound was prepared in the same manner as in the previous example (example 65) using Nα-isobutyl-Nε-benzyloxycarbonyl-D-lysine methyl ester and 4-methylbenzenesulfonyl-D-phenylalanine as the starting materials.

¹H NMR(DMSO-d6): δ 0.80 (d, J=6.5, 3H), 0.83 (d, J=6.8, 3H), 1.00–1.12 (m, 4H), 1.35–1.45 (m, 1H), 1.70–1.80 (m, 1H), 1.85–1.95 (m, 1H), 2.32 (s, 3H), 2.60–2.80 (m, 4H), 2.85 and 2.97 (ABX, J=14.5, 7.5, 2H), 3.90 (m, 1H), 4.15 (t, J=5.0, 1H), 7.10 (d, J=7.3, 2H), 7.12–7.25 (m, 5H), 7.36 (d, J=7.5, 2H), 7.50 (d, J=8.0, 2H), 7.68 (d, J=7.5, 2H), 7.75 (t, J=5.0, 1H), 7.92 (d, J=9.2, 1H).

Example 67

Preparation of Nα-isobutyl-Nα-(4-methylbenzenesulfonyl)-Nε-[N'α-(4-methylbenzenesulfonyl)-L-phenylalanyl]-D-lysine The title compound was prepared in the same manner as in the example 65 using Nα-isobutyl-Nε-benzyloxycarbonyl-D-lysine methyl ester and 4-methylbenzenesulfonyl-L-phenylalanine as the starting materials.

¹H NMR (CDCl₃): δ 0.77 (d, J=6.3, 3H), 0.80 (d, J=6.3, 3H), 1.00–1.11 (m, 4H), 1.23–1.25 (m, 1H), 1.70–1.74 (m, 1H), 1.89–1.93 (m, 1H), 2.30 (s, 3H), 2.32 (s, 3H), 2.59–2.67 (m, 2H), 2.87 and 2.93 (ABX, J=14.1, 4.2, 2H), 3.85 (t, J=5.9, 1H), 3.63 (t, J=6.9, 1H), 6.90–7.10 (m, 7H), 7.24 (d, J=8.0, 2H), 7.44 (d, J=8.1, 2H), 7.73 (d, J=8.1, 2H).

Example 68

Preparation of Nα-isobutyl-Nα-(4-methylbenzenesulfonyl)-Nε-[N'α-(4-methylbenzenesulfonyl)-L-phenylalanyl]-L-lysine methyl ester To a stirred solution of Nα-isobutyl-Nα-(4-methylbenzenesulfonyl)-L-lysine methyl ester (369 mg, 1 mmol, example 65, step C) in THF/K$_2$CO$_3$ (1M) (3 mL/3 mL) was added Nα-(4-methylbenzenesulfonyl)-L-phenylalanine N-hydroxysuccinimide ester (500 mg, 1.2 mmol). The reaction mixture was stirred overnight, then diluted with 1N HCl and extracted with EtOAc. The organic layer was dried (MgSO$_4$) and concentrated. The crude was purified by flash chromatography using hexane/EtOAc as eluent to afford the desired product (77% yield).

$^1$H NMR (DMSO-d$_6$): δ 0.83 (d, J=7.0, 3H), 0.86 (d, J=6.8, 3H), 1.22–1.50 (m, 4H), 1.60 (m, 1H), 1.80–1.95 (m, 2H), 2.40 (s, 3H), 2.42 (s, 3H), 2.85–3.05 (m, 4H), 3.12 (m, 2H), 3.50 (s, 3H), 3.88 (m, 3H), 3.49 (t, J=5.0, 1H), 5.22 (m, 1H), 6.42 (t, J=5.0, 1H), 6.96 (d, J=8.0, 2H), 7.12–7.20 (m, 5H), 7.30 (d, J=8.0, 2H), 7.51 (d, J=7.5, 2H), 7.72 (d, J=7.8, 2H).

Example 69

Preparation of Nα-isobutyl-Nα-(4-methylbenzenesulfonyl)-Nε-[N'α-(4-methylbenzenesulfonyl)-L-tryptophanyl]-L-lysine methyl ester, To a stirred solution of Nα-isobutyl-Nα-(4-methylbenzenesulfonyl)-L-lysine methyl ester (369 mg, 1 mmol, example 65, step C) in THF/K$_2$CO$_3$ (1M) (3 mL/3 mL) was added Nα-(4-methylbenzenesulfonyl)-L-tryptophan N-hydroxysuccinimide ester (547 mg, 1.2 mmol). The reaction mixture was stirred overnight, then diluted with 1N HCl and extracted with EtOAc. The organic layer was dried (MgSO$_4$) and concentrated. The crude was purified by flash chromatography using hexane/EtOAc as eluent to afford the desired product (71% yield).

$^1$H NMR (DMSO-d$_6$): δ 0.77 (t, J=7.5, 6H), 1.00–1.10 (m, 4H), 1.40 (m, 1H), 1.70 (m, 1H), 1.85 (m, 1H), 2.29 (s, 3H), 2.38 (s, 3H), 2.87–3.00 (, 3H), 3.44 (s, 3H), 3.85 (m, 1H), 4.24 (t, J=7.3, 1H), 5.74 (s, 2H), 6.88–7.101 (m, 3H), 7.15 (d, J=8.2, 2H), 7.25–7.46 (m, 6H), 7.65 (d, J=8.2, 2H), 7.75 (br s, 1H), 7.84 (d, J=8.6, 1H), 10.71 (s, 1H).

Example 70

Preparation of Nα-isobutyl-Nα-(4-methylbenzenesulfonyl)-Nε-(N'α-benzoyl-L-phenylalanyl)-L-lysine methyl ester To a stirred solution of Nα-isobutyl-Nα-(4-methylbenzenesulfonyl)-L-lysine methyl ester (369 mg, 1 mmol, example 65, step C) in THF/K$_2$CO$_3$ (1M) (3 mL/3 mL) was added Nα-benzoyl-L-phenylalanine N-hydroxysuccinimide ester (440 mg, 1.2 mmol). The reaction mixture was stirred overnight, then diluted with 1N HCl and extracted with EtOAc. The organic layer was dried (MgSO$_4$) and concentrated. The crude was purified by flash chromatography using hexane/EtOAc as eluent to afford the desired product (82% yield).

$^1$H NMR (DMSO-d$_6$): δ 0.83 (d, J=6.3, 3H), 0.85 (d, J=6.8, 3H), 1.22–1.50 (m, 4H), 1.55–1.70 (m, 1H), 1.80–2.00 (m, 2H), 2.43 (s, 3H), 2.90 and 3.00 (ABX, J=14.0, 7.5, 2H), 3.12–3.30 (m, 4H), 3.50 (s, 3H), 4.39 (m, 1H), 4.82 (m, 1H), 5.95 (br s, 1H), 6.98 (br s, 1H), 7.20–7.52 (m, 10H), 7.65–7.75 (m, 4H).

Example 71

Preparation of Nα-isobutyl-Nα-(4-methylbenzenesulfonyl)-Nε-[N'α-(4-methylbenzenesulfonyl)-L-thiophenylalanyl]-L-lysine methyl ester The title compound was prepared from Nα-isobutyl-Nα-(4-methylbenzenesulfonyl)-Nε-[N'α-(4-methylbenzenesulfonyl)-L-phenylalanyl]-L-lysine methyl ester, product of example 68, following the indications of general procedure F. The thioamide was obtained in 64% yield.

$^1$H NMR (DMSO-d$_6$): δ 0.83 (d, J=6.8, 3H), 0.86 (d, J=6.8, 3H), 1.30 (m, 2H), 1.48–1.60 (m, 2H), 1.70 (m, 1H), 1.80–1.95 (m, 2H), 2.42 (s, 3H), 2.46 (s, 3H), 2.88 and 3.20 (ABX, J=13.5, 7.5, 2H), 3.00 (m, 2H), 3.45 (m, 2H), 3.52 (s, 3H), 4.18 (m, 1H), 4.40 (m, 1H), 5.37 (d, J=7.0, 1H), 7.00 (d, J=8.0, 2H), 7.18 (m, 5H), 7.32 (d, J=7.5, 2H), 7.50 (d, J=7.5, 2H), 7.75 (d, J=8.0, 2H), 7.97 (br s, 1H).

Example 72

Preparation of Nα-isobutyl-Nα-(4-methylbenzenesulfonyl)-Nε-[N'α-(4-methylbenzenesulfonyl)-L-thiophenylalanyl]-L-lysine Saponification of Nα-isobutyl-Nα-(4-methylbenzenesulfonyl)-Nε-[N'α-(4-methylbenzenesulfonyl)-L-thiophenylalanyl]-L-lysine methyl ester (example 71) using the conditions described in example 65 (step E) yielded 87% of the desired material.

$^1$H NMR (DMSO-d$_6$): δ 0.80 (d, J=6.5, 3H), 0.83 (d, J=6.8, 3H), 1.00–1.42 (m, 5H), 1.78 (m, 1H), 1.90 (m, 1H), 2.33 (s, 3H), 2.37 (s, 3H), 2.75 (m, 1H), 2.82–3.15 9m, 6H), 4.15 (t, J=7.2, 1H), 4.30 (m, 1H), 7.00–7.25 (m, 7H), 7.38 (d, J=8.2, 2H), 7.50 (d, J=8.3, 2H), 7.68 (d, J=8.2, 2H), 7.75 (d, J=9.0, 1H), 9.77 (s, 1H), 12.70 (br s, 1H).

Example 73

Preparation of Nα-isobutyl-Nα-(4-methylbenzenesulfonyl)-Nε-[N'α-(4-methylbenzenesulfonyl)-L-thiotryptophanyl]-L-lysine Saponification of Nα-isobutyl-Nα-(4-methylbenzenesulfonyl)-Nε-[N'α-(4-methylbenzenesulfonyl)-L-thiotryptophanyl]-L-lysine methyl ester (example 75) using the conditions described in example 65 (step E) yielded 88% of the desired material.

$^1$H NMR (DMSO-d$_6$): δ 0.80 (d, J=6.5, 3H), 0.83 (d, J=6.8, 3H), 1.00–1.42 (m, 5H), 1.73 (m, 1H), 1.83 (m, 1H), 2.28 (s, 3H), 2.37 (s, 3H), 2.80–3.02 (m, 3H), 3.03–3.15 (m, 3H), 4.15 (t, J=6.5, 1H), 4.30 (m, 1H), 6.90 (t, J=7.4, 1H), 7.00 (t, J=7.4, 1H), 7.10 (s, 1H), 7.20 (d, J=8.0, 2H), 7.28 (d, J=8.2, 1H), 7.30–7.42 (m, 4H), 7.67 (m, 4H), 9.68 (s, 1H), 10.72 (s, 1H), 12.76 (br s, 1H).

Example 74

Preparation of Nα-isobutyl-Nα-(4-methylbenzenesulfonyl)-Nε-(N'α-benzenesulfonyl[-L-thiotryptophanyl)-L-lysine The title compound was prepared from Nα-isobutyl-Nα-(4-methylbenzenesulfonyl)-Nε-(N'α-benzenesulfonyl-L-tryptophanyl)-L-lysine, product of example 4, following the indications of general procedure F. The thioamide was obtained in 34% yield.

$^1$H NMR (DMSO-d$_6$): δ 0.80 (d, J=6.5, 3H), 0.83 (d, J=6.8, 3H), 1.00–1.42 (m, 5H), 1.73 (m, 1H), 1.83 (m, 1H), 2.37 (s, 3H), 2.85–3.02 (m, 3H), 3.03–3.15 (m, 3H), 4.15 (t, J=6.5, 1H), 4.30 (m, 1H), 6.90 (t, J=7.4, 1H), 7.00 (t, J=7.4, 1H), 7. 10 (s, 1H), 7.27 (d, J=8.0, 2H), 7.32–7.50 (m, 5H), 7.55 (d, J=8.5, 2H), 7.67 (d, J=8.5, 2H), 7.81 (d, J=8.5, 2H), 9.69 (s, 1H), 10.72 (s, 1H), 12.76 (br s, 1H).

Example 75

Preparation of Nα-isobutyl-Nα-(4-methylbenzenesulfonyl)-Nε-[N'α-(4-methylbenzenesulfonyl)-L-thiotryptophanyl]-L-lysine methyl ester The title compound was prepared from Nα-isobutyl-Nα-(4-methylbenzenesulfonyl)-Nε-[N'α-(4-methylbenzenesulfonyl)-L-tryptophanyl]-L-lysine methyl ester, product of example 69, following the indications of general procedure F. The thioamide was obtained in 55% yield.

$^1$H NMR (CDCl$_3$): δ 0.83 (d, J=6.8, 3H), 0.87 (d, J=6.8, 3H), 1.20–1.62 (m, 5H), 1.80–1.98 (m, 2H), 2.33. (s, 3H), 2.44 (s, 3H), 2.88 and 3.02 (ABX, J=13.5, 7.5, 2H), 3.22 and 3.33 (ABX, J=14.0, 7.5, 2H), 3.40–3.52 (m, 2H), 3.49 (s, 3H), 4.25 (m, 1H), 4.39 (m, 1H), 5.30 (s, 1H), 5.40 (d, J=6.0, 1H), 7.00–7.20 (m, 5H), 7.25–7.50 (m, 5H), 5.70 (d, J=7.5, 2H), 7.90 (t, J=5.0, 1H), 8.48 (s, 1H).

Example 76

Preparation of Nα-isobutyl-Nα-(4-methylbenzenesulfonyl)-Nε-(N'α-thiobenzoyl-L-thiophenylalanyl)-L-lysine methyl ester The title compound was prepared from Nα-isobutyl-Nα-(4-methylbenzenesulfonyl)-Nε-(N'α-benzoyl-L-phenylalanyl)-L-lysine methyl ester, product of example 70, following the indications of general procedure F. The thioamide was obtained in 81% yield.

$^1$H NMR (DMSO-d$_6$): δ 0.83 (d, J=6.3, 3H), 0.86 (d, J=6.8, 3H), 1.12–1.50 (m, 4H), 1.55–1.70 (m, 1H), 1.80–2.00 (m, 2H), 2.45 (s, 3H), 2.87 (dd, J=14.0, 7.5, 2H), 2.98–3.10 (m, 2H), 3.40–3.50 (m, 2H), 3.51 (s, 3H), 3.70 (m, 1H), 4.39 (m, 1H), 5.50 (br s, 1H), 7.20–7.50 (m, 10H), 7.65–7.75 (m, 4H), 9.15 (br s, 1H).

Example 77

Preparation of Nα-isobutyl-Nα-(4-methylbenzenesulfonyl)-Nα-(N'α-thiobenzoyl-L-thiophenylalanyl)-L-lysine Saponification of Nα-isobutyl-Nα-(4-methylbenzenesulfonyl)-Nε-(N'α-thiobenzoyl-L-thiophenylalanyl)-L-lysine methyl ester (example 76) using the conditions described in example 65 (step E) yielded 80% of the desired material.

$^1$H NMR (DMSO-d$_6$): δ 0.81 (t, J=6.5, 6H), 1.15–1.52 (, 5H), 1.80–1.90 (m, 2H), 2.36 (s, 3H), 2.92 and 2.98 (ABX, J=14.5, 7.5, 2H), 3.10 (m, 1H), 3.30–3.50 (m, 3H), 4.20 (t, J=7.0, 1H), 5.60 (m, 1H), 7.18–7.28 (m, 3H), 7.32–7.50 (m, 5H), 7.68 (m, 4H), 10.23 (m, 2H), 12.80 (br s, 1H).

Example 78

Preparation of Nα-isobutyl-Nα-(4-methylbenzenesulfonyl)-Nα-(N'α-tert-butoxycarbonyl-L-phenylalanyl)-L-lysine The title compound was prepared from Nα-isobutyl-Nα-(4-methylbenzenesulfonyl)-L-lysine hydrochloride (1.2 g, 3.1 mmol, example 1, step E) suspended in THF (50 mL) and 1N NaOH (0.5 mL, to reach pH 10) as described in general procedure Bc using commercially available Nα-benzyloxycarbonyl-L-phenylalanine (1.0 g, 3.5 mmol), N-hydroxysuccinimide (0.4 g, 3.5 mmol) and DCC (1.1 g, 4.8 mmol). The final product was triturated with ether to yield 1.61 g (95%) of the desired material.

$^1$H NMR (CDCl$_3$): δ 0.83 (m, 6H), 1.08–1.11 (m, 2H), 1.23–1.25 (m, 2H), 1.35 (s, 9H), 1.45–1.52 (m, 1H), 1.89–1.99 (m, 2H), 2.36 (s, 3H), 2.94–3.09 (m, 6H), 4.20–4.23 (m, 2H), 7.09–7.26 (m, 7H), 7.73 (d, J=8.1, 2H). LC-MS: 602.2 (M–H)$^-$, 95% pure.

Example 79

Preparation of Nα-isobutyl-Nα-(4-methylbenzenesulfonyl)-Nε-(L-phenylalanyl)-L-lysine This product was prepared from Nα-isobutyl-Nα-(4-methylbenzenesulfonyl)-Nε-(N'α-tert-butoxycarbonyl-L-phenylalanyl)-L-lysine (600 mg, 1.0 mmol, example 78) as described in general procedure C. The residue was triturated with ether and placed under high vacuum to yield a hard white foam (440 mg, 88%).

$^1$H NMR (CDCl$_3$): δ 0.78 (d, J=6.3, 3H), 0.81 (d, J=6.3, 3H), 1.00–1.11 (m, 2H), 1.23–1.25 (m, 2H), 1.44–1.47 (m, 1H), 1.70–1.74 (m, 1H), 1.89–1.93 (m, 1H), 2.32 (s, 3H), 2.82–2.89 (m, 2H), 2.91–2.95 (m, 2H), 3.88 (br s, 1H), 4.17 (t, J=5.9, 1H), 7.14 (d, J=8.0, 2H), 7.23 (t, J=4.9, 1H), 7.29 (t, J=4.8, 2H), 7.31 (d, J=5.0, 2H), 7.64 (d, J=8.1, 2H), 8.05 (br s, 3H). LC-MS: 502.2 (M–H)$^-$, 95% pure.

Example 80

Preparation of Nα-isobutyl-Nα-(4-methylbenzenesulfonyl)-Nε-[N'α-(carbotetrahydro-3-furanyloxy)-L-phenylalanyl]-L-lysine Step A. Preparation of Nα-(carbotetrahydro-3-furanyloxy)-L-phenylalanine L-phenylalanine was reacted with tetrahydro-3-furanyloxy-1-nitrophenyl carbonate under the conditions used in general procedure A giving the title compound which was recrystallised from DCM (28%). This compound was used without further purification in the next step.

Step B. Preparation of Nα-isobutyl-Nα-(4-methylbenzenesulfonyl)-Nε-[N'α-(carbotetrahydro-3-furanyloxy)-L-phenylalanyl]-L-lysine The title compound was prepared from Nα-isobutyl-Nα-(4-methylbenzenesulfonyl)-L-lysine (100 mg, 0.29 mmol, example 1, step E) as described in general procedure Bc using Nα-(carbotetrahydro-3-furanyloxy)-L-phenylalanine (84 mg, 0.3 mmol) which was prepared in step A of this example. The final product was triturated with ether to yield 51 mg (27%) of the desired material.

LC-MS: 618.9 (M+H)$^+$, 90% pure.

Example 81

Preparation of Nα-isobutyl-Nα-(4-methylbenzenesulfonyl)-Nε-(N'α-tert-butoxycarbonyl-N'α-methyl-L-phenylalanyl)-L-lysine The title compound was prepared from Nα-isobutyl-Nα-(4-methylbenzenesulfonyl)-L-lysine (100 mg, 0.29 mmol, example 1, step E) as described in general procedure Bc using commercially available Nα-tert-butoxycarbonyl-Nα-methyl-L-phenylalanine (83 mg, 0.3 mmol). The final product was triturated with ether to yield 176 mg (90%) of the desired material.

LC-MS: 616.8 (M–H)$^-$, 94% pure.

Example 82

Preparation of Nα-isobutyl-Nα-(4-methylbenzenesulfonyl)-Nε-(N'α-tert-butoxycarbonyl-L-methionyl)-L-lysine The title compound was prepared from Nα-isobutyl-Nα-(4-methylbenzenesulfonyl)-L-lysine (100 mg, 0.29 mmol, example 1, step E) as described in general procedure Bc using commercially available Nα-tert-butoxycarbonyl-L-methionine (75 mg, 0.3 mmol). The final product was triturated with ether to yield 170 mg (96%) of the desired material.

LC-MS: 586.8 (M–H)⁻, 90% pure.

Example 83

Preparation of Nα-isobutyl-Nα-(4-methylbenzenesulfonyl)-Nε-[N'α-tert-butoxycarbonyl-S-(4-methylbenzyl)-L-cysteinyl]-L-lysine The title compound was prepared from Nα-isobutyl-Nα-(4-methylbenzenesulfonyl)-L-lysine (100 mg, 0.29 mmol, example 1, step E) as described in general procedure Bc using commercially available Nα-tert-butoxycarbonyl-S-(4-methylbenzyl)-L-cysteine (67 mg, 0.3 mmol). The final product was triturated with ether to yield 130 mg (65%) of the desired material.

LC-MS: 562.8 (M–H)⁻, 95% pure.

Example 84

Preparation of Nα-isobutyl-Nα-(4-methylbenzenesulfonyl)-Nε-(N'α-tert-butoxycarbonyl-O-benzyl-L-threonyl)-L-lysine The title compound was prepared from Nα-isobutyl-Nα-(4-methylbenzenesulfonyl)-L-lysine (100 mg, 0.29 mmol, example 1, step E) as described in general procedure Bc using commercially available Nα-tert-butoxycarbonyl-O-benzyl-L-threonine (93 mg, 0.3 mmol). The final product was triturated with ether to yield 195 mg (98%) of the desired material.

LC-MS: 646.9 (M–H)⁻, 95% pure.

Example 85

Preparation of Nα-isobutyl-Nα-(4-methylbenzenesulfonyl)-Nε-(N'α-tert-butoxycarbonyl-Nτ-benzyl-L-histidinyl)-L-lysine The title compound was prepared from Nα-isobutyl-Nα-(4-methylbenzenesulfonyl)-L-lysine (100 mg, 0.29 mmol, example 1, step E) as described in general procedure Bc using commercially available Nα-tert-butoxycarbonyl-Nτ-benzyl-L-histidine (100 mg, 0.3 mmol). The final product was triturated with ether to yield 133 mg (65%) of the desired material.

LC-MS: 682.2 (M–H)⁻, 90% pure.

Example 86

Preparation of Nα-isobutyl-Nα-(4-methylbenzenesulfonyl)-Nε-(N'α-tert-butoxycarbonyl-L-tryptophanyl)-L-lysine The title compound was prepared from Nα-isobutyl-Nα-(4-methylbenzenesulfonyl)-L-lysine (100 mg, 0.29 mmol, example 1, step E) as described in general procedure Bc using commercially available Nα-tert-butoxycarbonyl-L-tryptophan (90 mg, 0.3 mmol). The final product was triturated with ether to yield 157 mg (81%) of the desired material.

LC-MS: 641.8 (M–H)⁻-, 90% pure.

Example 87

Preparation of Nα-isobutyl-Nα-(4-methylbenzenesulfonyl)-Nε-(N'α-tert-butoxycarbonyl-O-benzyl-L-tyrosyl)-L-lysine The title compound was prepared from Nα-isobutyl-Nα-(4-methylbenzenesulfonyl)-L-lysine (100 mg, 0.29 mmol, example 1, step E) as described in general procedure Bc using commercially available Nα-tert-butoxycarbonyl-O-benzyl-L-tyrosine (111 mg, 0.3 mmol). The final product was triturated with ether to yield 145 mg (68%) of the desired material.

LC-MS: 708.2 (M–H)⁻, 95% pure.

Example 88

Preparation of Nα-isobutyl-Nα-(4-methylbenzenesulfonyl)-Nε-(N'α-methyl-L-phenylalanyl)-L-lysine This product was prepared from Nα-isobutyl-Nα-(4-methylbenzenesulfonyl)-Nε-(N'α-tert-butoxycarbonyl-N'α-methyl-L-phenylalanyl)-L-lysine (100 mg, 0.16 mmol, example 81) as described in general procedure C. The residue was triturated with ether and placed under high vacuum to yield a hard white foam (25 mg, 30%).

LC-MS: 516.3 (M–H)⁻, 95% pure.

Example 89

Preparation of Nα-isobutyl-Nα-(4methylbenzenesulfonyl)-Nε-(L-methionyl)-L-lysine This product was prepared from Nα-isobutyl-Nα-(4-methylbenzenesulfonyl)-Nε-(N'α-tert-butoxycarbonyl-L-methionyl)-L-lysine (95 mg, 0.16 mmol, example 82) as described in general procedure C. The residue was triturated with ether and placed under high vacuum to yield a hard white foam (40 mg, 51%).

LC-MS: 486.2 (M–H)⁻, 95% pure.

Example 90

Preparation of Nα-isobutyl-Nα-(4-methylbenzenesulfonyl)-Nε-[S-(4-methylbenzyl)-L-cysteinyl]-L-lysine This product was prepared from Nα-isobutyl-Nα-(4-methylbenzenesulfonyl)-Nε-[N'α-tert-butoxycarbonyl-S-(4-methylbenzyl)-L-cysteinyl]-L-lysine (91 mg, 0.16 mmol, example 83) as described in general procedure C. The residue was triturated with ether and placed under high vacuum to yield a hard white foam (60 mg, 66%).

LC-MS: 562.2 (M–H)⁻, 85% pure.

Example 91

Preparation of Nα-isobutyl-Nα-(4-methylbenzenesulfonyl)-Nε-(O-benzyl-L-threonyl)-L-lysine This product was prepared from Nα-isobutyl-Nα-(4-methylbenzenesulfonyl)-Nε-(N'α-tert-butoxycarbonyl-O-benzyl-L-threonyl)-L-lysine (110 mg, 0.18 mmol, example 84) as described in general procedure C. The residue was triturated with ether and placed under high vacuum to yield a hard white foam (40 mg, 41%).

LC-MS: 549.3 (M–H)⁻, 95% pure.

Example 92

Preparation of Nα-isobutyl-Nα-(4-methylbenzenesulfonyl)-Nε-(Nt-benzyl-L-histidinyl)-L-lysine This product was prepared from Nα-isobutyl-Nα-(4-methylbenzenesulfonyl)-Nε-(N'α-tert-butoxycarbonyl-Nτ- benzyl-L-histidinyl)-L-lysine (110 mg, 0.16 mmol, example 85) as described in general procedure C. The residue was triturated with ether and placed under high vacuum to yield a hard white foam (51 mg, 54%).

LC-MS: 582.1 (M−H)⁻, 95% pure.

Example 93

Preparation of Nα-isobutyl-Nα-(4-methylbenzenesulfonyl)-Nε-(L-tryptophanyl)-L-lysine This product was prepared from Nα-isobutyl-Nα-(4-methylbenzenesulfonyl)-Nε-(N'α-tert-butoxycarbonyl-L-tryptophanyl)-L-lysine (100 mg, 0.15 mmol, example 86) as described in general procedure C. The residue was triturated with ether and placed under high vacuum to yield a hard white foam (27 mg, 33%).

LC-MS: 541.6 (M−H)⁻, 90% pure.

Example 94

Preparation of Nα-isobutyl-Nα-(4-methylbenzenesulfonyl)-Nε-(O-benzyl-L-tyrosyl)-L-lysine This product was prepared from Nα-isobutyl-Nα-(4-methylbenzenesulfonyl)-Nε-(N'α-tert-butoxycarbonyl-O-benzyl-L-tyrosyl)-L-lysine (115 mg, 0. 16 mmol, example 87) as described in general procedure C. The residue was triturated with ether and placed under high vacuum to yield a hard white foam (19 mg, 19%).

LC-MS: 608.2 (M−H)⁻, 90% pure.

Example 95

Preparation of (2S, 2'S) 2-N-isobutyl-2-N-(4-methylbenzenesulfonyl)-6-N-(N'α-benzoyl-S-phenylalanyl)-2,6-diaminohexanol The product of example 70, Nα-isobutyl-Nα-(4-methylbenzenesulfonyl)-Nε-(N'α-benzoyl-L-phenylalanyl)-L-lysine methyl ester, was reduced with LiAlH₄ following the indications of general procedure G. The final product was obtained in 76% yield.

¹H NMR (DMSO-d₆): δ 0.77 (t, J=7.0, 6H), 0.90–1.30 (m, 5H), 1.48 (m, 1H), 1.85 (m, 1H), 2.38 (s, 3H), 2.55–2.70 (m, 3H), 2.75–2.85 (m, 2H), 2.93 (dd, J=13.5, 7.5, 1H), 3.35 (m, 1H), 3.50 (m, 1H), 3.86 (m, 1H), 4.65 (m, 1H), 7.10 (d, J=7.8, 2H), 7.12–7.22 (m, 6H), 7.35 (d, J=8.0, 2H), 7.50 (d, J=7.8, 2H), 7.67 (d, J=8.2, 2H), 7.72 (t, J=5.0, 1H), 7.70 (d, J=8.0, 1H).

Example 96

Preparation of (2S, 2'S) 2-N-isobutyl-2-N-(4-methylbenzenesulfonyl)-6-N-[N'α-(4-methylbenzenesulfonyl)-S-phenylalanyl]-2,6-diaminohexanol The product of example 68, Nα-isobutyl-Nα-(4-methylbenzenesulfonyl)-Nε-[N'α-(4-methylbenzenesulfonyl)-L-phenylalanyl]-L-lysine methyl ester, was reduced with LiAlH₄ following the indications of general procedure G. The final product was obtained in 76% yield.

¹H NMR (DMSO-d₆): δ 0.83 (t, J=7.0, 6H), 0.90–1.30 (m, 5H), 1.52 (m, 1H), 1.90 (m, 1H), 2.36 (s, 3H), 2.80 (dd, J=12.0, 8.0, 1H), 2.85–3.10 (m, 5H), 3.52 (m, 1H), 4.66 (m, 2H), 7.10–7.28 (m, 3 H), 7.30–7.55 (m, 7H), 7.67 (d, J=8.0, 2H), 7.80 (d, J=8.0, 2H), 7.96 (m, 1H), 8.51 (d, J=8.0, 1H).

Example 97

Preparation of (2S, 2'S) 2-N-isobutyl-2-N-(4-methylbenzenesulfonyl)-6-N-[N'α-(4-methylbenzenesulfonyl)-S-tryptophanyl]-2,6-diaminohexanol The product of example 69, Nα-isobutyl-Nα-(4-methylbenzenesulfonyl)-Nε-[N'α-(4-methylbenzenesulfonyl)-L-tryptophanyl]-L-lysine methyl ester, was reduced with LiAlH4 following the indications of general procedure G. The final product was obtained in 65% yield.

¹H NMR (DMSO-d₆): δ 0.82 (d, J=7.0, 3H), 0.85 (d, J=6.8, 3H), 0.88–1.20 (m, 5H), 1.45 (m, 1H), 2.30 (s, 3H), 2.36 (s, 3H), 2.62 (m, 2H), 2.76 (m, 2H), 2.90 (m, 2H), 2.90 (m, 2H), 3.20–3.40 (m, 2H), 3.50 (m, 1H), 3.85 (m, 1H), 4.67 (t, J=5.0, 1H), 6.90 (t, J=7.4, 1H), 7.03 (m, 2H), 7.13 (d, J=7.6, 2H), 7.27 (d, J=7.6, 2H), 7.35 (m, 3H), 7.46 (d, J=7.6, 2H), 7.68 (m, 3H), 7.82 (d, J=8.8, 1H), 10.70 (s, 1H).

Example 98

Preparation of Nα-isobutyl-Nα-(4-methylbenzenesulfonyl)-Nε-[N'α-(4-methylbenzenesulfonyl)-L-phenylalanyl-N-cyanoamidine]-L-lysine To a stirred solution of the thioamide, Nα-isobutyl-Nα-(4-methylbenzenesulfonyl)-Nε-[N'α-(4-methylbenzenesulfonyl)-L-thiophenylalanyl]-L-lysine, (227 mg, 0.33 mmol, example 72) in MeOH (3 mL) was added cyanamide (28 mg, 0.66 mmol). The mixture was stirred for 5 min, then mercuric acetate (209 mg, 0.66 mmol) was added. The reaction was stirred for 3 h then diluted with saturated NH₄Cl and extracted with EtOAc. The organic layer was washed with brine and concentrated then rediluted with THF/MeOH (2 mL/1 mL) and treated with 1N NaOH (0.8 mL). After stirring for 4 h, the reaction was acidified with 1N HCl and extracted with EtOAc. The organic layer was dried over MgSO₄, concentrated and purified by column chromatography to give 128 mg (57%) of the final product.

¹H NMR (DMSO-d₆): δ 0.80 (d, J=6.5, 3H), 0.83 (d, J=6.8, 3H), 1.00–1.12 (m, 4H), 1.35 (m, 1H), 1.71 (m, 1H), 1.88 (m, 1H), 2.37 (s, 3H), 2.50 (s, 3H), 2.60–2.80 (m, 4H), 2.90 and 2.97 (ABX, J=13.2, 7.0, 2H), 3.88 (m, 1H), 4.15 (t, J=7.0, 1H), 7.10 (d, J=8.2, 2H), 7.13–7.23 (m, 5H), 7.38 (d, J=8.2, 2H), 7.49 (d, J=7.9, 2H), 7.68 (d, J=8.2, 2H), 7.78 (m, 1H), 7.92 (d, J=8.3, 1H), 12.70 (br s, 1H).

Example 99

Preparation of Nα-isobutyl-Nα-(4-methylbenzenesulfonyl)-Nε-(N'α-acetyl-L-tryptophanyl)-L-lysine Step A. Preparation of Nα-acetyl-L-tryptophan L-tryptophan was reacted with acetyl chloride under the conditions used in general procedure A giving the title compound which was recrystallised from DCM (65%).

¹H NMR (CDCl₃): δ 1.92 (s, 3H), 3.11–3.46 (m, 2H), 4.73 (t, J=4.5, 1H), 6.92–7.10 (m, 3H), 7.28 (d, J=6.0, 1H), 7.55 (d, J=6.0, 1H).

Step B. Preparation of Nα-isobutyl-Nα-(4-methylbenzenesulfonyl)-Nε-(N'α-acetyl-L-tryptophanyl)-L-lysine The title compound was prepared from Nα-isobutyl-Nα-(4-methylbenzenesulfonyl)-L-lysine hydrochloride (400 mg, 1.0 mmol, example 1, step E) suspended in THF (20 mL) and 1N NaOH (0.5 mL, to reach pH 10) as described in general procedure Bc using Nα-acetyl-L-tryptophan (300 mg, 1.4 mmol) prepared in step A of this example, N-hydroxysuccinimide (115 mg, 1.0 mmol) and DCC (210 mg, 1.0 mmol). The crude material (600 mg) was purified by preparative HPLC to yield 411 mg (45%) of the desired material.

$^1$H NMR (CDCl$_3$): δ 0.82 (d, J=6.8, 3H), 0.84 (d, J=6.8, 3H), 1.08–1.11 (m, 2H), 1.18–1.22 (m, 2H), 1.45–1.52 (m, 1H), 1.94 (s, 3H), 2.32 (s, 3H), 2.84–3.09 (m, 4H), 3.15–3.18 (m, 1H), 4.19 (t, J=7.5, 1H), 4.57 (t, J=7.1, 1H), 6.85 (t, J=7.2, 1H), 7.04 (s, 2H), 7.32 (d, J=8.1, 2H), 7.56 (d, J=8.1, 1H), 7.69 (d, J=7.2, 2H). LC-MS: 583.8 (M−H)⁻, 99% pure.

Example 100

Preparation of Nα-isobutyl-Nα-(4-methylbenzenesulfonyl)-Nε-(N'α-pivaloyl-L-tryptophanyl)-L-lysine Step A. Preparation of Nα-pivaloyl-L-tryptophan L-tryptophan was reacted with pivaloyl chloride under the conditions used in general procedure A giving the title compound which was recrystallised from DCM (50%).

$^1$H NMR (CDCl$_3$): δ 1.02 (s, 9H), 3.21–3.46 (m, 2H), 4.73 (t, J=4.5, 1H), 6.92–7.10 (m, 3H), 7.28 (d, J=6.0, 1H), 7.55 (d, J=6.0, 1H).

Step B. Preparation of Nα-isobutyl-Nα-(4-methylbenzenesulfonyl)-Nε-(N'α-pivaloyl-L-tryptophanyl)-L-lysine The title compound was prepared from Nα-isobutyl-Nα-(4-methylbenzenesulfonyl)-L-lysine hydrochloride (400 mg, 1.0 mmol, example 1, step E) suspended in THF (20 mL) and 1N NaOH (0.5 mL, to reach pH 10) as described in general procedure Bc using Nα-pivaloyl-L-tryptophan (350 mg, 1.5 mmol) prepared in step A of this example, N-hydroxysuccinimide (115 mg, 1.0 mmol) and DCC (210 mg, 1.0 mmol). The crude material (488 mg) was purified by preparative HPLC to yield 244 mg (50%) of the desired material.

$^1$H NMR (CDCl$_3$): δ 0.82 (d, J=6.8, 3H), 0.84 (d, J=6.8, 3H), 1.06 (s, 9H), 1.08–1.11 (m, 2H), 1.18–1.22 (m, 2H), 1.45–1.52 (m, 1H), 2.38 (s, 3H), 2.84–3.09 (m, 4H), 3.15–3.18 (m, 1H), 4.24 (t, J=7.5, 1H), 4.57 (t, J=7.1, 1H), 6.85 (t, J=7.2, 1H), 7.04 (s, 2H), 7.32 (d, J=8.1, 2H), 7.56 (d, J=8.1, 1H), 7.69 (d, J=7.2, 2H). LC-MS: 625.8 (M−H)⁻, 99% pure.

Example 101

Preparation of Nα-isobutyl-Nα-(4-methylbenzenesulfonyl)-Nε-(N'α-trifluoroacetyl-L-phenylalanyl)-L-lysine Nα-isobutyl-Nα-(4-methylbenzenesulfonyl)-Nε-(N'α-tert-butoxycarbonyl-L-phenylalanyl)-L-lysine (50 mg, 0.08 mmol, example 78) is added to a mixture of of trifluoroacetic anhydride and TFA and was stirred for a period of 30 min. Afterwards, the reactant were evaporated and the residue triturated with ether to give 40 mg (74%) of the title compound.

LC-MS: 598.7 (M−H)⁻, 99% pure.

Example 102

Preparation of (2S, 2'S) 2-N-isobutyl-2-N-(4-methylbenzenesulfonyl)-6-N-[N'α-(4-methylbenzenesulfonyl)-S-thiotryptophanyl]-2,6-diaminohexanol The product of example 75, Nα-isobutyl-Nα-(4-methylbenzenesulfonyl)-Nε-[N'α-(4-methylbenzenesulfonyl)-L-thiotryptophanyl]-L-lysine methyl ester, was reduced with LiAlH$_4$ following the indications of general procedure G. The final product was obtained in 61% yield.

$^1$H NMR (CDCl$_3$): δ 0.83 (d, J=7.0, 3H), 0.85 (d, J=7.0, 3H), 0.88–1.25 (m, 5H), 1.50 (m, 1H), 1.88 (m, 1H), 2.30 (s, 3H), 2.37 (s, 3H), 2.80 and 2.95 (ABX, J=14.5, 7.3, 2H), 2.90 and 3.10 (ABX, J=14.5, 7.8, 2H), 3.05 (m, 2H), 3.20–3.40 (m, 2H), 3.51 (m, 1H), 4.30 (m, 1H), 4.68 (m, 1H), 6.90 (t, J=7.5, 1H), 7.02 (t, J=7.5, 1H), 7.06 (s, 1H), 7.09 (d, J=8.0, 2H), 7.28 (d, J=7.7, 1H), 7.32–7.42 (m, 5H), 7.70 (d, J=8.10, 4H), 10.71 (s, 1H).

Example 103

Preparation of Nα-isobutyl-Nα-(4-methylbenzenesulfonyl)-Nε-[N'α-(4-methylbenzenesulfonyl)-L-tryptophanyl-N-cyanoamidine]-L-lysine To a stirred solution of thioamide Nα-isobutyl-Nα-(4-methylbenzenesulfonyl)-Nα-[N'α-(4-methylbenzenesulfonyl)-L-thiotryptophanyl]-L-lysine (240 mg, 0.33 mmol, example 73) in MeOH (3 mL) was added cyanamide (28 mg, 0.66 mmol). The mixture was stirred for 5 min, then mercuric acetate (209 mg, 0.66 mmol) was added. The reaction was stirred for 3 h then diluted with saturated NH$_4$Cl and extracted with EtOAc. The organic layer was washed with brine and concentrated then rediluted with THF/MeOH (2 mL/1 mL) and treated with 1N NaOH (0.8 mL). After stirring for 4 h, the reaction was acidified with 1N HCl and extracted with EtOAc. The organic layer was dried over MgSO$_4$, concentrated and purified by column chromatography to give 154 mg (65%) of the final product.

$^1$H NMR (DMSO-d$_6$): δ 0.80 (d, J=6.5, 3H), 0.83 (d, J=6.8, 3H), 1.00–1.14 (m, 4H), 1.38 (m 1H), 1.72 (m, 1H), 1.88 (m, 1H), 2.30 (s, 3H), 2.37 (s, 3H), 2.70 (dd, J=13.5, 7.0, 1H), 2.92 (m, 3H), 3.87 (m, 1H), 4.12 (t, J=7.0, 1H), 6.90 (t, J=7.5, 1H), 7.00 (t, J=7.5, 1H), 7.04 (s, 1H), 7.13 (d, J=8.3, 2H), 7.28 (d, J=8.3, 1H), 7.38 (m, 3H), 7.47 (d, J=8.0, 2H), 7.65 (d, J=8.0, 2H), 7.72 (t, J=5.0, 1H), 7.85 (d, J=8.1, 1H), 10.73 (s, 1H), 12.70 (br s, 1H).

Example 104

Preparation of Nα-isobutyl-Nα-(4-methylbenzenesulfonyl)-Nε-(N'α-benzenesulfonyl-L-tryptophanyl)-L-lysine 2,3-dihydroxypropyl ester Nα-isobutyl-Nα-(4-methylbenzenesulfonyl)-Nε-(N'α-benzenesulfonyl-L-tryptophanyl)-L-lysine (170 mg, 0.25 mmol) dissolved in a solution of DMF (1 mL) was treated with glycerol (100 μL, 1.37 mmol) and EDC (100 mg, 0.5 mmol) and stirred overnight. Then, the solution was poured in 5% citric acid and extracted with EtOAc. The solvent was evaporated and the residue purified by preparative HPLC to give 150 mg (79%) of the final product.

$^1$H NMR (CDCl$_3$): δ 0.81 (d, J=6.3, 3H), 0.83 (d, J=6.3, 3H), 0.94–1.03 (m, 4H), 1.32–1.35 (m, 1H), 1.46–1.49 (m, 1H), 1.81–1.93 (m, 2H), 2.35 (s, 3H), 2.75 (br s, 11H), 2.82–2.99 (m, 4H), 3.45 (br s, 2H), 3.65 (br s, 1H), 3.82 (br s, 2H), 4.21 (t, J=7.2, 1H), 6.85 (t, J=4.5, 1H), 7.00 (t, J=4.5, 1H), 7.23–7.31 (m, 6H), 7.42 (t, J=4.5, 1H), 7.60 (d, J=6.8, 2H), 7.73 (d, J=6.8, 2H).

Example 105

Preparation of Nα-isobutyl-Nα-(4-methylbenzenesulfonyl)-Nε-(N'α-phenylglycyl)-L-lysine Step A. Preparation of Nα-isobutyl-Nα-(4-methylbenzenesulfonyl)-Nε-chloroacetyl-L-lysine The title compound was prepared from Nα-isobutyl-Nα-(4-methylbenzenesulfonyl)-L-lysine potassium salt (2.0 g, 5.1 mmol) suspended in a mixture of THF (20 mL), DIEA (1.5 mL, 8.6 mmol) and chloroacetyl chloride (0.8 mL, 10.1 mmol). The reaction mixture was stirred for a period of 30 min. Then, a solution of 2N HCl (20 mL) was added and the solution extracted with EtOAc (25 mL, 3×). The organic phase was dried with MgSO$_4$, filtered and evaporated to a brown oil. The crude material was purified by flash chromatography using a solvent gradient from 39:1 to 19:1 CH$_2$Cl$_2$/MeOH. The product was isolated as a yellowish oil (1.7 g, 78% yield).

Rf=0.43 (EtOAc/hexane, 9:1). LC-MS: 464 (M+H)$^+$, 90% pure.

Step B. Preparation of Nα-isobutyl-Nα-(4-methylbenzenesulfonyl)-Nε-iodoacetyl-L-lysine To a solution of Nα-isobutyl-Nα-(4-methylbenzenesulfonyl)-Nε-chloroacetyl-L-lysine (1.7 g, 3.9 mmol) in dry acetone (20 mL) was added NaI (1.5 g, 10.0 mmol). The resulting mixture was stirred at room temperature for a period of 24 h. The precipitate NaCl was filtered off and the solvent evaporated to an oil. The crude material was dissolved in CH$_2$Cl$_2$ to precipitate the remaining NaI which was filtered off. The filtrate was washed with a 5% aqueous solution of NaHSO$_3$ (10 mL) and with water (25 mL, 3×). The organic solvent was dried, filtered and evaporated to a brown oil (1.98 g, 96% yield) which was used without further purification in the next step.

$^1$H NMR (DMSO-d$_6$): δ 0.81 (d, J=6.5, 3H), 0.83 (d, J=6.3, 3H), 1.20 (m, 2H), 1.33 (m, 2H), 1.45 (m, 1H), 1.81 (m, 1H), 1.89 (m, 1H), 2.38 (s, 3H), 2.95 (m, 4H), 3.60 (s, 2H), 4.18 (t, J=7.2, 1H), 7.38 (d, J=7.6, 2H), 7.67 (d, J=7.6, 2H), 8.17 (t, J=5.0, 1H), 12.70 (br s, 1H). LC-MS: 556 (M+H)$^+$, 99% pure.

Step C. Preparation of Nα-isobutyl-Nα-(4-methylbenzenesulfonyl)-Nε-(N'α-phenylglycyl)-L-lysine The title compound was prepared from Nα-isobutyl-Nα-(4-methylbenzenesulfonyl)-Nε-iodoacetyl-L-lysine (200 mg, 0.38 mmol, product of step B above) by following the indications of general procedure H using DIEA (0.19 mL, 1.09 mmol) and aniline (0.16 mL, 1.76 mmol). The crude material was purified by preparative HPLC. The product was isolated as a solid (90 mg, 48% yield).

$^1$H NMR (DMSO-d$_6$): δ 0.79 (d, J=6.7, 3H), 0.81 (d, J=6.9, 3H), 1.15 (m, 2H), 1.32 (m, 2H), 1.41 (m, 1H), 1.77 (m, 1H), 1.88 (m, 1H), 2.37 (s, 3H), 2.90–3.01 (m, 4H), 3.58 (d, J=3.1, 2H), 4.14 (t, J=7.1, 1H), 5.86 (s, 1H), 6.52 (t, J=7.7, 2H), 6.57 (t, J=7.1, 1H), 7.08 (t, J=7.6, 2H), 7.36 (d, J=7.6, 2H), 7.66 (d, J=8.2, 2H), 7.80 (t, J=5.0, 1H), 12.5 (s, 1H). LC-MS: 490 (M+H)$^+$, 99% pure.

Example 106

Preparation of Nα-isobutyl-Nα-(4-methylbenzenesulfonyl)-Nε-[N'α-(3-pyridyl)glycyl]-L-lysine The title compound was prepared from Nα-isobutyl-Nα-(4-methylbenzenesulfonyl)-Nε-iodoacetyl-L-lysine (200 mg, 0.38 mmol, example 105, step B) by following the indications of general procedure H using DIEA (0.19 mL, 1.09 mmol) and 3-aminopyridine (175 mg, 1.36 mmol). The crude material was purified by preparative HPLC. The product was isolated as a solid (42 mg, 22% yield).

$^1$H NMR (DMSO-d$_6$): δ 0.75 (d, J=6.7, 3H), 0.81 (d, J=6.7, 3H), 1.23–1.37 (m, 4H), 1.46 (m, 1H), 1.84 (m, 1H), 1.99 (m, 1H), 2.31 (s, 3H), 2.85 (m, 1H), 3.07 (m, 3H), 3.95 (t, J=6.6, 1H), 5.21 (d, J=9.3, 2H), 7.01 (s, 2H), 7.26 (d, J=8.0, 2H), 7.55 (d, J=8.6, 2H), 7.62 (t, J=7.0, 1H), 7.75 (d, J=7.8, 2H), 8.03 (d, J=5.4, 1H), 8.21 (s, 1H), 9.28 (t, J=4.8, 1H). LC-MS: 491 (M+H)$^+$, 95% pure.

Example 107

Preparation of Nα-isobutyl-Nα-(4-methylbenzenesulfonyl)-Nε-[N'α-(2,3-dimethoxybenzyl)glycyl]-L-lysine The title compound was prepared from Nα-isobutyl-Nα-(4-methylbenzenesulfonyl)-Nε-iodoacetyl-L-lysine (150 mg, 0.29 mmol, example 105, step B) by following the indications of general procedure H using DIEA (0.14 mL, 0.81 mmol) and 2,3-dimethoxybenzylamine (0.12 mL, 0.81 mmol). The crude material was purified by preparative HPLC. The product was isolated as a solid (25 mg, 16% yield).

$^1$H NMR (DMSO-d$_6$): δ 0.79 (d, J=6.9, 3H), 0.81 (d, J=6.9, 3H), 1.20 (m, 2H), 1.30–1.50 (m, 3H), 1.75–1.95 (m, 2H), 2.36 (s, 3H), 2.90–3.05 (m, 4H), 3.09 (s, 2H), 3.68 (s, 2H), 3.72 (s, 3H), 3.79 (s, 3H), 4.16 (t, J=6.6, 1H), 6.95 (m, 2H), 7.01 (d, J=7.6, 1H), 7.35 (d, J=7.9, 2H), 7.67 (d, J=8.0, 2H), 7.80 (t, J=5.4, 1H). LC-MS: 564 (M+H)$^+$, 98% pure.

Example 108

Preparation of Nα-isobutyl-Nα-(4-methylbenzenesulfonyl)-Nε-[N'α-(2-pyridyl)glycyl]-L-lysine The title compound was prepared from Nα-isobutyl-Nα-(4-methylbenzenesulfonyl)-Nε-iodoacetyl-L-lysine (200 mg, 0.38 mmol, example 105, step B) by following the indications of general procedure H using DIEA (0.19 mL, 1.09 mmol) and 2-aminopyridine (170 mg, 1.31 mmol). The crude material was purified by preparative HPLC. The product was isolated as a solid (88 mg, .47% yield).

$^1$H NMR (DMSO-d$_6$): δ 0.79 (d, J=6.1, 3H), 0.82 (d, J=6.4, 3H), 1.26 (m, 2H), 1.39–1.50 (m, 3H), 1.75–1.90 (m, 2H), 2.37 (s, 3H), 2.87–3.04 (m, 4H), 4.21 (t, J=6.6, 1H), 4.90 (s, 2H), 6.88 (t, J=6.5, 1H), 7.05 (d, J=8.9, 1H), 7.37 (d, J=7.9, 2H), 7.67 (d, J=8.1, 2H), 7.88 (t, J=8.1, 1H), 7.95 (d, J=6.3, 1H,), 8.33 (t, J=5.6 1H), 8.41 (s, 2H), 12.7 (s, 1H). LC-MS: 491 (M+H)$^+$, 99% pure.

Example 109

Preparation of Nα-isobutyl-Nα-(4-methylbenzenesulfonyl)-Nε-(N'α-benzylglycyl)-L-lysine The title compound was prepared from Nα-isobutyl-Nα-(4-methylbenzenesulfonyl)-Nε-iodoacetyl-L-lysine (200 mg, 0.38 mmol, example 105, step B) by following the indications of general procedure H using DEEA (0.20 mL, 1.10 mmol) and benzylamine (320 mg, 2.99 mmol). The crude material was purified by preparative HPLC. The product was isolated as a solid (137 mg, 71% yield).

$^1$H NMR (CDCl$_3$): δ 0.81 (s, 6H), 1.26–1.60 (m, 5H), 1.80–2.05 (m, 2H), 2.40 (s, 3H), 2.90–3.00 (m, 3H), 3.04 (s,

1H), 3.19 (m, 2H), 3.87 (s, 1H), 4.26 (s, 2H), 6.16 (s, 4H), 7.28 (d, J=5.3, 2H), 7.38 (m, 3H), 7.48 (d, J=4.5, 2H), 7.70 (d, J=7.5, 2H), 8.90 (s, 1H). LC-MS: 502 (M−H)⁻, 99% pure.

Example 110

Preparation of Nα-isobutyl-Nα-(4-methylbenzenesulfonyl)-Nε-[N'α-(piperidinyl-N-ethyl)glycyl]-L-lysine trifluoroacetic acid salt The title compound was prepared from Nα-isobutyl-Nα-(4-methylbenzenesulfonyl)-Nε-iodoacetyl-L-lysine (150 mg, 0.29 mmol, example 105, step B) by following the indications of general procedure H using DIEA (0.12 mL, 0.69 mmol) and 1-(2-aminoethyl)piperidine (0.12 mL, 0.84 mmol). The crude material was purified by preparative HPLC. The product was isolated as a solid (65 mg, 33% yield).

$^1$H NMR (DMSO-d$_6$): δ 0.80 (d, J=6.3, 3H), 0.82 (d, J=6.7, 3H), 1.24–2.00 (m, 13H), 2.38 (s, 3H), 2.85–3.40 (m, 12H), 3.76 (s, 2H), 4.21 (t, J=6.7, 1H), 7.37 (d, J=7.9, 2H), 7.67 (d, J=8.0, 2H), 8.49 (t, J=5.0, 1H), 9.25 (s, 2H). LC-MS: 525 (M+H)⁺, 99% pure.

Example 111

Preparation of Nα-isobutyl-Nα-(4-methylbenzenesulfonyl)-Nε-[N'α-(4-morpholinyl-N-ethyl)glycyl]-L-lysine The title compound was prepared from Nα-isobutyl-Nα-(4-methylbenzenesulfonyl)-Nε-iodoacetyl-L-lysine (150 mg, 0.29 mmol, example 105, step B) by following the indications of general procedure H using DIEA (0.12 mL, 0.69 mmol) and 4-(2-aminoethyl)morpholine (0.11 mL, 0.84 mmol). The crude material was purified by preparative HPLC. The product was isolated as a solid (51 mg, 34% yield).

$^1$H NMR (DMSO-d$_6$): δ 0.80 (d, J=6.1, 3H), 0.82 (d, J=7.0, 3H), 1.24–1.30 (m, 2H), 1.35–1.55 (m, 3H), 1.75–1.95 (m, 2H), 2.38 (s, 3H), 2.80–3.25 (m, 10H), 3.30 (s, 2H), 3.75 (s, 6H), 4.21 (t, J=7.1, 1H), 7.37 (d, J=8.3, 2H), 7.68 (d, J=8.4, 2H), 8.47 (m, 1H). LC-MS: 525 (M−H)⁻, 99% pure.

Example 112

Preparation of Nα-isobutyl-Nα-(4-methylbenzenesulfonyl)-Nε-[N'α-(4-pyridyl)glycyl]-L-lysine The title compound was prepared from Nα-isobutyl-Nα-(4-methylbenzenesulfonyl)-Nε-iodoacetyl-L-lysine (150 mg, 0.29 mmol, example 105, step B) by following the indications of general procedure H using DIEA (0.10 mL, 0.57 mmol) and 4-aminopyridine (76 mg, 0.59 mmol). The crude material was purified by preparative HPLC. The product was isolated as a solid (39 mg, 28% yield).

$^1$H NMR (DMSO-d$_6$): δ 0.79 (d, J=6.8, 3H), 0.81 (d, J=6.5, 3H), 1.25 (m, 2H), 1.35–1.51 (m, 3H), 1.78–1.91 (m, 2H), 2.37 (s, 3H), 2.90 (m, 1H), 3.00 (m, 3H), 4.20 (t, J=7.1, 1H), 4.85 (s, 2H), 6.80 (d, J=6.7, 2H), 7.37 (d, J=8.2, 2H), 7.67 (d, J=7.6, 2H), 8.02 (d, J 7.0, 2H), 8.15 (s, 2H), 8.37 (t, J=4.9, 1H), 12.74 (br s, 1H). LC-MS: 489 (M−H)⁻, 99% pure.

Example 113

Preparation of Nα-isobutyl-Nα-(4-methylbenzenesulfonyl)-Nε-[N'α-(3-quinolyl)glycyl]-L-lysine The title compound was prepared from Nα-isobutyl-Nα-(4-methylbenzenesulfonyl)-Nε-iodoacetyl-L-lysine (200 mg, 0.38 mmol, example 105, step B) by following the indications of general procedure H using DEEA (0.19 mL, 1.09 mmol) and 3-aminoquinoline (260 mg, 1.80 mmol). The crude material was purified by preparative HPLC. The product was isolated as a solid (24 mg, 12% yield).

$^1$H NMR (DMSO-d$_6$): δ 0.76 (d, J=5.9, 3H), 0.82 (d, J=6.5, 3H), 1.26–1.50 (m, 5H), 1.80–2.10 (m, 2H), 2.34 (s, 3H), 2.86 (m, 1H), 3.04–3.20 (m, 2H), 4.00 (m, 1H), 5.67 (d, J=4.8, 2H), 6.85 (s, 2H), 7.29 (d, J=7.8, 2H), 7.75 (m, 4H), 8.02 (s, 1H), 8.07 (d, J=8.0, 1H), 8.12 (d, J=8.5, 1H), 8.97 (m, 1H), 9.05 (s, 1H). LC-MS: 539 (M−H)⁻, 95% pure.

Example 114

Preparation of Nα-isobutyl-Nα-(4-methylbenzenesulfonyl)-Nε-(N'α-benzyl-N'α-phenylglycyl)-L-lysine Step A. Preparation of N-benzyl-N-phenylglycine Commercially available N-phenylglycine (1.51 g, 10.0 mmol) dissolved in THF (20 mL) was treated with butyllithium 2.5M in hexane (8.8 mL, 22.0 mmol) under an inert atmophere of argon at −78° C. The mixture was stirred for 15 min before the addition of benzylbromide (1.3 mL, 11 mmol). The reaction mixture was stirred for 2 h while warming up to room temperature. Then, 2N HCl (25 mL) was added and the mixture extracted with EtOAc (30 mL, 3×). The organic phase was dried over MgSO$_4$, filtered and concentrated to an oil. The crude material was purified by flash chromatography using a solvent gradient from 19:1 to 9:1 CH$_2$Cl$_2$/MeOH. The product was isolated as a brown and hardy oil (1.98 g, 82%).

$^1$H NMR (CDCl$_3$): δ 4.16 (s, 2H), 4.68 (s, 2H), 6.76 (d, J=8.5, 2H), 6.83 (t, J=7.2, 1H), 7.27 (t, J=6.1, 2H), 7.33 (m, 3H), 7.38 (t, J=7.6, 2H), 10.70 (s, 1H).

Step B. Preparation of Nα-isobutyl-Nα-(4-methylbenzenesulfonyl)-Nε-(N'α-benzyl-N'α-phenylglycyl)-L-lysine The title compound was prepared from solid phase bound Nα-isobutyl-Nα-(4-methylbenzenesulfonyl)-Nε-(9-fluorenylmethoxycarbonyl)-L-lysine (200 mg) in a similar fashion to general procedure Bb using N-benzyl-N-phenylglycine (100 mg, 0.45 mmol) prepared in step A of this example with DCC (200 mg, 0.97 mmol) and HOBt (100 mg, 0.74 mmol) as the activating reagents. The final product was purified by preparative HPLC to yield 21 mg (75%) of the desired material.

$^1$H NMR (DMSO-d$_6$): δ 0.79 (d, J=6.9, 3H), 0.82 (d, J=7.2, 3H), 1.17 (m, 2H), 1.33 (m, 2H), 1.42 (m, 1H), 1.77 (m, 1H), 1.88 (m, 1H), 2.37 (s, 3H), 2.90–3.01 (m, 4H), 3.94 (s, 2H), 4.16 (t, J=7.2, 1H), 4.62 (s, 2H), 6.59 (m, 3H), 7.11 (t, J=7.5, 2H), 7.24 (m, 3H), 7.31 (t, J=7.3, 2H), 7.36 (d, J=7.6, 2H), 7.66 (d, J=8.5, 2H), 7.87 (t, J=5.3, 1H), 12.6 (s, 1H). LC-MS: 578 (M+H)⁺, 85% pure.

Example 115

Preparation of Nα-isobutyl-Nα-(4-methylbenzenesulfonyl)-Nε-(N'α-methyl-N'α-phenylglycyl)-L-lysine Step A. Preparation of N-methyl-N-phenylglycine The title compound was prepared from N-phenylglycine (200 mg, 1.3 mmol) as described for the preparation of N-benzyl-N-phenylglycine (example 114, step A) using methyl iodide (1 mL, 6.6 mmol) instead of benzylbromide. The crude material was purified by preparative HPLC. The product was isolated as a solid (90 mg, 41% yield).

$^1$H NMR (CDCl$_3$): δ 3.07 (s, 3H), 4.09 (s, 2H), 6.73 (d, J=7.7, 2H), 6.80 (t, J=7.2, 1H), 7.27 (t, J=7.3, 2H), 8.45 (s, 1H).

Step B. Preparation of Nα-isobutyl-Nα-(4-methylbenzenesulfonyl)-Nε-(N'α-methyl-N'α-phenylglycyl)-L-lysine The title compound was prepared from solid phase bound Nα-isobutyl-Nα-(4-methylbenzenesulfonyl)-Nε-(9-fluorenylmethoxycarbonyl)-L-lysine (200 mg) in a similar fashion to general procedure Bb using N-methyl-N-phenylglycine (75 mg, 0.45 mmol) prepared in step A of this example with DCC (200 mg, 0.97 mmol) and HOBt (100 mg, 0.74 mmol) as the activating reagents. The final product was purified by preparative HPLC to yield 7 mg (25%) of the desired material.

$^1$H NMR (DMSO-$d_6$): δ 0.79 (d, J=6.5, 3H), 0.82 (d, J=7.0, 3H), 1.16 (m, 2H), 1.32 (m, 2H), 1.41 (m, 1H), 1.77 (m, 1H), 1.88 (m, 1H), 2.37 (s, 3H), 2.90–3.01 (m, 4H), 2.96 (s, 3H), 3.82 (s, 2H), 4.16 (t, J=7.0, 1H), 6.62 (11, 3H), 7.16 (t, J=7.4, 2H), 7.36 (d, J=8.1, 2H), 7.66 (d, J=8.0, 2H), 7.80 (t, J=4.3, 1H), 12.7 (s, 1H). LC-MS: 502 (M+H)$^+$, 98% pure.

Example 116

Preparation of (2S, 2'S) 2-N-isobutyl-2-N-(4-methylbenzenesulfonyl)-6-N-[N'α-(4-methylbenzenesulfonyl)-S-tryptophanyl]-2,6-diaminohexanal Step A. Preparation of (2S) 2-N-isobutyl-2-N-(4-methylbenzenesulfonyl)-2,6-diaminohexanal A solution of Nα-isobutyl-Nα-(4-methylbenzenesulfonyl)-L-lysine (12.0 g, 30.5 mmol, example 1, step E) dissolved in MeOH (100 mL) was treated with of trimethylsilyl chloride (20 mL). The mixture was refluxed 5 h before stirring at room temperature for 5 h. Afterwards, the solution was evaporated and placed under high vacuum until a hard foam was obtained (13.6 g). This was dissolved in dry THF (100 mL) and added dropwise to a solution of LiAlH$_4$ (5.0 g, 131.6 mmol) in THF (300 mL). The solution was stirred for 2 h, then heated to reflux for 20 min. After cooling in an ice bath the solution was quenched by addition of MeOH (5 mL), water (5 mL), then 10% NaOH (5 mL). The solvent was evaporated and the precipitate dissolved in MeOH (200 mL) was stirred for 2 h at 60° C. The granular precipitate formed was filtered off through celite, and the liquor was concentrated to form a clear oil which solidified on standing (8.48 g, 81%).

$^1$H NMR (CDCl$_3$): δ 0.85 (d, J=6.3, 3H), 0.90 (d, J=6.3, 3H), 1.00–1.08 (m, 1H), 1.29–1.34 (m, 3H), 1.92–1.97 (m, 1H), 2.35 (s, 3H), 2.50 (t, J=6.7, 2H), 2.80–3.09 (m, 4H), 3.52 (d, J=5.1, 2H), 3.60–3.62 (t, J=6.8, 1H), 7.22 (d, J=7.8, 2H), 7.63 (d, J=7.8, 2H).

Step B. Preparation of (2S, 2'S) 2-N-isobutyl-2-N-(4-methylbenzenesulfonyl)-6-N-[N'α-(4-methylbenzenesulfonyl)-S-tryptophanyl]-2,6-diaminohexanol The title product was prepared from (2S) 2-N-isobutyl-2-N-(4-methylbenzenesulfonyl)-2,6-diaminohexanol (400 mg, 1.2 mmol, step A) following the indications of general procedure Bd using Nα-(4-methylbenzenesulfonyl)-L-tryptophan (450 mg, 1.3 mmol, example 2, step A), EDC (290 mg, 1.5 mmol) and HOBt (100 mg, 1.5 mmol). The crude material was purified by flash chromatography using a solvent gradient from 39:1 to 19:1 CH$_2$Cl$_2$/MeOH. The product was isolated as a yellowish oil (420 mg, 48% yield).

$^1$H NMR (CDCl$_3$): δ 0.93 (t, J=6.8, 6H), 0.98 (m, 1H), 1.26 (m, 3H), 1.42 (m, 1H), 1.93 (m, 4H), 2.38 (s, 3H), 2.42 (s, 3H), 2.91 (m, 1H), 3.05 (m, 3H), 3.13 (m, 2H), 3.56 (m, 2H), 3.66 (m, 1H), 3.91 (d, J=5.6, 1H), 5.08 (d, J=5.9, 1H), 6.32 (t, J=4.1, 1H), 6.95 (s, 1H), 7.02 (t, J=7.5, 1H), 7.12 (d, J=7.4, 2H), 7.19 (t, J=7.5, 1H), 7.29 (d, J=8.6, 2H), 7.35 (d, J=7.8, 1H), 7.51 (d, J=7.3, 2H), 7.72 (d, J=7.9, 2H), 8.54 (s, 1H). LC-MS: 681 (M–H)$^-$, 98% pure.

Step C. Preparation of (2S, 2'S) 2-N-isobutyl-2-N-(4-methylbenzenesulfonyl)-6-N-[N'α-(4-methylbenzenesulfonyl)-S-tryptophanyl]-2,6-diaminohexanal The title compound was prepared from the previous derivative (400 mg, 0.59 mmol) by oxidation under Swern's reaction conditions using oxalyl chloride (110 μL, 1.2 mmol), DMSO (166 μL, 2.4 mmol), and triethylamine (2 mL) (Organic Syntheses, Collective Volume VII, p. 258–263). The crude material was purified by flash chromatography using a solvent gradient from 39:1 to 19:1 CH$_2$Cl$_2$/MeOH. The product was isolated as a yellowish solid (330 mg, 83% yield).

$^1$H NMR (DMSO-$d_6$): δ 0.82 (t, J=7.6, 6H), 0.92 (m, 1H), 1.09 (m, 1H), 1.31 (m, 3H), 1.72 (m, 1H), 1.83 (m, 1H), 2.33 (s, 3H), 2.37 (s, 3H), 2.73 (d, J=4.8, 1H), 2.96 (m, 5H), 4.08 (t, J=6.1, 1H), 4.72 (n, 1H), 6.93 (t, J=7.4, 1H), 6.99 (t, J=7.3, 1H), 7.15 (d, J=7.6, 1H), 7.37 (m, 6H), 7.61 (d, J=7.5, 1H), 7.72 (d, J=7.6, 2H), 8.02 (t, J=5.7, 1H), 9.51 (s, 1H), 11.35 (s, 1H).

Example 117

Preparation of (2S, 2'S) 2-N-isobutyl-2-N-(4-methylbenzenesulfonyl)-6-N-(N'α-pivaloyl-S-tryptophanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-pivaloyl-L-tryptophan (example 100, step A). Purification by HPLC gave 85 mg (48%) of the desired material.

$^1$H NMR (CDCl$_3$): δ 0.90–0.98 (m, 6H), 1.09–1.16 (m, 1H), 1.23 (s, 9H), 1.25–1.29 (m, 1H), 1.45–1.52 (m, 1H), 1.92–1.97 (m, 1H), 2.38 (s, 3H), 2.82–3.10 (m, 4H), 3.11–3.26 (m, 3H), 3.51–3.55 (m, 1H), 3.51 (d, J=7.0, 2H), 4.64 (br s, 1H), 6.97–7.21 (m, 6H), 7.35 (q, J=6.7, 1H), 7.61 (d, J=7.1, 1H), 7.69 (d, J=7.6, 1H). LC-MS: 611.2 (M–H)$^-$, 95% pure.

Example 118

Preparation of (2S, 2'S) 2-N-isobutyl-2-N-(4-methylbenzenesulfonyl)-6-N-(N'α-acetyl-S-phenylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-acetyl-L-phenylalanine (example 30, step A). Purification by HPLC gave 82 mg (51%) of the desired material.

$^1$H NMR (CDCl$_3$): δ 8.79 (d, J=6.3, 3H), 0.82 (d, J=6.3, 3H), 1.08–1.11 (m, 2H), 1.23–1.31 (m, 2H), 1.45–1.52 (m, 1H), 1.92–1.97 (m, 1H), 1.98 (d, J=9.0, 3H), 2.38 (s, 3H), 2.84–3.09 (m, 6H), 3.51 (d, J=7.1, 2H), 3.61–3.64 (m, 1H), 4.51 (q, J=6.9, 1H), 7.09–7.26 (m, 7H), 7.73 (d, J=8.1, 2H). LC-MS: 530.4 (M–H)$^-$, 99% pure.

Example 119

Preparation of (2S, 2'S) 2-N-isobutyl-2-N-(4-methylbenzenesulfonyl)-6-N-(N'α-pivaloyl-S-phenylalanyl)-2,6-diaminohexanol The title product was prepared from (2S) 2-N-isobutyl-2-N-(4-methylbenzenesulfonyl)-2,6-diaminohexanal (example 116, step A) following the indications of general procedure Bd using Nα-pivaloyl-L-phenylalanine (example 52, step A). Purification by HPLC gave 65 mg (37%) of the desired material.

$^1$H NMR (CDCl$_3$): δ 0.79 (d, J=6.3, 3H), 0.82 (d, J=6.3, 3H), 1.08–1.11 (m, 2H), 1.13 (s, 9H), 1.23–1.31 (m, 2H), 1.45–1.52 (m, 1H), 1.92–1.97 (m, 1H), 2.38 (s, 3H), 2.84–3.09 (m, 6H), 3.51 (d, J=7.1, 2H), 3.2 (t, J=6.1, 1H), 4.51 (q, J=6.9, 1H), 7.09–7.26 (m, 7H), 7.73 (d, J=7.9, 2H). LC-MS: 572.2 (M–H)$^-$, 99% pure.

Example 120

Preparation of (2S, 2'S) 2-N-isobutyl-2-N-(4-methylbenzenesulfonyl)-6-N-[N'α-(4-morpholinecarbonyl)-S-phenylalanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-morpholinecarbonyl)-L-phenylalanine (example 51, step A). Purification by HPLC gave 69 mg (38%) of the desired material.

$^1$H NMR (CDCl$_3$): δ 0.79 (d, J=6.3, 3H), 0.82 (d, J=6.3, 3H), 1.08–1.11 (m, 2H), 1.23–1.31 (m, 2H), 1.45–1.52 (m, 1H), 1.92–1.97 (m, 1H), 2.39 (s, 3H), 2.84–3.09 (m, 6H), 3.21–3.31 (m, 4H), 3.45–3.64 (m, 7H), 4.48 (br s, 1H), 7.09–7.26 (m, 7H), 7.73 (d, J=8.1, 2H). LC-MS: 601.1 (M–H)$^-$, 99% pure.

Example 121

Preparation of (2S, 2'S) 2-N-isobutyl-2-N-(4-methylbenzenesulfonyl)-6-N-[N'α-(4-acetylaminobenzenesulfonyl)-S-phenylalanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-acetamidobenzenesulfonyl)-L-phenylalanine (example 3, step A). Purification by HPLC gave 103 mg (49%) of the desired material.

$^1$H NMR (CDCl$_3$): δ 0.79 (d, J=6.3, 3H), 0.82 (d, J=6.3, 3H), 1.08–1.11 (m, 2H), 1.23–1.31 (m, 2H), 1.45–1.52 (m, 1H), 1.92–1.97 (m, 1H), 2.20 (s, 3H), 2.38 (s, 3H), 2.85–3.02 (m, 6H), 3.51 (d, J=7.1, 2H), 3.64 (q, J=6.4, 1H), 3.88 (q, J=6.9, 1H), 6.89 (br s, 2H), 7.19 (br s, 3H), 7.24 (d, J=8.0, 2H), 7.54–7.61 (m, 4H), 7.73 (d, J=8.1, 2H). LC-MS: 685.2 (M–H)$^-$, 99% pure.

Example 122

Preparation of (2S, 2'S) 2-N-isobutyl-2-N-(4-methylbenzenesulfonyl)-6-N-[N'α-(2-thiophenesulfonyl)-S-phenylalanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(2-thiophenesulfonyl)-L-phenylalanine (example 24, step A). Purification by HPLC gave 69 mg (36%) of the desired material.

$^1$H NMR (CDCl$_3$): δ 0.79 (d, J=6.3, 3H), 0.82 (d, J=6.3, 3H), 1.08–1.11 (m, 2H), 1.28–1.35 (m, 2H), 1.45–1.52 (m, 1H), 1.92–1.97 (m, H), 2.39 (s, 3H), 2.85–3.18 (m, 6H), 3.51 (d, J=7.0, 2H), 3.64 (q, J=6.4, 1H), 3.94 (q, J=6.9, 1H), 6.91–6.98 (m, 3H), 7.19 (br s, 3H), 7.24 (d, J=8.0, 2H), 7.35 (s, 1H), 7.52 (d, J=4.1, 1H), 7.73 (d, J=8.1, 2H). LC-MS: 634.2 (M–H)$^-$, 99% pure.

Example 123

Preparation of (2S, 2'S) 2-N-isobutyl-2-N-(4-methylbenzenesulfonyl)-6-N-(N'α-benzenesulfonyl-S-phenylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-benzenesulfonyl-L-phenylalanine (example 8, step A). Purification by HPLC gave 68 mg (36%) of the desired material.

$^1$H NMR (CDCl$_3$): δ 0.79 (d, J=6.3, 3H), 0.82 (d, J=6.3, 3H), 1.08–1.11 (m, 2H), 1.28–1.35 (m, 2H), 1.45–1.52 (m, 1H), 1.92–1.97 (m, 1H), 2.41 (s, 3H), 2.85–3.18 (m, 6H), 3.51 (d, J=7.0, 2H), 3.64 (q, J=6.4, 1H), 3.84 (q, J=6.9, 1H), 6.88 (d, J=6.6, 2H), 7.14–7.19 (m, 3H), 7.24 (d, J=8.0, 2H), 7.35 (t, J=6.8, 2H), 7.52 (t, J=7.1, 1H), 7.60 (d, J=6.8, 2H), 7.72 (d, J=8.0, 2H). LC-MS: 628.2 (M–H)$^-$, 99% pure.

Example 124

Preparation of (2S, 2'S) 2-N-isobutyl-2-N-(4-methylbenzenesulfonyl)-6-N-[N'α-(4-methylbenzenesulfonyl)-S-4-nitrophenylalanyl]-2,6-diaminohexanal The title product was prepared from (2S) 2-N-isobutyl-2-N-(4-methylbenzenesulfonyl)-2,6-diaminohexanol (example 116, step A) following the indications of general procedure Bd using Nα-(4-methylbenzenesulfonyl)-L-4-nitrophenylalanine (example 26, step A). Purification by HPLC gave 101 mg (48%) of the desired material.

$^1$H NMR (CDCl$_3$): δ 0.89–0.97 (m, 6H), 1.18–1.21 (m, 2H), 1.35–1.45 (m, 3H), 1.92–1.97 (m, 1H), 2.33 (s, 3H), 2.39 (s, 3H), 2.85–3.01 (m, 3H), 3.15–3.24 (m, 3H), 3.51 (d, J=7.0, 2H), 3.71 (q, J=6.4, 1H), 3.98 (br s, 1H), 7.01 (d, J=7.6, 2H), 7.19 (d, J=8.0, 2H), 7.24 (d, J=8.0, 2H), 7.39 (d, J=7.7, 2H), 7.73 (d, J=8.1, 2H), 7.88 (d, J=7.9, 2H). LC-MS: 687.8 (M–H)$^-$, 99% pure.

Example 125

Preparation of (2S, 2'S) 2-N-isobutyl-2-N-(4-methylbenzenesulfonyl)-6-N-[N'α-(4-fluorobenzenesulfonyl)-S-phenylalanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-fluorobenzenesulfonyl)-L-phenylalanine (example 18, step A). Purification by HPLC gave 66 mg (34%) of the desired material.

$^1$H NMR (CDCl$_3$): δ 0.79 (d, J=6.3, 3H), 0.82 (d, J=6.3, 3H), 1.09–1.16 (m, 2H), 1.35–1.39 (m, 2H), 1.45–1.52 (m, 1H), 1.92–1.97 (m, 1H), 2.42 (s, 3H), 2.82–3.18 (m, 6H), 3.51 (d, J=7.0, 2H), 3.64 (q, J=6.3, 1H), 3.79 (q, J=6.9, 1H), 6.91 (d, J=7.0, 2H), 7.00 (t, J=6.8, 2H), 7.15–7.21 (m, 3H), 7.35 (s, 1H), 7.52 (d, J=7.1, 1H), 7.54 (q, J=6.6, 2H), 7.73 (d, J=8.1, 2H). LC-MS: 647.6 (M–H)$^-$, 99% pure.

Example 126

Preparation of (2S, 2'S) 2-N-isobutyl-2-N-(4-methylbenzenesulfonyl)-6-N-[N'α-(4-methoxybenzenesulfonyl)-S-phenylalanyl]-2,6-diaminohexanol Step A. Preparation of Nα-(4-methoxybenzenesulfonyl)-L-phenylalanine L-phenylalanine was reacted with 4-methoxybenzenesulfonyl chloride under the conditions used in general procedure A giving the title compound which was used without purification in the next step.

Step B. Preparation of (2S, 2'S) 2-N-isobutyl-2-N-(4-methylbenzenesulfonyl)-6-N-[N'α-(4-methoxybenzenesulfonyl)-S-phenylalanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-methoxybenzenesulfonyl)-L-phenylalanine (this example, step A). Purification by HPLC gave 107 mg (53%) of the desired material.

$^1$H NMR (CDCl$_3$): δ 0.79 (d, J=6.3, 3H), 0.82 (d, J=6.3, 3H), 1.09–1.16 (m, 2H), 1.35–1.39 (m, 2H), 1.45–1.52 (m, 1H), 1.94–1.97 (m, 1H), 2.40 (s, 3H), 2.82–3.18 (m, 6H), 3.51 (d, J=7.0, 2H), 3.64 (q, J=6.3, 1H), 3.79 (q, J=6.9, 1H), 3.92 (s, 3H), 6.87 (d, J=6.9, 2H), 6.89 (d, J=7.0, 2H), 7.15–7.21 (m, 3H), 7.35 (d, J=7.1, 2H), 7.50 (d, J=7.1, 1H), 7.73 (d, J=8.1, 2H). LC-MS: 658.3 (M–H)$^-$, 99% pure.

Example 127

Preparation of (2S, 2'S) 2-N-isobutyl-2-N-(4-methylbenzenesulfonyl)-6-N-[N'α-(4-trifluoromethylbenzenesulfonyl)-S-phenylalanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-trifluoromethylbenzenesulfonyl)-L-phenylalanine (example 23, step A). Purification by HPLC gave 49 mg (23%) of the desired material.

$^1$H NMR (CDCl$_3$): δ 0.79 (d, J=6.3, 3H), 0.82 (d, J=6.3, 3H), 1.09–1.16 (m, 2H), 1.25–1.40 (m, 4H), 1.92–1.97 (m, 1H), 2.44 (s, 3H), 2.78–3.18 (m, 6H), 3.51 (d, J=6.8, 2H), 3.64 (q, J=6.3, 1 H), 3.84 (q, J=5.9, 1H), 6.91 (d, J=7.0, 2H), 7.03–7.21 (m, 3H), 7.30 (d, J=6.8, 2H), 7.52 (d, J=7.1, 2H), 7.60 (d, J=6.9, 2H), 7.71 (d, J=7.1, 2H). LC-MS: 696.2 (M–H)$^-$, 99% pure.

Example 128

Preparation of (2S, 2'S) 2-N-isobutyl-2-N-(4-methylbenzenesulfonyl)-6-N-(N'α-benzenesulfonyl-S-tryptophanyl)-2,6-diaminohexanol The title product was prepared from (2S) 2-N-isobutyl-2-N-(4-methylbenzenesulfonyl)-2,6-diaminohexanal (example 116, step A) following the indications of general procedure Bd using Nα-benzenesulfonyl-L-tryptophan (example 4, step A). Purification by HPLC gave 93 mg (46%) of the desired material.

1H NMR (CDCl$_3$): δ 0.84 (d, J=6.3, 3H), 0.89 (d, J=6.3, 3H), 0.94–1.03 (m, 1H), 1.09–1.16 (m, 2H), 1.46–1.49 (m, 1H), 1.93–1.98 (m, 1H), 2.39 (s, 3H), 2.82–3.15 (m, 6H), 3.51 (d, J=6.8, 2H), 3.64 (q, J=6.3, 1H), 3.94 (q, J=5.5, 1H), 6.95 (t, J=4.5, 1H), 7.19 (t, J=4.5, 1H), 7.23–7.31 (m, 6H), 7.42 (t, J=4.5, 1H), 7.60 (d, J=6.8, 2H), 7.73 (d, J=6.8, 2H). LC-MS: 667.5 (M–H)$^-$, 99% pure.

Example 129

Preparation of (2S, 2'S) 2-N-isobutyl-2-N-(4-methylbenzenesulfonyl)-6-N-[N'α-(2-thiophenesulfonyl)-S-tryptophanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(2-thiophenesulfonyl)-L-tryptophan (example 53, step A). Purification by HPLC gave 81 mg (40%) of the desired material.

$^1$H NMR (CDCl$_3$): δ 0.84 (d, J=6.3, 3H), 0.89 (d, J=6.3, 3H), 0.94–1.03 (m, 1H), 1.09–1.16 (m, 2H), 1.46–1.49 (m, 1H), 1.93–1.98 (m, 1H), 2.40 (s, 3H), 2.82–3.15 (m, 6H), 3.51 (d, J=6.8, 2H), 3.64 (q, J=6.3, 1H), 4.05 (t, J=7.2, 1H), 6.89 (t, J=4.6, 1H), 6.97 (s, 1H), 7.03 (t, J=4.5, 1H), 7.19 (t, J=4.5, 1H), 7.23–7.28 (m, 3H), 7.34–7.42 (m, 4H), 7.73 (d, J=6.8, 2H). LC-MS: 674.2 (M–H)$^-$, 99% pure.

Example 130

Preparation of (2S, 2'S) 2-N-isobutyl-2-N-(4-methylbenzenesulfonyl)-6-N-[N'α-(4-nitrobenzenesulfonyl)-S-tryptophanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-nitrobenzenesulfonyl)-L-tryptophan (example 5, step A). Purification by HPLC gave 101 mg (47%) of the desired material.

$^1$H NMR (CDCl$_3$): δ 0.90–0.98 (m, 6H), 1.09–1.16 (m, 2H), 1.35–1.39 (m, 2H), 1.45–1.52 (m, 1H), 1.92–1.97 (m, 1H), 2.46 (s, 3H), 2.82–3.10 (m, 4H), 3.11–3.26 (m, 3H), 3.51 (d, J=7.0, 2H), 3.74 (q, J=6.3, 1H), 3.95 (br s, 1H), 6.91 (t, J=7.0, 1H), 6.97 (s, 1H), 7.01 (t, J=6.8, 1H), 7.15 (d, J=6.6, 1H), 7.20–7.30 (m, 3H), 7.52 (d, J=7.1, 1H), 7.71 (d, J=6.9, 2H), 7.79 (d, J=7.1, 2H). LC-MS: 713.1 (M–H)$^-$, 99% pure.

Example 131

Preparation of (2S, 2'S) 2-N-isobutyl-2-N-(4-methylbenzenesulfonyl)-6-N-(N'α-acetyl-S-tryptophanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-acetyl-L-tryptophan (example 99, step A). Purification by HPLC gave 68 mg (39%) of the desired material.

$^1$H NMR (CDCl$_3$): δ 0.90–0.98 (m, 6H), 1.09–1.16 (m, 1H), 1.25–1.29 (m, 1H), 1.45–1.52 (m, 1H), 1.92–1.97 (m, 1H), 2.0 (s, 3H), 2.38 (s, 3H), 2.82–3.10 (m, 4H), 3.11–3.26 (m, 3H), 3.51 (d, J=7.0, 2H), 3.64 (q, J=6.3, 1H), 3.75 (br s, 1H), 6.97–7.21 (m, 6H), 7.35 (q, J=6.7, 1H), 7.61 (d, J=7.1, 1H), 7.69 (d, J=7.6, 1H). LC-MS: 569.1 (M–H)$^-$, 98% pure.

Example 132

Preparation of Nα-isobutyl-Nα-(4-methylbenzenesulfonyl)-Nε-[N'α-(4-methoxyphenylacetyl)-L-phenylalanyl]-L-lysine Step A. Preparation of Nα-(4-methoxyphenylacetyl)-L-phenylalanine L-phenylalanine was reacted with 4-methoxyphenylacetyl chloride under the conditions used in general procedure A giving the title compound which was recrystallised neat (80%) and used as such in the next step.

Step B. Preparation of Nα-isobutyl-Nα-(4-methylbenzenesulfonyl)-Nε-[N'α-(4-methoxyphenylacetyl)-L-phenylalanyl]-L-lysine The title compound was prepared from Nα-isobutyl-Nα-(4-methylbenzenesulfonyl)-L-lysine hydrochloride (100 mg, 0.25 mmol, example 1, step E) as described in general procedure Bc using Nα-(4-methoxyphenylacetyl)-L-phenylalanine (80 mg, 0.25 mmol) which was prepared in step A of this example. The final product was triturated with ether to yield 85 mg (18%) of the desired material.

$^1$H NMR (CDCl$_3$): δ 0.83 (d, J=6.9, 6H), 1.08–1.11 (m, 2H), 1.33–1.55 (m, 2H), 1.45–1.52 (m, 1H), 1.79–1.89 (m, 2H), 2.36 (s, 3H), 2.85–3.27 (m, 6H), 3.55 (s, 2H), 3.79 (s, 3H), 4.21 (s, 2H), 4.53 (t, J=5.9, 1H), 6.79 (d, J=8.2, 2H), 6.99–7.09 (m, 3H), 7.15–7.26 (in, 7H), 7.73 (d, J=8.1, 2H). LC-MS: 650.1 (M–H)$^-$, 98% pure.

Example 133

Preparation of Nα-isobutyl-Nα-(4-methylbenzenesulfonyl)-Nε-(N'α-dihydrocinnamoyl-L-tryptophanyl)-L-lysine Step A. Preparation of Nα-dihydrocinnamoyl-L-tryptophan L-tryptophan was reacted with Nα-dihydrocinnamoyl chloride under the conditions used in general procedure A giving the title compound which was recrystallised from DCM (55%). This material was used without further purification in the next step.

Step B. Preparation of Nα-isobutyl-Nα-(4-methylbenzenesulfonyl)-NE -(N'α-dihydrocinnamoyl-L-tryptophanyl)-L-lysine The title compound was prepared from Nα-isobutyl-Nα-(4-methylbenzenesulfonyl)-L-lysine hydrochloride (400 mg, 1.0 mmol, example 1, step E) as described in general procedure Bc using Nα-dihydrocinnamoyl-L-tryptophan (360 mg, 1.0 mmol) which was prepared in step A of this example. The final product was triturated with ether to yield 612 mg (85% pure) of the crude material. Purification of 100 mg of the crude material by HPLC gave 45 mg (45%) of pure adduct.

$^1$H NMR. (CDCl$_3$): δ 0.82 (d, J=6.8, 3H), 0.84 (d, J=6.8, 3H), 1.08–1.11 (m, 2H), 1.18–1.22 (m, 2H), 1.45–1.52 (m, 1H), 1.94–1.99 (m, 2H), 2.34 (s, 3H), 2.48–2.52 (m, 2H), 2.89–3.09 (m, 4H), 3.15–3.18 (m, 2H), 4.29 (br s, 1H), 4.77 (br s, 1H), 6.95 (t, J=7.2, 1H), 7.04–7.34 (m, 8H), 7.36 (d, J=8.1, 1H), 7.69 (d, J=7.2, 1H), 7.99 (d, J=8.1, 2H). LC-MS: 673.1 (M–H)$^-$, 98% pure.

Example 134

Preparation of (2S, 2'S) 2-N-isobutyl-2-N-(4-methylbenzenesulfonyl)-6-N-(N'α-tert-butoxycarbonyl-S-2-pyridylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-2-pyridylalanine (Peptech Corporation). Purification by HPLC gave 54 mg (30%) of the desired material.

$^1$H NMR (CDCl$_3$): δ 0.90–0.98 (m, 6H), 1.09–1.16 (m, 1H), 1.25–1.29 (m, 2H), 1.45 (s, 9H), 1.92–1.97 (m, 1H), 2.38 (s, 3H), 2.82–3.10 (m, 4H), 3.26 (br s, 2H), 3.51 (d, J=7.0, 2H), 3.64 (q, J=6.3, 1H), 4.55 (br s, 1H), 7.18–7.38 (m, 4H), 7.70 (t, J=6.8, 1H), 7.74 (d, J=7.5, 2H), 8.45 (s, 1H). LC-MS: 591.3 (M+H)$^+$, 98% pure.

Example 135

Preparation of (2S, 2'S) 2-N-isobutyl-2-N-(4-methylbenzenesulfonyl)-6-N-(N'α-tert-butoxycarbonyl-S-3-pyridylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-3-pyridylalanine (Peptech Corporation). Purification by HPLC gave 45 mg (25%) of the desired material.

$^1$H NMR (CDCl$_3$): δ 0.90–0.98 (m, 6H), 1.09–1.16 (m, 1H), 1.25–1.29 (m, 2H), 1.45 (s, 9H), 1.92–1.97 (m, 1H), 2.37 (s, 3H), 2.82–3.30 (m, 6H), 3.51 (d, J=7.0, 2H), 3.64 (q, J=6.3, 1H), 4.35 (br s, 1H), 7.18–7.38 (m, 4H), 7.60 (br s, 1H), 7.74 (d, J=7.5, 2H), 8.56 (d, J=6.6, 2H). LC-MS: 591.3 (M+H)$^+$, 95% pure.

Example 136

Preparation of (2S, 2'S) 2-N-isobutyl-2-N-(4-methylbenzenesulfonyl)-6-N-(N'α-tert-butoxycarbonyl-S-4-pyridylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-4-pyridylalanine (Peptech Corporation). Purification by HPLC gave 65 mg (36%) of the desired material.

$^1$H NMR (CDCl$_3$): δ 0.90–0.98 (m, 6H), 1.09–1.16 (m, 1H), 1.25–1.29 (m, 2H), 1.49 (s, 9H), 1.92–1.97 (m, 1H), 2.37 (s, 3H), 2.82–3.30 (m, 6H), 3.49–3.51 (m, 2H), 3.64 (br s, 1H), 4.35 (br s, 1H), 7.16 (s, 2H), 7.18–7.22 (m, 2H), 7.74 (d, J=7.5, 2H), 8.56 (br s, 2H). LC-MS: 591.3 (M+H)$^+$, 98% pure.

Example 137

Preparation of (2S, 2'S) 2-N-isobutyl-2-N-(4-methylbenzenesulfonyl)-6-N-(N'α-tert-butoxycarbonyl-S-4-thiazolylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-4-thiazolylalanine (Peptech Corporation). Purification by HPLC gave 50 mg (29%) of the desired material.

$^1$H NMR (CDCl$_3$): δ 0.90–0.98 (m, 6H), 1.09–1.16 (m, 1H), 1.25–1.29 (m, 2H), 1.49 (s, 9H), 1.92–1.97 (m, 1H), 2.37 (s, 3H), 2.82–3.30 (m, 6H), 3.49–3.51 (m, 2H), 3.64 (br s, 1H), 4.35 (br s, 1H), 7.06 (s, 1H), 7.18–7.22 (m, 3H), 7.74 (d, J=7.5, 2H). LC-MS: 697.3 (M+H)$^+$, 99% pure.

Example 138

Preparation of (2S, 2'S) 2-N-isobutyl-2-N-(4-methylbenzenesulfonyl)-6-N-(N'α-tert-butoxycarbonyl-S-2-fluorophenylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-2-fluorophenylalanine (Peptech Corporation). Purification by HPLC gave 62 mg (34%) of the desired material.

$^1$H NMR (CDCl$_3$): δ 0.79 (d, J=6.3, 3H), 0.82 (d, J=6.3, 3H), 1.08–1.11 (m, 2H), 1.29–1.34 (m, 3H), 1.41 (s, 9H), 1.92–1.97 (m, 1H), 2.38 (s, 3H), 2.84–3.09 (m, 6H), 3.51 (d, J=7.1, 2H), 3.72 (t, J=6.1, 1H), 4.35 (br s, 1H), 7.00–7.08(m, 42H), 7.14–7.28(m, 4H), 7.73(d, J=7.9, 2H). LC-MS: 608.4 (M+H)$^+$, 99% pure.

Example 139

Preparation of (2S, 2'S) 2-N-isobutyl-2-N-(4-methylbenzenesulfonyl)-6-N-(N'α-tert-butoxycarbonyl-S-3-fluorophenylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-3-fluorophenylalanine (Peptech Corporation). Purification by HPLC gave 88 mg (48%) of the desired material.

$^1$H NMR (CDCl$_3$): δ 0.85 (d, J=6.3, 3H), 0.90 (d, J=6.3, 3H), 1.08–1.11 (m, 2H), 1.29–1.34 (m, 3H), 1.41 (s, 9H), 1.92–1.97 (m, 1H), 2.41 (s, 3H), 2.84–3.09 (m, 6H), 3.51 (d, J=7.1, 2H), 3.62 (t, J=6.1, 1H), 4.35 (br s, 1H), 6.91 (d, J=6.6, 2H), 7.00 (d, J=6.7, 2H), 7.14–7.28 (m, 3H), 7.73 (d, J=7.9, 2H). LC-MS: 608.4 (M+H)$^+$, 99% pure.

Example 140

Preparation of (2S, 2'S) 2-N-isobutyl-2-N-(4-methylbenzenesulfonyl)-6-N-(N'α-tert-butoxycarbonyl-S-4-fluorophenylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-4-fluorophenylalanine (Peptech Corporation). Purification by HPLC gave 65 mg (35%) of the desired material.

$^1$H NMR (CDCl$_3$): δ 0.85 (d, J=6.3, 3H), 0.90 (d, J=6.3, 3H), 1.08–1.11 (m, 2H), 1.29–1.34 (m, 3H), 1.41 (s, 9H), 1.92–1.97 (m, 1H), 2.41 (s, 3H), 2.84–3.09 (m, 6H), 3.51 (d, J=7.1, 2H), 3.60–3.62 (m, 1H), 4.24 (br s, 1H), 6.94 (t, J=7.6, 2H), 7.14–7.18 (m, 2H), 7.20–7.30 (m, 2H), 7.73 (d, J=7.9, 2H). LC-MS: 608.4 (M+H)$^+$, 99% pure.

Example 141

Preparation of (2S, 2'S) 2-N-isobutyl-2-N-(4-methylbenzenesulfonyl)-6-N-(N'α-tert-butoxycarbonyl-S-1,2,3,4-tetrahydronorharman-3-carbonyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-1,2,3,4-tetrahydronorharman-3-carboxylic acid (Peptech Corporation). Purification by HPLC gave 75 mg (39%) of the desired material.

$^1$H NMR (CDCl$_3$): δ 0.85 (d, J=6.3, 3H), 0.90 (d, J=6.3, 3H), 1.08–1.11 (m, 2H), 1.29–1.34 (m, 3H), 1.36 (s, 9H), 1.92–1.97 (m, 1H), 2.35 (s, 3H), 2.40 (t, J=6.7, 1H), 2.80–3.09 (m, 6H), 3.52 (d, J=5.1, 2H), 3.60–3.62 (m, 1H), 4.23 (br s, 1H), 7.28 (d, J=7.8, 2H), 7.73 (d, J=7.9, 2H). LC-MS: 641.5 (M+H)$^+$, 99% pure.

Example 142

Preparation of (2S, 2'S) 2-N-isobutyl-2-N-(4-methylbenzenesulfonyl)-6-N-(N'α-tert-butoxycarbonyl-S-4tert-butylphenylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-4-tert-butylphenylalanine (Peptech Corporation). Purification by HPLC gave 81 mg (42%) of the desired material.

$^1$H NMR (CDCl$_3$): δ 0.85 (d, J=6.3, 3H), 0.90 (d, J=6.3, 3H), 1.08–1.11 (m, 2H), 1.29–1.34 (m, 3H), 1.36 (s, 9H), 1.92–1.97 (m, 1H), 2.40 (s, 3H), 2.80–3.29 (m, 8H), 3.52 (d, J=5.1, 2H), 3.60–3.62 (m, 1H), 4.23 (br s, 1H), 6.90–7.28 (m, 5H), 7.55 (d, J=6.6, 1H)), 7.73 (d, J=7.9, 2H). LC-MS: 646.5 (M+H)$^+$, 99% pure.

Example 143

Preparation of (2S, 2'S) 2-N-isobutyl-2-N-(4-methylbenzenesulfonyl)-6-N-(N'α-tert-butoxycarbonyl-S-pentafluorophenylalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-pentafluorophenylalanine (Peptech Corporation). Purification by HPLC gave 55 mg (27%) of the desired material.

$^1$H NMR (CDCl$_3$): δ 0.85 (d, J=6.3, 3H), 0.90 (d, J=6.3, 3H), 1.08–1.11 (m, 2H), 1.29–1.34 (m, 3H), 1.41 (s, 9H), 1.92–1.97 (m, 1H), 2.41 (s, 3H), 2.80–3.09 (m, 6H), 3.51 (d, J=7.1, 2H), 3.60–3.62 (m, 1H), 4.31 (br s, 1H), 7.09 (s, 2H), 7.10–7.28 (m, 5H), 7.68 (d, J=7.5, 2H). LC-MS: 680.2 (M+H)$^+$, 99% pure.

Example 144

Preparation of (2S, 2'S) 2-N-isobutyl-2-N-(4-methylbenzenesulfonyl)-6-N-[N'α-tert-butoxycarbonyl-S-4-(9-fluorenemethoxycarbonylaminomethyl)phenylalanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-tert-butoxycarbonyl-L-4-(9-fluorenemethoxycarbonylaminomethyl) phenylalanine (Peptech Corporation). Purification by HPLC gave 41 mg (16%) of the desired material.

LC-MS: 842.8 (M+H)$^+$, 99% pure.

Example 145

Preparation of (2S, 2'S) 2-N-(4-aminobenzenesulfonyl)-2-N-isobutyl-6-N-[N'α-(4-methylbenzenesulfonyl)-S-tryptophanyl]-2,6-diaminohexanol Step A. Preparation of Nα-isobutyl-Nα-(4-nitrobenzenesulfonyl)-Nε-benzyloxycarbonyl-L-lysine methyl ester This product was prepared following the procedure described for the preparation of Nα-isobutyl-Nα-(4-methylbenzenesulfonyl)-Nε-benzyloxycarbonyl-L-lysine methyl ester (example 65, step B) using 4-nitrobenzenesulfonyl chloride instead of 4-methylbenzenesulfonyl chloride. The yield of this reaction was 42%.

$^1$H NMR (CDCl$_3$): δ 0.83 (d, J=6.6, 3H), 0.86 (d, J=6.5, 3H), 1.35–1.69 (m, 5H), 1.88–2.00 (m, 2H), 2.90 and 3.04 (ABX, J=14.5, 7.5, 2H), 3.18 (m, 2H), 3.49 (s, 3H), 4.45 (t, J=6.0, 1H), 4.83 (s, 1H), 5.10 (s, 2H), 7.30–7.40 (m, 5H), 8.00 (d, J=8.5, 2H), 8.33 (d, J=8.5, 2H).

Step B. Preparation of Nα-(4-aminobenzenesulfonyl)-Nα-isobutyl-L-lysine methyl ester The title compound was obtained by catalytic hydrogenation of Nα-isobutyl-Nα-(4-nitrobenzenesulfonyl)-Nε-benzyloxycarbonyl-L-lysine methyl ester (step A) as described for the preparation of Nα-isobutyl-Nα-(4-methylbenzenesulfonyl)-L-lysine methyl ester (example 65, step C). This compound was used without purification in the next step.

Step C. Preparation of Nα-(4-aminobenzenesulfonyl)-Nα-isobutyl-Nε-[N'α-(4-methylbenzenesulfonyl)-L-tryptophanyl]-L-lysine methyl ester The title compound was prepared in the same manner than example 69 using Nα-(4-aminobenzenesulfonyl)-Nα-isobutyl-L-lysine methyl ester (step B) as the starting material. The yield of this reaction was 65%.

$^1$H NMR (DMSO-d$_6$): δ 0.77 (t, J=7.5, 6H), 0.90–1.10 (m, 4H), 1.40 (m, 1H), 1.70 (m, 1H), 1.85 (m, 1H), 2.29 (s, 3H), 2.87–3.00 (m, 3H), 3.44 (s, 3H), 3.85 (m, 1H), 4.10 (s, 2H), 4.24 (t, J=7.3, 1H), 5.74 (s, 2H), 6.60 (d, J=8.4, 2H), 6.90 (m, 1H), 7.00 (m, 2H), 7.15 (d, J=7.5, 2H), 7.30–7.45 (m, 6H), 7.70 (t, J=5.0, 1H), 7.82 (d, J=8.7, 1H), 10.70 (s, 1H).

Step D. Preparation of (2S, 2'S) 2-N-(4-aminobenzenesulfonyl)-2-N-isobutyl-6-N-[N'α-(4-methylbenzenesulfonyl)-S-tryptophanyl]-2,6-diaminohexanol Nα-(4-aminobenzenesulfonyl)-Nα-isobutyl-Nε-[N'α-(4-methylbenzenesulfonyl)-L-tryptophanyl]-L-lysine methyl ester (step C) was reduced with LiAlH$_4$ following the indications of general procedure G. The final product was obtained in 37% yield.

$^1$H NMR (DMSO-d$_6$): δ 0.80 (d, J=7.8, 3H), 0.83 (d, J=7.6, 3H), 0.88–1.22 (m, 5H), 1.48 (m, 1H), 1.85 (m, 1H), 2.30 (s, 3H), 2.65–2.80 (m, 4H), 2.85 (dd, J=14.5, 7.5, 1H), 2.93 (dd, J=14.3, 7.6, 1H), 3.20–3.40 (m, 2H), 3.45 (m, 1H), 3.88 (m, 1H), 4.60 (t, J=5.0, 1H), 5.90 (s, 2H), 6.60 (d, J=8.4, 2H), 6.90 (m, 1H), 7.00 (m, 2H), 7.15 (d, J=7.5, 2H), 7.30–7.45 (m, 6H), 7.70 (t, J=5.0, 1H), 7.82 (d, J=8.7, 1H), 10.70 (s, 1H).

Example 146

Preparation of (S, 2'S) 2-N-isobutyl-2-N-(4-methoxybenzenesulfonyl)-6-N-(S-tryptophanyl)-2,6-diaminohexanol trifluoroacetic acid salt This product was obtained quantitatively by treating (2S, 2'S) 2-N-isobutyl-2-N-(4-methoxybenzenesulfonyl)-6-N-(N'α-tert-butoxycarbonyl-S-tryptophanyl)-2,6-diaminohexanol (example 147) with TFA in CH$_2$Cl$_2$.

$^1$H NMR (DMSO-d$_6$): δ 0.80 (d, J=7.0, 3H), 0.83 (d, J=7.0, 3H), 0.92–1.60 (m, 6H), 1.88 (m, 1H), 2.78–3.00 (m, 4H), 3.05 and 3.20 (ABX, J=14.0, 7.0, 2H), 3.22 and 3.30 (ABX, J=14.2, 7.0, 2H), 3.50 (m, 1H), 3.80 (s, 3H), 3.90 (m, 1H), 4.35 (m, 1H), 6.95–7.12 (m, 4H), 7.18 (s, 1H), 7.38 (d, J=8.2, 1H), 7.60 (m, 1H), 7.70 (d, J=8.2, 2H), 8.05 (br s, 3H), 8.34 (m, 1H), 11.0 (s, 1H).

Example 147

Preparation of (2S, 2'S) 2-N-isobutyl-2-N-(4-methoxybenzenesulfonyl)-6-N-(N'α-tert-butoxycarbonyl-S-tryptophanyl)-2,6-diaminohexanol Step A. Preparation of Nα-isobutyl-Nα-(4-methoxybenzenesulfonyl)-Nε-benzyloxycarbonyl-L-lysine methyl ester This product was prepared following the procedure described for the preparation of Nα-isobutyl-Nα-(4-methylbenzenesulfonyl)-Nε-benzyloxycarbonyl-L-lysine methyl ester (example 65, step B) using 4-methoxybenzenesulfonyl chloride instead of 4-methylbenzenesulfonyl chloride. The yield of this reaction was 65%.

$^1$H NMR (CDCl$_3$): δ 0.84 (d, J=6.6, 3H), 0.85 (d, J=6.5, 3H), 1.30–1.65 (m, 5H), 1.85–1.95 (m, 2H), 2.90 and 3.04 (ABX, J=14.5, 7.5, 2H), 3.15 (m, 2H), 3.51 (s, 3H), 3.85 (s, 3H), 4.35 (t, J=5.5, 1H), 4.80 (br s, 1H), 5.09 (s, 2H), 6.94 (d, J=8.6, 2H), 7.30–7.40 (m, 5H), 7.25 (d, J=8.5, 2H).

Step B. Preparation of Nα-isobutyl-Nα-(4-methoxybenzenesulfonyl)-L-lysine methyl ester The title compound was obtained quantitatively by catalytic hydrogenation of Nα-isobutyl-Nα-(4-methoxybenzenesulfonyl)-Nε-benzyloxycarbonyl-L-lysine methyl ester (step A) as described for the preparation of Nα-isobutyl-Nα-(4-methylbenzenesulfonyl)-L-lysine methyl ester (example 65, step C). This compound was used without purification in the next step.

Step C. Preparation of Nα-isobutyl-Nα-(4-methoxybenzenesulfonyl)-Nε-(N'α-tert-butoxycarbonyl-L-tryptophanyl)-L-lysine methyl ester The title compound was prepared in the same manner as in the example 65 (step D) using Nα-isobutyl-Nα-(4-methoxybenzenesulfonyl)-L-lysine methyl ester (step B) and commercially available Nα-tert-butoxycarbonyl-L-tryptophan as the starting materials. The yield of this reaction was 86%.

$^1$H NMR (DMSO-d$_6$): δ 0.84 (t, J=7.0, 6H), 0.90–1.30 (m, 5H), 1.31 (s, 9H), 1.53 (m, 1H), 1.86 (m, 1H), 2.82–3.10 (m, 5H), 3.46 (s, 3H), 3.83 (s, 3H), 4.12 (m, 1H), 4.30 (t, J=5.0, 1H), 6.67 (d, J=8.2, 1H), 6.90–7.12 (m, 5H), 7.30 (d, J=8.0, 2H), 7.55 (m, 1H), 7.70 (m, 2H), 7.81 (m, 1H).

Step D. Preparation of (2S, 2'S) 2-N-isobutyl-2-N-(4-methoxybenzenesulfonyl)-6-N-(N'α-tert-butoxycarbonyl-S-tryptophanyl)-2,6-diaminohexanol Nα-isobutyl-Nα-(4-methoxybenzenesulfonyl)-Nα-(N'α-tert-butoxycarbonyl-L-tryptophanyl)-L-lysine methyl ester (step C) was reduced with LiAlH$_4$ following the indications of general procedure G. The final product was obtained in 81% yield.

$^1$H NMR (DMSO-d$_6$): δ 0.73 (t, J=7.0, 6H), 0.90–1.27 (m, 5H), 1.31 (s, 9H), 1.52 (m, 1H), 1.85 (m, 1H), 2.80 and 3.02 (ABX, J=14.0, 7.2, 2H), 2.90 (m, 2H), 3.50 (m, 1H), 3.82 (s, 3H), 4.15 (m, 1H), 4.65 (t, J=5.0, 1H), 6.65 (d, J=7.8, 1H), 6.92–7.12 (m, 5H), 7.30 (d, J=7.8, 1H), 7.58 (d, J=8.0, 1H), 7.70 (d, J=7.7, 2H), 7.73 (t, J=5.0, 1H), 10.77 (s, 1H).

Example 148

Preparation of (2S, 2'S) 2-N-isobutyl-2-N-(4-methoxybenzenesulfonyl)-6-N-(N'α-pivaloyl-S-tryptophanyl)-2,6-diaminohexanol Treatment of (2S, 2'S) 2-N-isobutyl-2-N-(4-methoxybenzenesulfonyl)-6-N-(S-tryptophanyl)-2,6-diaminohexanol trifluoroacetic acid salt (example 146) with pivaloyl chloride using the conditions described in example 65 (step B) afforded the desired product in 86% yield.

$^1$H NMR (DMSO-d$_6$): δ 0.80 (d, J=7.0, 3H), 0.83 (d, J=7.0, 3H), 1.02 (s, 9H), 1.03–1.30 (m, 5H), 1.53 (m, 1H), 1.88 (m, 1H), 2.80 (dd, J=14.5, 7.5, 1H), 2.83–3.10 (m, 5H), 3.27 and 3.32 (ABX, J=14.5, 7.2, 2H), 3.52 (m, 1H), 3.82 (s, 3H), 4.46 (m, 1H), 6.90–7.15 (m, 5H), 7.30 (d, J=8.1, 1H), 7.56 (d, J=8.0, 1H), 7.71 (d, J=8.2, 2H), 7.74 (t, J=5.0, 1H), 10.75 (s, 1H).

Example 149

Preparation of (2S, 2'S) 2-N-isobutyl-2-N-(4-methoxybenzenesulfonyl)-6-N-[N'α-(4-methylbenzenesulfonyl)-S-tryptophanyl]-2,6-diaminohexanol Treatment of (2S, 2'S) 2-N-isobutyl-2-N-(4-methoxybenzenesulfonyl)-6-N-(S-tryptophanyl)-2,6- diaminohexanol trifluoroacetic acid salt (example 146) with 4-methylbenzenesulfonyl chloride using the conditions described in example 65 (step B) afforded the desired product in 82% yield.

$^1$H NMR (DMSO-d$_6$): δ 0.80 (d, J=6.0, 3H), 0.83 (d, J=6.2, 3H), 0.88–1.50 (m, 6H), 1.88 (m, 1H), 2.30 (s, 3H), 2.65 (m, 2H), 2.78 (m, 2H), 2.93 (m, 2H), 3.22–3.40 (m, 2H), 3.50 (m, 1H), 3.82 (s, 3H), 3.86 (m, 1H), 4.67 (m, 1H), 6.90 (t, J=7.5, 1H), 7.00–7.18 (m, 6H), 7.28 (d, J=8.3, 1H), 7.34 (d, J=8.0, 1H), 7.45 (d, J=7.5,2H), 7.71 (m, 3H), 7.83 (d, J=7.4, 1H), 10.71 (s, 1H).

Example 150

Preparation of Nα-cyclopentylmethyl-Nα-(4-methoxybenzenesulfonyl)-Nε-(N'α-tert-butoxycarbonyl-L-tryptophanyl)-L-lysine methyl ester Step A. Preparation of Nα-cyclopentylmethyl-Nα-(4-methoxybenzenesulfonyl)-Nε-benzyloxycarbonyl-L-lysine methyl ester This product was prepared following the procedure described for the preparation of Nα-isobutyl-Nα-(4-methylbenzenesulfonyl)-Nε-benzyloxycarbonyl-L-lysine methyl ester (example 65, steps A and B) using cyclopentanecarboxaldehyde instead of isobutyraldehyde (for step A) and 4-methoxybenzenesulfonyl chloride instead of 4-methylbenzenesulfonyl chloride (for step B). The yield of this two-step sequence was 79%.

$^1$H NMR (CDCl$_3$): δ 1.03–1.45 (m, 6H), 1.48–1.71 (m, 8H), 1.56 (s, 9H), 1.92 (m, 1H), 2.18 (m, 1H), 3.03 and 3.13 (ABX, J=13.5, 7.0, 2H), 3.20 (m, 2H), 3.53 (s, 3H), 3.87 (s, 3H), 4.40 (t, J=6.5, 1H), 5.11 (s, 2H), 6.96 (d, J=8.7, 2H), 7.25–7.40 (m, 6H), 7.77 (d, J=8.7, 2H).

Step B. Preparation of Nα-cyclopentylmethyl-Nα-(4-methoxybenzenesulfonyl)-L-lysine methyl ester The title compound was obtained quantitatively by catalytic hydrogenation of Nα-cyclopentylmethyl-Nα-(4-methoxybenzenesulfonyl)-Nε-benzyloxycarbonyl-L-lysine methyl ester as described for the preparation of Nα-isobutyl-Nα-(4-methylbenzenesulfonyl)-L-lysine methyl ester (example 65, step C). This compound was used without purification in the next step.

Step C. Preparation of Nα-cyclopentylmethyl-Nα-(4-methoxybenzenesulfonyl)-Nε-(N'α-tert-butoxycarbonyl-L-tryptophanyl)-L-lysine methyl ester The title compound was prepared in the same manner as in example 65 (step D) using Nα-cyclopentylmethyl-Nα-(4-methoxybenzenesulfonyl)-L-lysine methyl ester (this example, step B) and Nα-tert-butoxycarbonyl-L-tryptophan-N-hydroxysuccinimide as the starting materials. The yield of the two last reactions was 82%.

$^1$H NMR (CDCl$_3$): δ 1.08–1.28 (m, 6H), 1.30 (s, 9H), 1.40–1.62 (m, 7H), 1.80 (m, 1H), 2.10 (m, 1H), 2.82–3.10 (m, 5H), 3.46 (s, 3H), 3.82 (s, 3H), 4.12 (m, 1H), 4.30 (m, 1H), 6.65 (d, J=8.2, 1H), 6.90–7.10 (m, 5H), 7.30 (d, J=8.0, 1H), 7.59 (d, J=8.2, 1H), 7.70 (d, J=8.1, 2H), 7.80 (t, J=5.0, 1H), 10.77 (s, 1H).

Example 151

Preparation of Nα-cyclopentylmethyl-Nα-(4-methoxybenzenesulfonyl)-Nε-(N'α-tert-butoxycarbonyl-L-tryptophanyl)-L-lysine A saponification of Nα-cyclopentylmethyl-Nα-(4-methoxybenzenesulfonyl)-Nε-(N'α-tert-butoxycarbonyl-L-tryptophanyl)-L-lysine methyl ester (example 150) using the conditions described in example 65 (step E) afforded the desired material quantitatively.

$^1$H NMR (DMSO-d$_6$): δ 1.08–1.28 (m, 6H), 1.21 (s, 9H), 1.40–1.65 (m, 7H), 1.80 (m, 1H), 2.18 (m, 1H), 2.88–3.10 (m, 6H), 3.82 (s, 3H), 4.12 (m, 1H), 4.20 (m, 1H), 6.62 (d, J=7.8, 1H), 6.90–7.15 (m, 5H), 7.3 (d, J=8.0, 1H), 7.55 (d, J=8.0, 1H), 7.70 (d, J=8.7, 2H), 7.80 (d, J=5.1, 1H), 10.77 (s, 1H), 12.70 (br s, 1H).

Example 152

Preparation of (2S, 2'S) 2-N-cyclopentylmethyl-2-N-(4-methoxybenzenesulfonyl)-6-N-(S-tryptophanyl)-2,6-diaminohexanol trifluoroacetic acid salt This product was obtained quantitatively by treating (2S, 2'S) 2-N-cyclopentylmethyl-2-N-(4-methoxybenzenesulfonyl)-6-N-(N'α-tert-butoxycarbonyl-S-tryptophanyl)-2,6-diaminohexanol (example 153) with TFA in CH$_2$Cl$_2$.

$^1$H NMR (DMSO-d$_6$): δ 1.10–1.38 (m, 7H), 1.40–1.68 (m, 7H), 2.18 (m, 1H), 2.84–3.02 (m, 4H), 3.10 and 3.18 (ABX, J=14.0, 7.0, 2H), 3.30 (m, 2H), 3.50 (m, 1H), 3.81 (s, 3H), 3.90 (m, 1H), 4.35 (m, 1H), 6.98–7.10 (m, 4H), 7.20 (s, 1H), 7.39 (d, J=8.3, 1H), 7.60 (m, 1H), 7.70 (d, J=8.2, 2H), 8.10 (br s, 3H), 8.36 (m, 1H), 11.0 (s, 1H).

Example 153

Preparation of (2S, 2'S) 2-N-cyclopentylmethyl-2-N-(4-methoxybenzenesulfonyl)-6-N-(N'α-tert-butoxycarbonyl- S-tryptophanyl)-2,6-diaminohexanol Nα-cyclopentylmethyl-Nα-(4-methoxybenzenesulfonyl)-Nε-(N'α- tert-butoxycarbonyl-L-tryptophanyl)-L-lysine methyl ester (example 150) was reduced with LiAlH$_4$ following the indications of general procedure G. The final product was obtained with 72% yield.

$^1$H NMR (DMSO-d$_6$): δ 0.95–1.28 (m, 7H), 1.30 (s, 9H), 1.42–1.65 (m, 6H), 2.15 (m, 1H), 2.85–3.10 (m, 6H), 3.35 (m, 1H), 3.53 (m, 1H), 3.80 (s, 3H), 4.15 (m, 1H), 4.65 (m, 1H), 6.75 (d,=8.2, 1H), 6.90–7.12 (m, 5H), 7.30 (d, J=8.0, 1H), 7.55 (d, J=8.4, 1H), 7.70 (d, J=8.0, 2H), 7.73 (t, J=5.0, 1H).

Example 154

Preparation of Nα-isobutyl-Nα-(4-methylbenzenesulfonyl)-Nε-[N'α-(4-methylbenzenesulfonyl)-L-phenylalanyl]-L-ornithine The title compound was prepared using the conditions described in example 65 (steps A, B, C, D and E) with, as the starting materials, Nε-benzyloxycarbonyl-L-ornithine methyl ester hydrochloride and, for step D, Nα-(4-methylbenzenesulfonyl)-L-phenylalanine.

$^1$H NMR (DMSO-d$_6$): δ 0.77 (d, J=6.5, 3H), 0.80 (d, J=6.8, 3H), 1.15–1.25 (m, 2H), 1.40 (m, 1H), 1.70 (m, 1H), 1.90 (m, 1H), 2.33 (s, 3H), 2.36 (s, 3H), 2.60–3.00 (m, 5H), 3.85 (m, 2H), 4.19 (m, 2H), 4.19 (m, 1H), 7.08–7.26 (m, 6H), 7.38 (d, J=8.2, 2H), 7.45 (m, 2H), 7.70 (d, J=8.3, 2H), 7.35 (t, J=5.0, 1H), 7.90 (d, J=8.5, 1H), 8.16 (d, J=8.6, 1H), 12.70 (br s, 1H).

Example 155

Preparation of Nα-isobutyl-Nα-(4-methylbenzenesulfonyl)-Nε-(N'α,N'α-dibenzylglycyl)-L-lysine The title compound was prepared from Nα-isobutyl-Nα-(4-methylbenzenesulfonyl)-Nε-(N'α-benzylglycyl)-L- lysine (100 mg, 0.20 mmol, example 109) by following the indications of general procedure H using Et₃N (70 μL, 0.50 mmol) and benzyl bromide (0.10 mL, 0.84 mmol). The crude material was purified by preparative HPLC. The product was isolated as a solid (21 mg, 18% yield).

¹H NMR (CDCl₃): δ 0.78 (d, J=6.7, 3H), 0.83 (d, J=6.8, 3H), 1.34 (m, 2H), 1.45 (m, 1H), 1.65 (m, 2H), 1.91 (m, 2H), 2.39 (s, 3H), 2.86 (dd, J=13.6, 7.3, 1Ha), 2.98 (dd, J=13.6, 7.3, 1Hb), 3.12 (s, 1H), 3.15 (m, 2H), 3.64 (s, 4H), 4.43 (t, J=7.0, 1H), 4.93 (s, 2H), 7.13 (s, 1H), 7.16 (d, J=7.7, 2H), 7.22–7.37 (m, 10H), 7.66 (d, J=7.6,2H). LC-MS: 592 (M–H)⁻, 99% pure.

Example 156

Preparation of (2S) 2-N-isobutyl-2-N-(4-methylbenzenesulfonyl)-6-N-(N'α-benzyl-N'α-phenylglycyl)-2,6-diaminohexanol The title product was prepared from (2S) 2-N-isobutyl-2-N-(4-methylbenzenesulfonyl)-2,6-diaminohexanol (350 mg, 1.0 mmol, example 116, step A) following the indications of general procedure Ba using N-benzyl-N-phenylglycine (241 mg, 1.0 mmol, example 114, step A) and N,N-carbonyldiimidazole (195 mg, 1.2 mmol). The crude material was purified by preparative HPLC. The product was isolated as a solid (135 mg, 24% yield).

¹H NMR (DMSO-d₆): δ 0.83 (t, J=6.8, 6H), 1.05 (m, 2H), 1.26 (m, 3H), 1.55 (m, 1H), 1.85 (m, 1H), 2.37 (s, 3H), 2.86 (m, 1H), 2.94 (m, 3H), 3.27 (m, 1H), 3.45 (m, 1H), 3.94 (s, 2H), 4.62 (s, 2H), 4.66 (t, J=5.1, 1H), 6.57 (d, J=8.3, 2H), 6.61 (t, J=7.5, 1H), 7.11 (t, J=7.5, 2H), 7.25 (m, 3 H), 7.31 (t, J=7.4, 2H), 7.35 (d, J=7.8, 2H), 7.66 (d, J=8.2, 2H), 8.81 (t, J=5.0, 1H). LC-MS: 566 (M+H)⁺, 99% pure.

Example 157

Preparation of Nα-isobutyl-Nα-(4-methylbenzenesulfonyl)-Nε-(N'α-cyclohexylglycyl)-L-lysine The title compound was prepared from Nα-isobutyl-Nα-(4-methylbenzenesulfonyl)-Nε-iodoacetyl-L-lysine (520 mg, 1.0 mmol, example 105, step B) by following the indications of general procedure H using cyclohexylamine (1.0 mL, 8.7 mmol). The crude material was purified by preparative HPLC. The product was isolated as a solid (300 mg, 64% yield).

¹H NMR (CDCl₃/MeOD 1:1): δ 0.85 (d, J=7.2, 3H), 0.88 (d, J=5.8, 3H), 1.23 (m, 1H,), 1.30–1.50 (m, 6H), 1.56 (m, 3H), 1.70 (m, 1H), 1.88 (m, 3H), 2.04 (m, 3H), 2.41 (s, 3H), 2.98 (m, 1H), 3.07 (m, 2H), 3.26 (t, J=6.4, 2H), 3.66 (s, 2H), 4.27 (t, J=7.3, 1H), 7.31 (d, J=8.4, 2H), 7.75 (d, J=8.8, 2H). LC-MS: 494 (M–H)⁻, 95% pure.

Example 158

Preparation of (2S) 2-N-isobutyl-2-N-(4-methylbenzenesulfonyl)-6-N-(N'α-benzoyl-N'α-benzylglycyl)-2,6-diaminohexanol Step A. Preparation of N-benzylglycine methyl ester A solution of methyl bromoacetate (2.0 mL, 20 mmol) in CH₂Cl₂ (25 mL) was treated with benzylamine (3.22 g, 30 mmol). The resulting mixture was stirred at room temperature for 16 h under an inert atmosphere of argon. Afterwards, the reaction was quenched with 2N HCl (10 mL). The product was extracted with EtOAc (15 mL, 3×), dried over MgSO₄, filtered and evaporated to an oil. The crude material was purified by flash chromatography using 9:1 hexane/EtOAc. The product was isolated as a yellowish liquid (3.24 g, 86% yield).

¹H NMR (CDCl₃): δ 3.44 (s, 2H), 3.74 (s, 3H), 3.82 (s, 2H), 7.27 (m, 1H), 7.34 (m, 4H).

Step B. Preparation of N-benzoyl-N-benzylglycine

To a solution of N-benzylglycine methyl ester (800 mg, 4.5 mmol, step A) in THF (10 mL) was added benzoique acid (820 mg, 6.7 mmol) and DCC (1.40 g, 6.8 mmol). The reaction mixture was stirred at room temperature for 5 IL Then, it was treated with a saturated NaHCO₃ solution and extracted with EtOAc (30 mL, 3×). The organic phase was evaporated to an oil. The ester intermediate was saponified following the indications of example 65 (step E). The crude material was purified by flash chromatography using EtOAc:hexane:CHCl₃ (5:5:2) to give 875 mg (73%) of the final product.

¹H NMR (DMSO-d₆): δ 3.84 (s, 0.66H), 4.20 (s, 1.33H) ; 4,64 (s, 1.33H), 4.82 (s, 0.66H), 7.21 (d, J=7.4,22H), 7.40 (m, 8H), 7.55 (d, J=7.2, 2H), 10.0 (s, 1H). LC-MS: 270 (M+H)⁺ and 292 (M+Na)⁺, 98% pure.

Step C. Preparation of (2S) 2-N-isobutyl-2-N-(4-methylbenzenesulfonyl)-6-N-(N'α-benzoyl-N'α-benzylglycyl)-2,6-diaminohexanol The title product was prepared from (2S) 2-N-isobutyl-2-N-(4-methylbenzenesulfonyl)-2,6-diaminohexanol (350 mg, 1.0 mmol, example 116, step A) following the indications of general procedure Ba using N-benzoyl-N-benzylglycine (269 mg, 1.0 mmol, step B) and N,N-carbonyldiimidazole (180 mg, 1.1 mmol). The crude material was purified by preparative HPLC. The product was isolated as a solid (98 mg, 17% yield).

¹H NMR (DMSO-d₆): δ 0.83 (t, J=7.1, 6H), 1.05 (m, 2H), 1.26 (m, 3H), 1.55 (m, 1H), 1.87 (m, 1H), 2.37 (s, 3H), 2.80–3.00 (m, 4H), 3.52 (m, 1H), 3.65 (s, 0.66H), 3.89 (s, 0.33H), 4.49 (s, 0.33H), 4.66 (s, 0.66H), 7.20 (m, 1H), 7.29 (m, 3H), 7.36 (d, J=7.3, 2H), 7.43 (m, 5H), 7.67 (d, J=7.5, 2H), 7.83 (m, 1H). LC-MS: 594 (M+H)⁺, 99% pure.

Example 159

Preparation of (2S) 2-N-isobutyl-2-N-(4-methylbenzenesulfonyl)-6-N-[N'α-benzyl-N'α-(4-methylbenzenesulfonyl)glycyl]-2,6-diaminohexanol Step A. Preparation of N-(4-methylbenzenesulfonyl)-N-benzylglycine A solution of N-benzylglycine methyl ester (1.00 g, 5.6 mmol, example 158, step A) in DCM (10 mL) was treated with triethylamine (1 mL, 7.2 mmol) and 4-methylbenzenesulfonyl chloride (1.28 g, 6.7 mmol). The reaction mixture was stirred for 3 h at room temperature. Afterwards, the reaction was quenched with 2N HCl (10 mL). The product was extracted with DCM (15 mL, 3×), dried over MgSO₄, filtered and evaporated. The ester intermediate was saponified following the indications of example 65 (step E). The crude material was diluted with 0.5N HCl (150 mL). The resulting precipitate was filtered off and dried under vacuum to give 1.46 g (82%) of the desired material (99% pure).

¹H NMR (DMSO-d₆): δ 2.40 (s, 3H), 3.80 (s, 2H), 4.40 (s, 2H), 7.21 (d, J=7.2, 1H), 7.30 (m, 3H), 7.40 (d, J=7.6 2H), 7.74 (d, J=8.2, 2H), 12.7 (s, 1H).

Step B. Preparation of (2S) 2-N-isobutyl-2-N-(4-methylbenzenesulfonyl)-6-N-[N'α-benzyl-N'α-(4-methylbenzenesulfonyl)glycyl]-2,6-diaminohexanol The title product was prepared from (2S) 2-N-isobutyl-2-N-(4-methylbenzenesulfonyl)-2,6-diaminohexanol (350 mg, 1.0 mmol, example 116, step A) following the indications of general procedure Ba using N-(4-methylbenzenesulfonyl)-N-benzylglycine (320 mg, 1.0 mmol, step A) and N,N-carbonyldiimidazole (180 mg, 1.1 mmol). The crude material was purified by preparative HPLC. The product was isolated as a solid (236 mg, 37% yield).

$^1$H NMR (DMSO-d$_6$): δ 0.83 (t, J=7.3, 6H), 1.05 (m, 2H), 1.12 (m, 2H), 1.23 (m, 1H), 1.55 (m, 1H), 1.85 (m, 1H), 2.36 (s, 3H), 2.40 (s, 3H), 2.80–3.00 (m, 4H), 3.34 (m, 2H), 3.52 (m, 1H), 3.65 (s, 2H), 4.39 (s, 2H), 7.25 (d, J=7.0, 1H), 7.27–7.40 (m, 7H), 7.60 (t, J=4.2, 1H), 7.66 (d, J=8.2, 2H), 7.75 (d, J=7.5, 2H). LC-MS: 644 (M+H)$^+$, 90% pure.

Example 160

Preparation of (2S) 2-N-isobutyl-2-N-(4methylbenzenesulfonyl)-6-N-(N'α-phenethyl-N'α-phenylglycyl]-2,6-diaminohexanol Step A. Preparation of 2-phenylethyl-4-methylbenzenesulfonate A solution of 2-phenylethanol (1.22 g, 10 mmol) in THF (10 mL) was added to a suspension of NaH (440 mg, 1.01 mmol, 60% in oil) in dry THF (5 mL) and stirred for 15 min. The resulting alcolate solution was added dropwise to a solution of 4-methylbenzenesulfonyl chloride (3.80 g, 20.0 mmol) in dry THF (10 mL) and stirred for a period of 1 h. Afterwards, the reaction was quenched with 2N HCl (5 mL). The product was extracted with EtOAc (25 mL, 3×), dried over MgSO$_4$, filtered and evaporated to an oil. The crude material was purified by flash chromatography using 9:1 hexane/EtOAc. The product was isolated as an oil (1.77 g, 64% yield).

$^1$H NMR (CDCl$_3$): δ 2.43 (s, 3H), 2.96 (t, J=7.3, 2H), 4.23 (t, J=7.2, 2H), 7.12 (d, J=7.3, 2H), 7.26 (m, 5H), 7.70 (d, J=7.6, 2H).

Step B. Preparation of N-phenethyl-N-phenylglycine

The title compound was prepared from N-phenylglycine (800 mg, 5.30 mmol) as described for the preparation of N-benzyl-N-phenylglycine (example 114, step A) using 2-phenylethyl-4-methylbenzenesulfonate (1.61 g, 5.81 mmol) instead of benzylbromide. The crude material was purified by flash chromatography using a solvent gradient from 19:1 to 9:1 CH$_2$Cl$_2$/MeOH. The product was isolated as a solid (550 mg, 41% yield).

$^1$H NMR (CDCl$_3$): δ 2.95 (t, J=7.5, 2H), 3.65 (t, J=7.5, 2H), 3.95 (s, 2H), 6.73 (d, J=8.1, 2H), 6.80 (t, J=7.0, 1H), 7.30 (m, 7H).

Step C. Preparation of (2S) 2-N-isobutyl-2-N-(4-methylbenzenesulfonyl)-6-N-(N'α-phenethyl-N'α-phenylglycyl]-2,6-diaminohexanol The title product was prepared from (2S) 2-N-isobutyl-2-N-(4-methylbenzenesulfonyl)-2,6-diaminohexanol (320 mg, 0.94 mmol, example 116, step A) following the indications of general procedure Ba using N-phenethyl-N-phenylglycine (200 mg, 1.0 mmol, step B) and N,N-carbonyldiimidazole (140 mg, 0.86 mmol). The crude material was purified by preparative HPLC. The product was isolated as a hardy oil (32 mg, 7% yield).

$^1$H NMR (DMSO-d$_6$): δ 0.83 (t, J=7.1, 6H), 1.05 (m, 2H), 1.25 (m, 3H), 1.55 ((m, 1H), 1.85 (m, 1H), 2.37 (s, 3H), 2.80–3.01 (m, 4H), 3.52 (m, 1H), 3.94 (s, 2H), 4.62 (s, 2H), 4.65 (t, J=4.3, 1H), 6.58 (d, J=7.8, 2 H), 6.61 (t, J=7.8, 1 H), 7.11 (t, J=7.3, 2H), 7.25 (m, 3 H), 7.31 (t, J=7.3, 2H), 7.35 (d, J=8.2, 2H), 7.66 (d, J=7.9, 2H), 7.81 (t, J=5.4, 1H). LC-MS: 579 (M+H)$^+$, 90% pure.

Example 161

Preparation of (2S, 2'S) 2-N-isobutyl-2-N-(4-methylbenzenesulfonyl)-6-N-[N'α-(4-aminobenzenesulfonyl)-S-tryptophanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-nitrobenzenesulfonyl)-L-tryptophan (example 5, step A). The intermediate was reduced by catalytic hydrogenation following the conditions of general procedure E. Purification by HPLC gave 30 mg (14%) of the desired material.

$^1$H NMR (CDCl$_3$): δ 0.84 (d, J=6.3, 3H), 0.89 (d, J=6.3, 3H), 0.94–1.03 (m, 1H), 1.09–1.16 (m, 2H), 1.46–1.49 (m, 1H), 1.93–1.98 (m, 1H), 2.39 (s, 3H), 2.82–3.15 (m, 6H), 3.51 (d, J=6.8, 2H), 3.64 (q, J=6.3, 1H), 3.89 (q, J=5.5, 1H), 6.48 (d, J=7.8, 2H), 6.95 (t, J=4.5, 1H), 7.19 (t, J=4.5, 1H), 7.23–7.31 (m, 6H), 7.42 (t, J=4.5, 1H), 7.73 (d, J=7.8, 2H).

Example 162

Preparation of (2S, 2'S) 2-N-isobutyl-2-N-(4-methylbenzenesulfonyl)-6-N-[N'α-(4-methoxyphenylacetyl)-S-phenylalanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-methoxyphenylacetyl)-L-phenylalanine (example 132, step A). Purification by HPLC gave 25 mg (13%) of the desired material.

$^1$H NMR (CDCl$_3$): δ 0.79 (d, J=6.3, 3H), 0.82 (d, J=6.3, 3H), 1.09–1.16 (m, 2H), 1.35–1.39 (m, 2H), 1.45–1.52 (m, 1H) 1.94–1.97 (m, 1H), 2.40 (s, 3H), 2.82–3.18 (m, 6H), 3.45 (s, 2H), 3.51 (d, J=7.0, 2H), 3.64 (q, J=6.3, 1H), 3.79 (q, J=6.9, 1H), 3.82 (s, 3H), 4.50 (q, J=5.6, 1H), 6.87 (d, J=6.9, 2H), 6.89 (d, J=7.0, 2H), 7.15–7.21 (m, 3H), 7.35 (d, J=7.1, 2H), 7.50 (d, J=7.1, 1H), 7.73 (d, J=8.1,2H).

Example 163

Preparation of Nα-(4-aminobenzenesulfonyl)-Nα-isobutyl-Nε-[N'α-(4-methoxyphenylacetyl)-L-phenylalanyl]-L-lysine The title compound was prepared from Nα-isobutyl-Nα-(4-nitrobenzenesulfonyl)-L-lysine hydrochloride (200 mg, 0.45 mmol, example 5, step C) as described in general procedure Bc using Nα-(4-methoxyphenylacetyl)-L-phenylalanine (example 132, step A). The final product, Nα-isobutyl-Nα-(4-nitrobenzenesulfonyl)-Nε-[N'α-(4-methoxyphenylacetyl)-L-phenylalanyl]-L-lysine was subsequently hydrogenolysed following the indications of general procedure E. Purification by HPLC gave the desired material (7 mg, 4%).

$^1$H NMR (CDCl$_3$): δ 0.79 (d, J=6.3, 3H), 0.82 (d, J=6.3, 3H), 1.09–1.16 (m, 2H), 1.35–1.39 (m, 2H), 1.45–1.52 (m, 1H), 1.94–1.97 (m, 1H), 2.40 (s, 3H), 2.82–3.18 (m, 6H), 3.45 (s, 2H), 3.64 (q, J=6.3, 1H), 3.82 (s, 3H), 4.33 (t, J=5.5, 1H), 4.50 (q, J=5.6, 1H), 6.87 (d, J=6.9, 2H), 6.89 (d, J=7.0, 2H), 7.15–7.21 (m, 3H), 7.35 (d, J=7.1, 2H), 7.50 (d, J=7.1, 1H), 7.73 (d, J=8.1, 2H).

Example 164

Preparation of Nα-isobutyl-Nα-(4-methylbenzenesulfonyl)-Nε-[N'α-(4-methoxyphenylacetyl)-L-tryptophanyl]-L-lysine Step A. Preparation of Nα-(4-methoxyphenylacetyl)-L-tryptophan L-tryptophan was reacted with 4-methoxyphenylacetyl chloride under the conditions used in general procedure A giving the title compound which was recrystallised from DCM (31%) and used as such in the next step.

Step B. Preparation of Nα-isobutyl-N(-(4-methylbenzenesulfonyl)-Nε-[N'α-(4-methoxyphenylacetyl)-L-tryptophanyl]-L-lysine The title compound was prepared from Nα-isobutyl-Nα-(4-methylbenzenesulfonyl)-L-lysine hydrochloride (100 mg, 0.25 mmol, example 1, step E) as described in general procedure Bc using Nα-(4-methoxyphenylacetyl)-L-tryptophan (90 mg, 0.25 mmol) which was prepared in step A of this example. The final product was triturated with ether to yield 21 mg (11%) of the desired material.

$^1$H NMR (CDCl$_3$): δ 0.79 (d, J=6.3, 3H), 0.82 (d, J=6.3, 3H), 1.09–1.16 (m, 2H), 1.35–1.39 (m, 2H), 1.94–1.97 (m, 2H), 2.30 (s, 3H), 2.82–3.18 (m, 6H), 3.45 (s, 2H), 3.82 (s, 3H), 4.25–4.20 (m, 1H), 4.50 (q, J=5.6, 1H), 6.77 (d, J=6.2, 2H), 6.89 (s, 1H), 6.97 (d, J=6.9, 2H), 7.00–7.11 (m, 3H), 7.15–7.21 (m, 3H), 7.35 (d, J=7.1, 2H), 7.50 (d, J=7.1, 1H), 7.73 (d, J=8.1, 2H).

Example 165

Preparation of (2S, 2'S) 2-N-isobutyl-2-N-(4-methylbenzenesulfonyl)-6-N-[N'α-(4-methoxyphenylacetyl)-S-tryptophanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-methoxyphenylacetyl)-L-tryptophan (example 164, step A). Purification by HPLC gave 20 mg (10%) of the desired material.

$^1$H NMR (CDCl$_3$): δ 0.79 (d, J=6.3, 3H), 0.82 (d, J=6.3, 3H), 1.09–1.16 (m, 2H), 1.35–1.39 (m, 2H), 1.94–1.97 (m, 2H), 2.30 (s, 3H), 2.82–3.18 (m, 6H), 3.45 (s, 2H), 3.51 (d, J=7.0, 2H), 3.82 (s, 3H), 4.50 (q, J=5.6, 1H), 6.77 (d, J=6.2, 2H), 6.89 (s, 1H), 6.97 (d, J=6.9, 2H), 7.00–7.11 (m, 3H), 7.15–7.21 (m, 3H), 7.35 (d, J=7.1, 2H), 7.50 (d, J=7.1, 1H), 7.73 (d, J=8.1, 2H).

Example 166

Preparation of (2S, 2'S) 2-N-(4-aminobenzenesulfonyl)-2-N-isobutyl-6-N-[N'α-(2-thiophenesulfonyl)-S-tryptophanyl]-2,6-diaminohexanol Step A. Preparation of Nα-isobutyl-Nα-(4-acetamidobenzenesulfonyl)-L-α-amino-ε-caprolactam Nα-isobutyl-L-α-amino-ε-caprolactam (4.14 g, 21.1 mmol, free base, example 1, step C) was dissolved in DCE (50 mL) and treated with diisopropylethylamine (6 mL, 0.3 mol) followed by freshly recrystallized 4-acetamidobenzenesulfonyl chloride (5.06 g, 21.6 mmol). The mixture was stirred overnight (TLC shows the reaction to be complete after 2 h). The solution was extracted with 1N HCl (50 mL) and the organic layer was dried and evaporated. The crude material (7.01 g, 83%) was of sufficient purity to be used as such in the next step.

$^1$H NMR (CDCl$_3$): δ 0.93 (d, J=6.0, 3H), 0.96 (d, J=6.0, 3H), 1.39 (t, J=12.0, 1H), 1.85–1.65 (m, 3H), 2.08–2.18 (m and s, 6H), 2.90–2.97 (m 1H), 3.00–3.06 (m, 2H), 3.35 (dd, J=14.2, 8.5, 1H), 4.65 (d, J=8.7, 1H), 6.3 (s, 1H), 7.42 (d, J=8.8, 2H), 7.6 (d, J=8.8, 2H).

Step B. Preparation of Nα-(4-aminobenzenesulfonyl)-Nα-isobutyl-L-lysine potassium salt A mixture of Nα-isobutyl-Nα-(4-acetamidobenzenesulfonyl)-L-α-amino-ε-caprolactam (6.8 g, 2 mmol) and 6N HCl (200 mL) was refluxed for 12 h until all solids had disappeared. Afterwards, the solution was evaporated to dryness. The resulting solid was dissolved in EtOH (15 mL), neutralized with KOH and precipitated from acetone to give 8.0 g (100%) of the pure potassium salt.

$^1$H NMR (DMSO-d$_6$): δ 0.72 (dd, J=5.8, 6.4, 6H), 1.13–1.27 (m, 3H), 1.37–1.44 (m 1H), 1.72–1.78 (m, 1H), 1.92–1.98 (m, 1H), 2.67–2.73 (m, 2H), 2.80–2.91 (m, 2H), 3.85 (t, J=7.2, 1H), 6.56 (d, J=8.5, 2H), 7.44 (d, J=8.5, 2H).

Step C. Preparation of (2S) 2-N-(4-aminobenzenesulfonyl)-2-N-isobutyl-2,6-diaminohexanol A solution of Nα-(4-aminobenzenesulfonyl)-Nα-isobutyl-L-lysine (13.0 g, 40.0 mmol, step B) dissolved in MeOH (200 mL) was treated with of trimethylsilyl chloride (25 mL). The mixture was refluxed 3 h before stirring at room temperature for 2 k Afterwards, the solution was evaporated and placed under high vacuum until a white solid was obtained (14.0 g). This was suspended in dry THF (100 mL) and added dropwise to a solution of LiAlH$_4$ (5.0 g, 150 mmol) in THF (300 mL). The solution was stirred for 4 h After cooling in an ice bath the solution was quenched by addition of MeOH (50 mL), water (5 mL), then 10% NaOH (5 mL). The solvent was evaporated and the product was extracted from the precipitate with MeOH using a Soxlet apparatus during 18 h. Then, the solvent was evaporated to form a white solid which was dissolved in EtOH, filtered to eliminate Al$_2$O$_3$ and, after cooling, crystallized on standing (12.0 g, 88%).

$^1$H NMR (DMSO-d$_6$): δ 0.82 (m, 6H), 0.97–1.12 (m, 2H), 1.15–1.30 (m, 3H), 1.57 (m, 1H), 1.84 (m, 1H), 2.40 (t, J=7.0, 2H), 2.75 (m, 1H), 2.85 (m, 1H), 3.21 (m, 1H), 3.44 (d, J=6.0, 2H), 5.92 (s, 2H), 6.59 (d, J=8.0, 2H), 7.39 (d, J=8.0, 2H).

Step D. Preparation of (2S, 2'S) 2-N-(4-aminobenzenesulfonyl)-2-N-isobutyl-6-N-[(N'α-(2-thiophenesulfonyl)-S-tryptophanyl]-2,6-diaminohexanol The title product was prepared from (2S) 2-N-(4-aminobenzenesulfonyl)-2-N-isobutyl-2,6-diaminohexanol (step C) following the indications of general procedure Bd using Nα-(2-thiophenesulfonyl)-L-tryptophan (example 53, step A). Purification by HPLC gave 200 mg (98%) of the desired material.

$^1$H NMR (CDCl$_3$): δ 0.84 (d, J=6.3, 3H), 0.89 (d, J=6.3, 3H), 0.94–1.03 (m, 1H), 1.09–1.16 (m, 2H), 1.46–1.49 (m, 1H), 1.93–1.98 (m, 1H), 2.82–3.15 (m, 6H), 3.51 (d, J=6.8, 2H), 3.64 (q, J=6.3, 1H), 4.05 (t, J=7.2, 1H), 6.76 (d, J=6.5, 2H), 6.89 (t, J=4.6, 1H), 6.97 (s, 1H), 7.03 (t, J=4.5, 1H), 7.19 (t, J=4.5, 1H), 7.23–7.28 (m, 3H), 7.34–7.42 (m, 4H), 7.73 (d, J=6.8, 2H).

Example 167

Preparation of (2S, 2'S) 2-N-(4-aminobenzenesulfonyl)-2-N-isobutyl-6-N-(N'α-benzenesulfonyl-S-tryptophanyl)-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-benzenesulfonyl-L-tryptophan (example 4, step A). Purification by HPLC gave 196 mg (96%) of the desired material.

$^1$H NMR (CDCl$_3$): δ 0.84 (d J=6.3, 3H), 0.89 (d, J=6.3, 3H), 0.94–1.03 (m, 1H), 1.09–1.16 (m, 2H), 1.46–1.49 (m, 1H), 1.93–1.98 (m, 1H), 2.82–3.15 (m, 6H), 3.51 (d, J=6.8, 2H), 3.64 (q, J=6.3, 1H), 3.94 (q, J=5.5, 1H), 6.76 (d, J=6.5, 2H), 6.95 (t, J=4.5, 1H), 7.19 (t, J=4.5, 1H), 7.23–7.31 (m, 6H), 7.42 (t, J=4.5, 1H), 7.60 (d, J=6.8, 2H), 7.73 (d, J=6.8, 2H).

Example 168

Preparation of (2S, 2'S) 2-N-(4-aminobenzenesulfonyl)-2-N-isobutyl-6-N-(N'α-acetyl-S-tryptophanyl)-2,6-diaminohexanol The title product was prepared from (2S) 2-N-(4-aminobenzenesulfonyl)-2-N-isobutyl-2,6-diaminohexanal (example 166, step C) following the indications of general procedure Bd using Nα-acetyl-L-tryptophan (example 99, step A). Purification by HPLC gave 165 mg (96%) of the desired material.

$^1$H NMR (CDCl$_3$): δ 0.90–0.98 (m, 6H), 1.09–1.16 (m, 1H), 1.25–1.29 (m, 1H), 1.45–1.52 (m, 1H) 1.92–1.97 (m, 1H), 2.0 (s, 3H), 2.38 (s, 3H), 2.82–3.10 (m, 4H), 3.11–3.26 (m, 3H), 3.51 (d, J=7.0, 2H), 3.64 (q, J=6.3, 1H), 3.75 (br s, 1H), 6.86 (d, J=5.5, 2H), 6.77 (t, J=5.1, 1H), 6.95 (t, J=5.2, 1H), 6.99 (s, 1 H), 7.15 (d, J=6.9, 1H), 7.31 (d, J=7.1, 1H), 7.45 (d, J=6.7, 1H).

Example 169

Preparation of (2S, 2'S) 2-N-(4-aminobenzenesulfonyl)-2-N-isobutyl-6-N-(N'α-pivaloyl-S-tryptophanyl)-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-pivaloyl-S-tryptophan (example 100, step A). Purification by HPLC gave 185 mg (97%) of the desired material.

$^1$H NMR (CDCl$_3$): δ 0.90–0.98 (m, 6H), 1.09–1.16 (m, 1H), 1.23 (s, 9H), 1.25–1.29 (m, 1H), 1.45–1.52 (m, 1H), 1.92–1.97 (m, 1H), 2.82–3.10 (m, 4H), 3.11–3.26 (m, 1H), 3.41–3.45 (m, 1H), 4.51 (q, J=5.0, 1H), 4.64 (br s, 1H), 6.86 (d, J=5.5, 2H), 6.77 (t, J=5.1, 1H), 6.85 (t, J=5.2, 1H), 6.99 (s, 1H), 7.15 (d, J=6.9, 1H), 7.31 (d, J=7.1, 1H), 7.45 (d, J=6.7, 1H).

Example 170

Preparation of (2S, 2'S) 2-N-(4-aminobenzenesulfonyl)-2-N-isobutyl-6-N-[N'α-(4-morpholinecarbonyl)-S-tryptophanyl]-2,6-diaminohexanol Step A. Preparation of Nα-(4-morpholinecarbonyl)-L-tryptophan L-tryptophan was reacted with 4-morpholinecarbonyl chloride under the conditions used in general procedure A giving the title compound as a thick oil. This material was used without further purification in the next step.

Step B. Preparation of (2S, 2'S) 2-N-(4-aminobenzenesulfonyl)-2-N-isobutyl-6-N-[N'α-(4-morpholinecarbonyl)-S-tryptophanyl]-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-(4-morpholinecarbonyl)-L-tryptophan (step A). Purification by HPLC gave 185 mg (97%) of the desired material.

$^1$H NMR (CDCl$_3$): δ 0.90–0.98 (m, 6H), 1.09–1.16 (m, 1H), 1.23 (s, 9H), 1.25–1.29 (m, 1H), 1.45–1.52 (m, 1H), 1.92–1.97 (m, 1H), 2.82–3.10 (m, 4H), 3.11–3.36 (m, 6H), 3.41–3.55 (m, 4H), 4.14 (br s, 1H), 6.86 (d, J=5.5, 2H), 6.77 (t, J=5.1, 1H), 6.85 (t, J=5.2, 1H), 6.99 (s, 1H), 7.15 (d, J=6.9, 1H), 7.31 (d, J=7.1, 1H), 7.45 (d, J=6.7, 1H).

Example 171

Preparation of (2S, 2'S) 2-N-isobutyl-2-N-(4-methylbenzenesulfonyl)-6-N-[N'α-(4-morpholinecarbonyl)-S-tryptophanyl]-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-(4-morpholinecarbonyl)-L-tryptophan (example 170, step A). Purification by HPLC gave 110 mg (57%) of the desired material.

$^1$H NMR (CDCl$_3$): δ 0.90–0.98 (m, 6H), 1.09–1.16 (m, 1H), 1.23 (s, 9H), 1.25–1.29 (m, 1H), 1.45–1.52 (m, 1H), 1.92–1.97 (m, 1H), 2.33 (s, 3H), 2.82–3.10 (m, 4H), 3.11–3.36 (m, 6H), 3.41–3.55 (r, 4H), 4.14 (br s, 1H), 6.86 (d, J=5.5, 2H), 6.77 (t, J=5.1, 1H), 6.85 (t, J=5.2, 1H), 6.99 (s, 1H), 7.15 (d, J=6.9, 1H), 7.31 (d, J=7.1, 1H), 7.45 (d, J=6.7, 1H).

Example 172

Preparation of (2S, 2'S) 2-N-isobutyl-2-N-(4-methoxybenzenesulfonyl)-6-N-(N'α-acetyl-S-tryptophanyl)-2,6-diaminohexanol Treatment of (2S, 2'S) 2-N-isobutyl-2-N-(4-methoxybenzenesulfonyl)-6-N-(S-tryptophanyl)-2,6-diaminohexanol trifluoroacetic acid salt (example 146) with acetyl chloride, using similar reaction conditions as for example 65 (step B) which uses 4-methylbenzenesulfonyl chloride, afforded the desired product in 86% yield.

$^1$H NMR (DMSO-d$_6$): δ 0.82 (t, J=7.0, 6H), 1.02 (s, 9H), 1.00–1.30 (m, 5H), 1.77 (s, 3H), 2.80–2.95 (m, 5H), 3.03 (dd, J=13.5, 7.0, 1H), 3.77 (m, 1H), 3.81 (s, 3H), 3.90 (m, 1H), 3.98 (m, 1H), 4.45 (m, 1H), 6.96 (t, J=7.5, 1H), 7.04 (t, J=7.5, 1H), 7.10 (d, J=8.0, 2H), 7.30 (d, J=7.5, 1H), 7.58 (d, J=7.5, 1H), 7.70 (d, J=8.6, 2H), 7.85 (t, J=5.5, 1H), 7.99 (d, J=8.5, 1H), 10.75 (s, 1H).

Example 173

Preparation of (2S, 2'S) 2-N-cyclopentylmethyl-2-N-(4-methoxybenzenesulfonyl)-6-N-(N'α-acetyl-S-tryptophanyl)-2,6-diaminohexanol Treatment of (2S, 2'S) 2-N-cyclopentylmethyl-2-N-(4-methoxybenzenesulfonyl)-6-N-(S-tryptophanyl)-2,6-diaminohexanol trifluoroacetic acid salt (example 152) with acetyl chloride, using similar reaction conditions as for example 65 (step B) which uses 4-methylbenzenesulfonyl chloride, afforded the desired product in 76% yield.

$^1$H NMR (DMSO-d$_6$): δ 0.93–1.30 (m, 7H), 1.40–1.68 (m, 7H), 1.77 (s, 3H), 2.18 (m, 1H), 2.84–3.10 (m, 5H), 3.30 (m, 2H), 3.50 (m, 1H), 3.81 (s, 3H), 4.45 (m, 1H), 4.65 (m, 1H), 6.95–7.13 (m, 5H), 7.30 (d, J=8.3, 1H), 7.56 (d, J=8.5, 1H), 7.71 (d, J=8.2, 2H), 7.85 (t, J=5.5, 1H), 7.98 (d, J=8.0, 1H), 10.75 (s, 1H).

Example 174

Preparation of Nα-isobutyl-Nα-(4-methylbenzenesulfonyl)-Nε-[N'α-(4-methoxybenzyl)-N'α-phenylglycyl]-L-lysine Step A. Preparation of Nα-(4-methoxybenzyl)-Nα-phenylglycine The title compound was prepared from N-phenylglycine (1.51 g, 10.0 mmol) as described for the preparation of N-benzyl-N-phenylglycine (example 114, step A) using 4-methoxybenzylchloride (1.72 g, 11.0 mmol) instead of benzylbromide. The crude material was purified by flash chromatography using 9:1 CH$_2$Cl$_2$/hexane. The product was isolated as a yellow solid (2.33 g, 86% yield).

$^1$H NMR (DMSO-d$_6$): δ 3.72 (s, 3H), 4.11 (s, 2H), 4.51 (s, 2H), 6.59 (m, 3H), 6.87 (d, J=7.5, 2H), 7.11 (t, J=7.9, 2H), 7.21 (d, J=8.2, 2H), 12.6 (s, 1H).

Step B. Preparation of Nα-isobutyl-Nα-(4-methylbenzenesulfonyl)-Nε-[N'α-(4-methoxybenzyl)-N'α-phenylglycyl]-L-lysine The title product was prepared from Nα-isobutyl-Nα-(4-methylbenzenesulfonyl)-L-lysine hydrochloride (360 mg, 1.0 mmol, example 1, step E) following the indications of general procedure Ba using Nα-(4-methoxybenzyl)-Nα-phenylglycine (271 mg, 1.0 mmol, step A) and N,N-carbonyldiimidazole (195 mg, 1.2 mmol). The crude material was purified by preparative HPLC. The product was isolated as a solid (39 mg, 6% yield).

$^1$H NMR (DMSO-$d_6$): δ 0.81 (t, J=6.9, 6H), 1.17 (m, 2H), 1.33 (m, 2H), 1.48 (m, 1H), 1.80 (m, 1H), 1.90 (m, 1H), 2.37 (s, 3H), 2.85–3.05 (m, 4H), 3.71 (s, 3H), 3.90 (s, 2H), 4.16 (t, J=7.2, 1H), 4.54 (s, 2H), 6.61 (t, J=8.7, 3H), 6.87 (d, J=8.4, 2H), 7.11 (t, J=7.4, 2H), 7.17 (d, J=8.6, 2H), 7.36 (d, J=7.6, 2H), 7.66 (d, J=8.3, 2H), 7.83 (t, J=5.1, 1H), 12.75 (s, 1H). LC-MS: 610 (M+H)$^+$, 99% pure.

Example 175

Preparation of (2S) 2-N-isobutyl-2-N-(4-methylbenzenesulfonyl)-6-N-[N'α-(4-methoxybenzyl)-N'α-phenylglycyl]-2,6-diaminohexanol The title product was prepared from (2S) 2-N-isobutyl-2-N-(4-methylbenzenesulfonyl)-2,6-diaminohexanol (345 mg, 1.0 mmol, example 116, step A) following the indications of general procedure Ba using Nα-(4-methoxybenzyl)-Nα-phenylglycine (271 mg, 1.0 mmol, example 174, step A) and N,N-carbonyldiimidazole (195 mg, 1.2 mmol). The crude material was purified by preparative HPLC. The product was isolated as a yellow solid (105 mg, 18% yield).

$^1$H NMR (DMSO-$d_6$): δ 0.82 (m, 6H), 1.01 (m, 2H), 1.23 (m, 3H), 1.48 (m, 1H), 1.86 (m, 1H), 2.36 (s, 3H), 2.85 (m, 1H), 2.95 (m, 3H), 3.26 (dd, J=11.2, 6.3, 1Ha), 3.32 (dd, J=11.2, 6.3, 1Hb), 3.52 (m, 1H), 3.71 (s, 3H), 3.89 (s, 2H), 4.35 (m, 1H), 4.54 (s, 2H), 6.61 (m, 3H), 6.86 (d, J=8.6, 2H), 7.11 (t, J=8.0, 2H), 7.17 (d, J=7.9, 2H), 7.36 (t, J=7.0, 2H), 7.66 (d, J=8.5, 2H), 7.78 (t, J=4.9, 1H). LC-MS: 596 (M+H)$^+$, 95% pure.

Example 176

Preparation of (2S) 2-N-(4-aminobenzenesulfonyl)-2-N-isobutyl-6-N-[N'α-(4-methoxybenzyl)-N'α-phenylglycyl]-2,6-diaminohexanol The title product was prepared from (2S) 2-N-(4-aminobenzenesulfonyl)-2-N-isobutyl-2,6-diaminohexanol (350 mg, 1.0 mmol example 166, step C) following the indications of general procedure Ba using Nα-(4-methoxybenzyl)-Nα-phenylglycine (271 mg, 1.0 mmol, example 174, step A) and N,N-carbonyldiimidazole (195 mg, 1.2 mmol). The crude material was purified by preparative HPLC. The product was isolated as a yellow solid (87 mg, 14% yield).

$^1$H NMR (DMSO-$d_6$): δ 0.81 (t, J=7.0, 6H), 1.10 (m, 2H), 1.27 (m, 3H), 1.51 (m, 1H), 1.85 (m, 1H), 2.75 (dd, J=14.1, 7.3, 1Ha), 2.83 (dd, J=14.1, 7.3, 1Hb), 2.98 (m, 2H), 3.22 (m, 1H), 3.30 (m, 1H), 3.45 (m, 1H), 3.71 (s, 3H), 3.90 (s, 2H), 4.54 (s, 2H), 6.60 (m, 5H), 6.86 (d, J=8.8, 2H), 7.11 (t, J=7.6, 2H), 7.17 (d, J=7.7, 2H), 7.39 (d, J=8.7, 2H), 7.80 (t, J=5.0, 1H). LC-MS: 597 (M+H)$^+$, 98% pure.

Example 177

Preparation of (2S, 2'S) 2-N-(4-aminobenzenesulfonyl)-2-N-isobutyl-6-N-(N'α-methoxycarbonyl-S-phenylalanyl)-2,6-diaminohexanol Step A. Preparation of Nα-methoxycarbonyl-L-phenylalanine L-phenylalanine was reacted with methyl chloroformate under the conditions used in general procedure A giving the title compound as an oil which was used without further purification in the next step.

Step B. Preparation of (2S, 2'S) 2-N-(4-aminobenzenesulfonyl)-2-N-isobutyl-6-N-(N'α-methoxycarbonyl-S-phenylalanyl)-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-methoxycarbonyl-L-phenylalanine (step A). Purification by HPLC gave 159 mg (98%) of the desired material.

$^1$H NMR (CDCl$_3$): δ 0.79 (d, J=6.3, 3H), 0.82 (d, J=6.3, 3H), 1.08–1.11 (m, 2H), 1.23–1.31 (m, 2H), 1.45–1.52 (m, 1H), 1.92–1.97 (m, 1H), 1.98 (d, J=9.0, 3H), 2.84–3.09 (m, 6H), 3.51 (d, J=7.1, 2H), 3.59 (s, 3H), 3.61–3.64 (m, 1H), 4.51 (q, J=6.9, 1H), 6.76 (d, J=8.1, 2H), 7.09–7.26 (m, 5H), 7.73 (d, J=8.1, 2H). LC-MS: 549.7 (M+H)$^+$, 98% pure.

Example 178

Preparation of (2S, 2'S) 2-N-(4-aminobenzenesulfonyl)-2-N-isobutyl-6-N-(N'α-methoxycarbonyl-S-tryptophanyl)-2,6-diaminohexanol Step A. Preparation of Nα-methoxycarbonyl-L-tryptophan L-tryptophan was reacted with methyl chloroformate under the conditions used in general procedure A giving the title compound as an oil which was used without further purification in the next step.

Step B. Preparation of (2S, 2'S) 2-N-(4-aminobenzenesulfonyl)-2-N-isobutyl-6-N-(N'α-methoxycarbonyl-S-tryptophanyl)-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-methoxycarbonyl-L-tryptophan (step A). Purification by HPLC gave 155 mg (87%) of the desired material.

$^1$H NMR (CDCl$_3$): δ 0.90–0.98 (m, 6H), 1.09–1.16 (m, 1H), 1.25–1.29 (m, 1H), 1.45–1.52 (m, 1H), 1.92–1.97 (m, 1H), 2.82–3.10 (m, 4H), 3.11–3.26 (m, 3H), 3.51 (d, J=7.0, 2H), 3.59 (s, 3H), 3.64 (q, J=6.3, 1H), 3.75 (br s, 1H), 6.86 (d, J=5.5, 2H), 6.77 (t, J=5.1, 1H), 6.95 (t, J=5.2, 1H), 7.15 (d, J=6.9, 1H), 7.31 (d, J=7.1, 1H), 7.45 (d, J=6.7, 1H). LC-MS: 588.7 (M+H)$^+$, 98% pure.

Example 179

Preparation of (2S, 2'S) 2-N-(4-aminobenzenesulfonyl)-2-N-isobutyl-6-N-[N'α-(4-nitrobenzenesulfonyl)-S-tryptophanyl]-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-(4-nitrobenzenesulfonyl)-L-tryptophan (example 5, step A). Purification by HPLC gave 255 mg (60%) of the desired material.

LC-MS: 715.8 (M+H)$^+$, 98% pure.

Example 180

Preparation of (2S, 2'S) 2-N-(4-aminobenzenesulfonyl)-2-N-isobutyl-6-N-[N'α-(4-morpholinecarbonyl)-S-phenylalanyl]-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-(4-morpholinecarbonyl)-L-phenylalanine (example 51, step A). Purification by HPLC gave 165 mg (91%) of the final product.

$^1$H NMR (CDCl$_3$): δ 0.79 (d, J=6.3, 3H), 0.82 (d, J=6.3, 3H), 1.08–1.11 (m, 2H), 1.23–1.31 (m, 2H), 1.45–1.52 (m, 1H), 1.92–1.97 (m, 1H), 2.84–3.09 (m, 6H), 3.21–3.31 (m, 4H), 3.45–3.64 (m, 7H), 4.48 (br s, 1H), 6.88 (d, J=8.1, 2H), 7.09–7.26 (m, 5H), 7.43 (d, J=8.1, 2H). LC-MS: 604.8 (M+H)$^+$, 98% pure.

Example 181

Preparation of (2S) 2-N-(4-aminobenzenesulfonyl)-2-N-isobutyl-6-N-(N'α-isobutyl-N'α-phenylglycyl)-2,6-diaminohexanol Step A. Preparation of N-isobutyl-N-phenylglycine The title compound was prepared from N-phenylglycine (1.0 g, 5.5 mmol) as described for the preparation of N-benzyl-N-phenylglycine (example 114, step A) using isobutyl iodide (2.0 mL, 17.3 mmol) instead of benzylbromide. The crude material was purified by flash chromatography using hexane/EtOAc/CHCl$_3$ (7:3:2) as the eluent. The product was isolated as a brown oil (560 mg, 41% yield).

$^1$H NMR (CDCl$_3$): δ 0.94 (m, 6H), 2.03 (m, 1H), 3.16 (d, J=7.2, 2H), 4.06 (s, 2H), 6.66 (d, J=8.2, 2H), 6.75 (t, J=7.2, 1H), 7.21 (t, J=8.0, 2H).

Step B. Preparation of (2S) 2-N-(4-aminobenzenesulfonyl)-2-N-isobutyl-6-N-(N'αc-isobutyl-N'α-phenylglycyl)-2,6-diaminohexanol A solution of N-isobutyl-N-phenylglycine (200 mg, 1.0 mmol, step A) in DMF (5.0 mL) was treated with EDC (290 mg, 1.5 mmol) and HOBt (100 mg, 0.75 mmol) for a period of 10 min under an inert atmosphere or argon. Then, (2S) 2-N-(4-aminobenzenesulfonyl)-2-N-isobutyl-2,6-diaminohexanol (345 mg, 1.0 mmol example 166, step C) was added and the reaction mixture was stirred for a period of 6 h. Afterwards, a 10% aqueous citric acid solution was added and the product extracted with EtOAc (10 mL, 3×). The organic phase was washed with water 10 mL (3×) and with brine (5 mL). The organic phase was dried with MgSO$_4$, filtered and evaporated to a solid. The crude material was purified by preparative HPLC. The product was isolated as a yellow solid (125 mg, 24% yield).

$^1$H NMR (DMSO-d$_6$): δ 0.81 (t, J=6.5, 6H), 0.88 (d, J=8.1, 6H), 1.05 (m, 1H), 1.13 (m, 1H), 1.26 (m, 3H), 1.55 (m, 1H), 1.84 (m, 1H), 1.98 (m, 1H), 2.74 (dd, J=13.6, 7.1, 1H), 2.83 (dd, J=14.2, 7.5, 1H), 2.95 (d, J=6.4, 2H), 3.18 (d, J=7.3, 2H), 3.23 (m, 1H), 3,44 (m, 1H), 3.85 (s, 2H), 4.59 (t, J=5.0, 1H), 5.90 (s, 2H), 6.58 (m, 5H), 7.11 (t, J=7.4, 2H), 7.38 (d, J=8.6, 2H), 7.67 (t, J=5.0, 1H). LC-MS: 553 (M+H)$^+$, 98% pure.

Example 182

Preparation of (2S) 2-N-(4-aminobenzenesulfonyl)-2-N-isobutyl-6-N-(N'α-benzyl-N'α-phenylglycyl)-2,6-diaminohexanol The title product was prepared from (2S) 2-N-(4-aminobenzenesulfonyl)-2-N-isobutyl-2,6-diaminohexanol (345 mg, 1.0 mmol, example 166, step C) as described above for the preparation of 2-N-(4-aminobenzenesulfonyl)-2-N-isobutyl-6-N-(N'α-isobutyl-N'α-phenylglycyl)-2,6-diaminohexanol (example 183) using N-benzyl-N-phenylglycine (241 mg, 1.0 mmol, example 114, step A) instead of N-isobutyl-N-phenylglycine. The crude material was purified by preparative HPLC. The product was isolated as a yellow solid (370 mg, 65% yield).

$^1$H NMR (DMSO-d$_6$): δ 0.81 (t, J=6.9, 6H), 1.05 (m, 1H), 1.13 (m, 1H), 1.28 (m, 3H), 1.55 (m, 1H), 1.84 (m, 1H), 2.74 (dd, J=12.6, 7.0, 1H), 2.85 (dd, J=11.3, 5.9, 1H), 2.98 (d, J=6.0, 2H), 3.24 (dd, J=11.7, 6.3, 1H), 3.30 (dd, J=8.9, 5.0, 1H), 3.45 (m, 1H), 3.94 (s, 2H), 4.62 (s, 2H), 5.35 (br s, 2H), 6.60 (m, 5H), 7.11 (t, J=7.7, 2H), 7.24 (m, 3H), 7.31 (t, J=7.5, 2H), 7.39 (d, J=7.6, 2H), 7.83 (t, J=5.1, 1H). LC-MS: 567 (M+H)$^+$, 99% pure.

Example 183

Preparation of (2S, 2'S) 2-N-isobutyl-2-N-(4methylbenzenesulfonyl)-6-N-(S-tryptophanyl)-2,6-diaminohexanol trifluoroacetic acid salt Step A. Preparation of Nα-isobutyl-Nα-(4-methylbenzenesulfonyl)-Nε-(N'α-tert-butoxycarbonyl-L-tryptophanyl)-L-lysine methyl ester To a stirred solution of Nα-isobutyl-Nα-(4-methylbenzenesulfonyl)-L-lysine methyl ester (370 mg, 1 mmol, example 65, step C) in THF/K$_2$CO$_3$ (1M) (3 mL/3 mL) was added Nα-tert-butoxycarbonyl-L-tryptophan N-hydroxysuccinimide ester (550 mg, 1.2 mmol). The reaction mixture was stirred overnight then diluted with 1N HCl and extracted with EtOAc. The organic layer was dried (MgSO$_4$) and concentrated. The crude was purified by flash chromatography using hexane/EtOAc as eluent to afford the desired product (85% yield).

$^1$H NMR (DMSO-d$_6$): δ 0.81 (t, J=7.0, 6H), 1.10–1.50 (m, 5H), 1.31 (s, 9H), 1.75–1.90 (m, 2H), 2.38 (s, 3H), 2.82–3.10 (m, 5H), 3.44 (s, 3H), 4.12 (m, 1H), 4.30 (t, J=5.0, 1H), 6.67 (d, J=8.2, 1H), 6.90–7.12 (m, 5H), 7.30 (d, J=8.0, 1H), 7.40 (d, J=7.5, 2H), 7.55 (m, 1H), 7.65 (d, J=7.5, 2H), 7.78 (m, 1H), 10.77 (s, 1H).

Step B. Preparation of (2S, 2'S) 2-N-isobutyl-2-N-(4-methylbenzenesulfonyl)-6-N-(N'α-tert-butoxycarbonyl-S-tryptophanyl)-2,6-diaminohexanol Nα-isobutyl-Nα-(4-methylbenzenesulfonyl)-Nε-(N'α-tert-butoxycarbonyl-L-tryptophanyl)-L-lysine methyl ester (step A) was reduced with LiAlH$_4$ following the indications of general procedure G. The final product was obtained with 78% yield.

$^1$HNMR(DMSO-d$_6$): δ 0.84 (t, J=7.0, 6H), 0.90–1.27 (m, 5H), 1.31 (s, 9H), 1.52 (m, 1H), 1.85 (m, 1H), 2.37 (s, 3H), 2.80 and 3.02 (ABX, J=14.0, 7.2, 2H), 2.90 (m, 2H), 3.33 (m, 1H), 3.50 (m, 1H), 4.15 (m, 11H), 4.65 (t, J=5.0, 1H), 6.65 (d, J=7.8, 1H), 6.92–7.12 (m, 5H), 7.30 (d, J=7.8, 1H), 7.35 (d, J=7.5, 2H), 7.57 (d, J=8.0, 1H), 7.67 (d, J=7.7, 2H), 7.73 (t, J=5.0, 1H), 10.77 (s, 1H).

Step C. Preparation of (2S, 2'S) 2-N-isobutyl-2-N-(4-methylbenzenesulfonyl)-6-N-(S-tryptophanyl)-2,6-diaminohexanol trifluoroacetic acid salt This product was obtained quantitatively by treating (2S, 2'S) 2-N-isobutyl-2-N-(4-methylbenzenesulfonyl)-6-N-(N'α-tert-butoxycarbonyl-S-tryptophanyl)-2,6-diaminohexanol (step B) with TFA in CH$_2$Cl$_2$.

$^1$H NMR (DMSO-d$_6$): δ 0.80 (d, J=7.0, 3H), 0.83 (d, J=7.0, 3H), 0.92–1.60 (m, 6H), 1.88 (m, 1H), 2.37 (s, 3H), 2.78–3.00 (m, 4H), 3.05 and 3.20 (ABX, J=14.0, 7.0, 2H), 3.22 and 3.30 (ABX, J=14.2, 7.0, 2H), 3.50 (m, 1H), 3.86–3.97 (m, 2H), 4.35 (m, 1H), 6.95–7.12 (m, 4H), 7.18 (s, 1H), 7.38 (d, J=8.2, 1H), 7.60 (m, 1H), 7.70 (d, J=8.2, 2H), 8.05 (br s, 3H), 8.34 (m, 1H), 10.99 (s, 1H).

Example 184

Preparation of (2S, 2'S) 2-N-(4-aminobenzenesulfonyl)-2-N-isobutyl-6-N-(N'α-isobutyryl-S-tryptophanyl)-2,6-diaminohexanol Step A. Preparation of Nα-isobutyryl-L-tryptophan L-tryptophan was reacted with isobutyryl chloride under the conditions used in general procedure A giving the title compound which was recrystallised from DCM (55%). This material was used without further purification in the next step.

Step B. Preparation of (2S, 2'S) 2-N-(4-aminobenzenesulfonyl)-2-N-isobutyl-6-N-(N'α-isobutyryl-S-tryptophanyl)-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-isobutyryl-L-tryptophan (step A). Purification by HPLC gave 121 mg (67%) of the desired material.

$^1$H NMR (DMSO-d$_6$): δ 0.80–0.90 (m, 9H), 0.95–0.97 (d, J=6.6, 3H), 1.09–1.16 (m, 1H), 1.25–1.29 (m, 1H), 1.45–1.52 (m, 1H), 1.92–1.97 (m, 1H), 2.33–2.45 (m, 1H), 2.82–2.99 (m, 4H), 3.26–3.33 (m, 1H), 3.51–3.55 (m, 1H), 4.64 (br s, 1H), 6.66 (d, J=5.5, 2H), 6.87 (t, J=5.1, 1H), 6.95 (t, J=5.2, 1H), 6.99 (s, 1H), 7.15 (d, J=6.9, 1H), 7.31 (d, J=7.1, 1H), 7.45 (d, J=6.7, 1H). LC-MS: 600.8 (M+H)$^+$, 99% pure.

Example 185

Preparation of (2S, 2'S) 2-N-(4-aminobenzenesulfonyl)-2-N-isobutyl-6-N-(N'α-tert-butylacetyl-S-tryptophanyl)-2,6-diaminohexanol Step A. Preparation of Nα-tert-butylacetyl-L-tryptophan L-tryptophan was reacted with tert-butylacetyl chloride under the conditions used in general procedure A giving the title compound which was recrystallised from DCM (81%). This material was used as such in the next step.

Step B. Preparation of (2S, 2'S) 2-N-(4-aminobenzenesulfonyl)-2-N-isobutyl-6-N-(N'α-tert-butylacetyl-S-tryptophanyl)-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-tert-butylacetyl-L-tryptophan (step A). Purification by HPLC gave 133 mg (70%) of the desired material.

$^1$HNMR(DMSO-d$_6$): δ 0.80–0.90 (m, 15H), 1.09–1.16 (m, 1H), 1.25–1.29 ((m, 1H), 1.45–1.52 (m, 1H), 1.82–1.87 (m, 1H), 1.97 (s, 2H), 2.33–2.45 (m, 1H), 2.82–2.99 (m, 4H), 3.26–3.33 (m, 1H), 3.51–3.55 (m, 1H), 4.64 (br s, 1H), 6.66 (d, J=5.5, 2H), 6.87 (t, J=5.1, 1H), 6.95 (t, J=5.2, 1H), 6.99 (s, 1H), 7.15 (d, J=6.9, 1H), 7.31 (d, J=7.1, 1H), 7.45 (d, J=6.7, 1H). LC-MS: 628.8 (M+H)$^+$, 98% pure.

Example 186

Preparation of (2S, 2'S) 2-N-(4-aminobenzenesulfonyl)-2-N-isobutyl-6-N-(N'α-benzoyl-S-tryptophanyl)-2,6-diaminohexanol Step A. Preparation of Nα-benzoyl-L-tryptophan L-tryptophan was reacted with benzoyl chloride under the conditions used in general procedure A giving the title compound which was recrystallised from DCM (51%). This compound was used without further purification in the next step.

Step B. Preparation of (2S, 2'S) 2-N-(4-aminobenzenesulfonyl)-2-N-isobutyl-6-N-(N'α-benzoyl-S-tryptophanyl)-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-benzoyl-L-tryptophan (step A). Purification by HPLC gave 122 mg (64%) of the desired material.

$^1$H NMR (CDCl$_3$): δ 0.84 (d, J=6.3, 3H), 0.89 (d, J=6.3, 3H), 0.94–1.03 (m, 1H), 1.09–1.16 (m, 2H), 1.46–1.49 (m, 1H), 1.93–1.98 (m, 1H), 2.39 (s, 3H), 2.82–3.15 (m, 6H), 3.51 (d, J=6.8, 2H), 3.64 (q, J=6.3, 1H), 3.94 (q, J=5.5, 1H), 6.95 (t, J=4.5, 1H), 7.19 (t, J=4.5, 1H), 7.23–7.31 (m, 6H), 7.42 (t, J=4.5, 1H), 7.60 (d, J=6.8, 2H), 7.73 (d, J=6.8, 2H). LC-MS: 634.8 (M+H)$^+$, 98% pure.

Example 187

Preparation of (2S, 2'S) 2-N-(4-aminobenzenesulfonyl)-2-N-isobutyl-6-N-[N'α-(4-aminobenzenesulfonyl)-S-tryptophanyl]-2,6-diaminohexanol The title compound was obtained from (2S, 2'S) 2-N-(4-aminobenzenesulfonyl)-2-N-isobutyl-6-N-[N'α-(4-nitrobenzenesulfonyl)-S-tryptophanyl]-2,6-diaminohexanol (200 mg, 0.28 mmol, example 179) by catalytic hydrogenation following the conditions of general procedure E. Purification by HPLC gave 191 mg (99%) of the desired material.

$^1$H NMR (DMSO-d$_6$): δ 0.73 (d, J=6.3, 3H), 0.75 (d, J=6.3, 3H), 1.00–1.11 (m, 4H), 1.32–1.35 (m, 1H), 1.66–1.69 (m, 1H), 1.83–1.88 (m, 1H), 2.48 (br s, 6H), 2.59–2.67 (m, 2H), 2.84–2.96 (m, 2H), 3.20 (d, J=6.5, 2H), 4.21 (t, J=7.2, 1H), 6.66 (d, J=7.1, 2H), 6.72 (d, J=7.1, 2H), 6.85 (t, J=4.0, 1H), 7.09 (t, J=4.0, 2H), 7.28 (d, J=7.1 , 1H), 7.33 (d, J=7.1, 2H), 7.60 (t, J=4.0, 1H). LC-MS: 685.8 (M+H)$^+$, 98% pure.

Example 188

Preparation of (2S, 2'S) 2-N-isobutyl-2-N-(4-methylbenzenesulfonyl)-6-N-(N'α-benzenesulfonyl-S-cyanoalanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-benzenesulfonyl-L-asparagine (example 25, step A). In this particular reaction an excess EDC (2.5 eq.) was used which dehydrated the amide function on the asparagine moiety. Purification by HPLC gave 6 mg (9%) of the desired material.

LC-MS: 579.2 (M+H)$^+$, 92% pure.

Example 189

Preparation of Nα-isobutyl-Nα-(4-methylbenzenesulfonyl)-Nε-(N'α-benzenesulfonyl-L-tryptophanyl)-L-lysine amide A solution of Nα-isobutyl-Nα-(4-methylbenzenesulfonyl)-Nε-(N'α-benzenesulfonyl-L-tryptophanyl)-L-lysine (100 mg, 0.15 mmol, example 4) dissolved in EtOAc (3 mL) was treated with DCC (30 mg, 0.15 mmol) and N-hydroxysuccinimide (17 mg, 0.15 mmol). The resulting solution was stirred overnight at room temperature. Then, the reaction mixture was filtered through celite. The organic solvent was evaporated and the crude residue dissolved in THF (5 mL) was treated with concentrated NH$_4$OH (1 mL). The reaction mixture was left in the refrigerator overnight. Afterwards, it was filtered through celite and the solvent was evaporated to give 98 mg (97%) of the desired title compound after purification by HPLC.

LC-MS: 682.8 (M+H)$^+$, 99% pure.

Example 190

Preparation of (2S, 2'S) 2-N-isobutyl-2-N-(4-methylbenzenesulfonyl)-6-N-(N'α-methoxycarbonyl-S-tryptophanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-methoxycarbonyl-L-tryptophan (example 178, step A). Purification by HPLC gave 21 mg (15%) of the desired material.

$^1$H NMR (CDCl$_3$): δ 0.90–0.98 (m, 6H), 1.09–1.16 (m, 1H), 1.25–1.29 (m, 1H), 1.45–1.52 (m, 1H), 1.92–1.97 (m, 1H), 2.38 (s, 3H), 2.82–3.10 (m, 4H)9 3.11–3.26 (m, 3H), 3.51 (d, J=7.0, 2H), 3.59 (s, 3H), 3.64 (q, J=6.3, 1H), 3.75 (br s, 1H), 6.77 (t, J=5.1, 1H), 6.95 (t, J=5.2, 1H), 6.99 (s, 1H), 7.15–7.25 (m, 3H), 7.31 (d, J=7.1, 1H), 7.75 (d, J=6.7, 1H). LC-MS: 587 (M+H)$^+$, 99% pure.

Example 191

Preparation of (2S, 2'S) 2-N-isobutyl-2-N-(4-methylbenzenesulfonyl)-6-N-(N'α-benzoyl-S-tryptophanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-benzoyl-L-tryptophan (example 186, step A). Purification by HPLC gave 41 mg (28%) of the desired material.

$^1$H NMR (CDCl$_3$): δ 0.90–0.98 (m, 6H), 1.09–1.16 (m, 1H), 1.25–1.29 (m, 1H), 1.45–1.52 (m, 1H), 1.92–1.97 (m, 1H), 2.82–3.10 (m, 4H), 3.11–3.26 (m, 3H), 3.51 (d, J=7.0, 2H), 3.59 (s, 3H), 3.64 (q, J=6.3, 1H), 4.08 (br s, 1H), 6.86 (d, J=5.5, 2H), 6.77 (t, J=5.1, 1H), 6.95 (t, J=5.2, 1H), 6.99 (s, 1H), 7.15 (d, J=6.9, 1H), 7.31 (d, J=7.1, 1H), 7.45 (d, J=6.7, 1H). LC-MS: 633.8 (M+H)$^+$, 99% pure.

Example 192

Preparation of (2S, 2'S) 2-N-isobutyl-2-N-(4-methylbenzenesulfonyl)-6-N-(N'α-isobutoxycarbonyl-S-tryptophanyl)-2,6-diaminohexanol Step A. Preparation of Nα-isobutoxycarbonyl-L-tryptophan L-tryptophan was reacted with isobutyl chloroformate under the conditions used in general procedure A giving the title compound which was recrystallised neat. This product was used without further purification in the next step.

Step B. Preparation of (2S, 2'S) 2-N-isobutyl-2-N-(4-methylbenzenesulfonyl)-6-N-(N'α-isobutoxycarbonyl-S-tryptophanyl)-2,6-diaminohexanol The title product was prepared from (2S) 2-N-isobutyl-2-N-(4-methylbenzenesulfonyl)-2,6-diaminohexanol (example 116, step A) following the indications of general procedure Bd using Nα-isobutoxycarbonyl-L-tryptophan (step A). Purification by HPLC gave 64 mg (40%) of the desired material.

$^1$H NMR (DMSO-d$_6$): δ 0.80–0.91 (m, 9H), 0.94–0.97 (d, J=6.6, 3H), 1.09–1.16 (m, 1H), 1.25–1.29 (m, 1H), 1.45–1.52 (m, 1H), 1.92–1.97 (m, 1H), 2.33–2.45 (m and s, 4H), 2.82–2.99 (m, 6H), 3.26–3.33 (m, 1H), 3.51–3.55 (m, 1H), 4.44 (br s, 1H), 6.87 (t, J=5.1, 1H), 6.95 (t, J=5.2, 1H), 6.99 (s, 1H), 7.15–7.22 (m, 3H), 7.31 (d, J=7.1, 1H), 7.65 (d, J=6.7, 1H). LC-MS: 629.8 (M+H)$^+$, 99% pure.

Example 193

Preparation of (2S, 2'S) 2-N-(4-aminobenzenesulfonyl)-2-N-isobutyl-6-N-(N'α-isobutoxycarbonyl-S-tryptophanyl)-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-isobutoxycarbonyl-L-tryptophan (example 192, step A). Purification by HPLC gave 151 mg (95%) of the final product.

$^1$H NMR (DMSO-d$_6$): δ 0.80–0.90 (m, 9H), 0.95–0.97 (d, J=6.6, 3H), 1.09–1.16 (m, 1H), 1.25–1.29 (m, 1H), 1.45–1.52 (m, 1H), 1.92–1.97 (m, 1H), 2.33–2.45 (m, 1H), 2.82–2.99 (m, 6H), 3.26–3.33 (m, 1H), 3.51–3.55 (m, 1H), 4.44 (br s, 1H), 6.66 (d, J=5.5, 2H), 6.87 (t, J=5.1, 1H), 6.95 (t, J=5.2, 1H), 6.99 (s, 1H), 7.15 (d, J=6.9, 1H), 7.31 (d, J=7.1, 1H), 7.45 (d, J=6.7, 1H). LC-MS: 630.2 (M+H)$^+$, 99% pure.

Example 194

Preparation of (2S, 2'S) 2-N-(4-aminobenzenesulfonyl)-2-N-isobutyl-6-N-[N'α-(4-nitrobenzenesulfonyl)-S-phenylalanyl]-2,6-diaminohexanol The title product was prepared from (2S) 2-N-(4-aminobenzenesulfonyl)-2-N-isobutyl-2,6-diaminohexanol (example 166, step C) following the indications of general procedure Bd using Nα-(4-nitrobenzenesulfonyl)-L-phenylalanine (example 10, step A). Purification by HPLC of about half (50 mg) of the crude material gave 20 mg (40%) of the final product.

LC-MS: 676.8 (M+H)$^+$, 95% pure.

Example 195

Preparation of (2S, 2'S) 2-N-(4-aminobenzenesulfonyl)-2-N-isobutyl-6-N-[N'α-(4-aminobenzenesulfonyl)-S-phenylalanyl]-2,6-diaminohexanol The title compound was obtained from (2S, 2'S) 2-N-(4-aminobenzenesulfonyl)-2-N-isobutyl-6-N-[N'α-(4-nitrobenzenesulfonyl)-S-phenylalanyl]-2,6-diaminohexanol (50 mg, 0.07 mmol, example 194) by catalytic hydrogenation following the conditions of general procedure E. Purification by HPLC gave 31 mg (77%) of the desired material.

LC-MS: 646.8 (M+H)$^+$, 99% pure.

Example 196

Preparation of Nα-isobutyl-Nα-(4-methylbenzenesulfonyl)-Nε-[N'α-(4-methoxyanilinecarbonyl)-L-phenylalanyl]-L-lysine The title compound was prepared from solid phase bound Nα-isobutyl-Nα-(4-methylbenzenesulfonyl)-Nε-(9-fluorenylmethoxycarbonyl)-L-lysine (450 mg, 0.125 mmol) as described in general procedure Bb using commercially available Nα-(9-fluorenylmethoxycarbonyl)-L-phenylalanine (400 mg, 0.9 mmol). After the coupling reaction, the resin was once more deprotected and activated with N,N-carbonyldiimidazole (5–10 fold excess) for 30 min. after which time the resin was washed with DCM (4×) before 4-methoxyaniline was added. The tube was sealed and left for a period of 12 h. Afterwards, the product was cleaved from the resin using TFA as indicated in general procedure Bb. The final product was purified by preparative HPLC to yield 11 mg (13%) of the desired material.

$^1$H NMR (CDCl$_3$): δ 0.83 (d, J=6.9, 6H), 1.08–1.11 (m, 2H), 1.33–1.55 (m, 2H), 1.45–1.52 (m, 1H), 1.79–1.89 (m, 2H), 2.36 (s, 3H), 2.85–3.27 (m, 6H), 3.55 (s, 2H), 3.79 (s, 3H), 4.21 (s, 2H), 4.33 (t, J=4.5, 1H), 6.69 (d, J=8.2, 2H), 6.99–7.19 (m, 3H), 7.15–7.26 (m, 7H), 7.73 (d, J=8.1, 2H). LC-MS: 651.8 (M–H)$^-$, 99% pure.

Example 197

Preparation of Nα-isobutyl-Nα-(4-methylbenzenesulfonyl)-Nε-(N'α-pyrrolidinecarbonyl-L-phenylalanyl)-L-lysine This compound was prepared as described for the preparation of Nα-isobutyl-Nα-(4-methylbenzenesulfonyl)-Nε-[N'α-(4-methoxyanilinecarbonyl)-L-phenylalanyl]-L-lysine (example 196) using pyrrolidine instead of 4-methoxyaniline. The crude material was purified by preparative HPLC to give 15 mg, 20% of the desired material.

LC-MS: 599.7 (M–H)$^-$, 99% pure.

Example 198

Preparation of Nα-isobutyl-Nα-(4-methylbenzenesulfonyl)-Nε-(N'α-methylaminocarbonyl-L-phenylalanyl)-L-lysine This compound was prepared as described for the preparation of Nα-isobutyl-Nα-(4-methylbenzenesulfonyl)-Nε-[N'α-(4-methoxyanilinecarbonyl)-L-phenylalanyl]-L-lysine (example 196) using methylamine instead of 4-methoxyaniline. The crude material was purified by preparative HPLC to give 4 mg, 6% of the desired material.

$^1$H NMR (CDCl$_3$): δ 0.83 (d, J=6.9, 6H), 1.08–1.11 (m, 2H), 1.23–1.25 (m, 2H), 1.45–1.52 (m, 1H), 1.89–1.99 (m, 2H), 2.32 (s, 3H), 2.70 (s, 3H), 2.94–3.09 (m, 6H), 4.23 (t, J=5.9, 1H), 4.61 (m, 1H), 7.09–7.26 (m, 7H), 7.73 (d, J=8.1, 2H). LC-MS: 559.2 (M–H)$^-$, 99% pure.

Example 199

Preparation of Nα-isobutyl-Nα-(4-methylbenzenesulfonyl)-Nε-(N'α-ethanolaminocarbonyl-L-phenylalanyl)-L-lysine This compound was prepared as described for the preparation of Nα-isobutyl-Nα-(4-methylbenzenesulfonyl)-Nε-[N'α-(4-methoxyanilinecarbonyl)-L-phenylalanyl]-L-lysine (example 196) using ethanolamine instead of 4-methoxyaniline. The crude material was purified by preparative HPLC to give 4.1 mg, 5% of the desired material.

$^1$H NMR (CDCl$_3$): δ 0.79 (d, J=6.3, 3H), 0.82 (d, J=6.3, 3H), 1.08–1.11 (m, 2H), 1.23–1.31 (m, 2H), 1.45–1.52 (m, 1H), 1.92–1.97 (m, 1H), 2.39 (s, 3H), 2.84–3.29 (m, 8H), 3.45–3.64 (m, 2H), 4.11 (br s, 1H), 4.48 (br s, 1H), 7.09–7.26 (m, 7H), 7.73 (d, J=8.1, 2H). LC-MS: 589.7 (M–H)$^-$, 99% pure.

Example 200

Preparation of Nα-benzenesulfonyl-Nα-isobutyl-Nε-[N'α-(4-methylbenzenesulfonyl)-L-phenylalanyl]-L-lysine Step A. Preparation of Nα-benzenesulfonyl-Nα-isobutyl-L-α-amino-ε-caprolactam Nα-isobutyl-L-α-amino-ε-caprolactam (example 1, step C) (4.0 g, 21.3 mmol, free base) was dissolved in DCM (100 mL) and treated with diisopropylethylamine (4.0 mL) followed by freshly recrystallized benzenesulfonyl chloride (3.5 g, 21 mmol). The mixture was stirred overnight (TLC shows the reaction to be complete after 2 h). The solution was extracted with 1N HCl and the organic layer was dried and evaporated to give 5.5 g (80%) of pure product. This compound was used without further purification in the next step.

Step B. Preparation of Nα-benzenesulfonyl-Nα-isobutyl-L-lysine

A mixture of Nα-benzenesulfonyl-Nα-isobutyl-L-α-amino-ε-caprolactam (5.0 g, 15 mmol) and 6N HCl (50 mL) was refluxed for 6 h until all solids had disappeared. Afterwards, the solution was evaporated and the resulting solid was triturated with THF to give 5.2 g, 96% of the desired material.

LC-MS: 346 (M+H)$^+$, 99% pure.

Step C. Preparation of Nα-benzenesulfonyl-Nα-isobutyl-Nε-[N'α-(4-methylbenzenesulfonyl)-L-phenylalanyl]-L-lysine A suspension of Nα-benzenesulfonyl-Nα-isobutyl-L-lysine (150 mg, 0.5 mmol), in THF (10 mL) was treated with a 1N NaOH (3.0 mL) to pH 10. A solution of commercially available Nα-(4-methylbenzenesulfonyl)-L-phenylalanine acid chloride (187 mg, 0.5 mmol), in dry THF (10 mL) was added to the suspension and stirred for 4 h. Afterwards, water (2 mL) was added resulting in a clear solution. Then, EtOAc (30 mL) was added and the organic phase was washed with 1N HCl. The organic phase was removed. Evaporation of the solvent gave a crude product which was purified by preparative HPLC to yield 19 mg (6%) of the title compound.

$^1$H NMR (CDCl$_3$): δ 0.76 (d, J=6.3, 3H), 0.80 (d, J=6.3, 3H), 1.10–1.20 (m, 2H), 1.26–1.33 (m, 2H), 1.70–1.74 (m, 1H), 1.89–1.93 (m, 2H), 2.38 (s, 3H), 2.79–2.90 (m, 2H), 3.85 (t, J=5.9, 1H), 4.29 (t, J=6.9, 1H), 6.90 (d, J=6.2, 2H), 7.08–7.29 (m, 6H), 7.35 (t, J=6.2, 2H), 7.44 (d, J=8.1, 2H), 7.73 (d, J=8.1, 2H). LC-MS: 642.8 (M–H)$^-$, 99% pure.

Example 201

Preparation of Nα-(4-aminobenzenesulfonyl)-Nα-isobutyl-Nε-[N'α-(4-methylbenzenesulfonyl)-L-phenylalanyl]-L-lysine A suspension of Nα-(4-aminobenzenesulfonyl)-Nα-isobutyl-L-lysine potassium salt (190 mg, 0.5 mmol, example 166, step B) in THF (10 mL) was treated with a solution of Nα-(4-methylbenzenesulfonyl)-L-phenylalanine acid chloride (187 mg, 0.5 mmol) in dry THF (10 mL). The suspension was stirred for 4 h. Afterwards, water (2 mL) was added resulting in a clear solution. Then, EtOAc (30 mL) was added and the organic phase was washed with 1N HCl. The organic phase was removed. Evaporation of the solvent gave a crude product which was purified by preparative HPLC to yield 15 mg (4.6%) of the title compound.

$^1$H NMR (CDCl$_3$): δ 0.74 (d, J=6.3, 3H), 0.80 (d, J=6.3, 3H), 1.00–1.11 (m, 4H), 1.23–1.25 (m, 1H), 1.70–1.74 (m, 1H), 1.89–1.93 (m, 1H), 2.32 (s, 3H), 2.65 (m, 2H), 2.84–2.95 (ABX, J=10.1, 7.1, 2H), 3.88 (t, J=6.0, 1H), 4.11 (t, J=6.9, 1H), 6.84 (d, J=6.6, 1H), 7.02–7.21 (m, 7H), 7.24 (d, J=8.0, 1H), 7.73 (d, J=8.1, 2H). LC-MS: 657.9 (M–H)$^-$, 99% pure.

TABLE 1

Anti-protease activity of Nε-amino acid substituted L-lysine derivatives and analogs of formula I.

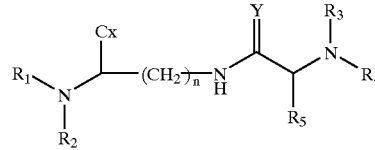

| Ex. No. | Cx | $R_1$ | $R_2$ | $R_3$ | $R_4$ | $R_5$ | Y | n | Ki (nM) | D, L, DL R, S, RS |
|---|---|---|---|---|---|---|---|---|---|---|
| 1 | COOH | i-$C_4H_9$ | 4-$CH_3C_6H_4SO_2$ | H | 4-$CH_3C_6H_4SO_2$ | $C_6H_5CH_2$ | O | 4 | 1.1 | L, L |
| 2 | COOH | i-$C_4H_9$ | 4-$CH_3C_6H_4SO_2$ | H | 4-$CH_3C_6H_4SO_2$ | Indole-3-$CH_2$ | O | 4 | 0.513 | L, L |
| 3 | COOH | i-$C_4H_9$ | 4-$CH_3C_6H_4SO_2$ | H | 4-$AcNHC_6H_4SO_2$ | $C_6H_5CH_2$ | O | 4 | 0.977 | L, L |
| 4 | COOH | i-$C_4H_9$ | 4-$CH_3C_6H_4SO_2$ | H | $C_6H_5SO_2$ | Indole-3-$CH_2$ | O | 4 | 1.0 | L, L |
| 5 | COOH | i-$C_4H_9$ | 4-$NH_2C_6H_4SO_2$ | H | 4-$NH_2C_6H_4SO_2$ | Indole-3-$CH_2$ | O | 4 | 0.459 | L, L |
| 6 | COOH | i-$C_4H_9$ | 4-$CH_3C_6H_4SO_2$ | H | 4-$NO_2C_6H_4SO_2$ | Indole-3-$CH_2$ | O | 4 | 7.3 | L, L |
| 7 | COOH | i-$C_4H_9$ | 4-$CH_3C_6H_4SO_2$ | H | 4-$CH_3C_6H_4SO_2$ | $C_6H_5CH_2$ | O | 4 | 120 | D, L |
| 8 | COOH | i-$C_4H_9$ | 4-$CH_3C_6H_4SO_2$ | H | $C_6H_5SO_2$ | $C_6H_5CH_2$ | O | 4 | 1.9 | L, L |
| 9 | COOH | i-$C_4H_9$ | 4-$CH_3C_6H_4SO_2$ | H | 4-$ClC_6H_4SO_2$ | $C_6H_5CH_2$ | O | 4 | 6.8 | L, L |
| 10 | COOH | i-$C_4H_9$ | 4-$CH_3C_6H_4SO_2$ | H | 4-$NO_2C_6H_4SO_2$ | $C_6H_5CH_2$ | O | 4 | 18 | L, L |
| 11 | COOH | i-$C_4H_9$ | 4-$CH_3C_6H_4SO_2$ | H | 4-$CH_3C_6H_4SO_2$ | 4-$HOC_6H_4CH_2$ | O | 4 | N/A | L, L |
| 12 | COOH | i-$C_4H_9$ | 4-$CH_3C_6H_4SO_2$ | H | 4-$NH_2C_6H_4SO_2$ | Indole-3-$CH_2$ | O | 4 | 0.311 | L, L |
| 13 | COOH | i-$C_4H_9$ | 4-$CH_3C_6H_4SO_2$ | H | 4-$NO_2C_6H_4SO_2$ | $CH_3$ | O | 4 | N/A | L, L |
| 14 | COOH | i-$C_4H_9$ | 4-$CH_3C_6H_4SO_2$ | H | $C_6H_5SO_2$ | $CH_3CH_2CH_2$ | O | 4 | 185 | L, L |
| 15 | COOH | i-$C_4H_9$ | 4-$CH_3C_6H_4SO_2$ | H | $C_6H_5SO_2$ | $CH_3CH_2CH_2CH_2$ | O | 4 | 34 | L, L |
| 16 | COOH | i-$C_4H_9$ | 4-$CH_3C_6H_4SO_2$ | H | 4-$NO_2C_6H_4SO_2$ | i-$C_4H_9$ | O | 4 | 34 | L, L |
| 17 | See Table 2 | | | | | | | | | |
| 18 | COOH | i-$C_4H_9$ | 4-$CH_3C_6H_4SO_2$ | H | 4-$FC_6H_4SO_2$ | $C_6H_5CH_2$ | O | 4 | 8.3 | L, L |
| 19 | COOH | i-$C_4H_9$ | 4-$CH_3C_6H_4SO_2$ | H | 2-Naphthyl-$SO_2$ | $C_6H_5CH_2$ | O | 4 | 11 | L, L |
| 20 | COOH | i-$C_4H_9$ | 4-$CH_3C_6H_4SO_2$ | H | 4-$BrC_6H_4SO_2$ | $C_6H_5CH_2$ | O | 4 | 19 | L, L |
| 21 | COOH | i-$C_4H_9$ | 4-$CH_3C_6H_4SO_2$ | H | 4-$CH_3C_6H_4SO_2$ | H | O | 4 | 21 | L |
| 22 | COOH | i-$C_4H_9$ | 4-$CH_3C_6H_4SO_2$ | H | $C_6H_5SO_2$ | i-$C_4H_9$ | O | 4 | 29 | L, L |
| 23 | COOH | i-$C_4H_9$ | 4-$CH_3C_6H_4SO_2$ | H | 4-$CF_3C_6H_4SO_2$ | $C_6H_5CH_2$ | O | 4 | 12 | L, L |
| 24 | COOH | i-$C_4H_9$ | 4-$CH_3C_6H_4SO_2$ | H | 2-Thiophene-$SO_2$ | $C_6H_5CH_2$ | O | 4 | 0.506 | L, L |
| 25 | COOH | i-$C_4H_9$ | 4-$CH_3C_6H_4SO_2$ | H | $C_6H_5SO_2$ | $H_2NC(O)CH_2$ | O | 4 | 5.3 | L, L |
| 26 | COOH | i-$C_4H_9$ | 4-$CH_3C_6H_4SO_2$ | H | 4-$CH_3C_6H_4SO_2$ | 4-$NO_2C_6H_4CH_2$ | O | 4 | 2.6 | L, L |
| 27 | COOH | i-$C_4H_9$ | 4-$CH_3C_6H_4SO_2$ | H | 4-$CH_3C_6H_4SO_2$ | $C_6H_5$ | O | 4 | 11 | L, L |
| 28 | COOH | i-$C_4H_9$ | 4-$NO_2C_6H_4SO_2$ | H | 4-$AcNHC_6H_4SO_2$ | $C_6H_5CH_2$ | O | 4 | 9.3 | L, L |
| 29 | COOH | i-$C_4H_9$ | 4-$NO_2C_6H_4SO_2$ | H | 2-Thiophene-$SO_2$ | $C_6H_5CH_2$ | O | 4 | 11 | L, L |
| 30 | COOH | i-$C_4H_9$ | 4-$CH_3C_6H_4SO_2$ | H | Ac | $C_6H_5CH_2$ | O | 4 | 0.483 | L, L |
| 31 | COOH | i-$C_4H_9$ | 4-$CH_3C_6H_4SO_2$ | H | $C_6H_5CH_2O_2C$ | $C_6H_5CH_2$ | O | 4 | 2.3 | L, L |
| 32 | COOH | i-$C_4H_9$ | 4-$CH_3C_6H_4SO_2$ | H | 4-$CH_3C_6H_4SO_2$ | $HOCH_2$ | O | 4 | 93 | L, L |
| 33 | COOH | i-$C_4H_9$ | 4-$CH_3C_6H_4SO_2$ | H | 4-$CH_3C_6H_4SO_2$ | $C_6H_{11}CH_2$ | O | 4 | 3.2 | L, L |
| 34 | COOH | i-$C_4H_9$ | 4-$CH_3C_6H_4SO_2$ | H | 4-$CH_3C_6H_4SO_2$ | $H_2NC(O)CH_2CH_2$ | O | 4 | 95 | L, L |
| 35 | COOH | i-$C_4H_9$ | 4-$CH_3C_6H_4SO_2$ | H | 4-$CH_3C_6H_4SO_2$ | 2-Thiophene-$CH_2$ | O | 4 | 21 | L, L |
| 36 | COOH | i-$C_4H_9$ | 4-$CH_3C_6H_4SO_2$ | H | Fmoc | $HOCH_2$ | O | 4 | 162 | L, L |
| 37 | COOH | i-$C_4H_9$ | 4-$CH_3C_6H_4SO_2$ | H | Fmoc | $C_6H_{11}CH_2$ | O | 4 | 28 | L, L |
| 38 | COOH | i-$C_4H_9$ | 4-$CH_3C_6H_4SO_2$ | H | 4-$CH_3C_6H_4SO_2$ | $HO_2CCH_2CH_2$ | O | 4 | 220 | |
| 39 | COOH | i-$C_4H_9$ | 4-$CH_3C_6H_4SO_2$ | H | 4-$CH_3C_6H_4SO_2$ | $H_2NCH_2CH_2CH_2CH_2$ | O | 4 | >300 | L, L |
| 40 | COOH | i-$C_4H_9$ | 4-$CH_3C_6H_4SO_2$ | H | 4-$CH_3C_6H_4SO_2$ | $C_6H_5CH_2OCH_2$ | O | 4 | 8.0 | L, L |
| 41 | COOH | i-$C_4H_9$ | 4-$CH_3C_6H_4SO_2$ | H | 4-$CH_3C_6H_4SO_2$ | $HO_2CCH_2$ | O | 4 | 172 | L, L |
| 42 | COOH | i-$C_4H_9$ | 4-$CH_3C_6H_4SO_2$ | H | 4-$CH_3C_6H_4SO_2$ | 2-Benzothiophene-$CH_2$ | O | 4 | 256 | L, L |
| 43 | COOH | i-$C_4H_9$ | 4-$NH_2C_6H_4SO_2$ | H | 4-$CH_3C_6H_4SO_2$ | Indole-3-$CH_2$ | O | 4 | 0.56 | L, L |
| 44 | COOH | i-$C_4H_9$ | 4-$NH_2C_6H_4SO_2$ | H | $C_6H_5SO_2$ | $C_6H_5CH_2$ | O | 4 | 3.6 | L, L |
| 45 | $COOCH_2CH(OH)CH_2OH$ | i-$C_4H_9$ | 4-$CH_3C_6H_4SO_2$ | H | 4-$CH_3C_6H_4SO_2$ | Indole-3-$CH_2$ | O | 4 | >300 | L, L |
| 46 | COOH | i-$C_4H_9$ | 4-$NH_2C_6H_4SO_2$ | H | 2-Thiophene-$SO_2$ | $C_6H_5CH_2$ | O | 4 | 0.477 | L, L |
| 47 | COOH | i-$C_4H_9$ | 4-$NH_2C_6H_4SO_2$ | H | 4-$CH_3C_6H_4SO_2$ | $H_2NC(O)CH_2$ | O | 4 | 54 | L, L |
| 48 | COOH | i-$C_4H_9$ | 4-$CH_3C_6H_4SO_2$ | H | $C_6H_5CH_2O_2C$ | $H_2NC(O)CH_2$ | O | 4 | 114 | L, L |
| 49 | $CONHNH_2$ | i-$C_4H_9$ | 4-$NH_2C_6H_4SO_2$ | H | 2-Thiophene-$SO_2$ | $C_6H_5CH_2$ | O | 4 | 17 | L, L |
| 50 | COOH | i-$C_4H_9$ | 4-$CH_3C_6H_4SO_2$ | H | $C_6H_5CO$ | $C_6H_5CH_2$ | O | 4 | 2.0 | L, L |
| 51 | COOH | i-$C_4H_9$ | 4-$CH_3C_6H_4SO_2$ | H | 4-Morpholine-CO | $C_6H_5CH_2$ | O | 4 | 0.9 | L, L |
| 52 | COOH | i-$C_4H_9$ | 4-$CH_3C_6H_4SO_2$ | H | t-butyl-CO | $C_6H_5CH_2$ | O | 4 | 0.545 | L, L |
| 53 | COOH | i-$C_4H_9$ | 4-$CH_3C_6H_4SO_2$ | H | 2-Thiophene-$SO_2$ | Indole-3-$CH_2$ | O | 4 | 13 | L, L |
| 54 | COOH | i-$C_4H_9$ | 2-Thiophene-$SO_2$ | H | 4-$CH_3C_6H_4SO_2$ | $C_6H_5CH_2$ | O | 4 | 17 | L, L |
| 55 | COOH | i-$C_4H_9$ | 4-$CH_3C_6H_4SO_2$ | i-$C_4H_9$ | 4-$CH_3C_6H_4SO_2$ | H | O | 4 | 14 | L |
| 56 | COOH | i-$C_4H_9$ | 4-$NH_2C_6H_4SO_2$ | H | 4-$AcNHC_6H_4SO_2$ | $C_6H_5CH_2$ | O | 4 | 1.9 | L, L |
| 57 | $COOCH_3$ | i-$C_4H_9$ | 4-$CH_3C_6H_4SO_2$ | H | 2-Thiophene-$SO_2$ | $C_6H_5CH_2$ | O | 4 | >300 | L, L |
| 58 | $CONH_2$ | i-$C_4H_9$ | 4-$CH_3C_6H_4SO_2$ | H | 2-Thiophene-$SO_2$ | $C_6H_5CH_2$ | O | 4 | 5.2 | L, L |
| 59 | CONHOH | i-$C_4H_9$ | 4-$CH_3C_6H_4SO_2$ | H | 2-Thiophene-$SO_2$ | $C_6H_5CH_2$ | O | 4 | 13 | L, L |
| 60 | $CONHCH_2CH_2OH$ | i-$C_4H_9$ | 4-$CH_3C_6H_4SO_2$ | H | 2-Thiophene-$SO_2$ | $C_6H_5CH_2$ | O | 4 | >300 | L, L |
| 61 | COOH | i-$C_4H_9$ | 4-$CH_3C_6H_4SO_2$ | H | 4-$CH_3C_6H_4SO_2$ | $H_2NC(O)CH_2$ | O | 4 | 296 | L, L |
| 62 | COOH | i-$C_4H_9$ | 4-$CH_3C_6H_4SO_2$ | H | t-butyl-CO | $H_2NC(O)CH_2$ | O | 4 | 212 | L, L |

TABLE 1-continued

Anti-protease activity of Ne-amino acid substituted L-lysine derivatives and analogs of formula I.

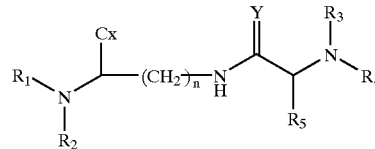

| Ex. No. | Cx | $R_1$ | $R_2$ | $R_3$ | $R_4$ | $R_5$ | Y | n | Ki (nM) | D, L, DL R, S, RS |
|---|---|---|---|---|---|---|---|---|---|---|
| 63 | COOH | i-$C_4H_9$ | 4-$CH_3C_6H_4SO_2$ | H | $C_6H_5CO$ | $H_2NC(O)CH_2$ | O | 4 | 193 | L, L |
| 64 | $CONHNH_2$ | i-$C_4H_9$ | 4-$CH_3C_6H_4SO_2$ | H | 2-Thiophene-$SO_2$ | $C_6H_5CH_2$ | O | 4 | >300 | L, L |
| 65 | See Table 2 | | | | | | | | | |
| 66 | COOH | i-$C_4H_9$ | 4-$CH_3C_6H_4SO_2$ | H | 4-$CH_3C_6H_4SO_2$ | $C_6H_5CH_2$ | O | 4 | >300 | D, D |
| 67 | COOH | i-$C_4H_9$ | 4-$CH_3C_6H_4SO_2$ | H | 4-$CH_3C_6H_4SO_2$ | $C_6H_5CH_2$ | O | 4 | >300 | L, D |
| 68 | $COOCH_3$ | i-$C_4H_9$ | 4-$CH_3C_6H_4SO_2$ | H | 4-$CH_3C_6H_4SO_2$ | $C_6H_5CH_2$ | O | 4 | >300 | L, L |
| 69 | $COOCH_3$ | i-$C_4H_9$ | 4-$CH_3C_6H_4SO_2$ | H | 4-$CH_3C_6H_4SO_2$ | Indole-3-$CH_2$ | O | 4 | >300 | L, L |
| 70 | $COOCH_3$ | i-$C_4H_9$ | 4-$CH_3C_6H_4SO_2$ | H | $C_6H_5CO$ | $C_6H_5CH_2$ | O | 4 | >300 | L, L |
| 71 | $COOCH_3$ | i-$C_4H_9$ | 4-$CH_3C_6H_4SO_2$ | H | 4-$CH_3C_6H_4SO_2$ | $C_6H_5CH_2$ | S | 4 | >300 | L, L |
| 72 | COOH | i-$C_4H_9$ | 4-$CH_3C_6H_4SO_2$ | H | 4-$CH_3C_6H_4SO_2$ | $C_6H_5CH_2$ | S | 4 | 33 | L, L |
| 73 | COOH | i-$C_4H_9$ | 4-$CH_3C_6H_4SO_2$ | H | 4-$CH_3C_6H_4SO_2$ | Indole-3-$CH_2$ | S | 4 | 14 | L, L |
| 74 | COOH | i-$C_4H_9$ | 4-$CH_3C_6H_4SO_2$ | H | $C_6H_5SO_2$ | Indole-3-$CH_2$ | S | 4 | 4.8 | L, L |
| 75 | $COOCH_3$ | i-$C_4H_9$ | 4-$CH_3C_6H_4SO_2$ | H | 4-$CH_3C_6H_4SO_2$ | Indole-3-$CH_2$ | S | 4 | >300 | L, L |
| 76 | $COOCH_3$ | i-$C_4H_9$ | 4-$CH_3C_6H_4SO_2$ | H | $C_6H_5CS$ | $C_6H_5CH_2$ | S | 4 | >300 | L, L |
| 77 | COOH | i-$C_4H_9$ | 4-$CH_3C_6H_4SO_2$ | H | $C_6H_5CS$ | $C_6H_5CH_2$ | S | 4 | 212 | L, L |
| 78 | COOH | i-$C_4H_9$ | 4-$CH_3C_6H_4SO_2$ | H | Boc | $C_6H_5CH_2$ | O | 4 | 2.5 | L, L |
| 79 | COOH | i-$C_4H_9$ | 4-$CH_3C_6H_4SO_2$ | H | H | $C_6H_5CH_2$ | O | 4 | 1.5 | L, L |
| 80 | COOH | i-$C_4H_9$ | 4-$CH_3C_6H_4SO_2$ | H | Carbotetrahydro-3-furanyloxy | $C_6H_5CH_2$ | O | 4 | 1.4 | L, L |
| 81 | COOH | i-$C_4H_9$ | 4-$CH_3C_6H_4SO_2$ | $CH_3$ | Boc | $C_6H_5CH_2$ | O | 4 | 3.8 | L, L |
| 82 | COOH | i-$C_4H_9$ | 4-$CH_3C_6H_4SO_2$ | H | Boc | $CH_3SCH_2CH_2$ | O | 4 | 65 | L, L |
| 83 | COOH | i-$C_4H_9$ | 4-$CH_3C_6H_4SO_2$ | H | Boc | 4-$CH_3C_6H_4CH_2SCH_2$ | O | 4 | 62 | L, L |
| 84 | COOH | i-$C_4H_9$ | 4-$CH_3C_6H_4SO_2$ | H | Boc | $BnOCH(CH_3)$ | O | 4 | 163 | L, L |
| 85 | COOH | i-$C_4H_9$ | 4-$CH_3C_6H_4SO_2$ | H | Boc | Nτ-Bn-imidazole-4-$CH_2$ | O | 4 | 124 | L, L |
| 86 | COOH | i-$C_4H_9$ | 4-$CH_3C_6H_4SO_2$ | H | Boc | Indole-3-$CH_2$ | O | 4 | 1.6 | L, L |
| 87 | COOH | i-$C_4H_9$ | 4-$CH_3C_6H_4SO_2$ | H | Boc | 4-BnO-$C_6H_4CH_2$ | O | 4 | 49 | L, L |
| 88 | COOH | i-$C_4H_9$ | 4-$CH_3C_6H_4SO_2$ | H | $CH_3$ | $C_6H_5CH_2$ | O | 4 | 2.1 | L, L |
| 89 | COOH | i-$C_4H_9$ | 4-$CH_3C_6H_4SO_2$ | H | H | $CH_3SCH_2CH_2$ | O | 4 | 33 | L, L |
| 90 | COOH | i-$C_4H_9$ | 4-$CH_3C_6H_4SO_2$ | H | H | 4-$CH_3C_6H_4CH_2SCH_2$ | O | 4 | 29 | L, L |
| 91 | COOH | i-$C_4H_9$ | 4-$CH_3C_6H_4SO_2$ | H | H | $BnOCH(CH_3)$ | O | 4 | 10 | L, L |
| 92 | COOH | i-$C_4H_9$ | 4-$CH_3C_6H_4SO_2$ | H | H | Nτ-Bn-imidazole-4-$CH_2$ | O | 4 | >300 | L, L |
| 93 | COOH | i-$C_4H_9$ | 4-$CH_3C_6H_4SO_2$ | H | H | Indole-3-$CH_2$ | O | 4 | 2.1 | L, L |
| 94 | COOH | i-$C_4H_9$ | 4-$CH_3C_6H_4SO_2$ | H | H | 4-BnO-$C_6H_4CH_2$ | O | 4 | 177 | L, L |
| 95 | $CH_2OH$ | i-$C_4H_9$ | 4-$CH_3C_6H_4SO_2$ | H | $C_6H_5CO$ | $C_6H_5CH_2$ | O | 4 | 54 | S, S |
| 96 | $CH_2OH$ | i-$C_4H_9$ | 4-$CH_3C_6H_4SO_2$ | H | 4-$CH_3C_6H_4SO_2$ | $C_6H_5CH_2$ | O | 4 | 16 | S, S |
| 97 | $CH_2OH$ | i-$C_4H_9$ | 4-$CH_3C_6H_4SO_2$ | H | 4-$CH_3C_6H_4SO_2$ | Indole-3-$CH_2$ | O | 4 | 3.6 | S, S |
| 98 | COOH | i-$C_4H_9$ | 4-$CH_3C_6H_4SO_2$ | H | 4-$CH_3C_6H_4SO_2$ | $C_6H_5CH_2$ | NC—N | 4 | 5.1 | L, L |
| 99 | COOH | i-$C_4H_9$ | 4-$CH_3C_6H_4SO_2$ | H | Ac | Indole-3-$CH_2$ | O | 4 | 0.438 | L, L |
| 100 | COOH | i-$C_4H_9$ | 4-$CH_3C_6H_4SO_2$ | H | t-butyl-CO | Indole-3-$CH_2$ | O | 4 | 0.388 | L, L |
| 101 | COOH | i-$C_4H_9$ | 4-$CH_3C_6H_4SO_2$ | H | $CF_3CO$ | $C_6H_5CH_2$ | O | 4 | 2.9 | L, L |
| 102 | $CH_2OH$ | i-$C_4H_9$ | 4-$CH_3C_6H_4SO_2$ | H | 4-$CH_3C_6H_4SO_2$ | Indole-3-$CH_2$ | S | 4 | 51 | S, S |
| 103 | COOH | i-$C_4H_9$ | 4-$CH_3C_6H_4SO_2$ | H | 4-$CH_3C_6H_4SO_2$ | Indole-3-$CH_2$ | NC—N | 4 | 1.1 | L, L |
| 104 | $COOCH_2CH(OH)CH_2OH$ | i-$C_4H_9$ | 4-$CH_3C_6H_4SO_2$ | H | $C_6H_5SO_2$ | Indole-$CH_2$ | O | 4 | >300 | L, L |
| 105 | COOH | i-$C_4H_9$ | 4-$CH_3C_6H_4SO_2$ | H | $C_6H_5$ | H | O | 4 | 7.7 | L |
| 106 | COOH | i-$C_4H_9$ | 4-$CH_3C_6H_4SO_2$ | H | 3-$C_5H_4N$ | H | O | 4 | >300 | L |
| 107 | COOH | i-$C_4H_9$ | 4-$CH_3C_6H_4SO_2$ | H | 2,3-$(CH_3O)_2Bn$ | H | O | 4 | 52 | DL |
| 108 | COOH | i-$C_4H_9$ | 4-$CH_3C_6H_4SO_2$ | H | 2-$C_5H_4N$ | H | O | 4 | >300 | L |
| 109 | COOH | i-$C_4H_9$ | 4-$CH_3C_6H_4SO_2$ | H | $C_6H_5CH_2$ | H | O | 4 | >300 | L |
| 110 | COOH | i-$C_4H_9$ | 4-$CH_3C_6H_4SO_2$ | H | $C_5H_{10}N$—$CH_2CH_2$ | H | O | 4 | >300 | L |
| 111 | COOH | i-$C_4H_9$ | 4-$CH_3C_6H_4SO_2$ | H | $OC_4H_8N$—$CH_2CH_2$ | H | O | 4 | >300 | L |
| 112 | COOH | i-$C_4H_9$ | 4-$CH_3C_6H_4SO_2$ | H | 4-$C_5H_4N$ | H | O | 4 | >300 | L |
| 113 | COOH | i-$C_4H_9$ | 4-$CH_3C_6H_4SO_2$ | H | 3-quinolyl | H | O | 4 | 12 | L |
| 114 | COOH | i-$C_4H_9$ | 4-$CH_3C_6H_4SO_2$ | $C_6H_5$ | $C_6H_5CH_2$ | H | O | 4 | 0.937 | L |
| 115 | COOH | i-$C_4H_9$ | 4-$CH_3C_6H_4SO_2$ | $CH_3$ | $C_6H_5$ | H | O | 4 | 12 | L |
| 116 | CHO | i-$C_4H_9$ | 4-$CH_3C_6H_4SO_2$ | H | 4-$CH_3C_6H_4SO_2$ | Indole-3-$CH_2$ | O | 4 | >300 | L, L |
| 117 | $CH_2OH$ | i-$C_4H_9$ | 4-$CH_3C_6H_4SO_2$ | H | t-butyl-CO | Indole-3-$CH_2$ | O | 4 | 0.428 | S, S |
| 118 | $CH_2OH$ | i-$C_4H_9$ | 4-$CH_3C_6H_4SO_2$ | H | Ac | $C_6H_5CH_2$ | O | 4 | 13 | S, S |
| 119 | $CH_2OH$ | i-$C_4H_9$ | 4-$CH_3C_6H_4SO_2$ | H | t-butyl-CO | $C_6H_5CH_2$ | O | 4 | 3.9 | S, S |
| 120 | $CH_2OH$ | i-$C_4H_9$ | 4-$CH_3C_6H_4SO_2$ | H | 4-Morpholine-CO | $C_6H_5CH_2$ | O | 4 | 2.4 | S, S |

TABLE 1-continued

Anti-protease activity of Nε-amino acid substituted L-lysine derivatives and analogs of formula I.

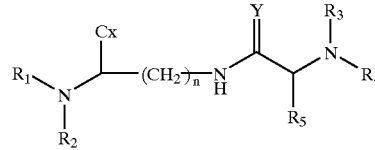

| Ex. No. | Cx | $R_1$ | $R_2$ | $R_3$ | $R_4$ | $R_5$ | Y | n | Ki (nM) | D, L, DL R, S, RS |
|---|---|---|---|---|---|---|---|---|---|---|
| 121 | $CH_2OH$ | $i-C_4H_9$ | $4-CH_3C_6H_4SO_2$ | H | $4-AcNHC_6H_4SO_2$ | $C_6H_5CH_2$ | O | 4 | 23 | S, S |
| 122 | $CH_2OH$ | $i-C_4H_9$ | $4-CH_3C_6H_4SO_2$ | H | $2$-Thiophene-$SO_2$ | $C_6H_5CH_2$ | O | 4 | 8.2 | S, S |
| 123 | $CH_2OH$ | $i-C_4H_9$ | $4-CH_3C_6H_4SO_2$ | H | $C_6H_5SO_2$ | $C_6H_5CH_2$ | O | 4 | 14 | S, S |
| 124 | $CH_2OH$ | $i-C_4H_9$ | $4-CH_3C_6H_4SO_2$ | H | $4-CH_3C_6H_4SO_2$ | $4-NO_2C_6H_4CH_2$ | O | 4 | 12 | S, S |
| 125 | $CH_2OH$ | $i-C_4H_9$ | $4-CH_3C_6H_4SO_2$ | H | $4-FC_6H_4SO_2$ | $C_6H_5CH_2$ | O | 4 | 39 | S, S |
| 126 | $CH_2OH$ | $i-C_4H_9$ | $4-CH_3C_6H_4SO_2$ | H | $4-CH_3OC_6H_4SO_2$ | $C_6H_5CH_2$ | O | 4 | 19 | S, S |
| 127 | $CH_2OH$ | $i-C_4H_9$ | $4-CH_3C_6H_4SO_2$ | H | $4-CF_3C_6H_4SO_2$ | $C_6H_5CH_2$ | O | 4 | 164 | S, S |
| 128 | $CH_2OH$ | $i-C_4H_9$ | $4-CH_3C_6H_4SO_2$ | H | $C_6H_5SO_2$ | Indole-3-$CH_2$ | O | 4 | 0.95 | S, S |
| 129 | $CH_2OH$ | $i-C_4H_9$ | $4-CH_3C_6H_4SO_2$ | H | $2$-Thiophene-$SO_2$ | Indole-3-$CH_2$ | O | 4 | 1.0 | S, S |
| 130 | $CH_2OH$ | $i-C_4H_9$ | $4-CH_3C_6H_4SO_2$ | H | $4-NO_2C_6H_4SO_2$ | Indole-3-$CH_2$ | O | 4 | 27 | S, S |
| 131 | $CH_2OH$ | $i-C_4H_9$ | $4-CH_3C_6H_4SO_2$ | H | Ac | Indole-3-$CH_2$ | O | 4 | 3.0 | S, S |
| 132 | COOH | $i-C_4H_9$ | $4-CH_3C_6H_4SO_2$ | H | $4-CH_3OC_6H_4CH_2CO$ | $C_6H_5CH_2$ | O | 4 | 0.257 | L, L |
| 133 | COOH | $i-C_4H_9$ | $4-CH_3C_6H_4SO_2$ | H | $C_6H_5CH_2CH_2CO$ | Indole-3-$CH_2$ | O | 4 | 0.606 | L, L |
| 134 | $CH_2OH$ | $i-C_4H_9$ | $4-CH_3C_6H_4SO_2$ | H | Boc | $C_5H_4N$-2-$CH_2$ | O | 4 | 30 | S, S |
| 135 | $CH_2OH$ | $i-C_4H_9$ | $4-CH_3C_6H_4SO_2$ | H | Boc | $C_5H_4N$-3-$CH_2$ | O | 4 | 144 | S, S |
| 136 | $CH_2OH$ | $i-C_4H_9$ | $4-CH_3C_6H_4SO_2$ | H | Boc | $C_5H_4N$-4-$CH_2$ | O | 4 | 110 | S, S |
| 137 | $CH_2OH$ | $i-C_4H_9$ | $4-CH_3C_6H_4SO_2$ | H | Boc | Thiazole-4-$CH_2$ | O | 4 | 96 | S, S |
| 138 | $CH_2OH$ | $i-C_4H_9$ | $4-CH_3C_6H_4SO_2$ | H | Boc | $2-FC_6H_5CH_2$ | O | 4 | 10 | S, S |
| 139 | $CH_2OH$ | $i-C_4H_9$ | $4-CH_3C_6H_4SO_2$ | H | Boc | $3-FC_6H_5CH_2$ | O | 4 | 4.1 | S, S |
| 140 | $CH_2OH$ | $i-C_4H_9$ | $4-CH_3C_6H_4SO_2$ | H | Boc | $4-FC_6H_5CH_2$ | O | 4 | 4.2 | S, S |
| 141 | See Table 2 | | | | | | | | | |
| 142 | $CH_2OH$ | $i-C_4H_9$ | $4-CH_3C_6H_4SO_2$ | H | Boc | $4$-t-Butyl-$C_6H_5CH_2$ | O | 4 | 93 | S, S |
| 143 | $CH_2OH$ | $i-C_4H_9$ | $4-CH_3C_6H_4SO_2$ | H | Boc | $C_6F_5CH_2$ | O | 4 | >300 | S, S |
| 144 | $CH_2OH$ | $i-C_4H_9$ | $4-CH_3C_6H_4SO_2$ | H | Boc | 4-Fmoc-$NHCH_2$—$C_6H_5CH_2$ | O | 4 | >300 | S, S |
| 145 | $CH_2OH$ | $i-C_4H_9$ | $4-NH_2C_6H_4SO_2$ | H | $4-CH_3C_6H_4SO_2$ | Indole-3-$CH_2$ | O | 4 | 1.9 | S, S |
| 146 | $CH_2OH$ | $i-C_4H_9$ | $4-CH_3OC_6H_4SO_2$ | H | H TFA | Indole-3-$CH_2$ | O | 4 | 15 | S, S |
| 147 | $CH_2OH$ | $i-C_4H_9$ | $4-CH_3OC_6H_4SO_2$ | H | Boc | Indole-3-$CH_2$ | O | 4 | 16 | S, S |
| 148 | $CH_2OH$ | $i-C_4H_9$ | $4-CH_3OC_6H_4SO_2$ | H | t-butyl-CO | Indole-3-$CH_2$ | O | 4 | 1.9 | S, S |
| 149 | $CH_2OH$ | $i-C_4H_9$ | $4-CH_3OC_6H_4SO_2$ | H | $4-CH_3C_6H_4SO_2$ | Indole-3-$CH_2$ | O | 4 | 7.5 | S, S |
| 150 | $COOCH_3$ | Cyclo-pentyl-$CH_2$ | $4-CH_3OC_6H_4SO_2$ | H | Boc | Indole-3-$CH_2$ | O | 4 | >300 | L, L |
| 151 | COOH | Cyclo-pentyl-$CH_2$ | $4-CH_3OC_6H_4SO_2$ | H | Boc | Indole-3-$CH_2$ | O | 4 | 5.3 | L, L |
| 152 | $CH_2OH$ | Cyclo-pentyl-$CH_2$ | $4-CH_3OC_6H_4SO_2$ | H | H TFA | Indole-3-$CH_2$ | O | 4 | 12 | S, S |
| 153 | $CH_2OH$ | Cyclo-pentyl-$CH_2$ | $4-CH_3OC_6H_4SO_2$ | H | Boc | Indole-3-$CH_2$ | O | 4 | 24 | S, S |
| 154 | COOH | $i-C_4H_9$ | $4-CH_3C_6H_4SO_2$ | H | $4-CH_3C_6H_4SO_2$ | $C_6H_5CH_2$ | O | 3 | >300 | L, L |
| 155 | COOH | $i-C_4H_9$ | $4-CH_3C_6H_4SO_2$ | $C_6H_5CH_2$ | $C_6H_5CH_2$ | H | O | 4 | N/A | L |
| 156 | $CH_2OH$ | $i-C_4H_9$ | $4-CH_3C_6H_4SO_2$ | $C_6H_5CH_2$ | $C_6H_5$ | H | O | 4 | 7.6 | S |
| 157 | COOH | $i-C_4H_9$ | $4-CH_3C_6H_4SO_2$ | H | $C_6H_{11}$ | H | O | 4 | N/A | L |
| 158 | $CH_2OH$ | $i-C_4H_9$ | $4-CH_3C_6H_4SO_2$ | $C_6H_5CH_2$ | $C_6H_5CO$ | H | O | 4 | 95 | S |
| 159 | $CH_2OH$ | $i-C_4H_9$ | $4-CH_3C_6H_4SO_2$ | $C_6H_5CH_2$ | $4-CH_3C_6H_4SO_2$ | H | O | 4 | 101 | S |
| 160 | $CH_2OH$ | $i-C_4H_9$ | $4-CH_3C_6H_4SO_2$ | $C_6H_5$ | $C_6H_5CH_2CH_2$ | H | O | 4 | 52 | S |
| 161 | $CH_2OH$ | $i-C_4H_9$ | $4-CH_3C_6H_4SO_2$ | H | $4-NH_2C_6H_4SO_2$ | Indole-3-$CH_2$ | O | 4 | 1.4 | S, S |
| 162 | $CH_2OH$ | $i-C_4H_9$ | $4-CH_3C_6H_4SO_2$ | H | $4-CH_3OC_6H_4CH_2CO$ | $C_6H_5CH_2$ | O | 4 | 1.2 | S, S |
| 163 | COOH | $i-C_4H_9$ | $4-NH_2C_6H_4SO_2$ | H | $4-CH_3OC_6H_4CH_2CO$ | $C_6H_5CH_2$ | O | 4 | 0.270 | L, L |
| 164 | COOH | $i-C_4H_9$ | $4-CH_3C_6H_4SO_2$ | H | $4-CH_3OC_6H_4CH_2CO$ | Indole-3-$CH_2$ | O | 4 | 0.320 | L, L |
| 165 | $CH_2OH$ | $i-C_4H_9$ | $4-CH_3C_6H_4SO_2$ | H | $4-CH_3OC_6H_4CH_2CO$ | Indole-3-$CH_2$ | O | 4 | 1.1 | S, S |
| 166 | $CH_2OH$ | $i-C_4H_9$ | $4-NH_2C_6H_4SO_2$ | H | $2$-Thiophene-$SO_2$ | Indole-3-$CH_2$ | O | 4 | 1.0 | S, S |
| 167 | $CH_2OH$ | $i-C_4H_9$ | $4-NH_2C_6H_4SO_2$ | H | $C_6H_5SO_2$ | Indole-3-$CH_2$ | O | 4 | 1.5 | S, S |
| 168 | $CH_2OH$ | $i-C_4H_9$ | $4-NH_2C_6H_4SO_2$ | H | Ac | Indole-3-$CH_2$ | O | 4 | 3.8 | S, S |
| 169 | $CH_2OH$ | $i-C_4H_9$ | $4-NH_2C_6H_4SO_2$ | H | t-butyl-CO | Indole-3-$CH_2$ | O | 4 | 1.2 | S, S |
| 170 | $CH_2OH$ | $i-C_4H_9$ | $4-NH_2C_6H_4SO_2$ | H | 4-Morpholine-CO | Indole-3-$CH_2$ | O | 4 | 1.1 | S, S |
| 171 | $CH_2OH$ | $i-C_4H_9$ | $4-NH_2C_6H_4SO_2$ | H | 4-Morpholine-CO | Indole-3-$CH_2$ | O | 4 | 7.9 | S, S |
| 172 | $CH_2OH$ | $i-C_4H_9$ | $4-CH_3OC_6H_4SO_2$ | H | Ac | Indole-3-$CH_2$ | O | 4 | >300 | S, S |

TABLE 1-continued

Anti-protease activity of Nε-amino acid substituted L-lysine derivatives and analogs of formula I.

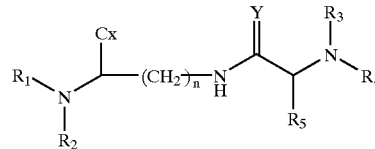

| Ex. No. | Cx | $R_1$ | $R_2$ | $R_3$ | $R_4$ | $R_5$ | Y | n | Ki (nM) | D, L, DL R, S, RS |
|---|---|---|---|---|---|---|---|---|---|---|
| 173 | $CH_2OH$ | Cyclopentyl-$CH_2$ | 4-$CH_3OC_6H_4SO_2$ | H | Ac | Indole-3-$CH_2$ | O | 4 | 11 | S, S |
| 174 | COOH | i-$C_4H_9$ | 4-$CH_3C_6H_4SO_2$ | $C_6H_5$ | 4-$CH_3OC_6H_4CH_2$ | H | O | 4 | 1.4 | L |
| 175 | $CH_2OH$ | i-$C_4H_9$ | 4-$CH_3C_6H_4SO_2$ | $C_6H_5$ | 4-$CH_3OC_6H_4CH_2$ | H | O | 4 | 6.3 | S |
| 176 | $CH_2OH$ | i-$C_4H_9$ | 4-$NH_2C_6H_4SO_2$ | $C_6H_5$ | 4-$CH_3OC_6H_4CH_2$ | H | O | 4 | 2.4 | S |
| 177 | $CH_2OH$ | i-$C_4H_9$ | 4-$NH_2C_6H_4SO_2$ | H | $CH_3O$—CO | $C_6H_5CH_2$ | O | 4 | 6.6 | S, S |
| 178 | $CH_2OH$ | i-$C_4H_9$ | 4-$NH_2C_6H_4SO_2$ | H | $CH_3O$-CO | Indole-3-$CH_2$ | O | 4 | 2.0 | S, S |
| 179 | $CH_2OH$ | i-$C_4H_9$ | 4-$NH_2C_6H_4SO_2$ | H | 4-$NO_2C_6H_4SO_2$ | Indole-3-$CH_2$ | O | 4 | 32 | S, S |
| 180 | $CH_2OH$ | i-$C_4H_9$ | 4-$NH_2C_6H_4SO_2$ | H | 4-Morpholine-CO | $C_6H_5CH_2$ | O | 4 | 2.4 | S, S |
| 181 | $CH_2OH$ | i-$C_4H_9$ | 4-$NH_2C_6H_4SO_2$ | i-$C_4H_9$ | $C_6H_5$ | H | O | 4 | 16 | S |
| 182 | $CH_2OH$ | i-$C_4H_9$ | 4-$NH_2C_6H_4SO_2$ | $C_6H_5CH_2$ | $C_6H_5$ | H | O | 4 | 2.4 | S |
| 183 | $CH_2OH$ | i-$C_4H_9$ | 4-$CH_3C_6H_4SO_2$ | H | H TFA | Indole-3-$CH_2$ | O | 4 | 4.4 | S, S |
| 184 | $CH_2OH$ | i-$C_4H_9$ | 4-$NH_2C_6H_4SO_2$ | H | i-Pr-CO | Indole-3-$CH_2$ | O | 4 | 1.6 | S, S |
| 185 | $CH_2OH$ | i-$C_4H_9$ | 4-$NH_2C_6H_4SO_2$ | H | t-butyl-$CH_2CO$ | Indole-3-$CH_2$ | O | 4 | 3.1 | S, S |
| 186 | $CH_2OH$ | i-$C_4H_9$ | 4-$NH_2C_6H_4SO_2$ | H | $C_6H_5CO$ | Indole-3-$CH_2$ | O | 4 | 1.7 | S, S |
| 187 | $CH_2OH$ | i-$C_4H_9$ | 4-$NH_2C_6H_4SO_2$ | H | 4-$NH_2C_6H_4SO_2$ | Indole-3-$CH_2$ | O | 4 | 0.200 | S, S |
| 188 | $CH_2OH$ | i-$C_4H_9$ | 4-$CH_3C_6H_4SO_2$ | H | $C_6H_5SO_2$ | NC—$CH_2$ | O | 4 | 79 | S, S |
| 189 | $CONH_2$ | i-$C_4H_9$ | 4-$CH_3C_6H_4SO_2$ | H | $C_6H_5SO_2$ | Indole-3-$CH_2$ | O | 4 | 1.9 | L, L |
| 190 | $CH_2OH$ | i-$C_4H_9$ | 4-$CH_3C_6H_4SO_2$ | H | $CH_3O$—CO | Indole-3-$CH_2$ | O | 4 | 2.2 | S, S |
| 191 | $CH_2OH$ | i-$C_4H_9$ | 4-$CH_3C_6H_4SO_2$ | H | $C_6H_5CO$ | Indole-3-$CH_2$ | O | 4 | 3.8 | S, S |
| 192 | $CH_2OH$ | i-$C_4H_9$ | 4-$CH_3C_6H_4SO_2$ | H | i-butylO—CO | Indole-3-$CH_2$ | O | 4 | 4.5 | S, S |
| 193 | $CH_2OH$ | i-$C_4H_9$ | 4-$NH_2C_6H_4SO_2$ | H | i-butylO—CO | Indole-3-$CH_2$ | O | 4 | 4.1 | S, S |
| 194 | $CH_2OH$ | i-$C_4H_9$ | 4-$NH_2C_6H_4SO_2$ | H | 4-$NO_2C_6H_4SO_2$ | $C_6H_5CH_2$ | O | 4 | 85 | S, S |
| 195 | $CH_2OH$ | i-$C_4H_9$ | 4-$NH_2C_6H_4SO_2$ | H | 4-$NH_2C_6H_4SO_2$ | $C_6H_5CH_2$ | O | 4 | 20 | S, S |
| 196 | COOH | i-$C_4H_9$ | 4-$CH_3C_6H_4SO_2$ | H | 4-$CH_3OC_6H_4NHCO$ | $C_6H_5CH_2$ | O | 4 | 0.500 | L, L |
| 197 | COOH | i-$C_4H_9$ | 4-$CH_3C_6H_4SO_2$ | H | Pyrrolidine-CO | $C_6H_5CH_2$ | O | 4 | 1.7 | L, L |
| 198 | COOH | i-$C_4H_9$ | 4-$CH_3C_6H_4SO_2$ | H | $CH_3NHCO$ | $C_6H_5CH_2$ | O | 4 | 1.1 | L, L |
| 199 | COOH | i-$C_4H_9$ | 4-$CH_3C_6H_4SO_2$ | H | $HOCH_2CH_2NHCO$ | $C_6H_5CH_2$ | O | 4 | 2.2 | L, L |
| 200 | COOH | i-$C_4H_9$ | $C_6H_4SO_2$ | H | 4-$CH_3C_6H_4SO_2$ | $C_6H_5CH_2$ | O | 4 | 31 | L, L |
| 201 | COOH | i-$C_4H_9$ | 4-$NH_2C_6H_4SO_2$ | H | 4-$CH_3C_6H_4SO_2$ | $C_6H_5CH_2$ | O | 4 | 4.1 | L, L |

TABLE 2

Anti-protease activity of amino acid derivatives of formula II.

II $$R_1\diagdown N\diagup \underset{R_2}{\phantom{N}}\overset{Cx}{\underset{}{\text{—}}}(CH_2)_n\text{—}\underset{H}{N}\overset{Y}{\text{—}}\underset{R_a}{\overset{R_4}{N}}$$

| Ex. No. | Cx | $R_1$ | $R_2$ | $R_4$ | $R_a$ | U | n | Ki(nM) | D, L, DL R, S, RS |
|---|---|---|---|---|---|---|---|---|---|
| 17 | COOH | i-$C_4H_9$ | 4-$CH_3C_6H_4SO_2$ | $C_6H_5SO_2$ | N'α$CH_2CH(OH)CH_2$ | O | 0 | 55 | L, L |
| 65 | COOH | i-$C_4H_9$ | 4-$CH_3C_6H_4SO_2$ | 4-$CH_3C_6H_4SO_2$ | —$H_2C$—(o-$C_6H_4$)—$CH_2$— | O | 4 | 24 | L, L |
| 141 | $CH_2OH$ | i-$C_4H_9$ | 4-$CH_3C_6H_4SO_2$ | Boc | Indole-(2-$CH_2$N'α)-3-$CH_2$ | O | 4 | 38 | S, S |

We claim:

1. A compound selected from the group consisting of a compound of formula Ia

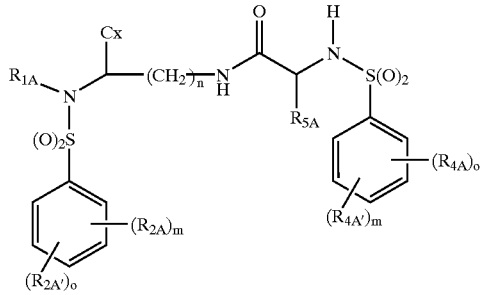

and when the compound of formula Ia has an amino group pharmaceutically acceptable ammonium salts thereof, wherein Cx is selected from the group consisting of —COOM and —CH$_2$OH, M being an alkali metal or alkaline earth metal, wherein R$_{1A}$ is selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, wherein R$_{2A}$, R$_{2A'}$, R$_{4A}$ and R$_{4A'}$ are independently selected from the group consisting of H, a straight or branched alkyl group of 1 to 4 carbon atoms, F, Cl, Br, I, —CF$_3$, —NO$_2$, —NR$_{10}$R$_{11}$, —NHCOR$_{10}$, —OR$_{10}$, —OCH$_2$C$_6$H$_5$, —SR$_{10}$, —COOR$_{10}$, —COR$_{10}$ and —CH$_2$OH, wherein R$_{5A}$ is selected from the group consisting of H, a straight or branched alkyl group of 1 to 8 carbon atoms, HOCH$_2$—, C$_6$H$_5$CH$_2$OCH$_2$—, benzyl-OCH(CH$_3$), HO$_2$CCH$_2$—, HO$_2$CCH$_2$CH$_2$—, NC—CH$_2$—, H$_2$NC(O)CH$_2$—, H$_2$NC(O)CH$_2$CH$_2$—, 4-CH$_3$C$_6$H$_4$CH$_2$SCH$_2$—, CH$_3$SCH$_2$CH$_2$—, H$_2$NCH$_2$CH$_2$CH$_2$—, C$_6$H$_5$—, C$_6$H$_5$CH$_2$—, C$_6$H$_5$CH(OH)—, C$_6$H$_5$CH(CN)—, C$_6$F$_5$CH$_2$—, 4-(9-fluorenylmethoxycarbonyl)-NHCH$_2$—C$_6$H$_4$CH$_2$— and benzyl substituted by a group selected from the group consisting of H, a straight or branched alkyl group of 1 to 4 carbon atoms, F, Cl, Br, I, —CF$_3$, —NO$_2$, —NR$_{10}$R$_{11}$, —NHCOR$_{10}$, —OR$_{10}$, —OCH$_2$C$_6$H$_5$, —SR$_{10}$, —COOR$_{10}$, —COR$_{10}$ and —CH$_2$OH, wherein each m is independently 0 or 1, wherein n is 3 or 4, wherein each o is independently 0 or 1, and wherein R$_{10}$ and R$_{11}$ are independently selected from the group consisting of H, a straight or branched alkyl group of 1 to 4 carbon atoms.

2. A compound selected from the group consisting of a compound of formula Ia'

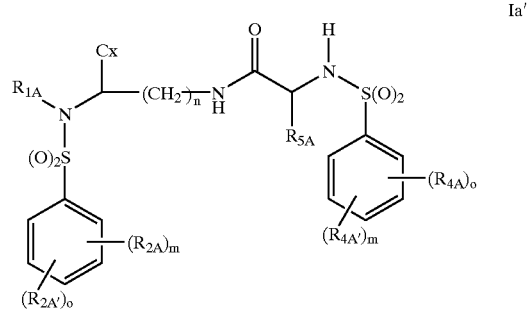

and when the compound of formula Ia' has an amino group pharmaceutically acceptable ammonium salts thereof, wherein Cx is selected from the group consisting of —COOM and —CH$_2$OH, M being an alkali metal or alkaline earth metal, wherein R$_{1A}$, R$_{2A}$, R$_{2A'}$, R$_{4A}$, R$_{4A'}$, R$_{10}$, R$_{11}$, m, n and o are as defined in claim 1, and wherein R$_{5A}$ is selected from the group consisting of indole-3-CH$_2$—, 2-benzothiophene-CH$_2$—, C$_5$H$_4$N-2-CH$_2$—, C$_5$H$_4$N-3-CH$_2$—, C$_5$H$_4$N-4-CH$_2$—, 2-thiophene-CH$_2$—, imidazole-4-CH$_2$—, thiazole-4-CH$_2$— and Nτ-benzyl-imidazole-4-CH$_2$— provided that when Cx is CH$_2$OH, R$_{5A}$ is not indole-3-CH$_2$—.

3. A compound of formula

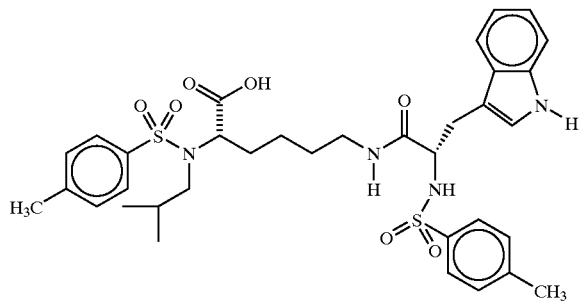

or a K, Na and Cs salt thereof.

4. A compound of formula

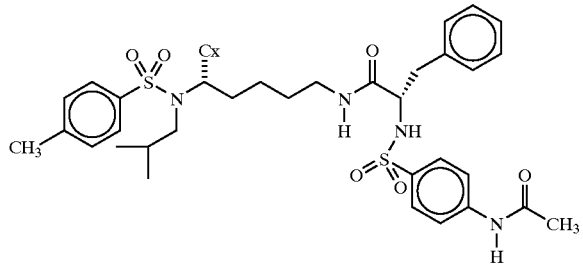

or a K, Na and Cs salt thereof, wherein Cx is selected from the group consisting of —COOH and —CH$_2$OH.

5. A compound of formula

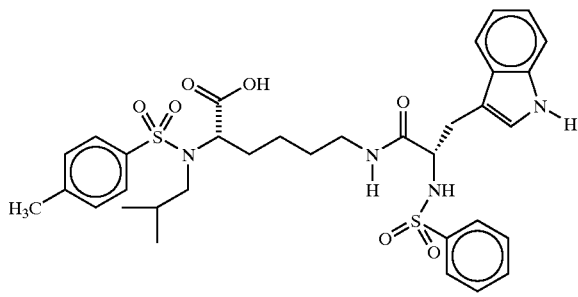

or a K, Na and Cs salt thereof.

6. A compound of formula

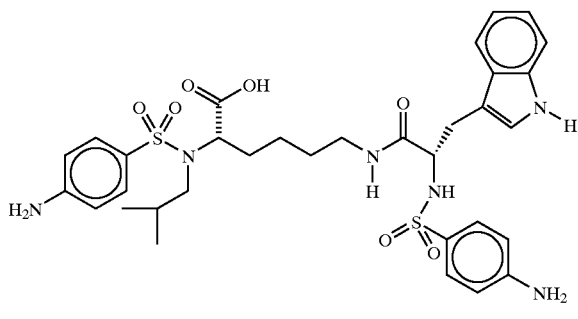

or a pharmaceutically acceptable ammonium, K, Na and Cs salt thereof.

7. A compound of formula

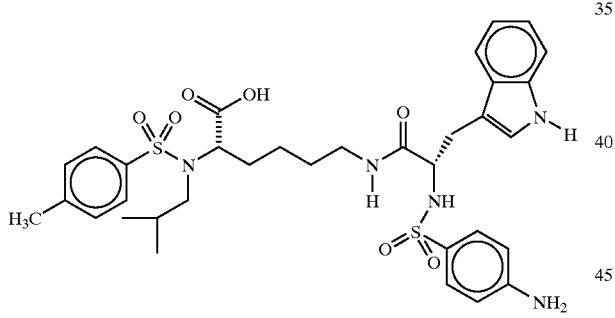

or a pharmaceutically acceptable ammonium, K, Na and Cs salt thereof.

8. A compound of formula

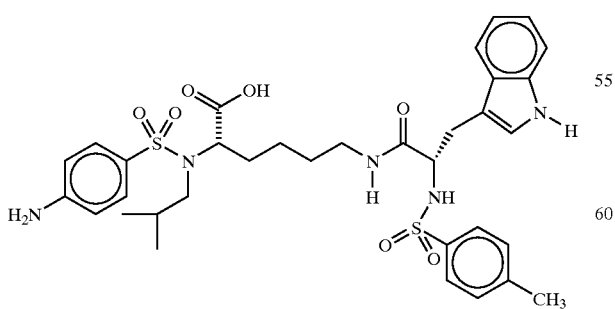

or a pharmaceutically acceptable ammonium, K, Na and Cs salt thereof.

9. A compound of formula

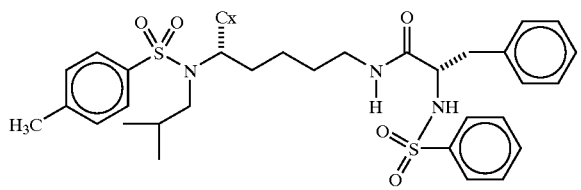

or a K, Na and Cs salt thereof, thereof, wherein Cx is selected from the group consisting of —COOH and —CH$_2$OH.

10. A compound selected from the group consisting of a compound of formula Ia″

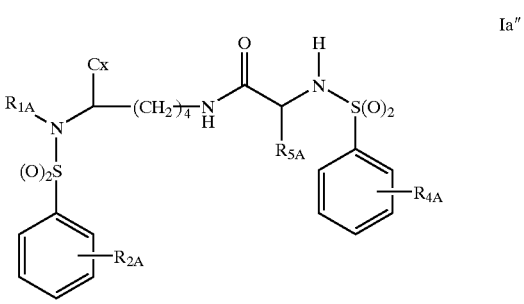

and when the compound of formula Ia″ has an amino group pharmaceutically acceptable ammonium salts thereof, wherein Cx is selected from the group consisting of —COOM and —CH$_2$OH, M being an alkali metal or alkaline earth metal, wherein $R_{1A}$ is selected from the group consisting of a straight or branched alkyl group of 1 to 6 carbon atoms, a cycloalkylalkyl group having 3 to 6 carbon atoms in the cycloalkyl part thereof and 1 to 3 carbon atoms in the alkyl part thereof, wherein $R_{2A}$ and $R_{4A}$ are independently selected from the group consisting of H, a straight or branched alkyl group of 1 to 4 carbon atoms, F, Cl, Br, I, —CF$_3$, —NO$_2$, —NR$_{10}$R$_{11}$, —NHCOR$_{10}$, —OR$_{10}$, —OCH$_2$C$_6$H$_5$, —SR$_{10}$, —COOR$_{10}$, —COR$_{10}$ and —CH$_2$OH, wherein $R_{5A}$ is selected from the group consisting of H, a straight or branched alkyl group of 1 to 8 carbon atoms, HOCH$_2$—, C$_6$H$_5$CH$_2$OCH$_2$—, benzyl-OCH(CH$_3$), HO$_2$CCH$_2$—, HO$_2$CCH$_2$CH$_2$—, NC—CH$_2$—, H$_2$NC(O)CH$_2$—, H$_2$NC(O)CH$_2$CH$_2$—, 4-CH$_3$C$_6$H$_4$CH$_2$SCH$_2$—, CH$_3$SCH$_2$CH$_2$—, H$_2$NCH$_2$CH$_2$CH$_2$CH$_2$—, C$_6$H$_5$—, C$_6$H$_5$CH$_2$—, C$_6$H$_5$CH(OH)—, C$_6$H$_5$CH(CN)—, C$_6$F$_5$CH$_2$—, 4-(9-fluorenylmethoxycarbonyl)-NHCH$_2$—C$_6$H$_4$CH$_2$—, C$_5$H$_4$N-2-CH$_2$—, C$_5$H$_4$N-3-CH$_2$—, C$_5$H$_4$N-4-CH$_2$—, 2-thiophene-CH$_2$—, indole-3-CH$_2$—, 2-benzothiophene-CH$_2$—, Nτ-benzyl-imidazole-4—CH$_2$—, imidazole-4-CH$_2$—, thiazole-4-CH$_2$— and benzyl substituted by a group selected from the group consisting of H, a straight or branched alkyl group of 1 to 4 carbon atoms, F, Cl, Br, I, —CF$_3$, —NO$_2$, —NR$_{10}$R$_{11}$, —NHCOR$_{10}$, —OR$_{10}$, —OCH$_2$C$_6$H$_5$, —SR$_{10}$, —COOR$_{10}$, —COR$_{10}$ and —CH$_2$OH, and wherein $R_{10}$ and $R_{11}$ are independently selected from the group consisting of H, a straight or branched alkyl group of 1 to 4 carbon atoms, provided that when Cx is CH$_2$OH, $R_{5A}$ is not indole-3-CH$_2$—.

* * * * *

UNITED STATES PATENT AND TRADEMARK OFFICE
CERTIFICATE OF CORRECTION

PATENT NO. : 6,608,100 B1
DATED : August 19, 2003
INVENTOR(S) : Brent Richard Stranix et al.

It is certified that error appears in the above-identified patent and that said Letters Patent is hereby corrected as shown below:

Column 2,
Line 58, the phrase "...It is the m objective of this invention..." should read -- It is the main objective of this invention... --;

Column 6,
Line 39, the phrase "...4-Brc$_6$H$_4$SO$_2$..." should read -- ...4-BrC$_6$H$_4$SO$_2$... --;

Column 9,
Line 21, the phrase "... C$_6$H5..." should read -- ... C$_6$H$_5$... --;

Column 11,
Line 5, the phrase "... of formulae IA, Ia, IB, Ic..." should read -- IA, Ia, Ib, Ic... --;

Columns 15 and 16,
The structure -- ...

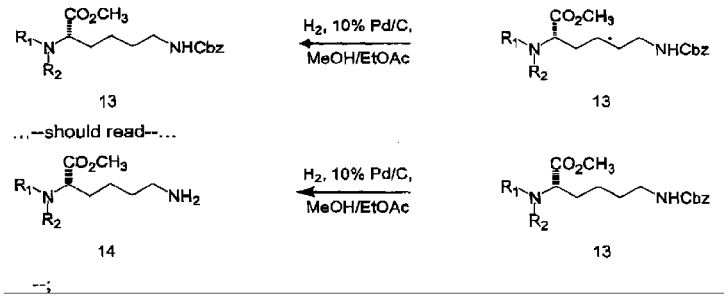

...--should read--...

--;

Column 17,
Line 50, the phrase "...a) For scheme 4,..." should read -- ...a) For scheme 5, ... --;

Columns 17 and 28,
Scheme 5, the phrase "...1. 30% piperdlne DMF..." should read -- ...1. 30% piperidine DMF --;

Column 27,
Line 4, the phrase "...for a further 20 mill..." should read -- ... for a further 20 min... --;

Column 36,
Line 29, the phrase "...1H NMR..." should read -- ...$^1$H NMR... --;
Line 52, the phrase "... prepared from No-isobutyl– Nα-..." should read -- ... prepared from Nα-isobutyl– Nα-... --;

UNITED STATES PATENT AND TRADEMARK OFFICE
CERTIFICATE OF CORRECTION

PATENT NO. : 6,608,100 B1
DATED : August 19, 2003
INVENTOR(S) : Brent Richard Stranix et al.

It is certified that error appears in the above-identified patent and that said Letters Patent is hereby corrected as shown below:

Column 37,
Line 19, the phrase "… Preparation of Nαc-benzenesulfonyl-L-norleucine…" should read -- … Preparation of Nα-benzenesulfonyl-L-norleucine… --.

Column 39,
Line 23, the phrase "…1HR NMR…" should read -- …$^1$H NMR… --;
Line 52, the phrase "…$^1$H NMR (CDCl$_3$): 0.79…" should read
-- …$^1$H NMR(CDCl$_3$): δ 0.79… --;

Column 52,
Line 67, the phrase "…-NF-[N'α-(2-thiophenesulfonyl)-L-…" should read
-- "…-Nε-[N'α-(2-thiophenesulfonyl)-L-… --;

Column 53,
Line 38, the phrase " …preparative H[PLC to…" should read --… preparative HPLC to… --;

Column 54,
Line 59, the phrase "…is based in scheme 4…" should read -- …in based on scheme 4…--;

Column 58,
Line 53, the phrase "…N'α-benzenesulfonyl[-…" should read
-- …N'α-benzenesulfonyl-… --;

Column 62,
Line 24, the phrase "…(4methylbenzenesulfonyl)…" should read -- …(4-methylbenzenesulfonyl)…--;
Line 63, the phrase "…-Nε-(Nt-benzyl-L-…"-- should read -- …-Nε-(Nτ-benzyl-L-…--;
Line 67, the phrase "…-(N'α-tert-butoxycarbonyl-Nr-…" should read
-- …-(N'α-tert-butoxycarbonyl-Nτ-… --;

Column 64,
Line 14, the phrase "…with LiAlH4 following…" should read -- … with LiAlH$_4$ following… --;

Column 68,
Line 62, the phrase "… H using DEEA…" should read -- H using DIEA… --;

UNITED STATES PATENT AND TRADEMARK OFFICE
CERTIFICATE OF CORRECTION

PATENT NO. : 6,608,100 B1
DATED : August 19, 2003
INVENTOR(S) : Brent Richard Stranix et al.

It is certified that error appears in the above-identified patent and that said Letters Patent is hereby corrected as shown below:

Column 70,
Line 2, the phrase "… H using DEEA…" should read -- H using DIEA… --;

Column 71,
Line 26, the phrase "… -2,6-diaminohexanal…" should read
-- … -2,6-diaminohexanol… --;

Column 75,
Line 47, the phrase " …-2,6-diaminohexanal…" should read -- … -2,6-diaminohexanol… --;

Column 77,
Line 23, the phrase "…- NE - (N'α-dihydrocinnamoyl-L-…"should read -- … -Nε-(N'α-dihydrocinnamoyl-L-… --;

Column 79,
Line 63, the phrase "…-S-4tert-…" should read -- …-S-4-tert.... --;

Column 81,
Line 43, the phrase "…Preparation of (S, 2'S) …" should read -- … Preparation of (2S, 2'S) … --;

Column 86,
Line 10, the phrase "… temperature for 5 IL…" should read -- temperature for
5 h. … --;

Column 90,
Line 14, the phrase "… for 2 k Afterwards, …" should read -- … for 2 h. Afterwards, ...--;

Column 93,
Line 8, the phrase "…carbonyldimidazole...-- should read
-- … carbonyldiimidazole… --;

UNITED STATES PATENT AND TRADEMARK OFFICE
CERTIFICATE OF CORRECTION

PATENT NO. : 6,608,100 B1
DATED : August 19, 2003
INVENTOR(S) : Brent Richard Stranix et al.

It is certified that error appears in the above-identified patent and that said Letters Patent is hereby corrected as shown below:

Columns 103 and 104,
TABLE 1, "...Anti-protease activity of Ne-amino acid..." should read -- ... Anti-protease activity of Nε-amino acid... --;

Columns 105 and 106,
TABLE 1-continued, at the phrase "...Anti-protease activity of Nε-amino acid..." should read -- ... Anti-protease activity of Nε-amino acid... --;

Columns 107 and 108,
TABLE 1-continued, at the phrase "...Anti-protease activity of Ne-amino acid...-- should read -- ... Anti-protease activity of Nε-amino acid... --; and Columns 109 and 110,
TABLE 1-continued, at the phrase "...Anti-protease activity of Ne-amino acid.." should read -- … Anti-protease activity of Nε-amino acid... --.

Signed and Sealed this

Fourteenth Day of September, 2004

JON W. DUDAS
*Director of the United States Patent and Trademark Office*